US012576074B2

(12) United States Patent
Belardinelli et al.

(10) Patent No.: US 12,576,074 B2
(45) **Date of Patent: *Mar. 17, 2026**

(54) KITS AND METHODS FOR INDUCTION OF CARDIOVERSION IN SUBJECTS WITH ATRIAL ARRHYTHMIAS

(71) Applicant: InCarda Therapeutics, Inc., Newark, CA (US)

(72) Inventors: Luiz Belardinelli, Palo Alto, CA (US); Carlos Schuler, Kensington, CA (US); Miguel Guzman, San Jose, CA (US)

(73) Assignee: InCarda Therapeutics, Inc., West Jordan, UT (US)

( * ) Notice: Subject to any disclaimer, the term of this patent is extended or adjusted under 35 U.S.C. 154(b) by 74 days.

This patent is subject to a terminal disclaimer.

(21) Appl. No.: 18/186,668

(22) Filed: Mar. 20, 2023

(65) Prior Publication Data

US 2023/0226032 A1 Jul. 20, 2023

Related U.S. Application Data

(63) Continuation of application No. 17/708,732, filed on Mar. 30, 2022, now Pat. No. 12,059,414, which is a continuation of application No. PCT/US2021/064213, filed on Dec. 17, 2021.

(60) Provisional application No. 63/153,492, filed on Feb. 25, 2021, provisional application No. 63/127,089, filed on Dec. 17, 2020.

(51) Int. Cl.

| | |
|---|---|
| ***A61K 31/4458*** | (2006.01) |
| ***A61K 31/138*** | (2006.01) |
| ***A61K 31/167*** | (2006.01) |
| ***A61K 31/18*** | (2006.01) |
| ***A61P 9/06*** | (2006.01) |

(52) U.S. Cl.

CPC ........ *A61K 31/4458* (2013.01); *A61K 31/138* (2013.01); *A61K 31/167* (2013.01); *A61K 31/18* (2013.01); *A61P 9/06* (2018.01)

(58) Field of Classification Search

CPC .. A61K 31/4458; A61K 31/18; A61K 31/167; A61K 31/138; A61P 9/06

See application file for complete search history.

(56) References Cited

U.S. PATENT DOCUMENTS

| | | | | |
|---|---|---|---|---|
| 7,951,137 | B2 | 5/2011 | Mehra et al. | |
| 8,106,099 | B2 | 1/2012 | Brendel et al. | |
| 8,974,828 | B2 | 3/2015 | Schuler et al. | |
| 9,597,302 | B1 | 3/2017 | Yan et al. | |
| 10,010,294 | B2 | 7/2018 | Narasimhan et al. | |
| 10,045,939 | B2 | 8/2018 | Schuler et al. | |
| 10,441,537 | B2 | 10/2019 | Schuler et al. | |
| 10,660,578 | B2 | 5/2020 | Narasimhan et al. | |
| 10,744,087 | B2 | 8/2020 | Belardinelli et al. | |
| 11,007,185 | B2 | 5/2021 | Hurrey et al. | |
| 11,020,384 | B2 | 6/2021 | Hurrey et al. | |
| 12,059,414 | B2 * | 8/2024 | Belardinelli | A61P 9/06 |
| 12,208,070 | B2 | 1/2025 | Khadtare et al. | |
| 2002/0161018 | A1 | 10/2002 | Smith et al. | |
| 2003/0077297 | A1 | 4/2003 | Chen et al. | |
| 2006/0032501 | A1 | 2/2006 | Hale et al. | |
| 2006/0062739 | A1 | 3/2006 | Hofmann et al. | |
| 2010/0183725 | A1 | 7/2010 | Mohsen et al. | |
| 2012/0003318 | A1 | 1/2012 | Schuler et al. | |
| 2015/0045305 | A1 | 2/2015 | Belardinelli et al. | |
| 2017/0238866 | A1 | 8/2017 | Narasimhan et al. | |
| 2019/0060230 | A1 | 2/2019 | Schuler et al. | |
| 2019/0290581 | A1 | 9/2019 | Belardinelli et al. | |
| 2021/0030732 | A1 | 2/2021 | Hurrey et al. | |
| 2021/0228825 | A1 | 7/2021 | Narasimhan et al. | |

FOREIGN PATENT DOCUMENTS

| | | | |
|---|---|---|---|
| EP | 2861254 | B1 | 4/2020 |
| WO | WO-2010107964 | A1 | 9/2010 |
| WO | WO-2013112932 | A1 | 8/2013 |
| WO | WO-2017136421 | A1 | 8/2017 |
| WO | WO-2018209107 | A1 | 11/2018 |
| WO | WO-2019183470 | A2 | 9/2019 |
| WO | WO-2019236694 | A1 | 12/2019 |
| WO | WO-2021022058 | A2 | 2/2021 |

OTHER PUBLICATIONS

Tikosyn (dofetilide) Capsules Drug Label (Pfizer Labs, Revised Jan. 2014, 30 pages) (Year: 2014).*

Betapace (sotalol hydrochloride) Tablets Drug Label (Covis Pharma, Revised May 2016, 22 pages) (Year: 2016).*

Flecainide Acetate Tablets Drug Label (County Line Pharmaceuticals, LLC, Sep. 2016, 6 pages) (Year: 2016).*

Corvert (Ibutilide fumarate injection) Drug Label (Pharmacia & Upjohn, Revised Oct. 2000, 6 pages) (Year: 2000).*

Narayan et al. J. Interv. Card. Electrophysiol., 2006, vol. 15, p. 175-178 (Year: 2006).*

Part 6: Advanced Cardiovascular Life Support Section 5: Pharmacology I: Agents for Arrhythmias. Resuscitation. 46(1):135-153 (2017).

European Application No. 21907959.7 European Search Report dated Oct. 10, 2024.

Belardinelli et al., A novel, potent, and selective inhibitor of cardiac late sodium current suppresses experimental arrhythmias. J Pharmacol Exp Ther. Jan. 2013;344(1):23-32. doi: 10.1124/jpet. 112.198887. Epub Sep. 25, 2012. PMID: 23010360.

Chan et al., Drug-induced QT prolongation and torsades de pointes: evaluation of a QT nomogram, QJM: An International Journal of Medicine, vol. 100, Issue 10, Oct. 2007, pp. 609-615.

(Continued)

*Primary Examiner* — James D. Anderson

(74) *Attorney, Agent, or Firm* — Wilson Sonsini Goodrich & Rosati

(57) ABSTRACT

Disclosed herein are methods and kits for treating or preventing a heart condition, e.g., cardiac arrhythmia, e.g., atrial arrhythmia, using potassium channel inhibitors and class I antiarrhythmic agents. Also disclosed herein are methods and kits for treating a heart condition via an intravenously, orally, or inhalationally administered fixed-dose combination of a sodium channel blocker and a class I antiarrhythmic agent.

24 Claims, 28 Drawing Sheets

(56) References Cited

OTHER PUBLICATIONS

Chiladakis et al., Ibutilide added to propafenone for the conversion of atrial fibrillation and atrial flutter. J Am Coll Cardiol. Aug. 18, 2004;44(4):859-63.
Fenrich et al. Flecainide and amiodarone: combined therapy for refractory tachyarrhythmias in infancy. J Am Coll Cardiol. Apr. 1995;25(5):1195-8.
Hongo et al., Use of Ibutilide in cardioversion of patients with atrial fibrillation or atrial flutter treated with class IC agents. J Am Coll Cardiol. Aug. 18, 2004;44(4):864-8.
International Search Report and Written Opinion issued in PCT/US2021064213 on May 4, 2022.
Johannesen et al., Late sodium current block for drug-induced long QT syndrome: Results from a prospective clinical trial. Clin Pharmacol Ther. Feb. 2016;99(2):214-23.
Korantzopoulos et al., Propafenone added to ibutilide increases conversion rates of persistent atrial fibrillation. Heart (British Cardiac Society). 92. 631-4 (2006).
Li Y, et al. Pharmacokinetic and pharmacodynamic properties of a single intravenous dose of ibutilide fumarate: a phase I, randomized, open-label, increasing-dose study in healthy Chinese men. Clin Ther. Sep. 2007;29(9):1957-66.
Liu et al., Synergistic Effect of Dofetilide and Mexiletine on Prevention of Atrial Fibrillation. Journal of the American Heart Association. 6. 10.1161/JAHA.117.005482, May 2017.
Reiffel et al., The actions of ibutilide and class Ic drugs on the slow sodium channel: new insights regarding individual pharmacologic effects elucidated through combination therapies. J Cardiovasc Pharmacol Ther. Jul. 2000;5(3):177-81.
Sahu et al., Ibutilide is Safe for Cardioversion of Atrial Fibrillation in Patents on Concomitant Antiarrhythmic Agents (Abstract). PACE 42:743, 1999.
Themistoclakis et al., Class IC Drug Plus Ibutilide for Acute Cardioversion of Atrial Fibrillation: What is the Rationale and What are the Results?. 10.1007/978-88-470-2103-7_59 (2002).
U.S. Appl. No. 17/708,732 Notice of Allowance dated May 8, 2024.
Wang T, et al. The development and testing of intravenous dosing regimens: application to flecainide for the suppression of ventricular arrhythmias. Clin Pharmacol Ther. May 1988;43(5):499-508. Erratum in: Clin Pharmacol Ther Jul. 1988;44(1):77.
Burashnikov, Alexander, and Charles Antzelevitch. New developments in atrial antiarrhythmic drug therapy. Nature Reviews Cardiology 7(3):139-148 (2010).
Burashnikov, Alexander et al. Atrium-selective sodium channel block as a strategy for suppression of atrial fibrillation: differences in sodium channel inactivation between atria and ventricles and the role of ranolazine. Circulation 116(13):1449-1457 (2007).
Burashnikov, Alexander et al. Inhibition of IKr potentiates development of atrial-selective INa block leading to effective suppression of atrial fibrillation. Heart Rhythm 12(4):836-844 (2015).
Burashnikov, Alexander et al. Synergistic effect of the combination of ranolazine and dronedarone to suppress atrial fibrillation. Journal of the American College of Cardiology 56(15):1216-1224 (2010).
Coumel, Philippe et al. Logic and Empiricism in the Selection of Antiarrhythmic Agents: The Role of Drug Combinations. Drugs 29(Suppl_4):68-76 (1985).
El-Bizri, Nesrine et al. Eleclazine exhibits enhanced selectivity for long QT syndrome type 3-associated late Na+ current. Heart Rhythm 15(2):277-286 (2018).
Fuster, Valentin et al. 2011 ACCF/AHA/HRS focused updates incorporated into the ACC/AHA/ESC 2006 Guidelines for the management of patients with atrial fibrillation: a report of the American College of Cardiology Foundation/American Heart Association Task Force on Practice Guidelines developed in partnership with the European Society of Cardiology and in collaboration with the European Heart Rhythm Association and the Heart Rhythm Society. Journal of the American College of Cardiology 57(11):e101-e198 (2011).
Kornyeyev, Dmytro et al. Contribution of the late sodium current to intracellular sodium and calcium overload in rabbit ventricular myocytes treated by anemone toxin. American Journal of Physiology-Heart and Circulatory Physiology 310(3):H426-H435 (2016).
Lee, Kai S. et al. Membrane activity of class III antiarrhythmic compounds; a comparison between ibutilide, d-sotalol, E-4031, sematilide and dofetilide. European journal of pharmacology 234(1):43-53 (1993).
Liu, Tengxian et al. Blinded validation of the isolated arterially perfused rabbit ventricular wedge in preclinical assessment of drug-induced proarrhythmias. Heart rhythm 3(8):948-956 (2006).
Mirams, Gary R. et al. Simulation of multiple ion channel block provides improved early prediction of compounds' clinical torsadogenic risk. Cardiovascular research 91(1):53-61 (2011).
Ni, Haibo et al. Populations of in silico myocytes and tissues reveal synergy of multiatrial-predominant K+-current block in atrial fibrillation. British journal of pharmacology 177(19):4497-4515 (2020).
Ni, Haibo. et al. Synergistic Anti-arrhythmic effects in human atria with combined use of sodium blockers and acacetin. Frontiers in Physiology 8:946, 1-21 (2017).
Oral, Hakan et al. Facilitating transthoracic cardioversion of atrial fibrillation with ibutilide pretreatment. New England Journal of Medicine 340(24):1849-1854 (1999).
Reiffel, James A. et al. The HARMONY trial: combined ranolazine and dronedarone in the management of paroxysmal atrial fibrillation: mechanistic and therapeutic synergism. Circulation: Arrhythmia and Electrophysiology 8(5):1048-1056 (2015).
Sun, Xue-Rong et al. Low-dose ibutilide combined with catheter ablation of persistent atrial fibrillation: procedural impact and clinical outcome. Cardiology research and practice 2019(1):3210803, 1-10 (2019).
Anno, Takafumi, and Luc M. Hondeghem. Interactions of flecainide with guinea pig cardiac sodium channels. Importance of activation unblocking to the voltage dependence of recovery. Circulation research 66(3):789-803 (1990).
Antzelevitch, Charles, and Luiz Belardinelli. The role of sodium channel current in modulating transmural dispersion of repolarization and arrhythmogenesis. Journal of Cardiovascular Electrophysiology 17(Suppl 1):S79-S85 (2006).
Belardinelli, Luiz. et al. Cardiac late Na(+) current: proarrhythmic effects, roles in long QT syndromes, and pathological relationship to CaMKII and oxidative stress. Heart Rhythm 12(2):440-448 (2015).
Breindahl, Torben. Therapeutic drug monitoring of flecainide in serum using high-performance liquid chromatography and electrospray mass spectrometry. Journal of Chromatography B: Biomedical Sciences and Applications 746(2):249-254 (2000).
Burashnikov, Alexander. et al. Effect of flecainide and ibutilide alone and in combination to terminate and prevent recurrence of atrial fibrillation. Circulation: Arrhythmia and Electrophysiology 17(1):e012454, 24-33 (2024). Published Online Dec. 26, 2023.
Burashnikov, Alexander. Late INa inhibition as an antiarrhythmic strategy. Journal of Cardiovascular Pharmacology 70(3):159-167 (2017).
Cogolludo, Angel L. et al. Antagonism by class I antiarrhythmic drugs of levcromakalim-induced relaxation in isolated rat aorta. The Journal of Pharmacology and Experimental Therapeutics 287(1):81-86 (1998).
Cohen, Alberto A. et al. Hemodynamic effects of intravenous flecainide in acute noncomplicated myocardial infarction. American Heart Journal 110(6):1193-1196 (1985).
Conard, G. J. et al. Plasma concentrations of flecainide acetate, a new antiarrhythmic agent, in humans. Clinical Therapeutics 6(5):643-652 (1984).
Conard, Gordon J., and Robert E. Ober. Metabolism of flecainide. The American Journal of Cardiology 53(5):41B-51B (1984).
Deneer, V. H. M. et al. Absorption kinetics and pharmacodynamics of two oral dosage forms of flecainide in patients with an episode of paroxysmal atrial fibrillation. European Journal of Clinical Pharmacology 60(10):693-701 (2004).
Echt, Debra S., and Jeremy N. Ruskin. Use of flecainide for the treatment of atrial fibrillation. The American Journal of Cardiology 125(7):1123-1133 (2020).

(56) References Cited

OTHER PUBLICATIONS

Falk, Rodney H. et al. Intravenous dofetilide, a class III antiarrhythmic agent, for the termination of sustained atrial fibrillation or flutter. Journal of the American College of Cardiology 29(2):385-390 (1997).
Follmer, C. H., and T. J. Colatsky. Block of delayed rectifier potassium current, IK, by flecainide and E-4031 in cat ventricular myocytes. Circulation 82(1):289-293 (1990).
Gossinger, Heinz David. et al. Combined sotalol and flecainide given at low dosage in patients with the Wolff-Parkinson-White syndrome. International journal of cardiology 26(3):380-382 (1990).
Hilliard, Fredrick A. et al. Flecainide inhibits arrhythmogenic Ca2+ waves by open state block of ryanodine receptor Ca2+ release channels and reduction of Ca2+ spark mass. Journal of Molecular and Cellular Cardiology 48(2):293-301 (2010). Oct. 14, 2009.
Hoffmeister, H. M. et al. Negative inotropic effect of class-I-antiarrhythmic drugs: comparison of flecainide with disopyramide and quinidine. European Heart Journal 8(10):1126-1132 (1987).
Jackson, N. et al. Hemodynamic dose-response effects of flecainide in acute myocardial infarction with and without left ventricular decompensation. Clinical Pharmacology & Therapeutics 37(6):619-624 (1985).
James, M. A. et al. Combined anti-arrhythmic therapy with class 1 and class 3 drugs. Postgraduate Medical Journal 65(766):519-524 (1989).
Johannesen, Lars. et al. Late sodium current block for drug-induced long QT syndrome: results from a prospective clinical trial. Clinical Pharmacology & Therapeutics 99(2):214-223 (2016). Published Online Nov. 28, 2015.
Josephson, Martin A. et al. Hemodynamic effects of intravenous flecainide relative to the level of ventricular function in patients with coronary artery disease. American Heart Journal 109(1):41-45 (1985).
Kihara, Yasuki. et al. Mechanisms of negative inotropic effects of class Ic antiarrhythmic agents: comparative study of the effects of flecainide and pilsicainide on intracellular calcium handling in dog ventricular myocardium. Journal of Cardiovascular Pharmacology 27(1):42-51 (1996).
Kowey, Peter R. et al. Safety and risk/benefit analysis of ibutilide for acute conversion of atrial fibrillation/flutter. The American Journal of Cardiology 78(8):46-52 (1996).
Lee, Kai S., and Esther W. Lee. Ionic mechanism of ibutilide in human atrium: evidence for a drug-induced Na+ current through a nifedipine-inhibited inward channel. The Journal of Pharmacology and Experimental Therapeutics 286(1): 9-22 (1998).
Legrand, Victor. et al. Comparative haemodynamic effects of intravenous flecainide in patients with and without heart failure and with and without beta-blocker therapy. European Heart Journal 6(8):664-671 (1985).
Legrand, Victor. et al. Hemodynamic effects of a new antiarrhythmic agent, flecainide (R-818), in coronary heart disease. The American Journal of Cardiology 51(3):422-426 (1983).
Li, Yishi. et al. Pharmacokinetic and pharmacodynamic properties of a single intravenous dose of ibutilide fumarate: a phase I, randomized, open-label, increasing-dose study in healthy Chinese men. Clinical Therapeutics 29(9):1957-1966 (2007).
Lynch Jr, Joseph J. et al. Comparison of binding to rapidly activating delayed rectifier K+ channel, IKr, and effects on myocardial refractoriness for class III antiarrhythmic agents. Journal of cardiovascular pharmacology 25(2):336-340 (1995).
Lynch Jr, Joseph J et al. Comparison of the intrinsic vasorelaxant and inotropic effects of the antiarrhythmic agents vernakalant and flecainide in human isolated vascular and cardiac tissues. Journal of Cardiovascular Pharmacology 61(3):226-232 (2013).
Marum, Alexandre A. et al. Optimizing flecainide plasma concentration profile for atrial fibrillation conversion while minimizing adverse ventricular effects by rapid, low-dose intratracheal or intravenous administration. International Journal of Cardiology 274:170-174 (2019).
Muhiddin, Khulood A. et al. Effect of flecainide on cardiac output. Clinical Pharmacology and Therapeutics 37(3):260-263 (1985).
Perez-Vizcaino, Francisco. et al. Effects of flecainide on isolated vascular smooth muscles of rat. British Journal of Pharmacology 104(3):726-730 (1991).
Perry, Matthew. et al. Structural determinants of HERG channel block by clofilium and ibutilide. Molecular Pharmacology 66(2):240-249 (2004).
Pham, Thai V. et al. Testosterone diminishes the proarrhythmic effects of dofetilide in normal female rabbits. Circulation 106(16):2132-2136 (2002).
Price, Jack F. et al. Flecainide and sotalol: a new combination therapy for refractory supraventricular tachycardia in children 1 year of age. Journal of the American College of Cardiology 39(3):517-520 (2002).
Reiffel, James A. and Mark Blitzer. The actions of ibutilide and class Ic drugs on the slow sodium channel: new insights regarding individual pharmacologic effects elucidated through combination therapies. Journal of Cardiovascular Pharmacology and Therapeutics 5(3):177-181 (2000).
Rythmol(propafenone hydrochloride tablets). Product Label Information. Reference ID: 4344605 (pp. 1-24) (Approval 1989/Revised 2018).
Santinelli, Vincenzo. et al. Effects of flecainide and propafenone on systolic performance in subjects with normal cardiac function. Chest 103(4):1068-1073 (1993).
Scamps, F. et al. Inhibition of ICa in single frog cardiac cells by quinidine, flecainide, ethmozin, and ethacizin. American Journal of Physiology-Cell Physiology 256(3):C549-C559 (1989).
Schulze, J. J. and J Knops. Effects of flecainide on contractile force and electrophysiological parameters in cardiac muscle. Arzneimittel-Forschung 32(9):1025-1029 (1982).
Serruys, P. W. et al. The haemodynamic effect of intravenous flecainide acetate in patients with coronary artery disease. British Journal of Clinical Pharmacology 16(1):51-59 (1983).
Stambler, Bruce S. et al. Efficacy and safety of repeated intravenous doses of ibutilide for rapid conversion of atrial flutter or fibrillation. Circulation 94(7):1613-1621 (1996).
Tisdale, James E. et al. Enhanced sensitivity to drug-induced QT interval lengthening in patients with heart failure due to left ventricular systolic dysfunction. The Journal of Clinical Pharmacology 52(9):1296-1305 (2012).
Tisdale, James E. et al. Pharmacokinetics of ibutilide in patients with heart failure due to left ventricular systolic dysfunction. Pharmacotherapy 28(12):1461-1470 (2008).
Tjandra-Maga, Tikma Budya et al. Flecainide: single and multiple oral dose kinetics, absolute bioavailability and effect of food and antacid in man. British Journal of Clinical Pharmacology 22(3):309-316 (1986).
Van Midendorp, Lars B. et al. Electrophysiological and haemodynamic effects of vernakalant and flecainide in dyssynchronous canine hearts. Europace 16(8):1249-1256 (2014).
Verdouw, Pieter D. et al. Antiarrhythmic and hemodynamic actions of flecainide acetate (R-818) in the ischemic porcine heart. Journal of Cardiovascular Pharmacology 1(4):473-486 (1979).
Vicente, Jose. et al. Electrocardiogramarkers for detection of drug-induced late sodium current block. Plos One 11(12):e0163619, 1-16 (2016).
Vicente, Jose. et al. Mechanistic model-informed proarrhythmic risk assessment of drugs: review of the "CiPA" initiative and design of a prospective clinical validation study. Clinical Pharmacology and Therapeutics 103(1):54-66 (2018).
Yang, Tao. et al. Ibutilide, a methanesulfonanilide antiarrhythmic, is a potent blocker of the rapidly activating delayed rectifier K+ current (IKr) in AT-1 cells: concentration-, time-, voltage-, and use-dependent effects. Circulation 91(6):1799-1806 (1995).

* cited by examiner

KITS AND METHODS FOR INDUCTION OF CARDIOVERSION IN SUBJECTS WITH ATRIAL ARRHYTHMIAS

CROSS-REFERENCE

This application is a continuation of U.S. application Ser. No. 17/708,732, filed Mar. 30, 2022, which is a continuation of International Patent Application No. PCT/US2021/064213, filed Dec. 17, 2021, which claims the benefit of U.S. Provisional Application No. 63/153,492, filed Feb. 25, 2021, and U.S. Provisional Application No. 63/127,089, filed Dec. 17, 2020, each of which is incorporated by reference herein in its entirety.

BACKGROUND

Atrial fibrillation (AF) is one of the most common sustained cardiac arrhythmias encountered in clinical practice and can lead to complications such as congestive heart failure or thromboembolism.

SUMMARY

In some embodiments, the present disclosure provides a pharmaceutical composition comprising a sodium channel blocker, ibutilide or a pharmaceutically acceptable salt thereof, and one or more pharmaceutically acceptable excipients, diluents, or carriers.

In some embodiments, the present disclosure provides a pharmaceutical composition comprising a sodium channel blocker, dofetilide or a pharmaceutically acceptable salt thereof, and one or more pharmaceutically acceptable excipients, diluents, or carriers.

In some embodiments, the present disclosure provides a pharmaceutical composition comprising a sodium channel blocker, sotalol or a pharmaceutically acceptable salt thereof, and one or more pharmaceutically acceptable excipients, diluents, or carriers.

In some embodiments, the present disclosure provides a method of treating a subject suffering from atrial arrhythmia, comprising administering to said subject:

(i) a sodium channel blocker in a first amount; and (ii) a potassium channel blocker in a second amount, wherein said potassium channel blocker is selected from the group consisting of: ibutilide or a pharmaceutically acceptable salt thereof, dofetilide or a pharmaceutically acceptable salt thereof, and sotalol or a pharmaceutically acceptable salt thereof, wherein said administration results in a $t_{max}$ of said sodium channel blocker in said subject that occurs no more than about 30 minutes apart from a $t_{max}$ of said potassium channel blocker in said subject, thereby inducing cardioversion of said atrial arrhythmia.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Figure 1:
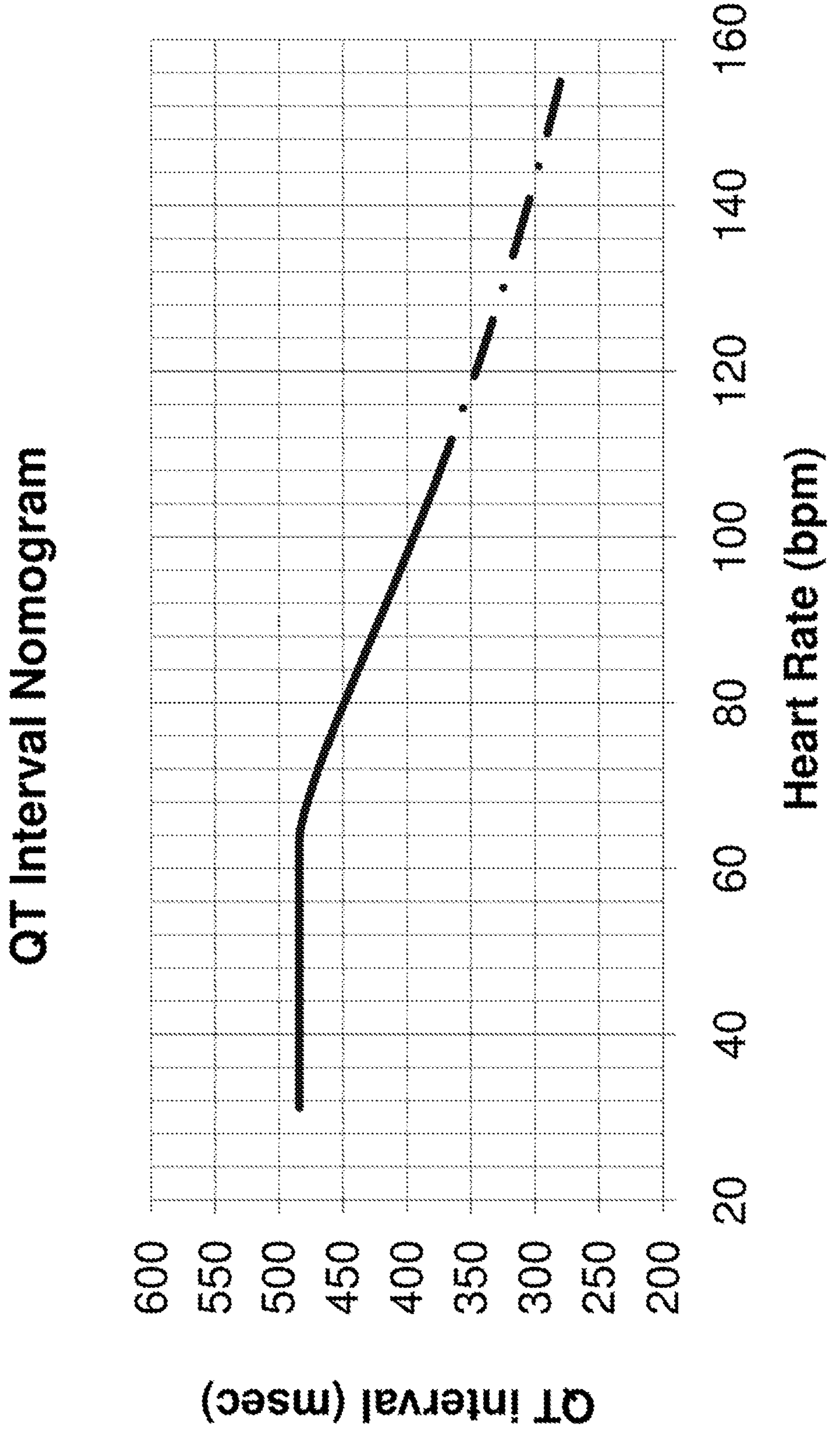
FIG. 1 depicts a QT interval nomogram that can be used for the evaluation of torsades de pointes (TdP) risk in a subject.

In some embodiments, the present disclosure relates to administration of a therapeutically effective amount of sodium channel blocker (or class I antiarrhythmic agent) and a potassium channel blocker to a subject suffering from cardiac arrhythmia as a fixed dose combination. In some embodiments, the cardiac arrhythmia is an atrial arrhythmia, which can include supraventricular tachycardia, paroxysmal supraventricular tachycardia, atrial fibrillation, paroxysmal atrial fibrillation, acute episodes in persistent atrial fibrillation, atrial flutter, paroxysmal atrial flutter, or lone atrial fibrillation. In some embodiments, the sodium channel blocker is flecainide, and the potassium channel blocker is ibutilide. In some embodiments, the sodium channel blocker is flecainide, and the potassium channel blocker is dofetilide. In some embodiments, the sodium channel blocker is flecainide, and the potassium channel blocker is sotalol. In some embodiments, a $Mg^{2+}$ source, such as, magnesium sulfate, is administered in combination with the sodium channel blocker and potassium channel blocker.

Pharmaceutical Agents.

In some embodiments, the method of treating cardiac arrhythmia, e.g., atrial fibrillation, includes administering a compound that lengthens the action potential duration (APD) of atrial myocytes, such as a potassium channel blocker. Non-limiting examples of potassium channel blockers that can be used in the methods and kits provided herein include ibutilide, dofetilide, sotalol, semilitide, methanandamide, anandamide, arachidonamide, A293 (2-(butylsulfonylamino)-N-[(1R)-1-(6-methoxy-3-pyridyl)propyl]-benzamide), bupivacaine, etidocaine, genistein, mepivacaine, phenytoin, quinidine, R-ropivacaine, S-ropivacaine, tetracaine, amiodarone, dronedarone, E-4031, vernakalant, and pharmaceutically acceptable salts and solvates thereof.

Among others, ibutilide or a pharmaceutically acceptable salt thereof, is a potassium channel blocker that can be used for the purpose of the present disclosure. Ibutilide is N-(4-(4-(ethyl(heptyl)amino)-1-hydroxybutyl)phenyl)methanesulfonamide, and has the following structural formula:

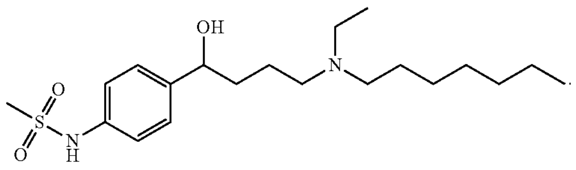 [SMILES: CCCCCCCN(CC)CCCC(O)c1ccc(NS(C)(=O)=O)cc1]

Ibutilide is a class IIIa antiarrhythmic drug (e.g., potassium channel blocker) that can inhibit delayed rectifier potassium current ($I_{Kr}$) and enhance inward depolarizing or non-inactivated component of the slow sodium current (e.g. late, persistent, or sustained sodium current). In some embodiments, ibutilide is used in the form of a pharmaceutically acceptable salt or solvate, for instance, ibutilide fumarate (e.g., ibutilide hemifumarate). Ibutilide can be a racemic combination of its two enantiomers R and S. In some embodiments, ibutilide can be a composition where (R)-ibutilide is in an enantiomeric excess over (S)-ibutilide. In some embodiments, ibutilide can be a composition where (S)-ibutilide is in an enantiomeric excess over (R)-ibutilide. In some embodiments, ibutilide can be a composition where the enantiomeric excess of (S)-ibutilide is at least 90%, such as at least 90, 95, 98, 99, 99.5, or 99.9 percent. In some embodiments, ibutilide can be a composition where the enantiomeric excess of (R)-ibutilide is at least 90%, such as at least 90, 95, 98, 99, 99.5, 99.9 percent.

Dofetilide, or a pharmaceutically acceptable salt thereof, is a potassium channel blocker belonging to the group of class IIIa antiarrhythmic agents, and can be used for the purpose of the present disclosure. Dofetilide is N-(4-(2-(methyl(2-(4-(methylsulfonamido)phenoxy)ethyl)amino)ethyl)phenyl)methanesulfonamide and has the following structural formula:

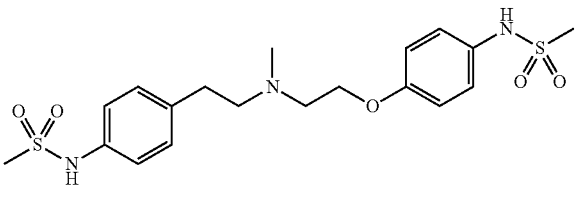

In some embodiments, dofetilide is used in the form of a pharmaceutically acceptable salt. Dofetilide can be a racemic combination of its two enantiomers R and S. In some embodiments, dofetilide can be a composition where (R)-dofetilide is in an enantiomeric excess over (S)-dofetilide. In some embodiments, dofetilide can be a composition where (S)-dofetilide is in an enantiomeric excess over (R)-dofetilide. In some embodiments, dofetilide can be a composition where the enantiomeric excess of (S)-dofetilide is at least 90%, such as at least 90, 95, 98, 99, 99.5, or 99.9 percent. In some embodiments, dofetilide can be a composition where the enantiomeric excess of (R)-dofetilide is at least 90%, such as at least 90, 95, 98, 99, 99.5, 99.9 percent.

Sotalol, or a pharmaceutically acceptable salt thereof, is a potassium channel blocker belonging to the group of class IIIa antiarrhythmic agents (i.e. $I_{kr}$ blocker) that non-selectively binds to both β1- and β2-adrenergic receptors. Sotalol is N-{4-[1-hydroxy-2-(propan-2-ylamino)ethyl]phenyl}methanesulfonamide and has the following structural formula:

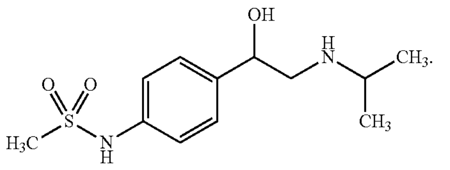 [SMILES: CC(C)NCC(O)c1ccc(NS(C)(=O)=O)cc1]

The anti-arrhythmic effects of sotalol is primarily due to its class III actions, that is, inhibition of $I_{kr}$, which results in prolongation of the action potential duration and effective refractory of atrial and ventricular cardiomyocytes. In addition, due to its beta-adrenergic receptors blocking activity, sotalol can also reduce the arrhythmogenic effects associated with conditions of increased sympathetic drive and/or catecholamines. Both the $I_{Kr}$ inhibition and beta-adrenergic receptor blocking activity can contribute to sotalol's antiarrhythmic effect, but the inhibition of the potassium current with resulting prolongation of the ERP is the predominant mechanism underlying the antiarrhythmic action of this drug.

Sotalol can be a racemic combination of its two enantiomers D-(+)-sotalol and L-(−)-sotalol, also known as d,l-Sotalol. The L-(−)-enantiomer of sotalol has both beta-blocking (class II) activity and potassium-channel-blocking (class III) properties. The D-(+)-enantiomer has class III properties similar to those of L-(−)-sotalol. However, the affinity of D-(+)-sotalol for beta-adrenergic receptors is 30 to 60 times lower than the affinity of L-(−)-sotalol.

In some embodiments, sotalol is used in the form of a pharmaceutically acceptable salt or solvate, for instance, sotalol hydrochloride. In some embodiments, sotalol can be a composition where D-(+)-sotalol is in an enantiomeric excess over L-(−)-sotalol. In some embodiments, sotalol can be a composition where L-(−)-sotalol is in an enantiomeric excess over D-(+)-sotalol. In some embodiments, sotalol can be a composition where the enantiomeric excess of L-(−)-sotalol is at least 90%, such as at least 90, 95, 98, 99, 99.5, or 99.9 percent. In some embodiments, sotalol can be a composition where the enantiomeric excess of D-(+)-sotalol is at least 90%, such as at least 90, 95, 98, 99, 99.5, 99.9 percent.

In some embodiments, the potassium channel blocker (e.g., ibutilide) is administered in combination with a sodium channel blocker for treatment of an atrial arrhythmia. A potassium channel blocker can be used to prolong atrial action potential, shorten diastolic interval (period between two consecutive atrial beats) and induce a corresponding delay in the recovery of sodium channels from inactivation. Consequently, these changes can slow unbinding of a sodium channel blocker (e.g. flecainide) from the bound sodium channels. For example, flecainide can exhibit a long unbinding time ($\tau_{off}$≈20.5 sec), and the fraction of sodium channels available for activation can be reduced when both a potassium channel blocker and sodium channel blocker are administered. Under these conditions, atrial myocyte excitability can be reduced and atrial arrhythmia can be terminated.

Sodium channel blockers of the present disclosure can include class Ia, class Ib, class Ic, or class Id antiarrhythmic agents, or pharmaceutically acceptable salts or solvates thereof. Class Ia antiarrhythmic agents include, but are not limited to, quinidine, procainamide, and disopyramide. Class Ib antiarrhythmic agents include, but are not limited to, lidocaine, tocainide, phenytoin, moricizine, and mexiletine. Class Ic antiarrhythmic agents include, but are not limited to, flecainide, propafenone, and moricizine. A class Id antiarrhythmic agent can be, for example, ranolazine.

Lidocaine, or a pharmaceutically acceptable salt thereof (e.g., lidocaine hydrochloride), is a sodium channel blocker belonging to the group of class Ib antiarrhythmic agents, and can be used for the purpose of the present disclosure. Lidocaine is 1 2-(diethylamino)-N-(2,6-dimethylphenyl)acetamide, and has the following structural formula:

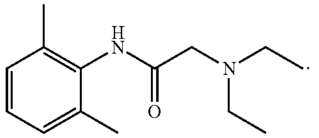 [SMILES: CCN(CC)CC(=O)Nc1c(C)cccc1C]

In some embodiments, a pharmaceutically acceptable salt of lidocaine is provided in a pharmaceutical composition of the disclosure. A salt of lidocaine can be for example, a magnesium salt, an acetate salt, a citrate salt, a nitrate salt, a hydrochloride salt, a sulfate salt, a maleate salt, a tartarate salt, a phosphate salt, a aconitate salt, adipate salt, an ascorbate salt, a benzoate salt, a caprylate salt, a cholate salt, a formate salt, a glutamate salt, a lactate salt, a propionate salt, a sorbate salt, a stearate salt, or a succinate salt.

Mexiletine, or a pharmaceutically acceptable salt thereof, is a sodium channel blocker belonging to the group of class Ib antiarrhythmic agents, and can be used for the purpose of the present disclosure. Mexiletine is 1-(2,6-dimethylphenoxy)propan-2-amine, and has the following structural formula:

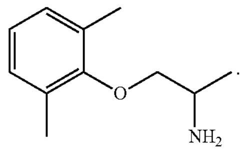

In some embodiments, mexiletine is used in the form of a pharmaceutically acceptable salt or solvate, for instance, mexiletine hydrochloride. Mexiletine can be a racemic combination of its two enantiomers R and S. In some embodiments, mexiletine can be a composition where (R)-mexiletine is in an enantiomeric excess over (S)-mexiletine. In some embodiments, mexiletine can be a composition where (S)-mexiletine is in an enantiomeric excess over (R)-mexiletine. In some embodiments, mexiletine can be a composition where the enantiomeric excess of (S)-mexiletine is at least 90%, such as at least 90, 95, 98, 99, 99.5, or 99.9 percent. In some embodiments, mexiletine can be a composition where the enantiomeric excess of (R)-mexiletine is at least 90%, such as at least 90, 95, 98, 99, 99.5, 99.9 percent.

Propafenone, or a pharmaceutically acceptable salt thereof, is a sodium channel blocker belonging to the group of class Ic antiarrhythmic agents, and can be used for the purpose of the present disclosure. Propafenone is 1-(2-(2-hydroxy-3-(propylamino)propoxy)phenyl)-3-phenylpropan-1-one, and has the following structural formula:

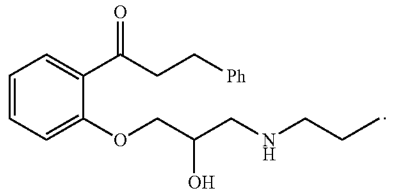 [SMILES: CCCNCC(O)COc1ccccc1C(=O)CCc1ccccc1]

Flecainide, or a pharmaceutically acceptable salt thereof, is a sodium channel blocker belonging to the group of class Ic antiarrhythmic agents, and can be used for the purpose of the present disclosure. Flecainide is N-(piperidin-2-ylmethyl)-2,5-bis(2,2,2-trifluoroethoxy)benzamide, and has the following structural formula:

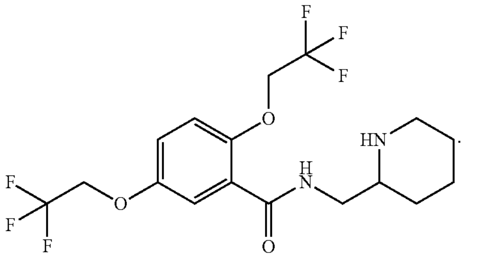 [SMILES: O=C(NCC1CCCCN1)c1cc(OCC(F)(F)F)ccc1OCC(F)(F)F]

In some embodiments, flecainide is used in the form of a pharmaceutically acceptable salt or solvate, for instance, flecainide acetate. Flecainide can be a racemic combination of its two enantiomers R and S. In some embodiments, flecainide can be a composition where (R)-flecainide is in an enantiomeric excess over (S)-flecainide. In some embodiments, flecainide can be a composition where (S)-flecainide is in an enantiomeric excess over (R)-flecainide. In some embodiments, flecainide can be a composition where the enantiomeric excess of (S)-flecainide is at least 90%, such as at least 90, 95, 98, 99, 99.5, or 99.9 percent. In some embodiments, flecainide can be a composition where the enantiomeric excess of (R)-flecainide is at least 90%, such as at least 90, 95, 98, 99, 99.5, 99.9 percent.

Pharmaceutically-Acceptable Salts.

The disclosure provides the use of pharmaceutically-acceptable salts of any therapeutic compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound of the disclosure. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the present disclosure. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrazole, imidazole, or pyrazine.

In some embodiments, an ammonium salt is a triethyl amine salt, a trimethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrazole salt, a pyridazine salt, a pyrimidine salt, an imidazole salt, or a pyrazine salt.

Acid addition salts can arise from the addition of an acid to a compound of the present disclosure. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisic acid, gluconic acid, glucuronic acid, saccharic acid, formic acid, benzoic acid, glutamic acid, pantothenic acid, acetic acid, trifluoroacetic acid, mandelic acid, cinnamic acid, aspartic acid, stearic acid, palmitic acid, glycolic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisate salt, a gluconate salt, a glucuronate salt, a saccharate salt, a formate salt, a benzoate salt, a glutamate salt, a pantothenate salt, an acetate salt, a trifluoroacetate salt, a mandelate salt, a cinnamate salt, an aspartate salt, a stearate salt, a palmitate salt, a glycolate salt, a propionate salt, a butyrate salt, a fumarate salt, a succinate salt, a methanesulfonate salt, an ethanesulfonate salt, a benzenesulfonate salt, a p-toluenesulfonate salt, a citrate salt, an oxalate salt, or a maleate salt.

Combination Therapies.

Flecainide can exhibit a voltage and use-dependent block of cardiac voltage-gated sodium channels (Nav1.5 subtype) characteristic of class Ic antiarrhythmics, as well as a corresponding inhibition of the transient peak inward sodium current due to preferential binding of the inactivated, open state of the channels. Characteristics of the sodium channel blocking activity of flecainide include slow dissociation kinetics of the bound drug from its target channel (e.g., up to several seconds). This can result in incomplete recovery of flecainide-bound channels during diastole and a smaller population of channels available for activation. This feature can make flecainide more effective in decreasing excitability of the myocytes when the frequency of action potentials is high, such as during tachyarrhythmias (e.g., AF). The voltage and frequency dependent potency of flecainide for inhibition of peak sodium current can be in the micromolar range of ~0.5 to 2.5 μM and the use-dependent block can occur at concentrations as low as 0.5 mM. In addition to inhibiting the transient peak sodium current, flecainide can also inhibit the slow inactivating component of sodium current (also referred to as late or persistent sodium current) at a potency of 3.4 μM. Flecainide can also inhibit the cardiac sarcoplasmic reticulum $Ca^{2+}$ release channel (ryanodine receptor RyR2) at a potency of ~20 μM.

The prolongation of atrial effective refractory period (ERP) caused by a sodium channel blocker (e.g., flecainide) can be intensified by the prolongation of the atrial action potential induced by a potassium channel inhibitor (e.g., ibutilide, dofetilide, or sotalol). The ERP can be especially prolonged by flecainide, given that atrial rate can increase during episodes of arrhythmia such as atrial fibrillation. In some cases, the inhibition of sodium channels by a sodium channel blocker (e.g., flecainide) can lead to delayed reactivation of the channels and prolongation of atrial ERP during AF, both of which can be further intensified by the prolongation of the atrial action potential (AP) and ERP caused by a potassium channel blocker such as ibutilide. In some embodiments, the combination of a sodium channel blocker and a delayed rectifier potassium channel $I_{Kr}$ inhibitor (e.g., flecainide and ibutilide) can cause an overall synergistic electrophysiological effect, e.g., an overall effect that is more than additive in suppressing AF.

A combination therapy containing flecainide and a potassium blocker such as ibutilide or dofetilide can increase antiarrhythmic efficacy while also reducing the risk of both proarrhythmic and hemodynamic adverse events that can be associated with each of the components as used in a monotherapy. In some embodiments, coadministration of flecainide and a potassium channel blocker (e.g., ibutilide or dofetilide) for acute treatment of recent onset atrial fibrillation reduces the risk of cardiovascular adverse events when compared to potassium channel blocker or flecainide monotherapy. For example, relative to ibutilide monotherapy, coadministration of flecainide and ibutilide can reduce risk of Torsades de Pointes (TdP), a polymorphic ventricular tachycardia (VT) that can be observed with ibutilide-promoted QT prolongation. In some embodiments, without wishing to be bound by a certain theory, while ibutilide can enhance late $I_{Na}$ and inhibit $I_{Kr}$, thereby prolonging ventricular cell action potential and QT interval, flecainide can exert an inhibitory effect on late $I_{Na}$ and counteract ibutilide-promoted QT prolongation. In some embodiments, flecainide attenuates ibutilide-, dofetilide-, or sotalol-promoted $I_{Kr}$ inhibition. For example, flecainide can decrease net inward current during a plateau phase of an action potential, as well as decrease inward current that could otherwise trigger delay after depolarization (DAD) required to initiate TdP. In addition, flecainide, as well as other sodium channel blockers such as mexiletine, ranolazine, tetrodotoxin, can reduce both the reverse use-dependent and beat-to-beat variability of ventricular repolarization (i.e. APD and QT interval) caused by $I_{Kr}$ blockers. Hence, by this action, sodium channel blockers can reduce the "torsadogenic" effect of potassium channel blockers, such as ibutilide, dofetilide, E-4031, sotalol, etc. (ref. Wu et al., Circulation 2011).

Inhibition of $I_{Kr}$ by ibutilide, dofetilide, or sotalol can also reduce the risk of adverse events associated with the use of flecainide to terminate atrial arrythmia (e.g. atrial fibrillation). For example, ibutilide, sotalol, or dofetilide can attenuate a decrease in intracellular calcium caused by sodium channel blockers and reduce flecainide-associated negative inotropic effect and hypotension. In some embodiments, administration of flecainide induces atrial flutter (AFL) with 1:1 AV transmission, and administration of ibutilide converts the flecainide-promoted atrial flutter to sinus rhythm.

A combination therapy containing flecainide and sotalol can increase antiarrhythmic efficacy while also reducing the risk of both proarrhythmic and hemodynamic adverse events that can be associated with each of the components as used in a monotherapy. In some embodiments, coadministration of flecainide and sotalol for acute treatment of recent onset atrial fibrillation reduces the risk of cardiovascular adverse events when compared to sotalol or flecainide monotherapy. For example, relative to sotalol monotherapy, coadministration of flecainide and sotalol can reduce risk of Torsades de Pointes (TdP), a polymorphic ventricular tachycardia (VT) that can be observed with sotalol-promoted QT prolongation. In some embodiments, without wishing to be bound by a certain theory, while sotalol can inhibit $I_{Kr}$, thereby prolonging ventricular cell action potential and QT interval, flecainide can exert an inhibitory effect on $I_{Na}$ and counteract sotalol-promoted QT prolongation. In some embodiments, flecainide attenuates sotalol-promoted $I_{Kr}$ inhibition. For example, flecainide can decrease net inward current during a plateau phase of an action potential, as well as decrease inward current that could otherwise trigger delay after depolarization (DAD) required to initiate TdP.

The potassium channel blocker can have increased half-life or decreased renal clearance. Renal clearance can be measured through standard measures of renal impairment such as creatinine clearance. For example, severe renal impairment is characterized by a creatinine clearance of less than 20 ml/minute. Thus, dosage of a potassium channel blocker (e.g., ibutilide or dofetilide) can be modified based on the measured creatinine clearance in a subject. In some embodiments, normal creatinine clearance is characterized by a clearance rate of about 80 to about 140 mL/minute. In some embodiments, creatinine clearance is about 80 mL/minute to about 140 mL/minute. In some embodiments, creatinine clearance is at least about 80 mL/minute. In some embodiments, creatinine clearance is at most about 140 mL/minute. In some embodiments, creatinine clearance is about 80 mL/minute to about 85 mL/minute, about 80 mL/minute to about 90 mL/minute, about 80 mL/minute to about 95 mL/minute, about 80 mL/minute to about 100 mL/minute, about 80 mL/minute to about 105 mL/minute, about 80 mL/minute to about 110 mL/minute, about 80 mL/minute to about 115 mL/minute, about 80 mL/minute to about 120 mL/minute, about 80 mL/minute to about 125 mL/minute, about 80 mL/minute to about 130 mL/minute, about 80 mL/minute to about 140 mL/minute, about 85 mL/minute to about 90 mL/minute, about 85 mL/minute to about 95 mL/minute, about 85 mL/minute to about 100 mL/minute, about 85 mL/minute to about 105 mL/minute, about 85 mL/minute to about 110 mL/minute, about 85 mL/minute to about 115 mL/minute, about 85 mL/minute to about 120 mL/minute, about 85 mL/minute to about 125 mL/minute, about 85 mL/minute to about 130 mL/minute, about 85 mL/minute to about 140 mL/minute, about 90 mL/minute to about 95 mL/minute, about 90 mL/minute to about 100 mL/minute, about 90 mL/minute to about 105 mL/minute, about 90 mL/minute to about 110 mL/minute, about 90 mL/minute to about 115 mL/minute, about 90 mL/minute to about 120 mL/minute, about 90 mL/minute to about 125 mL/minute, about 90 mL/minute to about 130 mL/minute, about 90 mL/minute to about 140 mL/minute, about 95 mL/minute to about 100 mL/minute, about 95 mL/minute to about 105 mL/minute, about 95 mL/minute to about 110 mL/minute, about 95 mL/minute to about 115 mL/minute, about 95 mL/minute to about 120 mL/minute, about 95 mL/minute to about 125 mL/minute, about 95 mL/minute to about 130 mL/minute, about 95 mL/minute to about 140 mL/minute, about 100 mL/minute to about 105 mL/minute, about 100 mL/minute to about 110 mL/minute, about 100 mL/minute to about 115 mL/minute, about 100 mL/minute to about 120 mL/minute, about 100 mL/minute to about 125 mL/minute, about 100 mL/minute to about 130 mL/minute, about 100 mL/minute to about 140 mL/minute, about 105 mL/minute to about 110 mL/minute, about 105 mL/minute to about 115 mL/minute, about 105 mL/minute to about 120 mL/minute, about 105 mL/minute to about 125 mL/minute, about 105 mL/minute to about 130 mL/minute, about 105 mL/minute to about 140 mL/minute, about 110 mL/minute to about 115 mL/minute, about 110 mL/minute to about 120 mL/minute, about 110 mL/minute to about 125 mL/minute, about 110 mL/minute to about 130 mL/minute, about 110 mL/minute to about 140 mL/minute, about 115 mL/minute to about 120 mL/minute, about 115 mL/minute to about 125 mL/minute, about 115 mL/minute to about 130 mL/minute, about 115 mL/minute to about 140 mL/minute, about 120 mL/minute to about 125 mL/minute, about 120 mL/minute to about 130 mL/minute, about 120 mL/minute to about 140 mL/minute, about 125 mL/minute to about 130 mL/minute, about 125 mL/minute to about 140 mL/minute, or about 130 mL/minute to about 140 mL/minute.

In some embodiments, the potassium channel blocker can cause an increase in the $QT_C$ interval, also known as $QT_C$ prolongation. Normal $QT_C$ values are less than 430 ms. Cessation of the potassium channel blocker (e.g., ibutilide or dofetilide) is considered when a $QT_C$ is elevated above 430 ms. $QT_C$ prolongations can be of a value of greater than about 450 ms, 460 ms, or 470 ms.

In some embodiments, the potassium channel blocked can increase $QT_C$ values and reduced clearance in a subject, wherein the subject has depressed creatinine clearance values.

In some embodiments, the sodium channel blocker (e.g. flecainide, mexiletine, or propafenone), the potassium channel blocker (e.g. ibutilide, dofetilide, or sotalol), or a combination of the sodium channel blocker and the potassium channel blocker is administered in combination with a $Mg^{2+}$ source. $Mg^{2+}$ sources can include, but are limited to salts comprising $Mg^{2+}$ and anions such as sulfate, pyrosulfate, oxide, hydroxide, bisulfate, sulfite, bisulfate, phosphate, monohydrogenphosphate, dihydrogenphosphate, metaphosphate, pyrophosphate, chloride, bromide, iodide, glycinate, threonate, aspartate, acetate, propionate, gluconate, decanoate, caprylate, acrylate, formate, isobutyrate, caproate, heptanoate, propiolate, oxalate, malonate, malate, succinate, suberate, sebacate, stearate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenyipropionate, phenylbutyrate, citrate, lactate, γ-hydroxybutyrate, glycolate, tartrate, methanesulfonate, propanesulfonate, naphthalene-1-sulfonate, naphthalene-2-sulfonate, and mandelates. In some embodiments, the $Mg^{2+}$ source is magnesium citrate, magnesium aspartate, magnesium threonate, magnesium glycinate, magnesium chloride, magnesium sulfate, magnesium oxide, or magnesium malate. In some embodiments, the $Mg^{2+}$ source comprises magnesium sulfate, or a hydrate thereof. In some embodiments, the $Mg^{2+}$ source comprises magnesium sulfate heptahydrate.

$Mg^{2+}$ ions are inhibitors of L-type calcium channels ($I_{CaL}$), and can increase voltage-dependent inactivation and stimulated dephosphorylation of $Ca_{V1.2}$ channels. In some embodiments, $Mg^{2+}$ acts directly on $Ca_{V1.2}$ channels, including proximal C-terminal domains. Overall, $Mg^{2+}$ can promote inhibition of $I_{CaL}$, effect under basal conditions (e.g., about 26% decrease in $I_{CaL}$), but can also cause a greater decrease (e.g., about 63%) in $I_{CaL}$, stimulated by cAMP (e.g., stimulated by beta-adrenergic agonists). $Mg^{2+}$ ions can also induce inward rectification of $K^+$-channels and prevent outward efflux of $K^+$ ions.

Administration of a $Mg^{2+}$ source (e.g. intravenous magnesium sulfate) can be effective in terminating or preventing TdP, including TdP caused by administration of ibutilide, dofetilide, or sotalol. $Mg^{2+}$ can decrease the amplitude of early after depolarization (EADs) by decreasing calcium influx (via L-type Calcium channels), thus suppressing EADs that can initiate TdP. By inhibition of $I_{CaL}$, and $K^+$ current, administration of $Mg^{2+}$ (e.g. IV magnesium sulfate) can lower ventricular rate and can induce cardioversion of atrial fibrillation.

As described above, flecainide can counter "torsadogenic" effects of ibutilide, sotalol, or dofetilide by inhibition of late $I_{Na}$. A combination of $Mg^{2+}$ and flecainide can also be more effective for the prevention of TdP induced by ibutilide, sotalol, or dofetilide relative to flecainide or $Mg^{2+}$ monotherapy. In some embodiments, administration of a $Mg^{2+}$ source reduces the risk of TdP associated with administration of ibutilide, sotalol, or dofetilide without compromising the efficacy of the combination of flecainide; and ibutilide, sotalol, or dofetilide. Weak inhibition of $I_{CaL}$, by $Mg^{2+}$ in combination with concomitant $I_{Kr}$ inhibition by ibutilide, sotalol, or dofetilide can also slow AV nodal conduction (e.g. prevent 1:1 AV transmission) in cases where flecainide converts AF into atrial flutter.

Methods.

One aspect of the disclosure provides a method of treating a subject suffering from atrial arrhythmia, comprising administering to the subject (i) a sodium channel blocker in a first amount, and (ii) a potassium channel blocker in a second amount, thereby inducing cardioversion of the atrial arrhythmia.

In some embodiments, the administration results in a $t_{max}$ of the sodium channel blocker in the subject that occurs no more than about 1 hour, no more than about 0.5 hours, no more than about 15 minutes, no more than about 5 minutes, no more than about 3 minutes, no more than about 2 minutes, no more than about 1 minute, or no more than about 30 seconds apart from a $t_{max}$ of the potassium channel blocker in the subject.

In some embodiments, the administration results in a $t_{max}$ of the sodium channel blocker in the subject that occurs no more than about 1 hour, no more than about 0.5 hours, no more than about 15 minutes, no more than about 5 minutes, no more than about 3 minutes, no more than about 2 minutes, no more than about 1 minute, or no more than about 30 seconds before a $t_{max}$ of the potassium channel blocker in the subject.

In some embodiments, the administration results in a $t_{max}$ of the sodium channel blocker in the subject that occurs no more than about 1 hour, no more than about 0.5 hours, no more than about 15 minutes, no more than about 5 minutes, no more than about 3 minutes, no more than about 2 minutes, no more than about 1 minute, or no more than about 30 seconds after a $t_{max}$ of the potassium channel blocker in the subject.

In some embodiments, $QT_c$ of the subject is no more than about 490 ms, about 495 ms, about 500 ms, about 505 ms, or about 510 ms between about 1 hour before and about 1 hour after $t_{max}$ of the potassium channel blocker in the subject. In some embodiments, $QT_c$ of the subject is no more than about 490 ms, about 495 ms, about 500 ms, about 505 ms, or about 510 ms during $t_{max}$ of the potassium channel blocker in the subject.

In some embodiments, the potassium channel blocker is an $I_{Kr}$ inhibitor. In some embodiments, the potassium channel blocker is ibutilide or a pharmaceutically acceptable salt thereof. In some embodiments, the potassium channel blocker is dofetilide or a pharmaceutically acceptable salt thereof. In some embodiments, the potassium channel blocker is sotalol or a pharmaceutically acceptable salt thereof. In some embodiments, the sodium channel blocker is a class Ib antiarrhythmic agent. In some embodiments, the sodium channel blocker is a class Ic antiarrhythmic agent. In some embodiments, the sodium channel blocker is flecainide or a pharmaceutically acceptable salt thereof. In some embodiments, the sodium channel blocker is propafenone or a pharmaceutically acceptable salt thereof.

In some embodiments, the potassium channel block also blocks beta adrenergic receptors.

In some embodiments, the sodium channel blocker is administered to the subject no more than 90 minutes, no more than 60 minutes, no more than 30 minutes, no more than 15 minutes, no more than 10 minutes, no more than 5 minutes, no more than 3 minutes, no more than 2 minutes, no more than 1 minute, or no more than 30 seconds from administration of the potassium channel blocker to the subject. In some embodiments, the sodium channel blocker is administered to the subject simultaneously with administration of the potassium channel blocker.

In some embodiments, the sodium channel blocker and the potassium channel blocker is administered to plurality of experimental subjects in a clinical study. The clinical study can further comprise a control cohort, which can include subjects that are administered the sodium channel blocker without ibutilide, or can include subjects that are administered the potassium channel blocker without the sodium channel blocker. In some embodiments, the clinical study can further comprise a control cohort, which can include subjects that are administered the sodium channel blocker without dofetilide, or can include subjects that are administered the potassium channel blocker without the sodium channel blocker. In some embodiments, the clinical study can further comprise a control cohort, which can include subjects that are administered the sodium channel blocker without sotalol, or can include subjects that are administered the potassium channel blocker without the sodium channel blocker.

In some embodiments, each subject in the plurality of experimental subjects is administered both the sodium channel blocker in the first amount and the potassium channel blocker in the second amount; and each subject in the control cohort is administered the sodium channel blocker in the first amount without the potassium channel blocker in the second amount, or each subject in the control cohort is administered the potassium channel blocker in the second amount without the sodium channel blocker in the first amount.

In some embodiments, the sodium channel blocker and ibutilide or pharmaceutically acceptable salt thereof are simultaneously administered to the plurality of experimental subjects. In some embodiments, the sodium channel blocker and dofetilide or pharmaceutically acceptable salt thereof are simultaneously administered to the plurality of experimental subjects. In some embodiments, the sodium channel blocker and the sotalol or pharmaceutically acceptable salt thereof are simultaneously administered to the plurality of experimental subjects. In some embodiments, the sodium channel blocker is administered to each subject of the plurality of experimental subjects no more than 90 minutes, no more than 60 minutes, no more than 30 minutes, no more than 15 minutes, no more than 10 minutes, no more than 5 minutes, no more than 3 minutes, no more than 2 minutes, no more than 1 minute, or no more than 30 seconds from administration of the potassium channel blocker to the each subject.

The plurality of experimental subjects can be, for example, at least two subjects, at least about 5 subjects, at least about 10 subjects, at least about 15 subjects, at least about 20 subjects, at least about 30 subjects, at least about 40 subjects, at least about 50 subjects, at least about 100 subjects, or at least about 150 subjects. The plurality of experimental subjects can be, for example, at least two subjects, at least about 5 subjects, from about 2 to about 15 subjects, from about 2 to about 20 subjects, from about 2 to about 30 subjects, from about 2 to about 40 subjects, from about 2 to about 50 subjects, from about 2 to about 100 subjects, from about 2 to about 150 subjects, from about 2 to about 300 subjects, from about 5 to about 15 subjects, from about 5 to about 20 subjects, from about 5 to about 30 subjects, from about 5 to about 40 subjects, from about 5 to about 50 subjects, from about 5 to about 100 subjects, from about 5 to about 150 subjects, or from about 5 to about 300 subjects.

The number subjects in the control cohort can be, for example, at least two subjects, at least about 5 subjects, at least about 10 subjects, at least about 15 subjects, at least about 20 subjects, at least about 30 subjects, at least about 40 subjects, at least about 50 subjects, at least about 100 subjects, or at least about 150 subjects. The plurality of experimental subjects can be, for example, at least two subjects, at least about 5 subjects, from about 2 to about 15 subjects, from about 2 to about 20 subjects, from about 2 to about 30 subjects, from about 2 to about 40 subjects, from about 2 to about 50 subjects, from about 2 to about 100 subjects, from about 2 to about 150 subjects, from about 2 to about 300 subjects, from about 5 to about 15 subjects, from about 5 to about 20 subjects, from about 5 to about 30 subjects, from about 5 to about 40 subjects, from about 5 to about 50 subjects, from about 5 to about 100 subjects, from about 5 to about 150 subjects, or from about 5 to about 300 subjects.

In some embodiments, the experimental subjects are healthy subjects. In some embodiments, wherein the experimental subjects suffer from atrial arrhythmia during the administering. In some embodiments, the subjects of the control cohort are healthy subjects. In some embodiments, the subjects of the control cohort suffer from atrial arrhythmia during the administering. In some embodiments, the experimental subjects is are human subjects. In some embodiments, the experimental subjects are animal subjects.

In some embodiments, the experimental subjects are pig subjects. In some embodiments, the experimental subjects are dog subjects.

In some embodiments, a $t_{max}$ of the sodium channel blocker in the plurality of experimental subjects occurs no more than about 1 hour, no more than about 30 minutes, no more than about 15 minutes, no more than about 10 minutes, no more than about 5 minutes, no more than about 3 minutes, no more than about 2 minutes, no more than about 1 minute, or no more than about 30 seconds apart from a $t_{max}$ of the potassium channel blocker in the subject.

In some embodiments, incidence of torsades de pointes (TdP) is decreased in the plurality of experimental subjects relative to incidence of TdP in the control cohort. In some embodiments, incidence of torsades de pointes (TdP) is decreased by at least about 2%, at least about 3%, at least about 4%, at least about 5%, at least about 10%, at least about 15%, at least about 20%, at least about 35%, or at least about 50% in the plurality of experimental subjects relative to incidence of TdP in the control cohort.

In some embodiments, incidence of above-nomogram QT interval is decreased in a plurality of experimental subjects in a clinical study relative to incidence above-nomogram QT interval in a control cohort of the clinical study. The risk of torsade de pointes (TdP) in a subject can be evaluated according to a QT nomogram as described in Chan et al. *QJM: An International Journal of Medicine*, Volume 100, Issue 10, October 2007, Pages 609-615, which is incorporated herein by reference in its entirety. In some embodiments, QT interval in a subject is plotted against heart rate on the nomogram according to FIG. 1, whereby if the resulting point is above the line of the nomogram (e.g. "above-nomogram"), then the subject is regarded at risk of TdP. In some embodiments, incidence of above-nomogram QT interval is decreased by at least about 2%, at least about 3%, at least about 4%, at least about 5%, at least about 10%, at least about 15%, at least about 20%, at least about 35%, or at least about 50% in the plurality of experimental subjects relative to incidence of TdP in the control cohort.

In some embodiments, incidence of hypotension is decreased in a plurality of experimental subjects in a clinical study relative to incidence of hypotension in a control cohort of the clinical study. In some embodiments, hypotension comprises, after the administering, a mean arterial pressure (MAP) of less than 70 mmHg sustained for at least 5 minutes. In some embodiments, incidence hypotension is decreased by at least about 2%, at least about 3%, at least about 4%, at least about 5%, at least about 10%, at least about 15%, at least about 20%, at least about 35%, or at least about 50% in the plurality of experimental subjects relative to incidence of TdP in the control cohort.

In some embodiments, an average magnitude of increase in QTc in a plurality of experimental subjects suffering from the atrial arrhythmia in a clinical study relative to average QTc in a control cohort of the clinical study is no more than about 1%, no more than about 2%, no more than about 3%, no more than about 4%, no more than about 5%, no more than about 10%, no more than about 15%, no more than about 20%, no more than about 30%, no more than about 40%, or no more than about 50%.

The method of any one of embodiments 25-41, wherein an average magnitude of increase in $QT_c$ in a plurality of experimental subjects in a clinical study relative to average $QT_c$ in a control cohort of the clinical study is no more than about 60 ms, no more than about 50 ms, no more than about 40 ms, no more than about 30 ms, no more than about 20 ms, no more than about 10 ms, or no more than about 6 ms. In some embodiments, $QT_c$ is calculated according to the Fridericia function.

In some embodiments, the present disclosure provides a method of mitigating a decrease in intracellular calcium in a cell caused by administration of a sodium channel blocker comprising treating the cell with a potassium channel blocker. In some embodiments, the potassium channel blocker is an $I_{Kr}$ inhibitor. In some embodiments, the potassium channel blocker is ibutilide or a pharmaceutically acceptable salt thereof. In some embodiments, the potassium channel blocker is dofetilide or a pharmaceutically acceptable salt thereof. In some embodiments, the potassium channel blocker is sotalol or a pharmaceutically acceptable salt thereof. In some embodiments, the sodium channel blocker is flecainide or a pharmaceutically acceptable salt thereof. In some embodiments, the cell is an atrial myocyte.

In some embodiments, the present disclosure provides a method of reducing the risk of ibutilide-promoted TdP in a subject suffering from atrial arrhythmia undergoing treatment with ibutilide, or a pharmaceutically acceptable salt thereof, comprising coadministering a therapeutically effective amount of flecainide, or a pharmaceutically acceptable salt thereof, with the ibutilide. In some embodiments, the method further comprises coadministering a $Mg^{2+}$ source with the flecainide and the ibutilide.

In some embodiments, the present disclosure provides a method of reducing the risk of dofetilide-promoted TdP in a subject suffering from atrial arrhythmia undergoing treatment with dofetilide, or a pharmaceutically acceptable salt thereof, comprising coadministering a therapeutically effective amount of flecainide, or a pharmaceutically acceptable salt thereof, with the dofetilide. In some embodiments, the method further comprises coadministering a $Mg^{2+}$ source with the flecainide and the dofetilide.

In some embodiments, the present disclosure provides a method of reducing the risk of sotalol-promoted TdP in a subject suffering from atrial arrhythmia undergoing treatment with sotalol, or a pharmaceutically acceptable salt thereof, comprising coadministering a therapeutically effective amount of flecainide, or a pharmaceutically acceptable salt thereof, with the sotalol. In some embodiments, the method further comprises coadministering a $Mg^{2+}$ source with the flecainide and the sotalol.

In some embodiments, the present disclosure provides a method of reducing the risk of ibutilide-promoted TdP in a subject suffering from atrial arrhythmia undergoing treatment with ibutilide, or a pharmaceutically acceptable salt thereof, comprising coadministering a therapeutically effective amount of propafenone, or a pharmaceutically acceptable salt thereof, with the ibutilide. In some embodiments, the method further comprises coadministering a $Mg^{2+}$ source with the propafenone and the ibutilide.

In some embodiments, the present disclosure provides a method of reducing the risk of dofetilide-promoted TdP in a subject suffering from atrial arrhythmia undergoing treatment with dofetilide, or a pharmaceutically acceptable salt thereof, comprising coadministering a therapeutically effective amount of propafenone, or a pharmaceutically acceptable salt thereof, with the dofetilide. In some embodiments, the method further comprises coadministering a $Mg^{2+}$ source with the propafenone and the dofetilide.

In some embodiments, the present disclosure provides a method of reducing the risk of sotalol-promoted TdP in a subject suffering from atrial arrhythmia undergoing treatment with sotalol, or a pharmaceutically acceptable salt thereof, comprising coadministering a therapeutically effective amount of propafenone, or a pharmaceutically acceptable salt thereof, with the sotalol. In some embodiments, the method further comprises coadministering a $Mg^{2+}$ source with the propafenone and the sotalol.

In some embodiments, administering a dose of sodium channel blocker and a dose of a potassium channel blocker induces cardioversion of an atrial arrhythmia in a subject faster than administering the dose of the sodium channel blocker to the subject without the dose of the potassium channel blocker. In some embodiments, administering a dose of sodium channel blocker and a dose of the potassium channel blocker induces cardioversion of an atrial arrhythmia in a subject faster than administering the dose of the potassium channel blocker to the subject without the dose of the sodium channel blocker. In some embodiments, a therapeutically effective amount of a sodium channel blocker administered to a subject concurrently or simultaneously with a potassium channel blocker is less than a therapeutically effective amount of the sodium channel blocker administered to the subject when not administered in combination or sequence with the potassium channel blocker. In some embodiments, a therapeutically effective amount of a potassium channel blocker administered to a subject concurrently or simultaneously with a sodium channel blocker is less than a therapeutically effective amount of the potassium channel blocker administered to the subject when not administered in combination with the sodium channel blocker. In some embodiments, the administration of both a potassium channel blocker and a sodium channel blocker lowers the minimum therapeutically effective dose of the potassium channel blocker or the sodium channel blocker by 10%, 20%, 30%, 40%, 50%, 60%, 70%, 80%, 90%, or 95% of their respective minimum therapeutically effective dose when used alone without the other agent in a corresponding subject.

Figure 2:
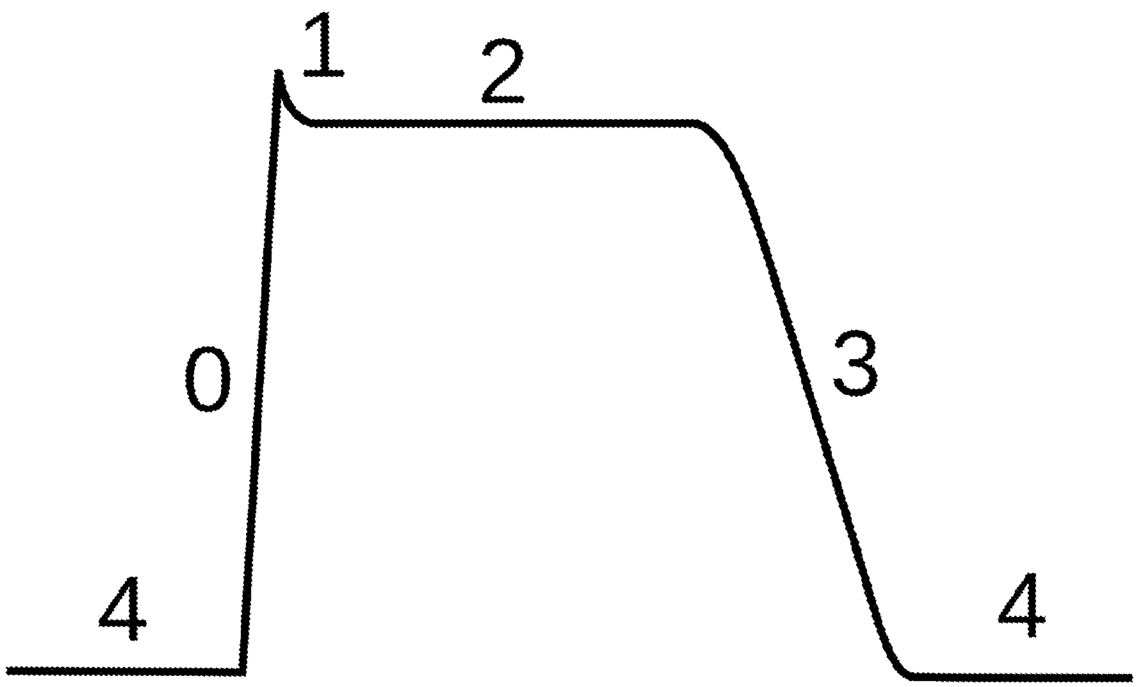
FIG. 2 is an example action potential.

In some embodiments, the administration of a potassium channel blocker and a sodium channel blocker can prolong the action potential duration or the effective refractory period of atrial myocytes. As used herein, the "effective refractory period" can refer to the amount of time where the atrial myocyte cannot respond to a new conducted stimulus and elicit a de-novo action potential. Quantitatively, the effective refractory period can be considered the summation of the duration of phases 0, 1, 2, and 3 of an action potential. An example action potential where 0, 1, 2, 3, and 4 correspond to their respective phases is illustrated in FIG. 2. In some embodiments, the administration of a potassium channel blocker and a sodium channel blocker can prolong the effective refractory period of atrial myocytes by at least 5%, such as about 5%, about 10%, about 15%, about 20%, about 25%, about 35% or about 40%. In some instances, the prolongation effect is measured as an average before and after the administration of the potassium channel blocker and the sodium channel blocker. For example, the effective refractory period before and after the administration can be quantified as an average during a period of at least 2, 4, 6, 8, 10, 12, 15, 18, 20, 22, 25, 28, 30, 35, 40, 45, 50, or 60 min, or during a period consisting of at least 10, 20, 30, 40, 50, 60, 80, or 100 myocyte action potentials. In some embodiments, the post-administration average effective refractory period is measured about 1, 2, 3, 4, 5, 6, 8, 10, 12, 15, 18, 20, 22, 25, 28, 30, 35, 40, 45, 50, or 60 min after the administration.

In some embodiments, the administration can prevent recurrence of the atrial arrhythmia for at least 1 hour after the administering, such as about 1, 2, 3, 4, 5, 6, 7, 8, 9, 10, 11, 12, 14, 16, 18, 20, 22, 24 hours after administering, or such as about 1, 2, 3, 4, 5, 6, or 7 days after administering.

In some embodiments, the administration does not induce ventricular arrhythmia. As used herein, "ventricular arrhythmia" can include ventricular fibrillation, sustained polymorphic ventricular tachycardia, and sustained monomorphic ventricular tachycardia.

In some embodiments, a subject suffering from atrial arrhythmia is administered with a first unit dose of sodium channel blocker (e.g. flecainide). In some embodiments, a second unit dose comprising a potassium channel blocker (e.g. ibutilide, sotalol, or dofetilide) is administered when the first unit dose does not induce cardioversion in the subject. In some embodiments, first unit dose or the second unit dose further comprises a $Mg^{2+}$ source.

In some embodiments, a unit dose of sodium channel blocker is administered to a subject suffering from atrial arrhythmia and induces cardioversion in the subject when administered concurrently with a potassium channel blocker and a $Mg^{2+}$ source. In some of these cases, the unit dose of sodium channel blocker does not induce cardioversion in the subject when the sodium channel blocker is not administered concurrently with the potassium channel blocker and the $Mg^{2+}$ source.

In some embodiments, the subject methods and compositions find use in treating subjects suffering from arrhythmia, e.g., atrial arrhythmia, that are nonresponsive to sodium channel blocker monotherapy (e.g. flecainide monotherapy). For example, in an average population, there are approximately 30% patients suffering from paroxysmal atrial fibrillation exhibiting resistance to flecainide monotherapy. In some embodiments, a subject suffers from atrial arrhythmia that is nonresponsive to sodium channel blocker monotherapy (a "sodium channel blocker non-responsive" subject), if the subject does not undergo cardioversion from atrial arrhythmia to normal sinus rhythm when administered a sodium channel blocker monotherapy, e.g., without a potassium channel blocker.

In some embodiments, a subject suffers from atrial arrhythmia that is nonresponsive to flecainide monotherapy (a "flecainide non-responsive" subject), if the subject does not undergo cardioversion from atrial arrhythmia to normal sinus rhythm when administered flecainide monotherapy, e.g., without a potassium channel blocker. For instance, the subject can be nonresponsive to flecainide treatment when flecainide is administered alone orally, via intravenous injection, or via inhalation at dosages that are otherwise therapeutically effective in most patients. For example, an otherwise therapeutically effective oral dose that does not induce cardioversion in a flecainide-nonresponsive subject can be at least about 25 mg per day, such as about 25 mg per day, 50 mg per day, 75 mg per day, 100 mg per day, 125 mg per day, 150 mg per day, 175 mg per day, 200 mg per day, 225 mg per day, 250 mg per day, 275 mg per day, 300 mg per day, 325 mg per day, 350 mg per day, 375 mg per day, and 400 mg per day. For example, an otherwise therapeutically effective intravenous dose of flecainide that does not induce cardioversion in a flecainide-nonresponsive subject without a potassium channel blocker can be, for example, at least about 0.1 mg/kg, such as about 0.1 mg/kg, 0.5 mg/kg, 1 mg/kg, 1.5 mg/kg, 2 mg/kg, 2.5 mg/kg, or 3 mg/kg. In some examples, an otherwise therapeutically effective inhalation dose of flecainide that does not induce cardioversion in a flecainide-nonresponsive subject without a potassium channel blocker can be, for example, about 0.1 mg to about 100 mg administered over multiple inhalations.

In some embodiments, the potassium channel blocker is administered simultaneously with a $Mg^{2+}$ source. In some embodiments, the potassium channel blocker is administered simultaneously with both a $Mg^{2+}$ source and a sodium channel blocker. In some embodiments, a subject suffering from cardiac arrhythmia, e.g., atrial arrhythmia, is administered with a sodium channel blocker, a potassium channel blocker, and a $Mg^{2+}$ source, either concurrently or simultaneously. In some embodiments, provided herein is a kit for treating cardiac arrhythmia, e.g., atrial arrhythmia, comprising a first unit dose of a sodium channel blocker, a second unit dose of a potassium channel blocker, and a third unit dose of a $Mg^{2+}$ source.

Definitions

As used herein, "heart condition" can refer to a condition where a heart has an abnormal function and/or structure, for example, a heart is beating in an irregular rhythm, experiencing arrhythmia, atrial fibrillation, and/or tachycardia, there is myocardial infarction, and/or coronary heart disease. As used herein, "atrial arrhythmia" can refer to an arrhythmia that affects at least one atrium and does not include bradycardia. For instance, atrial arrhythmia may originate in and affect at least one atrium. As used herein, "tachycardia" can refer to an arrhythmia in which the heart beat is too fast. For instance, tachycardia may involve a resting heart rate of over 100 beats per minute, such as greater than 110, greater than 120, or greater than 130 beats minute. In some embodiments, tachycardia can comprise sinus tachycardia, atrial fibrillation, atrial flutter, AV nodal reentrant tachycardia, accessory pathway mediated tachycardia, atrial tachycardia, multifocal atrial tachycardia, junctional tachycardia, ventricular tachycardia, supraventricular tachycardia, or any combination thereof.

As used herein, the phrase "cardiac arrhythmia" can refer to an arrhythmia in which the heart beat is irregular. As used herein, the term "atrial fibrillation" can refer to an abnormal heart rhythm characterized by rapid and irregular beating of the atria. As used herein, the term "cardioversion" can refer to a process by which an abnormally fast heart rate (tachycardia) or other cardiac arrhythmia is converted to a normal sinus rhythm. Cardioversion can be accomplished by electricity, drugs, or both.

As used herein, the singular forms "a," "an," and "the" can include plural referents unless the context clearly dictates otherwise. Thus, for example, reference to "an antiarrhythmic agent" can include not only a single active agent but also a combination or mixture of two or more different active agents.

Reference herein to "one embodiment," "one version," or "one aspect" can include one or more such embodiments, versions or aspects, unless otherwise clear from the context.

As used herein, the term "pharmaceutically acceptable solvate" can refer to a solvate that retains one or more of the biological activities and/or properties of the antiarrhythmic pharmaceutical agent and that is not biologically or otherwise undesirable. Examples of pharmaceutically acceptable solvates include, but are not limited to, antiarrhythmic pharmaceutical agents in combination with water, isopropanol, ethanol, methanol, DMSO, ethyl acetate, acetic acid, ethanolamine, or combinations thereof.

As used herein, the term "pharmaceutically acceptable salt" can refer to those salts that retain one or more of the biological activities and properties of the free acids and bases and that are not biologically or otherwise undesirable. Illustrative examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, di nitrobenzoates, hydroxybenzoates, methoxybenzoates, phthalates, sulfonates, xylenesulfonates, phenylacetates, phenyipropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

The term "about" in relation to a reference numerical value can include a range of values plus or minus 10% from that value. For example, the amount "about 10" includes amounts from 9 to 11, including the reference numbers of 9, 10, and 11. The term "about" in relation to a reference numerical value can also include a range of values plus or minus 10%, 9%, 8%, 7%, 6%, 5%, 4%, 3%, 2%, or 1% from that value.

As used herein, the amount of an agent as described herein in the "coronary circulation of the heart" can be measured by collecting a blood sample from any vascular region of the coronary circulation of the heart (e.g., arteries, veins, including coronary sinus) by using a catheter or cannula. The amount of the agent in the sample can then be determined by known means, such as bioanalytical techniques that employ analytical equipment such as LC-MS/MS. Thus, the amount of the agent in the blood in the heart can be measured for any particular time.

As used herein, the terms "treating" and "treatment" can refer to restoration of sinus rhythm, reduction in severity and/or frequency of symptoms, elimination of symptoms and/or underlying cause, reduction in likelihood of the occurrence of symptoms and/or underlying cause, and/or remediation of damage. Thus, "treating" a patient with an active agent as provided herein can include prevention of a particular condition, disease, or disorder in a susceptible individual as well as treatment of a clinically symptomatic individual.

As used herein, "nominal amount" can refer to the amount contained within the unit dose receptacle(s) that are administered.

As used herein, a "therapeutically effective amount" of an active agent can refer to an amount that is effective to achieve a desired therapeutic result. A therapeutically effective amount of a given active agent can vary with respect to factors such as the type and severity of the disorder or disease being treated and the age, gender, and weight of the patient.

In one embodiment, the pharmaceutical compostion of the disclosure is administered via oral inhalation. In some embodiments, "inhalation" (e.g., "oral inhalation" or "nasal inhalation") refers to a period starting from when the patient begins inhalation of the pharmaceutical composition and ending when the patient ceases inhalation of the pharmaceutical composition. In some embodiments, a patient is administered a pharmaceutical agent contained in one unit dose receptacle in one inhalation, which, in some instances, can comprise inhalational administration via tidal breathing from a period that is, for example, from 0.1 minutes to 15 minutes. In some cases, the antiarrhythmic pharmaceutical agent is delivered over two or more inhalations. In some cases, time between the two or more inhalations is from about 0.1 to 10 minutes. The antiarrhythmic pharmaceutical agent is administered in the described dose in less than 60 minutes, less than 50 minutes, less than 40 minutes, less than 30 minutes, less than 20 minutes, less than 15 minutes, less than 10 minutes, less than 7 minutes, less than 5 minutes, in less than 3 minutes, in less than 2 minutes, or in less than 1 minute. In some cases, delivery of the required dose of antiarrhythmic pharmaceutical agent is completed with 1, 2, 3, 4, 5, or 6 inhalations. In some cases, each inhalation is performed for about 0.5, 1, 1.2, 1.5, 1.8, 2, 2.2, 2.5, 2.8, 3, 3.2, 3.5, 3.8, 4, 4.2, 4.5, 4.8, or 5 minutes. In some cases, each inhalation is performed for longer than 5 minutes. In some cases, each inhalation is performed for up to 4.5 minutes. In some cases, each inhalation comprises at least 60 inhalation breaths, 50 inhalation breaths, 40 inhalation breaths, 30 inhalation breaths, 20 inhalation breaths, 10 inhalation breaths, 8 inhalation breaths, 6 inhalation breaths, 4 inhalation breaths, 3 inhalation breaths, 2 inhalation breaths or 1 inhalation breath. In some cases, each inhalation comprises no more than 100 inhalation breaths, 90 inhalation breaths, 80 inhalation breaths, 70 inhalation breaths, 60 inhalation breaths, 50 inhalation breaths, 40 inhalation breaths, 30 inhalation breaths, or 20 inhalation breaths. In some cases, inhalation of the antiarrhythmic pharmaceutical agent is performed with deep lung breath that lasts for longer than 1 second, 2 seconds, 3 seconds, or 4 seconds. In some cases, inhalation of the antiarrhythmic pharmaceutical agent is performed with deep lung breath that lasts for about 1 second, 2 seconds, 3 seconds, or 4 seconds.

In some embodiments, during inhalational delivery of the antiarrhythmic pharmaceutical agent, the subject takes, or is instructed to take, a break between two inhalations. In such embodiments, the break between two inhalations lasts for about 0.1 to 10 minutes, such as, 0.2 to 5, 1 to 5, 1.5 to 5, 2 to 5, 3 to 5, 4 to 5, 1 to 1.5, 1 to 2, 1 to 2.5, 1 to 3, 1 to 3.5, 1 to 4, 1.5 to 2, 1.5 to 2.5, or 1.5 to 3 minutes. In some cases, the subject takes, or is instructed to take, a break for about 1 minute between two inhalations. In some cases, the inhalation pattern for delivery of a single dose goes as follows: a first inhalation for about 4 to 4.5 minutes, a break for about 1 minute, and a second inhalation for about 4 to 4.5 minutes; a first inhalation for about 4 to 4.5 minutes, a break for about 30 seconds, and a second inhalation for about 4 to 4.5 minutes; a first inhalation for about 4 to 4.5 minutes, a first break for about 1 minute, and a second inhalation for about 4 to 4.5 minutes; a second break for about 1 minutes, and a third inhalation for about 4 to 4.5 minutes; or a first inhalation for about 4 to 4.5 minutes, a first break for about 30 seconds, and a second inhalation for about 4 to 4.5 minutes; a second break for about 30 seconds, and a third inhalation for about 4 to 4.5 minutes.

In some embodiments, the subject inhales, or is instructed to inhale an aerosolized pharmaceutical composition of the disclosure via tidal breathing for a certain duration of time. In some embodiments, after inhaling the pharmaceutical composition for a first duration of time (e.g, about 3.5 minutes), the subject pauses inhalation of the aerosolized pharmaceutical composition for another duration of time, such as a period equivalent to a break as specified above (e.g., about 1 minute), and then subsequently resumes inhaling the aerosolized pharmaceutical composition for another duration of time (e.g., about 3.5 minutes). In some embodiments, the subject inhales the aerosolized pharmaceutical composition for 3.5 minutes, pauses inhalation of the aerosolized pharmaceutical composition for about 1 minute, and then resumes inhaling the aerosolized pharmaceutical composition for a subsequent 3.5 minutes.

In some embodiments, the subject inhales an aerosolized pharmaceutical composition of the disclosure via tidal breathing. As used herein, "tidal breathing" can refer to inhalation and exhalation during restful breathing. For example, tidal breathing can include inhaling the arosolized pharmaceutical composition while breathing at a rate of 10 to 14 breaths a minute.

As used herein, the phrase "minimum effective amount" can mean the minimum amount of a pharmaceutical agent necessary to achieve an effective amount.

As used herein, "mass median diameter" or "MMD" can refer to the median diameter of a plurality of particles, typically in a polydisperse particle population, e.g., consisting of a range of particle sizes. MMD values as reported herein are determined by laser diffraction (Sympatec Helos, Clausthal-Zellerfeld, Germany), unless the context indicates otherwise. For instance, for powders the samples are added directly to the feeder funnel of the Sympatec RODOS dry powder dispersion unit. This can be achieved manually or by agitating mechanically from the end of a VIBRI vibratory feeder element. Samples are dispersed to primary particles via application of pressurized air (2 to 3 bar), with vacuum depression (suction) maximized for a given dispersion pressure. Dispersed particles are probed with a 632.8 nm laser beam that intersects the dispersed particles' trajectory at right angles. Laser light scattered from the ensemble of particles is imaged onto a concentric array of photomultiplier detector elements using a reverse-Fourier lens assembly. Scattered light is acquired in time-slices of 5 ms. Particle size distributions are back-calculated from the scattered light spatial/intensity distribution using a proprietary algorithm.

As used herein, "geometric diameter" can refer to the diameter of a single particle, as determined by microscopy, unless the context indicates otherwise.

As used herein, "mass median aerodynamic diameter" or "MMAD" can refer to the median aerodynamic size of a plurality of particles or particles, typically in a polydisperse population. The "aerodynamic diameter" can be the diameter of a unit density sphere having the same settling velocity, generally in air, as a powder and is therefore a useful way to characterize an aerosolized powder or other dispersed particle or particle formulation in terms of its settling behavior. The aerodynamic diameter encompasses particle or particle shape, density, and physical size of the particle or particle. As used herein, MMAD refers to the median of the aerodynamic particle or particle size distribution of aerosolized particles determined by cascade impaction, unless the context indicates otherwise.

By a "pharmaceutically acceptable" component is meant a component that is not biologically or otherwise undesirable, e.g., the component may be incorporated into a pharmaceutical formulation of the invention and administered to a patient as described herein without causing any significant undesirable biological effects or interacting in a deleterious manner with any of the other components of the formulation in which it is contained. When the term "pharmaceutically acceptable" is used to refer to an excipient, it can imply that the component has met the required standards of toxicological and manufacturing testing or that it is included on the Inactive Ingredient Guide prepared by the U.S. Food and Drug Administration.

The therapy provided herein can comprise or be suitable for parenteral injection, oral or nasal administration (e.g., oral or nasal inhalation), or intranasal spray administration. As provided herein, the term "oral or nasal administration" can refer to oral inhalation, nasal inhalation, or intranasal spray administration. In some embodiments, during administration via oral inhalation, the pharmaceutical agent is inhaled by the patient through the mouth and absorbed by the lungs. In some embodiments, during administration via nasal inhalation, the pharmaceutical agent is inhaled by the patient through the nose and absorbed by the nasal mucous and/or the lungs. In some embodiments, during intranasal spray administration, pharmaceutical agent is sprayed into the nose of the patient and subsequently absorbed by the nasal mucous and/or the lungs. In some embodiments, during intranasal spray administration, the pharmaceutical agent is passively administered to the patient, e.g., the patient does not actively inhale the sprayed agent. In some embodiments, during intranasal spray administration, the pharmaceutical agent is both passively and actively administered to the patient, e.g., the agent is at least partially actively inhaled by the patient through the nose after being sprayed intranasally.

As used herein, "parenteral injection" may refer to administration performed using a needle or indwelling catheter, which may include, for example, intracardiac, intra-arterial, intravenous, intramuscular, and subcutaneous administration.

As used herein, "QT interval" can refer to the time interval between the beginning of a QRS complex to an end of a subsequent T wave as measured by electrocardiogram (ECG). QT interval can vary among subjects due to factors not directly associated with disease pathology or drug-related effects, including age, sex, and ventricular rate. In some embodiments, measurement of QT interval is corrected for heart rate ($QT_c$) according to the Bazett function $QT_c=QT/(\sqrt{RR})$, where RR is an interval between two successive R waves and QT is the QT interval as defined above. In some embodiments, measurement of QT interval is corrected for heart rate ($QT_c$) according to the Fridericia function $QT_c=QT/\sqrt[3]{RR}$), where RR is an interval between two successive R waves and QT is the QT interval as defined above. In some embodiments, measurement of QT interval is corrected for heart rate ($QT_c$) according to the Framingham function $QT_c=QT+0.154*(1-RR)$, where RR is an interval between two successive R waves and QT is the QT interval as defined above. In some embodiments, measurement of QT interval is corrected for heart rate according to the Hodges function Hodges [$QTc=QT+1.75*(HR-60)$, wherein HR is heart rate in beats per minute, and QT is as defined above. In some embodiments, measurement of QT interval is corrected for heart rate ($QT_c$) according to the van de Water function $QT_c=QT-0.087(RR-1000)$, where RR is an interval between two successive R waves and QT is the QT interval as defined above. In some embodiments, the risk of torsade de pointes (TdP) in a subject is evaluated according to the magnitude of prolongation of the $QT_c$ interval. In some embodiments, a subject is at risk for TdP when the $QT_c$ of the subject is greater than 480 msec.

Routes of Administration.

Oral or Nasal Inhalation.

In some aspects of the present disclosure, the compositions or formulations of the pharmaceutical agents, e.g., potassium channel blocker, class I antiarrhythmic agent, or both, are administered via inhalation. The pharmaceutical formulations can be aerosolized prior to administration or can be presented to a user in the form of an aerosol.

The inhalation or intranasal spray administration routes can avoid first-pass hepatic metabolism, hence dosing variability can be eliminated. Unlike the case for oral tablets or pills, the patient's metabolic rates may not matter as the administration is independent of the metabolic paths experienced when a drug is administered via oral route through gastrointestinal tract, e.g., as tablets, pills, solution, or suspension.

A fast onset of action, a potential improvement in efficacy, and/or a reduction in dose can be achieved with the fast absorption of drugs from the nasal mucosa and/or lungs.

The fast absorption rate of drugs through the lungs can be achieved because of the large surface area available in the lungs for aerosols small enough to penetrate central and peripheral lung regions. For nasal delivery or intranasal spray delivery, the nasal mucosa can have a relatively high permeable epithelium layer, and a sub-epithelial layer that is highly vascularized, which can provide direct access of drugs for absorption into the systemic circulation. Consequently, the rate and extent of absorption of drugs delivered via the oral or nasal administration routes can yield plasma concentrations vs. time profiles that are comparable with the IV route of administration.

The time for onset of action can be short. For instance, the patient may have normal sinus rhythm within 20 minutes of initiating the administering, such as within 15 minutes, within 10 minutes, or within 5 minutes of initiating the administering. In some embodiments, the rapid onset of action is advantageous because the longer a patient has had arrhythmia, the longer it can take to convert the patient to normal sinus rhythm.

In some embodiments, the method of the present disclosure allows the patient to avoid other therapies, such as ablation and/or electrical cardioversion. In other embodiments, the method of the present invention is used in combination with other therapies, such as before or after electrical cardioversion and/or ablation therapy.

The pharmaceutical compositions can be administered using an aerosolization device. The aerosolization device can be a nebulizer, a metered dose inhaler, a liquid dose instillation device, or a dry powder inhaler. The aerosolization device can comprise the extrusion of the pharmaceutical preparation through micron or submicron-sized holes with subsequent Rayleigh break-up into fine droplets. The pharmaceutical composition can be delivered by a nebulizer as described in WO 99/16420, by a metered dose inhaler as described in WO 99/16422, by a liquid dose instillation apparatus as described in WO 99/16421, and by a dry powder inhaler as described in U.S. Published Application Nos. 20020017295 and 20040105820, WO 99/16419, WO 02/83220, and U.S. Pat. No. 6,546,929, which are incorporated herein by reference in their entireties. As such, an inhaler can comprise a canister containing the particles or particles and propellant, and wherein the inhaler comprises a metering valve in communication with an interior of the canister. The propellant can be a hydrofluoroalkane.

For instance, the pharmaceutical formulation can be in liquid solution, and can be administered with nebulizers, such as that disclosed in PCT WO 99/16420, the disclosure of which is hereby incorporated in its entirety by reference, in order to provide an aerosolized medicament that can be administered to the pulmonary air passages of a patient in need thereof. Nebulizers known in the art can easily be employed for administration of the claimed formulations. Breath-activated or breath-actuated nebulizers, as well as those comprising other types of improvements which have been, or will be, developed are also compatible with the formulations of the present disclosure and are contemplated as being within the scope thereof.

In some embodiments, the nebulizer is a breath activated or breath-actuated nebulizer. In some embodiments, the nebulizer is a hand-held inhaler device (e.g., AeroEclipse® II Breath Actuated Nebulizer (BAN)). In some embodiments, the nebulizer has a compressed air source. In some embodiments, the nebulizer converts liquid medication into an aerosol. In some embodiments, the nebulizer converts liquid medication into an aerosol by extruding the pharmaceutical preparation through micron or submicron-sized holes. In some embodiments, the nebulizer converts liquid medication into an aerosol so it can be inhaled into the lungs. In some embodiments, the nebulizer is a small volume nebulizer. In some embodiments, the nebulizer is a small volume jet nebulizer. In some embodiments, aerosolized medication is only produced when inhaled through the device. In some embodiments, the medication is contained in the cup between breaths or during breaks in treatment. In some embodiments, the medication is contained in the cup until ready to be inhaled.

Nebulizers can impart energy into a liquid pharmaceutical formulation to aerosolize the liquid, and to allow delivery to the pulmonary system, e.g., the lungs, of a patient. A nebulizer comprises a liquid delivery system, such as a container having a reservoir that contains a liquid pharmaceutical formulation. The liquid pharmaceutical formulation generally comprises an active agent that is either in solution or suspended within a liquid medium.

In one type of nebulizer that can be used in the subject methods and kits, generally referred to as a jet nebulizer, compressed gas is forced through an orifice in the container. The compressed gas forces liquid to be withdrawn through a nozzle, and the withdrawn liquid can mix with the flowing gas to form aerosol droplets. A cloud of droplets can then be administered to the respiratory tract of the patient.

In another type of nebulizer that can be used in the subject methods and kits, generally referred to as a vibrating mesh nebulizer, energy, such as mechanical energy, vibrates a mesh. This vibration of the mesh aerosolizes the liquid pharmaceutical formulation to create an aerosol cloud that is administered to the patient's lungs. In another type of nebulizer that can be used in the subject methods and kits, the nebulizing comprises extrusion through micron or submicron-sized holes followed by Rayleigh break-up into fine droplets.

Alternatively or additionally, the pharmaceutical formulation may be in a liquid form and may be aerosolized using a nebulizer as described in WO 2004/071368, which is herein incorporated by reference in its entirety, as well as U.S. Published application Nos. 2004/0011358 and 2004/0035413, which are both herein incorporated by reference in their entireties. Other examples of nebulizers include, but are not limited to, the Aeroneb® Go or Aeroneb® Pro nebulizers, available from Aerogen Ltd. of Galway, Ireland; the PARI eFlow and other PARI nebulizers available from PARI Respiratory Equipment, Inc. of Midlothian, Va.; the Lumiscope® Nebulizer 6600 or 6610 available from Lumiscope Company, Inc. of East Brunswick, N.J.; and the Omron NE-U22 available from Omron Healthcare, Inc. of Kyoto, Japan. Other examples of nebulizers include devices produced by Medspray (Enschede, The Netherlands).

It has been found that a nebulizer of the vibrating mesh type, such as one that that forms droplets without the use of compressed gas, such as the Aeroneb® Pro provides unexpected improvement in dosing efficiency and consistency. By generating fine droplets by using a vibrating perforated or unperforated membrane, rather than by introducing compressed air, the aerosolized pharmaceutical formulation can be introduced without substantially affecting the flow characteristics. In addition, the generated droplets when using a nebulizer of this type are introduced at a low velocity, thereby decreasing the likelihood of the droplets being driven to an undesired region. It has been found that when using a nebulizer of the extrusion/Rayleigh jet breakup type, the generated droplets are also introduced at a low velocity, thereby decreasing the likelihood of the droplets being driven to an undesired region.

In some embodiments, the nebulizer that can be used in the subject methods and kits is of the vibrating mesh type. In some embodiments, the nebulizer that can be used in the subject methods and kits is of the pressurized jet type. In some embodiments, the nebulizer that can be used in the subject methods and kits is of the extrusion/Rayleigh breakup type. In some embodiments, the nebulizer is lightweight (at most 60 g, at most 100 g, at most 200 g, at most 250 g) and nearly silent. In some embodiments, the nebulizer has a sound level less than 35 A-weighted decibels (dBA) at 1 meter. In some embodiments, the nebulizer has a medication cup capacity of 6 mL. In some embodiments, the nebulizer has a residual volume of less than 0.3 mL. In some embodiments, the nebulizer generates an average flow rate of 0.4 mL/min. In some embodiments, the nebulizer generates an average flow rate of 0.5 mL/min. In some embodiments, the nebulizer generates an average flow rate of 0.6 mL/min. In some embodiments, the nebulizer generates an average flow rate of 0.7 mL/min. In some embodiments, the nebulizer generates an average flow rate of 0.8 mL/min. In some embodiments, the nebulizer generates an average flow rate of 0.9 mL/min. In some embodiments, the nebulizer generates an average flow rate of 1.0 mL/min. In some embodiments, the nebulizer generates an average flow rate of 1.1 mL/min. In some embodiments, the nebulizer generates an average flow rate of 1.2 mL/min. In some embodiments, the nebulizer generates an average particle size of 3.0 μm MMAD. In some embodiments, the nebulizer generates an average particle size between 3.0 μm MMAD and 4.0 μm MMAD. In some embodiments, the nebulizer generates an average particle size of 3.0 μm MMAD. In some embodiments, the nebulizer generates an average particle size between 3.0 μm MMAD and 5.0 μm MMAD. In some embodiments, the nebulizer generates an average particle size of 3.0 μm MMAD. In some embodiments, the nebulizer generates an average particle size between 3.0 μm MMAD and 6.0 μm MMAD.

In still another type of nebulizer that can be used in the subject methods and kits, ultrasonic waves are generated to directly vibrate and aerosolize the pharmaceutical formulation.

Alternatively or additionally, the present disclosure can involve a dry powder inhaler. A specific version of a dry powder aerosolization apparatus is described in U.S. Pat. Nos. 4,069,819 and 4,995,385, which are incorporated herein by reference in their entireties. Another useful device, which has a chamber that is sized and shaped to receive a capsule so that the capsule is orthogonal to the inhalation direction, is described in U.S. Pat. No. 3,991,761, which is incorporated herein by reference in its entirety. As also described in U.S. Pat. No. 3,991,761, a puncturing mechanism may puncture both ends of the capsule. In another version, a chamber can receive a capsule in a manner where air flows through the capsule as described for example in U.S. Pat. Nos. 4,338,931 and 5,619,985, which are incorporated herein by reference in their entireties. In another version, the aerosolization of the pharmaceutical composition can be accomplished by pressurized gas flowing through the inlets, as described for example in U.S. Pat. Nos. 5,458,135; 5,785,049; and 6,257,233, or propellant, as described in WO 00/72904 and U.S. Pat. No. 4,114,615, which are incorporated herein by reference. These types of dry powder inhalers are generally referred to as active dry powder inhalers.

Other dry powder inhalers can include those available from Boehringer Ingelheim (e.g., Respimat inhaler), Hovione (e.g., FlowCaps inhaler), Plastiape (e.g., Osmohaler inhaler), and MicroDose. The present invention may also utilize condensation aerosol devices, available from Alexza, Mountain View, Calif. Yet another useful inhaler is disclosed in WO 2008/051621, which is incorporated herein by reference in its entirety.

The pharmaceutical formulations disclosed herein can also be administered to the lungs of a patient via aerosolization, such as with a metered dose inhaler. The use of such formulations provides for superior dose reproducibility and improved lung deposition as disclosed in WO 99/16422, hereby incorporated in its entirety by reference. Metered dose inhalers (MDIs) known in the art can be employed for administration of the claimed pharmaceutical compositions. Breath-activated or breath-actuated MDIs and pressurized MDIs (pMDIs), as well as those comprising other types of improvements which have been, or will be, developed are also compatible with the formulations of the present disclosure and, as such, are contemplated as being within the scope thereof.

Along with DPIs, MDIs and nebulizers, it will be appreciated that the formulations of one or more embodiments of the present invention can be used in conjunction with liquid dose instillation or LDI techniques as disclosed in, for example, WO 99/16421, which is incorporated herein by reference in its entirety. Liquid dose instillation involves the direct administration of a formulation to the lung. With respect to LDI the formulations are preferably used in conjunction with partial liquid ventilation or total liquid ventilation. Moreover, one or more embodiments of the present invention may further comprise introducing a therapeutically beneficial amount of a physiologically acceptable gas (such as nitric oxide or oxygen) into the pharmaceutical microdispersion prior to, during or following administration.

The pharmaceutical composition of one or more embodiments of the present disclosure can have improved emitted dose efficiency. Accordingly, high doses of the pharmaceutical composition can be delivered using a variety of aerosolization devices and techniques.

The emitted dose (ED) of the particles of the present invention may be greater than about 30%, such as greater than about 40%, greater than about 50%, greater than about 60%, or greater than about 70%.

Intranasal Spray Administration.

In another aspect of the disclosure, the present disclosure relates to intranasal spray administration of the pharmaceutical compositions for treatment of a subject suffering from a heart condition, e.g., cardiac arrhythmia, e.g., atrial arrhythmia. Nasal spray device can be used for the purpose of spraying the pharmaceutical formula in aerosol form into nasal cavity. For nasal administration, a useful device can be a small, hard bottle to which a metered dose sprayer is attached. In some embodiments, the metered dose is delivered by drawing the pharmaceutical solution described herein into a chamber of defined volume, which chamber has an aperture dimensioned to aerosolize and aerosol formulation by forming a spray when a liquid in the chamber is compressed. The chamber is compressed to administer the pharmaceutical agents, e.g., potassium channel blocker, class I antiarrhythmic agent, or both. In some embodiments, the chamber is a piston arrangement. Such devices are commercially available. Alternatively, a plastic squeeze bottle with an aperture or opening dimensioned to aerosolize an aerosol formulation by forming a spray when squeezed. The opening can be found in the top of the bottle, and the top is generally tapered to partially fit in the nasal passages for efficient administration of the aerosol formulation. The nasal inhaler can provide a metered amount of the aerosol formulation, for administration of a measured dose of the drug.

In some embodiments, the Aptar/Pfeiffer Unitdose delivery device is used to deliver the disclosed compositions. Other devices that can be used according to the present disclosure include, but not limited to, those as described in Djupesland, Drug Deliv Transl Res. (2013) February; 3(1). In some embodiments, the nasal spray device delivers a volume of about 50 μL, about 60 μL, about 80 μL, about 100 μL, about 150 μL, about 200 μL, about 300 μL, about 400 μL, about 500 μL, about 600 μL, about 700 μL, about 800 μL per spray. In some embodiments, the nasal spray device is configured to deliver the pharmaceutical formula in more than one sprays, for instance, 2, 3, 4, 5, 6, 7, 8, 9, 10, or even more sprays. The direct product contact components of the container closure can comprise a container (glass vial), manufactured using FIOLAX glass by MGLAS or NUOVA OMPI, a plunger (Stopper).

The nasal spray device can be intended for use by both medical and non-medical personnel. The device can have one or more features selected from being single-use, needle-free, ready-to-use, disposable, and combinations thereof. The device may be configured to administer the disclosed compositions as a single spray per naris. The device can comprise one or more unit dose containers, each container delivering about one 100 μL spray. In other aspects, the devices may be modified to deliver amounts of between about 50 μL to about 800 μL spray, and can utilize solutions of varying concentration. Any nasal spray device known in the art can be used to deliver the nasal spray and compositions described herein. In one aspect, the nasal spray device is an Aptar/Pfeiffer Unitdose device. The nasal spray provided herein can comprise a preserved solution with pH and osmolality appropriate for nasal administration. Similarly, it can be prepared as a sterile solution without an antimicrobial preservative.

Intravenous Administration.

The potassium channel blocker may also be administered by a parenteral route, which can include intravenous injection. Intravenous administration of the potassium channel blocker also can be accompanied by administration of a sodium channel blocker (e.g., flecainide). The sodium channel blocker can be administered prior to, subsequent to, or concurrently with intravenous administration of the potassium channel blocker. The sodium channel blocker can be administered by inhalation, intravenous injection, or by tablets, pills, solutions, or suspensions for oral ingestion. Intravenous administration of the potassium channel blocker concurrent to administration of a sodium channel blocker can comprise administration of a fixed dose combination of potassium channel blocker and a sodium channel blocker (e.g., ibutilide and flecainide) formulated for intravenous injection.

Oral Administration

The potassium channel blocker may also be administered by an oral route. Oral administration can include, but is not limited to, pills, tablets, capsules, or syrups. Oral administration of the potassium channel blocker also can be accompanied by administration of a sodium channel blocker (e.g., flecainide). The sodium channel blocker can be administered prior to, subsequent to, or concurrently with intravenous administration of the potassium channel blocker. The sodium channel blocker can be administered by inhalation, intravenous injection, or by tablets, pills, solutions, or suspensions for oral ingestion. Oral administration of the potassium channel blocker concurrent to administration of a sodium channel blocker can comprise administration of a fixed dose combination of potassium channel blocker and a sodium channel blocker (e.g., ibutilide/dofetilide and flecainide) formulated for oral administration.

The potassium channel blocker and the sodium channel blocker can be combined into a single oral administration, such as a tablet. In some embodiments, the tablet comprises a potassium channel blocker and a sodium channel blocker. In some embodiments, the tablet comprises ibutilide and flecainide, flecainide and dofetilide, flecainide and sotalol, mexiletine and sotalol, mexiletine and dofetilide, or mexiletine and ibutilide.

Oral administration (e.g., tablet, capsules, etc.) can be formulated to adjust the release an absorption of a drug upon administration to a subject. The tablet can be, but is not limited to formulations for timed release, controlled delivery, controlled release, delayed release, long-acting, long-acting release, modified release, prolonged release, sustained action, sustained release, timed release, immediate release, extended release, or slow release.

Administration Regimen.

The potassium channel blocker, e.g., a class IIIa antiarhytmic agent, provided herein can be coadministered with another antiarrhythmic therapy, e.g., a sodium channel blocker, which can be, for example, a class I antiarrhythmic agent. For example, the patient could self-administer a sodium channel blocker (e.g. flecainide) within a few minutes (e.g., 5-15 min) of self-administering a potassium channel blocker such as, for example, ibutilide or dofetilide.

In some embodiments, the administration of the potassium channel blocker takes place concurrently with the administration of sodium channel blocker, e.g., class I antiarrhythmic agent. For instance, an aerosolization device that is configured to deliver two separate drug formulations at the same time can be used. In such a device, the two drug formulations, e.g., containing a potassium channel blocker and a class I antiarrhythmic agent, respectively, can be received in two separate receptacles, and the device can form an aerosol containing both of the two formulations, which ensures the subject inhaling the two drugs at the same time. In other examples, one combination pharmaceutical composition is provided, containing both of the two drugs, e.g., potassium channel blocker and class I antiarrhythmic agent. In such cases, the combination composition is administered to the subject via intravenous injection, inhalation, or intranasal spray administration, thereby achieving therapeutic effects of co-administration of the two active agents.

The methods provided herein can comprise administration of an antiarrhythmic agent, e.g., a class I antiarrhythmic agent, for induction of cardioversion. The methods provided herein can further comprise application of an electric current for induction of cardioversion. The cardioversion provided herein can comprise both pharmaceutic and electrical.

The pharmaceutical composition can be administered to the patient on an as-needed basis. For instance, the methods, kits, and compositions can find particular use in treating a subject experiencing a heart condition, e.g., cardiac arrhythmia, e.g., atrial arrhythmia. In some embodiments, a subject is administered with the therapy described herein when he/she is experiencing atrial arrhythmia. In some embodiments, the therapy, for instance, the combination inhalational therapy with both a potassium channel blocker and class I antiarrhythmic is administered to a subject after the onset of an episode of cardiac arrhythmia. In other cases, the subject is treated between episodes of cardiac arrhythmias.

In some embodiments, the therapy provided herein is provided to a subject for more than once on an as-needed basis. For instance, the present invention may involve a follow-up inhalation if no cardioversion occurs after an initial inhalation. In some instances, if no cardioversion occurs within 30 minutes of the initial inhalation, the follow-up dosage is higher, lower, or the same as the initial dosage.

The dosing can be guided by how the patient feels. Also or alternatively, dosing can be guided by using a portable/mobile ECG device. For instance, the dosing may be guided by using a wearable device such as, for example, a Holter monitor, Apple Watch, the AliveCor® KardiaMobile® 6L, QardioCore® ECG, Fitbit® charge 5, or Oura® Ring.

The amount of $Mg^{2+}$ source suitable for the disclosed methods, kits, and compositions can be sufficient to deliver to the subject, for example, from about 50 mg to about 3000 mg $Mg^{2+}$ cation, such as from about 50 mg to about 2000 mg, from about 100 mg to about 2000 mg, from about 200 mg to about 2000 mg, from about 300 mg to about 2000 mg, from about 500 mg to about 2000 mg, 50 mg to about 1000 mg, from about 100 mg to about 1000 mg, from about 200 mg to about 1000 mg, from about 300 mg to about 1000 mg, or from about 500 mg to about 1000 mg $Mg^{2+}$ cation. The amount of $Mg^{2+}$ source suitable for the disclosed methods, kits, and compositions can be sufficient to deliver to the subject can be, for example, about 50 mg, about 100 mg, about 150 mg, about 200 mg, about 300 mg, about 100 mg, about 500 mg, about 600 mg, about 700 mg, about 800 mg, about 900 mg, about 1000 mg, about 1500 mg, or about 2000 mg $Mg^{2+}$ cation.

The amount of magnesium sulfate for the disclosed methods, kits, and compositions can range, for example, from about 1 mg to about 10,000 mg magnesium sulfate, such as from about 1 mg to about 8000 mg, from about 1 mg to about 6000 mg, from about 1 mg to about 4000 mg, from about 1 mg to about 2000 mg, from about 1 mg to about 1000 mg, from about 1 mg to about 700 mg, from about 1 mg to about 600 mg, from about 1 mg to about 500 mg, from about 5 mg to about 6000 mg, from about 5 mg to about 4000 mg, from about 5 mg to about 2000 mg, from about 5 mg to about 1000 mg, from about 1000 mg to about 10,000 mg, from about 2000 mg to about 10,000 mg, from about 3000 mg to about 10,000 mg, from about 4000 mg to about 10,000 mg, from about 5000 mg to about 10,000 mg, from about 5 mg to about 700 mg, from about 5 mg to about 600 mg, from about 5 mg to about 500 mg, from about 20 mg to about 6000 mg, from about 20 mg to about 4000 mg, from about 20 mg to about 2000 mg, from about 20 mg to about 1000 mg, from about 20 mg to about 700 mg, from about 20 mg to about 600 mg, from about 20 mg to about 500 mg magnesium sulfate. The amount of magnesium sulfate suitable for the disclosed methods, kits, and compositions can be, for example, about 0.5 g, about 1 g, about 1.5 g, about 2 g, about 2.5 g, about 3 g, about 3.5 g, about 4 g, about 5 g, about 6 g, about 7 g, about 8 g, about 9 g, or about 10 g.

The amount of magnesium sulfate suitable for the disclosed methods, kits, and compositions can range, for example, from about 1 mg per kilogram of subject body weight (mg/kg) to about 200 mg/kg, such as from about 1 mg/kg to about 150 mg/kg, from about 1 mg/kg to about 150 mg/kg, from about 10 mg/kg to about 150 mg/kg, from about 20 mg/kg to about 150 mg/kg, from about 50 mg/kg to about 150 mg/kg, from about 100 mg/kg to about 150 mg/kg, from about 1 mg/kg to about 100 mg/kg, from about 1 mg/kg to about 80 mg/kg, from about 1 mg/kg to about 60 mg/kg, from about 1 mg/kg to about 40 mg/kg, or from about 1 mg/kg to about 20 mg/kg. The amount of magnesium sulfate suitable for the disclosed methods, kits, and compositions can be, for example, about 1 mg/kg, about 5 mg/kg, about 10 mg/kg, about 20 mg/kg, about 30 mg/kg, about 40 mg/kg, about 50 mg/kg, about 75 mg/kg, or about 100 mg/kg.

The amount of ibutilide or a pharmaceutically acceptable salt thereof (e.g. ibutilide fumarate) suitable for the disclosed methods, kits, and compositions can range, for example, from about 0.002 mg to 100 mg, such as from about 0.002 mg to about 50 mg, from about 0.002 mg to about 25 mg, from about 0.002 mg to about 15 mg, from about 0.002 mg to about 10 mg, from about 0.002 mg to about 5 mg, from about 0.002 mg to about 2 mg, from about 0.002 mg to about 1 mg, from about 0.01 mg to about 50 mg, from about 0.01 mg to about 25 mg, from about 0.01 mg to about 15 mg, from about 0.01 mg to about 5 mg, from about 0.01 mg to about 2 mg, from about 0.01 mg to about 1 mg, from about 0.01 mg to about 0.5 mg, from about 0.05 mg to about 50 mg, from about 0.05 mg to about 25 mg, from about 0.05 mg to about 10 mg, from about 0.05 mg to about 5 mg, from about 0.05 mg to about 1 mg, from about 0.05 mg to about 0.5 mg, from about 0.05 mg to about 0.1 mg, from about 0.01 mg to about 0.5 mg, from about 0.25 mg to about 50 mg, from about 0.25 mg to about 25 mg, from about 0.25 mg to about 10 mg, from about 0.25 mg to about 5 mg, from about 0.25 mg to about 1 mg, from about 0.25 mg to about 0.5 mg, or from about 0.25 mg to about 0.1 mg ibutilide or a pharmaceutically acceptable salt thereof. The amount of ibutilide or a pharmaceutically acceptable salt thereof suitable for the disclosed methods, kits, and compositions can be, for example, about 0.002 mg, about 0.01 mg, about 0.02 mg, about 0.05 mg, about 0.01 mg, about 0.02 mg, about 0.03 mg, about 0.04 mg, about 0.05 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 1.5 mg or about 2 mg.

The amount of ibutilide or a pharmaceutically acceptable salt thereof (e.g. ibutilide fumarate) suitable for the disclosed methods, kits, and compositions can range, for example, from about 0.0001 mg per kilogram of subject body weight (mg/kg) to about 5 mg/kg, such as from about 0.001 mg/kg to about 0.25 mg/kg, from about 0.005 mg/kg to about 0.25 mg/kg, from about 0.01 mg/kg to about 0.25 mg/kg, from about 0.1 mg/kg to about 0.25 mg/kg, from about 0.001 mg/kg to about 0.2 mg/kg, from about 0.001 mg/kg to about 0.1 mg/kg, from about 0.001 mg/kg to about 0.05 mg/kg, from about 0.001 mg/kg to about 0.01 mg/kg, or from about 0.001 mg/kg to about 0.005 mg/kg. The amount of ibutilide or a pharmaceutically acceptable salt thereof (e.g. ibutilide fumarate) suitable for the disclosed methods, kits, and compositions can be, for example, about 0.0001 mg/kg, about 0.0005 mg/kg, about 0.001 mg/kg, about 0.005 mg/kg, about 0.01, about 0.05 mg/kg, about 0.1 mg/kg, or about 0.2 mg/kg.

The amount of dofetilide or a pharmaceutically acceptable salt suitable for the disclosed methods, kits, and compositions can range, for example, from about 0.002 mg to 100 mg, such as from about 0.002 mg to about 50 mg, from about 0.002 mg to about 25 mg, from about 0.002 mg to about 15 mg, from about 0.002 mg to about 10 mg, from about 0.002 mg to about 5 mg, from about 0.002 mg to about 2 mg, from about 0.002 mg to about 1 mg, from about 0.01 mg to about 50 mg, from about 0.01 mg to about 25 mg, from about 0.01 mg to about 15 mg, from about 0.01 mg to about 5 mg, from about 0.01 mg to about 2 mg, from about 0.01 mg to about 1 mg, from about 0.01 mg to about 0.5 mg, from about 0.05 mg to about 50 mg, from about 0.05 mg to about 25 mg, from about 0.05 mg to about 10 mg, from about 0.05 mg to about 5 mg, from about 0.05 mg to about 1 mg, from about 0.05 mg to about 0.5 mg, from about 0.05 mg to about 0.1 mg, from about 0.01 mg to about 0.5 mg, from about 0.25 mg to about 50 mg, from about 0.25 mg to about 25 mg, from about 0.25 mg to about 10 mg, from about 0.25 mg to about 5 mg, from about 0.25 mg to about 1 mg, from about 0.25 mg to about 0.5 mg, or from about 0.25 mg to about 0.1 mg dofetilide or a pharmaceutically acceptable salt thereof. The amount of dofetilide or a pharmaceutically acceptable salt thereof suitable for the disclosed methods, kits, and compositions can be, for example, about 0.002 mg, about 0.01 mg, about 0.02 mg, about 0.05 mg, about 0.01 mg, about 0.02 mg, about 0.03 mg, about 0.04 mg, about 0.05 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 1.5 mg or about 2 mg.

The amount of dofetilide or a pharmaceutically acceptable salt thereof suitable for the disclosed methods, kits, and compositions can range, for example, from about 1 μg per kilogram of subject body weight (μg/kg) to about 10 μg/kg, such as from about 1 μg/kg to about 2 μg/kg, about 1 μg/kg to about 3 μg/kg, about 1 μg/kg to about 4 μg/kg, about 1 μg/kg to about 5 μg/kg, about 1 μg/kg to about 6 μg/kg, about 1 μg/kg to about 7 μg/kg, about 1 μg/kg to about 8 μg/kg, about 1 μg/kg to about 9 μg/kg, about 1 μg/kg to about 10 μg/kg, about 2 μg/kg to about 3 μg/kg, about 2 μg/kg to about 4 μg/kg, about 2 μg/kg to about 5 μg/kg, about 2 μg/kg to about 6 μg/kg, about 2 μg/kg to about 7 μg/kg, about 2 μg/kg to about 8 μg/kg, about 2 μg/kg to about 9 μg/kg, about 2 μg/kg to about 10 μg/kg, about 3 μg/kg to about 4 μg/kg, about 3 μg/kg to about 5 μg/kg, about 3 μg/kg to about 6 μg/kg, about 3 μg/kg to about 7 μg/kg, about 3 μg/kg to about 8 μg/kg, about 3 μg/kg to about 9 μg/kg, about 3 μg/kg to about 10 μg/kg, about 4 μg/kg to about 5 μg/kg, about 4 μg/kg to about 6 μg/kg, about 4 μg/kg to about 7 μg/kg, about 4 μg/kg to about 8 μg/kg, about 4 μg/kg to about 9 μg/kg, about 4 μg/kg to about 10 μg/kg, about 5 μg/kg to about 6 μg/kg, about 5 μg/kg to about 7 μg/kg, about 5 μg/kg to about 8 μg/kg, about 5 μg/kg to about 9 μg/kg, about 5 μg/kg to about 10 μg/kg, about 6 μg/kg to about 7 μg/kg, about 6 μg/kg to about 8 μg/kg, about 6 μg/kg to about 9 μg/kg, about 6 μg/kg to about 10 μg/kg, about 7 μg/kg to about 8 μg/kg, about 7 μg/kg to about 9 μg/kg, about 7 μg/kg to about 10 μg/kg, about 8 μg/kg to about 9 μg/kg, about 8 μg/kg to about 10 μg/kg, or about 9 μg/kg to about 10 μg/kg. The amount of dofetilide or a pharmaceutically acceptable salt suitable for the disclosed methods, kits, and compositions can be, for example, about 1 μg/kg, about 2 μg/kg, about 3 μg/kg, about 4 μg/kg, about 5 μg/kg, about 6 μg/kg, about 7 μg/kg, about 8 μg/kg, about 9 μg/kg, or about 10 μg/kg.

The concentration of dofetilide or a pharmaceutically acceptable salt thereof suitable for the disclosed methods, kits, and compositions can range, for example, from about 1 μg/mL to about 40 μg/mL. In some embodiments, concentration of dofetilide is about 1 μg/mL to about 40 μg/mL. In some embodiments, concentration of dofetilide is at least about 1 μg/mL. In some embodiments, concentration of dofetilide is at most about 40 μg/mL. In some embodiments, concentration of dofetilide is about 1 μg/mL to about 2 μg/mL, about 1 μg/mL to about 3 μg/mL, about 1 μg/mL to about 4 μg/mL, about 1 μg/mL to about 5 μg/mL, about 1 μg/mL to about 10 μg/mL, about 1 μg/mL to about 15 μg/mL, about 1 μg/mL to about 20 μg/mL, about 1 μg/mL to about 25 μg/mL, about 1 μg/mL to about 30 μg/mL, about 1 μg/mL to about 35 μg/mL, about 1 μg/mL to about 40 μg/mL, about 2 μg/mL to about 3 μg/mL, about 2 μg/mL to about 4 μg/mL, about 2 μg/mL to about 5 μg/mL, about 2

μg/mL to about 10 μg/mL, about 2 μg/mL to about 15 μg/mL, about 2 μg/mL to about 20 μg/mL, about 2 μg/mL to about 25 μg/mL, about 2 μg/mL to about 30 μg/mL, about 2 μg/mL to about 35 μg/mL, about 2 μg/mL to about 40 μg/mL, about 3 μg/mL to about 4 μg/mL, about 3 μg/mL to about 5 μg/mL, about 3 μg/mL to about 10 μg/mL, about 3 μg/mL to about 15 μg/mL, about 3 μg/mL to about 20 μg/mL, about 3 μg/mL to about 25 μg/mL, about 3 μg/mL to about 30 μg/mL, about 3 μg/mL to about 35 μg/mL, about 3 μg/mL to about 40 μg/mL, about 4 μg/mL to about 5 μg/mL, about 4 μg/mL to about 10 μg/mL, about 4 μg/mL to about 15 μg/mL, about 4 μg/mL to about 20 μg/mL, about 4 μg/mL to about 25 μg/mL, about 4 μg/mL to about 30 μg/mL, about 4 μg/mL to about 35 μg/mL, about 4 μg/mL to about 40 μg/mL, about 5 μg/mL to about 10 μg/mL, about 5 μg/mL to about 15 μg/mL, about 5 μg/mL to about 20 μg/mL, about 5 μg/mL to about 25 μg/mL, about 5 μg/mL to about 30 μg/mL, about 5 μg/mL to about 35 μg/mL, about 5 μg/mL to about 40 μg/mL, about 10 μg/mL to about 15 μg/mL, about 10 μg/mL to about 20 μg/mL, about 10 μg/mL to about 25 μg/mL, about 10 μg/mL to about 30 μg/mL, about 10 μg/mL to about 35 μg/mL, about 10 μg/mL to about 40 μg/mL, about 15 μg/mL to about 20 μg/mL, about 15 μg/mL to about 25 μg/mL, about 15 μg/mL to about 30 μg/mL, about 15 μg/mL to about 35 μg/mL, about 15 μg/mL to about 40 μg/mL, about 20 μg/mL to about 25 μg/mL, about 20 μg/mL to about 30 μg/mL, about 20 μg/mL to about 35 μg/mL, about 20 μg/mL to about 40 μg/mL, about 25 μg/mL to about 30 μg/mL, about 25 μg/mL to about 35 μg/mL, about 25 μg/mL to about 40 μg/mL, about 30 μg/mL to about 35 μg/mL, about 30 μg/mL to about 40 μg/mL, or about 35 μg/mL to about 40 μg/mL.

The amount of sotalol or a pharmaceutically acceptable salt suitable for the disclosed methods, kits, and compositions can range, for example, from about 0.002 mg to 200 mg, such as from out 0.002 mg to about 200 mg. In some embodiments, at least about 0.002 mg. In some embodiments, at most about 200 mg. In some embodiments, about 0.002 mg to about 1 mg, about 0.002 mg to about 5 mg, about 0.002 mg to about 10 mg, about 0.002 mg to about 25 mg, about 0.002 mg to about 50 mg, about 0.002 mg to about 100 mg, about 0.002 mg to about 125 mg, about 0.002 mg to about 150 mg, about 0.002 mg to about 175 mg, about 0.002 mg to about 200 mg, about 1 mg to about 5 mg, about 1 mg to about 10 mg, about 1 mg to about 25 mg, about 1 mg to about 50 mg, about 1 mg to about 100 mg, about 1 mg to about 125 mg, about 1 mg to about 150 mg, about 1 mg to about 175 mg, about 1 mg to about 200 mg, about 5 mg to about 10 mg, about 5 mg to about 25 mg, about 5 mg to about 50 mg, about 5 mg to about 100 mg, about 5 mg to about 125 mg, about 5 mg to about 150 mg, about 5 mg to about 175 mg, about 5 mg to about 200 mg, about 10 mg to about 25 mg, about 10 mg to about 50 mg, about 10 mg to about 100 mg, about 10 mg to about 125 mg, about 10 mg to about 150 mg, about 10 mg to about 175 mg, about 10 mg to about 200 mg, about 25 mg to about 50 mg, about 25 mg to about 100 mg, about 25 mg to about 125 mg, about 25 mg to about 150 mg, about 25 mg to about 175 mg, about 25 mg to about 200 mg, about 50 mg to about 100 mg, about 50 mg to about 125 mg, about 50 mg to about 150 mg, about 50 mg to about 175 mg, about 50 mg to about 200 mg, about 100 mg to about 125 mg, about 100 mg to about 150 mg, about 100 mg to about 175 mg, about 100 mg to about 200 mg, about 125 mg to about 150 mg, about 125 mg to about 175 mg, about 125 mg to about 200 mg, about 150 mg to about 175 mg, about 150 mg to about 200 mg, or about 175 mg to about 200 mg.

The amount of sotalol or a pharmaceutically acceptable salt thereof suitable for the disclosed methods, kits, and compositions can range, for example, from about 1 μg per kilogram of subject body weight (mg/kg) to about 10 mg/kg, such as from about 1 mg/kg to about 2 mg/kg, about 1 mg/kg to about 3 mg/kg, about 1 mg/kg to about 4 mg/kg, about 1 mg/kg to about 5 mg/kg, about 1 mg/kg to about 6 mg/kg, about 1 mg/kg to about 7 mg/kg, about 1 mg/kg to about 8 mg/kg, about 1 mg/kg to about 9 mg/kg, about 1 mg/kg to about 10 mg/kg, about 2 mg/kg to about 3 mg/kg, about 2 mg/kg to about 4 mg/kg, about 2 mg/kg to about 5 mg/kg, about 2 mg/kg to about 6 mg/kg, about 2 mg/kg to about 7 mg/kg, about 2 mg/kg to about 8 mg/kg, about 2 mg/kg to about 9 mg/kg, about 2 mg/kg to about 10 mg/kg, about 3 mg/kg to about 4 mg/kg, about 3 mg/kg to about 5 mg/kg, about 3 mg/kg to about 6 mg/kg, about 3 mg/kg to about 7 mg/kg, about 3 mg/kg to about 8 mg/kg, about 3 mg/kg to about 9 mg/kg, about 3 mg/kg to about 10 mg/kg, about 4 mg/kg to about 5 mg/kg, about 4 mg/kg to about 6 mg/kg, about 4 mg/kg to about 7 mg/kg, about 4 mg/kg to about 8 mg/kg, about 4 mg/kg to about 9 mg/kg, about 4 mg/kg to about 10 mg/kg, about 5 mg/kg to about 6 mg/kg, about 5 mg/kg to about 7 mg/kg, about 5 mg/kg to about 8 mg/kg, about 5 mg/kg to about 9 mg/kg, about 5 mg/kg to about 10 mg/kg, about 6 mg/kg to about 7 mg/kg, about 6 mg/kg to about 8 mg/kg, about 6 mg/kg to about 9 mg/kg, about 6 mg/kg to about 10 mg/kg, about 7 mg/kg to about 8 mg/kg, about 7 mg/kg to about 9 mg/kg, about 7 mg/kg to about 10 mg/kg, about 8 mg/kg to about 9 mg/kg, about 8 mg/kg to about 10 mg/kg, or about 9 mg/kg to about 10 mg/kg. The amount of sotalol or a pharmaceutically acceptable salt suitable for the disclosed methods, kits, and compositions can be, for example, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg.

The concentration of sotalol or a pharmaceutically acceptable salt thereof suitable for the disclosed methods, kits, and compositions can range, for example, from about 1 mg/mL to about 40 mg/mL. In some embodiments, concentration of sotalol is at least about 1 mg/mL. In some embodiments, concentration of sotalol is at most about 40 mg/mL. In some embodiments, concentration of sotalol is about 1 mg/mL to about 2 mg/mL, about 1 mg/mL to about 3 mg/mL, about 1 mg/mL to about 4 mg/mL, about 1 mg/mL to about 5 mg/mL, about 1 mg/mL to about 10 mg/mL, about 1 mg/mL to about 15 mg/mL, about 1 mg/mL to about 20 mg/mL, about 1 mg/mL to about 25 mg/mL, about 1 mg/mL to about 30 mg/mL, about 1 mg/mL to about 35 mg/mL, about 1 mg/mL to about 40 mg/mL, about 2 mg/mL to about 3 mg/mL, about 2 mg/mL to about 4 mg/mL, about 2 mg/mL to about 5 mg/mL, about 2 mg/mL to about 10 mg/mL, about 2 mg/mL to about 15 mg/mL, about 2 mg/mL to about 20 mg/mL, about 2 mg/mL to about 25 mg/mL, about 2 mg/mL to about 30 mg/mL, about 2 mg/mL to about 35 mg/mL, about 2 mg/mL to about 40 mg/mL, about 3 mg/mL to about 4 mg/mL, about 3 mg/mL to about 5 mg/mL, about 3 mg/mL to about 10 mg/mL, about 3 mg/mL to about 15 mg/mL, about 3 mg/mL to about 20 mg/mL, about 3 mg/mL to about 25 mg/mL, about 3 mg/mL to about 30 mg/mL, about 3 mg/mL to about 35 mg/mL, about 3 mg/mL to about 40 mg/mL, about 4 mg/mL to about 5 mg/mL, about 4 mg/mL to about 10 mg/mL, about 4 mg/mL to about 15 mg/mL, about 4 mg/mL to about 20 mg/mL, about 4 mg/mL to about 25 mg/mL, about 4 mg/mL to about 30 mg/mL, about 4 mg/mL to about 35 mg/mL, about 4 mg/mL to about 40 mg/mL, about 5 mg/mL to about 10 mg/mL, about 5 mg/mL to about 15 mg/mL, about 5 mg/mL to about 20 mg/mL, about 5 mg/mL to about 25 mg/mL, about 5 mg/mL to about 30 mg/mL, about 5 mg/mL to about 35 mg/mL, about 5 mg/mL to about 40 mg/mL, about 10 mg/mL to about 15 mg/mL, about 10 mg/mL to about 20 mg/mL, about 10 mg/mL to about 25 mg/mL, about 10 mg/mL to about 30 mg/mL, about 10 mg/mL to about 35 mg/mL, about 10 mg/mL to about 40 mg/mL, about 15 mg/mL to about 20 mg/mL, about 15 mg/mL to about 25 mg/mL, about 15 mg/mL to about 30 mg/mL, about 15 mg/mL to about 35 mg/mL, about 15 mg/mL to about 40 mg/mL, about 20 mg/mL to about 25 mg/mL, about 20 mg/mL to about 30 mg/mL, about 20 mg/mL to about 35 mg/mL, about 20 mg/mL to about 40 mg/mL, about 25 mg/mL to about 30 mg/mL, about 25 mg/mL to about 35 mg/mL, about 25 mg/mL to about 40 mg/mL, about 30 mg/mL to about 35 mg/mL, about 30 mg/mL to about 40 mg/mL, or about 35 mg/mL to about 40 mg/mL.

The amount of flecainide or a pharmaceutically acceptable salt thereof (e.g. flecainide acetate) suitable for the disclosed methods, kits, and compositions can range, for example, from about 1 mg to 400 mg, such as from about 1 mg to 300 mg, from about 5 mg to about 300 mg, from about 5 mg to about 250 mg, from about 5 mg to about 200 mg, from about 5 mg to about 150 mg, from about 5 mg to about 140 mg, from about 5 mg to about 120 mg, from about 5 mg to about 100 mg, from about 5 mg to about 80 mg, from about 5 mg to about 60 mg, from about 5 mg to about 50 mg, from about 5 mg to about 40 mg, from about 5 mg to about 30 mg, or from about 5 mg to about 20 mg. The amount of flecainide or a pharmaceutically acceptable salt thereof (e.g. flecainide acetate) suitable for the disclosed methods, kits, and compositions can be, for example, about 5 mg, about 10 mg, about 15 mg, about 20 mg, about 25 mg, about 30 mg, about 40 mg, about 50 mg, about 60 mg, about 80 mg, about 100 mg, about 120 mg, about 150 mg, about 200 mg, about 250 mg, or about 300 mg.

The amount of ibutilide or a pharmaceutically acceptable salt thereof (e.g. ibutilide acetate) suitable for the disclosed methods, kits, and compositions can be, for example, from about 0.01 mg per kilogram of subject body weight (mg/kg) to about 3 mg/kg, such as from about 0.05 mg/kg to about 2 mg/kg, from about 0.05 mg/kg to about 1.5 mg/kg, from about 0.05 mg/kg to about 1 mg/kg, from about 0.05 mg/kg to about 0.5 mg/kg, from about 0.05 mg/kg to about 0.25 mg/kg, from about 0.05 mg/kg to about 0.1 mg/kg, from about 0.1 mg/kg to about 2 mg/kg, from about 0.1 mg/kg to about 1.5 mg/kg, from about 0.1 mg/kg to about 1 mg/kg, from about 0.1 mg/kg to about 0.5 mg/kg, or from about 0.1 mg/kg to about 0.25 mg/kg. The amount of ibutilide or a pharmaceutically acceptable salt thereof (e.g. ibutilide acetate) suitable for the disclosed methods, kits, and compositions can be, for example, about 0.01 mg/kg, about 0.05 mg/kg, about 0.1 mg/kg, about 0.2 mg/kg, about 0.25 mg/kg, about 0.3 mg/kg, about 0.4 mg/kg, about 0.5 mg/kg, about 0.75 mg/kg, about 1 mg/kg, about 1.25 mg/kg, about 1.5 mg/kg, about 1.75 mg/kg, or about 2 mg/kg.

The amount of dofetilide or a pharmaceutically acceptable salt thereof suitable for the disclosed methods, kits, and compositions can be, for example, from about 1 μg per kilogram of subject body weight (μg/kg) to about 10 μg/kg, such as from about 1 μg/kg to about 2 μg/kg, about 1 μg/kg to about 3 μg/kg, about 1 μg/kg to about 4 μg/kg, about 1 μg/kg to about 5 μg/kg, about 1 μg/kg to about 6 μg/kg, about 1 μg/kg to about 7 μg/kg, about 1 μg/kg to about 8 μg/kg, about 1 μg/kg to about 9 μg/kg, about 1 μg/kg to about 10 μg/kg, about 2 μg/kg to about 3 μg/kg, about 2 μg/kg to about 4 μg/kg, about 2 μg/kg to about 5 μg/kg, about 2 μg/kg to about 6 μg/kg, about 2 μg/kg to about 7 μg/kg, about 2 μg/kg to about 8 μg/kg, about 2 μg/kg to about 9 μg/kg, about 2 μg/kg to about 10 μg/kg, about 3 μg/kg to about 4 μg/kg, about 3 μg/kg to about 5 μg/kg, about 3 μg/kg to about 6 μg/kg, about 3 μg/kg to about 7 μg/kg, about 3 μg/kg to about 8 μg/kg, about 3 μg/kg to about 9 μg/kg, about 3 μg/kg to about 10 μg/kg, about 4 μg/kg to about 5 μg/kg, about 4 μg/kg to about 6 μg/kg, about 4 μg/kg to about 7 μg/kg, about 4 μg/kg to about 8 μg/kg, about 4 μg/kg to about 9 μg/kg, about 4 μg/kg to about 10 μg/kg, about 5 μg/kg to about 6 μg/kg, about 5 μg/kg to about 7 μg/kg, about 5 μg/kg to about 8 μg/kg, about 5 μg/kg to about 9 μg/kg, about 5 μg/kg to about 10 μg/kg, about 6 μg/kg to about 7 μg/kg, about 6 μg/kg to about 8 μg/kg, about 6 μg/kg to about 9 μg/kg, about 6 μg/kg to about 10 μg/kg, about 7 μg/kg to about 8 μg/kg, about 7 μg/kg to about 9 μg/kg, about 7 μg/kg to about 10 μg/kg, about 8 μg/kg to about 9 μg/kg, about 8 μg/kg to about 10 μg/kg, or about 9 μg/kg to about 10 μg/kg. The amount of dofetilide or a pharmaceutically acceptable salt suitable for the disclosed methods, kits, and compositions can be, for example, about 1 μg/kg, about 2 μg/kg, about 3 μg/kg, about 4 μg/kg, about 5 μg/kg, about 6 μg/kg, about 7 μg/kg, about 8 μg/kg, about 9 μg/kg, or about 10 μg/kg.

The amount of sotalol or a pharmaceutically acceptable salt thereof suitable for the disclosed methods, kits, and compositions can be, for example, from about 0.01 mg per kilogram of subject body weight (mg/kg) to about 3 mg/kg, such as from about 0.05 mg/kg to about 2 mg/kg, from about 0.05 mg/kg to about 1.5 mg/kg, from about 0.05 mg/kg to about 1 mg/kg, from about 0.05 mg/kg to about 0.5 mg/kg, from about 0.05 mg/kg to about 0.25 mg/kg, from about 0.05 mg/kg to about 0.1 mg/kg, from about 0.1 mg/kg to about 2 mg/kg, from about 0.1 mg/kg to about 1.5 mg/kg, from about 0.1 mg/kg to about 1 mg/kg, from about 0.1 mg/kg to about 0.5 mg/kg, or from about 0.1 mg/kg to about 0.25 mg/kg. The amount of sotalol or a pharmaceutically acceptable salt thereof suitable for the disclosed methods, kits, and compositions can be, for example, about 0.01 mg/kg, about 0.05 mg/kg, about 0.1 mg/kg, about 0.2 mg/kg, about 0.25 mg/kg, about 0.3 mg/kg, about 0.4 mg/kg, about 0.5 mg/kg, about 0.75 mg/kg, about 1 mg/kg, about 1.25 mg/kg, about 1.5 mg/kg, about 1.75 mg/kg, or about 2 mg/kg.

Indications and Subjects.

Examples of cardiac arrhythmias the methods, compositions, and kits provided herein can treat include, but are not limited to, tachycardia, supraventricular tachycardia (SVT), paroxysmal supraventricular tachycardia (PSVT), atrial fibrillation (AF), paroxysmal atrial fibrillation (PAF), persistent atrial fibrillation, permanent atrial fibrillation, atrial flutter, paroxysmal atrial flutter, and lone atrial fibrillation. In some embodiments, the methods, compositions, and kits provided herein find use in treating a subject suffering from atrial arrhythmia, e.g., atrial fibrillation. Examples of atrial arrhythmias may include, for example, paroxysmal atrial fibrillation and persistent atrial fibrillation.

Thus, the pharmaceutical compositions according to some examples of the present disclosure can be used to treat a broad range of patients. A suitable patient for, receiving treatment as described herein is any mammalian patient in need thereof, preferably such mammal is a human. Examples of subjects include, but are not limited to, pediatric patients, adult patients, and geriatric patients. In some embodiments, the composition is intended only as a treatment for rapid resolution of symptoms and restoration of normal sinus rhythm, and is not taken as a preventative, e.g., when the patient is well, there is no need for drug—this can increase the benefit-risk ratio of the therapy and overall safety due to the sporadic or intermittent dosing, and the focus on reducing disabling symptoms and restoring sinus rhythm only when needed.

The dosage necessary and the frequency of dosing of the antiarrhythmic pharmaceutical agent depend on the composition and concentration of the antiarrhythmic pharmaceutical agent within the composition. In some embodiments, the inhalation dose is less than about 10%, 20%, 30%, 40%, 50%, 60%, 70%, 80%, 90%, or 95% of its normal intravenous dose. In some embodiments, the inhalation dose is about 5% to about 10%, is about 10% to about 20%, is about 20% to about 30%, is about 30% to about 40%, is about 50% to about 60%, is about 60% to about 70%, is about 70% to about 80%, is about 80% to about 90%, or is about 90% to about 95% of the intravenous dose.

In some embodiments, the present invention involves a rapid acting inhaled product with a fast onset of action compared to oral medicine. The product is expected to be at least as fast as intravenous medicine. In some embodiments, an amount of the at least one antiarrhythmic pharmaceutical agent peaks in the coronary sinus of the heart at a time ranging from 10 seconds to 30 minutes, such as 30 seconds to 20 minutes, 1 minute to 10 minutes, 2 minutes to 8 minutes, or 2.5 minutes to 5 minutes, from initiation of the administering. In certain embodiments, an electrophysiologic effect is observed, via electrocardiography, at a time ranging from 10 seconds to 30 minutes, such as 30 seconds to 20 minutes, 1 minute to 10 minutes, 2 minutes to 8 minutes, or 2.5 minutes to 5 minutes, from initiation of the administering. In some embodiments, a cardiac score from a monitor implementing an arrhythmia detection algorithm shows a transition from an arrhythmic state to normal sinus rhythm in the patient at a time ranging from 10 seconds to 30 minutes, such as 30 seconds to 20 minutes, 1 minute to 10 minutes, 2 minutes to 8 minutes, or 2.5 minutes to 5 minutes, from initiation of the administering. In some embodiments, a short form-36 quality of life score of the patient improves at a time ranging from 10 seconds to 30 minutes, such as 30 seconds to 20 minutes, 1 minute to 10 minutes, 2 minutes to 8 minutes, or 2.5 minutes to 5 minutes, from initiation of the administering. In certain embodiments, the patient has normal sinus rhythm within 30 minutes, such as within 10 minutes, of initiating the administering.

A peak concentration of the pharmaceutical agents can be seen early in time after its delivery according to the present disclosure. In some embodiments, a concentration of the potassium channel blocker in the coronary arterial circulation of the heart is between about 0.001 mg/L and about 0.1 mg/L, about 0.001 mg/L and about 0.09 mg/L, about 0.001 mg/L and about 0.08 mg/L, about 0.001 mg/L and about 0.07 mg/L, about 0.001 mg/L and about 0.06 mg/L, about 0.001 mg/L and about 0.05 mg/L, about 0.001 mg/L and about 0.04 mg/L, about 0.001 mg/L and about 0.03 mg/L, about 0.001 mg/L and about 0.02 mg/L, about 0.001 mg/L and about 0.01 mg/L, about 0.001 mg/L and about 0.009 mg/L, about 0.001 mg/L and about 0.008 mg/L, about 0.001 mg/L and about 0.007 mg/L, about 0.001 mg/L and about 0.006 mg/L, about 0.001 mg/L and about 0.005 mg/L, about 0.001 mg/L and about 0.004 mg/L, about 0.001 mg/L and about 0.003 mg/L, about 0.001 mg/L and about 0.002 mg/L, about 0.002 mg/L and about 0.1 mg/L, about 0.005 mg/L and about 0.1 mg/L, about 0.01 mg/L and about 0.1 mg/L, about 0.02 mg/L and about 0.1 mg/L, about 0.03 mg/L and about 0.1 mg/L, about 0.04 mg/L and about 0.1 mg/L, about 0.05 mg/L and about 0.1 mg/L, about 0.06 mg/L and about 0.1 mg/L, about 0.07 mg/L and about 0.1 mg/L, about 0.08 mg/L and about 0.1 mg/L, about 0.09 mg/L and about 0.1 mg/L, about 0.01 mg/L and about 0.1 mg/L, about 0.01 mg/L and about 0.09 mg/L, about 0.01 mg/L and about 0.08 mg/L, about 0.01 mg/L and about 0.07 mg/L, about 0.01 mg/L and about 0.06 mg/L, about 0.01 mg/L and about 0.05 mg/L, about 0.01 mg/L and about 0.04 mg/L, about 0.01 mg/L and about 0.03 mg/L, about 0.01 mg/L and about 0.02 mg/L, about 0.03 mg/L and about 0.09 mg/L, about 0.05 mg/L and about 0.09 mg/L, or about 0.05 mg/L and about 0.08 mg/L at 2.5 minutes after the administering. In some embodiments, a concentration of the potassium channel blocker in the coronary arterial circulation of the heart is between about 0.01 mg/L and about 0.1 mg/L at 2.5 minutes after the administration.

In some embodiments, the peak concentration of the potassium channel blocker in the coronary arterial circulation of the heart peaks at between about 0.001 mg/L and about 0.1 mg/L, such as, between about 0.001 mg/L and about 0.1 mg/L, about 0.001 mg/L and about 0.09 mg/L, about 0.001 mg/L and about 0.08 mg/L, about 0.001 mg/L and about 0.07 mg/L, about 0.001 mg/L and about 0.06 mg/L, about 0.001 mg/L and about 0.05 mg/L, about 0.001 mg/L and about 0.04 mg/L, about 0.001 mg/L and about 0.03 mg/L, about 0.001 mg/L and about 0.02 mg/L, about 0.001 mg/L and about 0.01 mg/L, about 0.001 mg/L and about 0.009 mg/L, about 0.001 mg/L and about 0.008 mg/L, about 0.001 mg/L and about 0.007 mg/L, about 0.001 mg/L and about 0.006 mg/L, about 0.001 mg/L and about 0.005 mg/L, about 0.001 mg/L and about 0.004 mg/L, about 0.001 mg/L and about 0.003 mg/L, about 0.001 mg/L and about 0.002 mg/L, about 0.002 mg/L and about 0.1 mg/L, about 0.005 mg/L and about 0.1 mg/L, about 0.01 mg/L and about 0.1 mg/L, about 0.02 mg/L and about 0.1 mg/L, about 0.03 mg/L and about 0.1 mg/L, about 0.04 mg/L and about 0.1 mg/L, about 0.05 mg/L and about 0.1 mg/L, about 0.06 mg/L and about 0.1 mg/L, about 0.07 mg/L and about 0.1 mg/L, about 0.08 mg/L and about 0.1 mg/L, about 0.09 mg/L and about 0.1 mg/L, about 0.01 mg/L and about 0.1 mg/L, about 0.01 mg/L and about 0.09 mg/L, about 0.01 mg/L and about 0.08 mg/L, about 0.01 mg/L and about 0.07 mg/L, about 0.01 mg/L and about 0.06 mg/L, about 0.01 mg/L and about 0.05 mg/L, about 0.01 mg/L and about 0.04 mg/L, about 0.01 mg/L and about 0.03 mg/L, about 0.01 mg/L and about 0.02 mg/L, about 0.03 mg/L and about 0.09 mg/L, about 0.05 mg/L and about 0.09 mg/L, or about 0.05 mg/L and about 0.08 mg/L. In some embodiments, the peak concentration of the potassium channel blocker in the coronary arterial circulation of the heart peaks at between about 0.01 mg/L and about 0.1 mg/L.

Formulations and Kits.

In one aspect, provided herein are pharmaceutical compositions for treatment of a heart condition, e.g., cardiac arrhythmia, e.g., atrial arrhythmia.

The pharmaceutical composition can include a therapeutically effective amount of a potassium channel blocker. The therapeutically effective amount of potassium channel blocker can be effective for treatment of a heart condition, e.g., cardiac arrhythmia, e.g., atrial arrhythmia, when it is administered to a subject in need thereof via inhalation or intranasal spray administration. In some embodiments, the therapeutically effective amount of potassium channel blocker is effective for treatment of atrial arrhythmia by inducing cardioversion and slowing AV node conduction when it is administered to a subject in need thereof via inhalation or intranasal spray administration.

In some embodiments, provided herein are pharmaceutical composition including a therapeutically effective amount of potassium channel blocker and a therapeutically effective amount of an antiarrhythmic agent, e.g., class I antiarrhythmic agent. In some embodiments, the therapeutically effective amount of the potassium channel blocker and the therapeutically effective amount of the class I antiarrhythmic agent are effective for treatment of atrial arrhythmia by inducing cardioversion and slowing AV node conduction when it is administered to a subject in need thereof via inhalation or intranasal spray administration.

The potassium channel blocker can be in a liquid solution. In some embodiments, the potassium channel blocker in the pharmaceutical composition is ibutilide or a pharmaceutically acceptable salt thereof (e.g. ibutilide fumarate), and the concentration of ibutilide or a pharmaceutically acceptable salt thereof in the pharmaceutical compositions or formulations provided herein is from about 0.0005 mg/mL to about 5 mg/mL, such as from about 0.0005 mg/mL to about 2.5 mg/mL, from about 0.0005 mg/mL to about 2 mg/mL, from about 0.0005 mg/mL to about 1 mg/mL, from about 0.0005 mg/mL to about 0.5 mg/mL, from about 0.0005 mg/mL to about 0.25 mg/mL, from about 0.0005 mg/mL to about 0.2 mg/mL, from about 0.0005 mg/mL to about 0.1 mg/mL, from about 0.0005 mg/mL to about 0.05 mg/mL, from about 0.0005 mg/mL to about 0.02 mg/mL, from about 0.0005 mg/mL to about 0.01 mg/mL, from about 0.0005 mg/mL to about 0.001 mg/mL, from about 0.001 mg/mL to about 2.5 mg/mL, from about 0.001 mg/mL to about 2 mg/mL, from about 0.001 mg/mL to about 1 mg/mL, from about 0.001 mg/mL to about 0.5 mg/mL, from about 0.001 mg/mL to about 0.25 mg/mL, from about 0.001 mg/mL to about 0.2 mg/mL, from about 0.001 mg/mL to about 0.1 mg/mL, from about 0.001 mg/mL to about 0.05 mg/mL, from about 0.001 mg/mL to about 0.02 mg/mL, or from about 0.001 mg/mL to about 0.01 mg/mL. In some embodiments, the potassium channel blocker in the pharmaceutical composition is ibutilide or a pharmaceutically acceptable salt thereof (e.g. ibutilide fumarate), and the concentration of ibutilide or a pharmaceutically acceptable salt thereof in the pharmaceutical compositions or formulations provided herein is about 0.001 mg/mL, about 0.005 mg/mL, about 0.01 mg/mL, about 0.02 mg/mL, about 0.025 mg/mL, about 0.03 mg/mL, about 0.04 mg/mL, about 0.05 mg/mL, about 0.1 mg/mL, about 0.2 mg/mL, about 0.25 mg/mL, about 0.3 mg/mL, about 0.4 mg/mL, about 0.5 mg/mL, about 0.75 mg/mL, or about 1 mg/mL. In some embodiments, the potassium channel blocker in the pharmaceutical composition is sotalol or a pharmaceutically acceptable salt thereof, and the concentration of ibutilide or a pharmaceutically acceptable salt thereof in the pharmaceutical compositions or formulations provided herein is about 0.001 mg/mL, about 0.005 mg/mL, about 0.01 mg/mL, about 0.02 mg/mL, about 0.025 mg/mL, about 0.03 mg/mL, about 0.04 mg/mL, about 0.05 mg/mL, about 0.1 mg/mL, about 0.2 mg/mL, about 0.25 mg/mL, about 0.3 mg/mL, about 0.4 mg/mL, about 0.5 mg/mL, about 0.75 mg/mL, about 1 mg/mL, about 2 mg/mL, or about 5 mg/mL.

Dofetilide or a pharmaceutically acceptable salt thereof, can be in a liquid solution. In some embodiments, the potassium channel blocker in the pharmaceutical composition is dofetilide. The concentration of dofetilide or a pharmaceutically acceptable salt thereof in the pharmaceutical compositions or formulations provided herein is from about 1 μg/mL to about 40 μg/mL. In some embodiments, concentration of dofetilide is at least about 1 μg/mL. In some embodiments, concentration of dofetilide is at most about 40 μg/mL. In some embodiments, concentration of dofetilide is about 1 μg/mL to about 2 μg/mL, about 1 μg/mL to about 3 μg/mL, about 1 μg/mL to about 4 μg/mL, about 1 μg/mL to about 5 μg/mL, about 1 μg/mL to about 10 μg/mL, about 1 μg/mL to about 15 μg/mL, about 1 μg/mL to about 20 μg/mL, about 1 μg/mL to about 25 μg/mL, about 1 μg/mL to about 30 μg/mL, about 1 μg/mL to about 35 μg/mL, about 1 μg/mL to about 40 μg/mL, about 2 μg/mL to about 3 μg/mL, about 2 μg/mL to about 4 μg/mL, about 2 μg/mL to about 5 μg/mL, about 2 μg/mL to about 10 μg/mL, about 2 μg/mL to about 15 μg/mL, about 2 μg/mL to about 20 μg/mL, about 2 μg/mL to about 25 μg/mL, about 2 μg/mL to about 30 μg/mL, about 2 μg/mL to about 35 μg/mL, about 2 μg/mL to about 40 μg/mL, about 3 μg/mL to about 4 μg/mL, about 3 μg/mL to about 5 μg/mL, about 3 μg/mL to about 10 μg/mL, about 3 μg/mL to about 15 μg/mL, about 3 μg/mL to about 20 μg/mL, about 3 μg/mL to about 25 μg/mL, about 3 μg/mL to about 30 μg/mL, about 3 μg/mL to about 35 μg/mL, about 3 μg/mL to about 40 μg/mL, about 4 μg/mL to about 5 μg/mL, about 4 μg/mL to about 10 μg/mL, about 4 μg/mL to about 15 μg/mL, about 4 μg/mL to about 20 μg/mL, about 4 μg/mL to about 25 μg/mL, about 4 μg/mL to about 30 μg/mL, about 4 μg/mL to about 35 μg/mL, about 4 μg/mL to about 40 μg/mL, about 5 μg/mL to about 10 μg/mL, about 5 μg/mL to about 15 μg/mL, about 5 μg/mL to about 20 μg/mL, about 5 μg/mL to about 25 μg/mL, about 5 μg/mL to about 30 μg/mL, about 5 μg/mL to about 35 μg/mL, about 5 μg/mL to about 40 μg/mL, about 10 μg/mL to about 15 μg/mL, about 10 μg/mL to about 20 μg/mL, about 10 μg/mL to about 25 μg/mL, about 10 μg/mL to about 30 μg/mL, about 10 μg/mL to about 35 μg/mL, about 10 μg/mL to about 40 μg/mL, about 15 μg/mL to about 20 μg/mL, about 15 μg/mL to about 25 μg/mL, about 15 μg/mL to about 30 μg/mL, about 15 μg/mL to about 35 μg/mL, about 15 μg/mL to about 40 μg/mL, about 20 μg/mL to about 25 μg/mL, about 20 μg/mL to about 30 μg/mL, about 20 μg/mL to about 35 μg/mL, about 20 μg/mL to about 40 μg/mL, about 25 μg/mL to about 30 μg/mL, about 25 μg/mL to about 35 μg/mL, about 25 μg/mL to about 40 μg/mL, about 30 μg/mL to about 35 μg/mL, about 30 μg/mL to about 40 μg/mL, or about 35 μg/mL to about 40 μg/mL.

The sodium channel blocker (e.g. flecainide) can be in a liquid solution. In some embodiments, the sodium channel blocker in the pharmaceutical compositions or formulations provided herein is flecainide or a pharmaceutically acceptable salt thereof (e.g. flecainide acetate), and the concentration of flecainide or a pharmaceutically acceptable salt thereof in the pharmaceutical compositions or formulations provided herein is about 1 mg/mL to about 150 mg/mL, such as from about 1 mg/mL to about 5 mg/mL, from about 1 mg/mL to about 100 mg/mL, from about 1 mg/mL to about 50 mg/mL, from about 1 mg/mL to about 40 mg/mL, from about 1 mg/mL to about 30 mg/mL, from about 1 mg/mL to about 20 mg/mL, from about 1 mg/mL to about 10 mg/mL, from about 1 mg/mL to about 5 mg/mL, from about 10 mg/mL to about 50 mg/mL, from about 10 mg/mL to about 40 mg/mL, from about 10 mg/mL to about 30 mg/mL, from about 10 mg/mL to about 20 mg/mL, from about 20 mg/mL to about 50 mg/mL, from about 20 mg/mL to about 40 mg/mL, or from about 20 mg/mL to about 30 mg/mL. The sodium channel blocker (e.g. flecainide) can be in a liquid solution. In some embodiments, the sodium channel blocker in the pharmaceutical compositions or formulations provided herein is flecainide or a pharmaceutically acceptable salt thereof (e.g. flecainide acetate), and the concentration of flecainide or a pharmaceutically acceptable salt thereof in the pharmaceutical compositions or formulations provided herein is about 1 mg/mL, about 5 mg/mL, about 10 mg/mL, about 15 mg/mL, about 20 mg/mL, about 25 mg/mL, about 30 mg/mL, about 40 mg/mL, about 50 mg/mL, about 75 mg/mL, about 100 mg/mL, about 125 mg/mL, or about 150 mg/mL.

The $Mg^{2+}$ source can be in a liquid solution. In some embodiments, the $Mg^{2+}$ source in the pharmaceutical compositions or formulations provided herein is magnesium sulfate, and the concentration of magnesium sulfate in the pharmaceutical compositions or formulations provided herein is from about 5 mg/mL to about 1000 mg/mL, such as about 10 mg/mL to about 100 mg/mL, about 10 mg/mL to about 200 mg/mL, about 10 mg/mL to about 300 mg/mL, about 10 mg/mL to about 400 mg/mL, about 10 mg/mL to about 500 mg/mL, about 100 mg/mL to about 200 mg/mL, about 100 mg/mL to about 300 mg/mL, about 100 mg/mL to about 400 mg/mL, about 100 mg/mL to about 500 mg/mL, about 200 mg/mL to about 300 mg/mL, about 200 mg/mL to about 400 mg/mL, about 200 mg/mL to about 500 mg/mL, about 300 mg/mL to about 400 mg/mL, about 300 mg/mL to about 500 mg/mL, about 400 mg/mL to about 500 mg/mL, about 400 mg/mL to about 600 mg/mL, about 5 mg/mL to about 700 mg/mL, about 10 mg/mL to about 700 mg/mL, about 20 mg/mL to about 700 mg/mL, about 100 mg/mL to about 700 mg/mL, about 400 mg/mL to about 700 mg/mL, about 500 mg/mL to about 700 mg/mL. In some embodiments, the $Mg^{2+}$ source in the pharmaceutical compositions or formulations provided herein is magnesium sulfate, and the concentration of magnesium sulfate in the pharmaceutical compositions or formulations provided herein is about 5 mg/mL, about 10 mg/mL, about 15 mg/mL, about 20 mg/mL, about 30 mg/mL, about 40 mg/mL, about 50 mg/mL, about 75 mg/mL, about 100 mg/mL, about 200 mg/mL, about 300 mg/mL, about 400 mg/mL, about 500 mg/mL, about 600 mg/mL, about 700 mg/mL, about 800 mg/mL, about 900 mg/mL, or about 1000 mg/mL.

In some embodiments, ibutilide, sotalol, or a pharmaceutically acceptable salt thereof is coformulated with flecainide or a pharmaceutically acceptable salt thereof in a coformulation. In some embodiments, the mass to mass ratio of flecainide acetate to ibutilide fumarate in the coformulation is 1 to about 0.005, 1 to about 0.01, 1 to about 0.02, 1 to about 0.03, 1 to about 0.04, 1 to about 0.05, 1 to about 0.06, 1 to about 0.07, 1 to about 0.08, 1 to about 0.09, 1 to about 0.1, 1 to about 0.2, 1 to about 0.3, 1 to about 0.3, 1 to about 0.4, 1 to about 0.5, 1.5 to about 0.005, 1.5 to about 0.01, 1.5 to about 0.02, 1.5 to about 0.03, 1.5 to about 0.04, 1.5 to about 0.05, 1.5 to about 0.06, 1.5 to about 0.07, 1.5 to about 0.08, 1.5 to about 0.09, 1.5 to about 0.1, 1.5 to about 0.2, 1.5 to about 0.3, 1.5 to about 0.3, 1.5 to about 0.4, 1.5 to about 0.5, 2 to about 0.005, 2 to about 0.01, 2 to about 0.02, 2 to about 0.03, 2 to about 0.04, 2 to about 0.05, 2 to about 0.06, 2 to about 0.07, 2 to about 0.08, 2 to about 0.09, 2 to about 0.1, 2 to about 0.2, 2 to about 0.3, 2 to about 0.3, 2 to about 0.4, or 2 to about 0.5.

In some embodiments, dofetilide or a pharmaceutically acceptable salt thereof is coformulated with flecainide or a pharmaceutically acceptable salt thereof in a coformulation. In some embodiments, the mass to mass ratio of flecainide acetate to dofetilide in the coformulation is about 1,000 to about 4,000. In some embodiments, the mass to mass ratio of flecainide acetate to dofetilide in the coformulation is at least about 1,000. In some embodiments, the mass to mass ratio of flecainide acetate to dofetilide in the coformulation is at most about 4,000. In some embodiments, the mass to mass ratio of flecainide acetate to dofetilide in the coformulation is about 1,000 to about 1,250, about 1,000 to about 1,500, about 1,000 to about 2,000, about 1,000 to about 2,500, about 1,000 to about 3,000, about 1,000 to about 3,500, about 1,000 to about 4,000, about 1,250 to about 1,500, about 1,250 to about 2,000, about 1,250 to about 2,500, about 1,250 to about 3,000, about 1,250 to about 3,500, about 1,250 to about 4,000, about 1,500 to about 2,000, about 1,500 to about 2,500, about 1,500 to about 3,000, about 1,500 to about 3,500, about 1,500 to about 4,000, about 2,000 to about 2,500, about 2,000 to about 3,000, about 2,000 to about 3,500, about 2,000 to about 4,000, about 2,500 to about 3,000, about 2,500 to about 3,500, about 2,500 to about 4,000, about 3,000 to about 3,500, about 3,000 to about 4,000, or about 3,500 to about 4,000.

Another aspect of the disclosure provides unit doses of pharmaceutical compositions described herein for treatment of heart condition, e.g., cardiac arrhythmia, e.g., atrial arrhythmia, via oral or nasal inhalation, or intranasal spray administration.

In one aspect, provided herein are formulations for treatment of a heart condition, e.g., cardiac arrhythmia, e.g., atrial arrhythmia. The formulations can include the pharmaceutical compositions provided herein and a pharmaceutically acceptable carrier, excipient, diluent, or any other suitable component for the intended administration routes, such as oral or nasal inhalation, or intranasal spray administration. For example, the pharmaceutical composition can comprise neat particles of potassium channel blocker and/or antiarrhythmic pharmaceutical agents (e.g., particles containing only the potassium channel blocker and/or antiarrhythmic pharmaceutical agents), can comprise neat particles of potassium channel blocker and/or sodium channel blockers with other particles, and/or can comprise particles comprising potassium channel blocker and/or sodium channel blockers and one or more active ingredients and/or one or more pharmaceutically acceptable excipients. Examples of pharmaceutically acceptable excipients include, but are not limited to, lipids, metal ions, surfactants, amino acids, carbohydrates, buffers, salts, polymers, and the like, and combinations thereof.

The therapy according to the present disclosure can markedly reduce the variability of absorption typically observed when delivered orally. Because of the fast absorption through the nasal mucosa or through the lungs the $T_{max}$ can be short, 0.5 to 5 minutes post inhalation.

The antiarrhythmic agent can be administered via any route, such as intravenous, intramuscular, transdermal, and oral delivery.

The pharmaceutical formulation according to one or more embodiments of the disclosure may comprise one or more potassium channel blocker and sodium channel blocker and, optionally, one or more other active ingredients and, optionally, one or more pharmaceutically acceptable excipients. For example, the pharmaceutical formulation may comprise particles of antiarrhythmic pharmaceutical agent with no other ingredients added (neat particles), may comprise neat particles of antiarrhythmic pharmaceutical agent together with other particles, and/or may comprise particles comprising antiarrhythmic pharmaceutical agent and one or more active ingredients and/or one or more pharmaceutically acceptable excipients.

In some instances, the potassium channel blocker is co-formulated with another antiarrhythmic agent (e.g., sodium channel blocker) as either solutions or suspensions for inhalation or parenteral injection for treatment of cardiac arrhythmia. In some instances, the potassium channel blocker and the other antiarrhythmic agent are formulated as separate, individual formulations. In some embodiments, the individual formulations are administered to a subject simultaneously. In some embodiments, the individual formulations are combined and optionally diluted with an excipient prior to administration.

The potassium channel blocker, when administered concomitantly via oral or nasal administration prior to or along with an antiarrhythmic therapy, e.g., administration of a Class Ic antiarrhythmic drug, can achieve one or more of the following results unmet by current commercially available products: rapid cardioversion of atrial arrhythmia and avoidance of the proarrhythmic effects of class Ic inhibitors due to the reduced minimum therapeutically effective dose of a class Ic inhibitor when used in combination with a potassium channel blocker.

In one aspect, also provided herein are kits for treatment of heart conditions via inhalation or intranasal administration. The kits can include one or more pharmaceutical agents, for instance, a potassium channel blocker, an antiarrhythmic agent, or both, or some additional active agent(s) as described herein. In some embodiments, the kits include container for the pharmaceutical agents or compositions. In some embodiments, unit doses of the pharmaceutical agents as discussed above are provided in the kits. In some embodiments, the kits also include containers/receptacles for containing the pharmaceutical agents.

In some embodiments, the kits include separate containers/receptacles for containing the potassium channel blocker and the class I antiarrhythmic agent. In some embodiments, the kits include an aerosolization device for forming an aerosol of the pharmaceutical compositions. The aerosolization device can be any device as provided herein, and In some embodiments, used for inhalation of the pharmaceutical compositions. In some embodiments, the kits include nasal spray device as provided herein. In some embodiments, the pharmaceutical composition(s) is/are present in aerosol form in the kits. In some other cases, the kits include a single container for containing the potassium channel blocker and the class I antiarrhythmic agent, e.g., the potassium channel blocker and the class I antiarrhythmic agent are present in one single pharmaceutical composition, e.g., a single solution. The kits can further include instructions for methods of using the kit. The instructions can be presented in the form of a data sheet, a manual, in a piece of paper, printed on one or more containers or devices of the kit. Alternatively, the instructions can be provided in electronic form, for instance, available in a disc or online with a weblink available from the kit.

Examples of carbohydrates include, but are not limited to, monosaccharides, disaccharides, and polysaccharides. For example, monosaccharides such as dextrose (anhydrous and monohydrate), galactose, mannitol, D-mannose, sorbitol, sorbose and the like; disaccharides such as lactose, maltose, sucrose, trehalose, and the like; trisaccharides such as raffinose and the like; and other carbohydrates such as starches (hydroxyethylstarch), cyclodextrins, and maltodextrins. In some embodiments, carbohydrates such as cyclodextrins are used for stabilizing or increasing dissolution rate of the pharmaceutical agent in liquid solvent, e.g., water.

Non-limiting examples of lipids include phospholipids, glycolipids, ganglioside GM1, sphingomyelin, phosphatidic acid, cardiolipin; lipids bearing polymer chains such as polyethylene glycol, chitin, hyaluronic acid, or polyvinylpyrrolidone; lipids bearing sulfonated mono-, di-, and polysaccharides; fatty acids such as palmitic acid, stearic acid, and oleic acid; cholesterol, cholesterol esters, and cholesterol hemisuccinate.

In some embodiments, the phospholipid comprises a saturated phospholipid, such as one or more phosphatidylcholines. Exemplary acyl chain lengths are 16:0 and 18:0 (e.g., palmitoyl and stearoyl). The phospholipid content can be determined by the active agent activity, the mode of delivery, and other factors.

Phospholipids from both natural and synthetic sources can be used in varying amounts. When phospholipids are present, the amount is typically sufficient to coat the active agent(s) with at least a single molecular layer of phospholipid. In general, the phospholipid content ranges from about 5 wt % to about 99.9 wt %, such as about 20 wt % to about 80 wt %.

Generally, compatible phospholipids can comprise those that have a gel to liquid crystal phase transition greater than about 40° C., such as greater than about 60° C., or greater than about 80° C. The incorporated phospholipids can be relatively long chain (e.g., $C_{16}$-$C_{22}$) saturated lipids. Exemplary phospholipids useful in the present invention include, but are not limited to, phosphoglycerides such as dipalmitoylphosphatidylcholine, di stearoylphosphatidylcholine, diarachidoylphosphatidylcholine, dibehenoylphosphatidylcholine, diphosphatidyl glycerols, short-chain phosphatidylcholines, hydrogenated phosphatidylcholine, E-100-3 (available from Lipoid KG, Ludwigshafen, Germany), long-chain saturated phosphatidylethanolamines, long-chain saturated phosphatidylserines, long-chain saturated phosphatidylglycerols, long-chain saturated phosphatidylinositols, phosphatidic acid, phosphatidylinositol, and sphingomyelin.

Examples of metal ions include, but are not limited to, divalent cations, including calcium, magnesium, zinc, iron, and the like. For instance, when phospholipids are used, the pharmaceutical composition can also comprise a polyvalent cation, as disclosed in WO 01/85136 and WO 01/85137, which are incorporated herein by reference in their entireties. The polyvalent cation can be present in an amount effective to increase the melting temperature ($T_m$) of the phospholipid such that the pharmaceutical composition exhibits a $T_m$ which is greater than its storage temperature ($T_m$) by at least about 20° C., such as at least about 40° C. The molar ratio of polyvalent cation to phospholipid can be at least about 0.05:1, such as about 0.05:2 to about 2.0:1 or about 0.25:2 to about 1.0:1. An example of the molar ratio of polyvalent cation:phospholipid is about 0.50:1. When the polyvalent cation is calcium, it can be in the form of calcium chloride. Although metal ion, such as calcium, is often included with phospholipid, none is required.

As noted above, the pharmaceutical composition can include one or more surfactants. For instance, one or more surfactants can be in the liquid phase with one or more being associated with solid particles or particles of the composition. By "associated with" it is meant that the pharmaceutical compositions can incorporate, adsorb, absorb, be coated with, or be formed by the surfactant. Surfactants include, but are not limited to, fluorinated and nonfluorinated compounds, such as saturated and unsaturated lipids, nonionic detergents, nonionic block copolymers, ionic surfactants, and combinations thereof. It should be emphasized that, in addition to the aforementioned surfactants, suitable fluorinated surfactants are compatible with the teachings herein and can be used to provide the desired preparations.

Examples of nonionic detergents include, but are not limited to, sorbitan esters including sorbitan trioleate (Span™ 85), sorbitan sesquioleate, sorbitan monooleate, sorbitan monolaurate, polyoxyethylene (20) sorbitan monolaurate, and polyoxyethylene (20) sorbitan monooleate, oleyl polyoxyethylene (2) ether, stearyl polyoxyethylene (2) ether, lauryl polyoxyethylene (4) ether, glycerol esters, and sucrose esters. Other suitable nonionic detergents can be easily identified using McCutcheon's Emulsifiers and Detergents (McPublishing Co., Glen Rock, N.J.), which is incorporated herein by reference in its entirety.

Examples of block copolymers include, but are not limited to, diblock and triblock copolymers of polyoxyethylene and polyoxypropylene, including poloxamer 188 (Pluronic™ F-68), poloxamer 407 (Pluronic™ F-127), and poloxamer 338.

Examples of ionic surfactants include, but are not limited to, sodium sulfosuccinate, and fatty acid soaps.

Examples of amino acids include, but are not limited to hydrophobic amino acids. Use of amino acids as pharmaceutically acceptable excipients is known in the art as disclosed in WO 95/31479, WO 96/32096, and WO 96/32149, which are incorporated herein by reference in their entireties.

Examples of buffers include, but are not limited to, tris or citrate.

Examples of acids include, but are not limited to, carboxylic acids.

Examples of salts include, but are not limited to, sodium chloride, salts of carboxylic acids, (e.g., sodium citrate, sodium ascorbate, magnesium gluconate, sodium gluconate, tromethamine hydrochloride, etc.), ammonium carbonate, ammonium acetate, ammonium chloride, and the like.

Examples of organic solids include, but are not limited to, camphor, and the like.

The pharmaceutical composition of one or more embodiments of the present invention can also include a biocompatible, such as biodegradable polymer, copolymer, or blend or other combination thereof. In this respect useful polymers comprise polylactides, polylactide-glycolides, cyclodextrins, polyacrylates, methylcellulose, carboxymethylcellulose, polyvinyl alcohols, polyanhydrides, polylactams, polyvinyl pyrrolidones, polysaccharides (dextrans, starches, chitin, chitosan, etc.), hyaluronic acid, proteins, (albumin, collagen, gelatin, etc.). Those skilled in the art will appreciate that, by selecting the appropriate polymers, the delivery efficiency of the composition and/or the stability of the dispersions can be tailored to optimize the effectiveness of the antiarrhythmic pharmaceutical agent(s).

For solutions, the compositions can include one or more osmolality adjuster, such as sodium chloride. For instance, sodium chloride can be added to solutions to adjust the osmolality of the solution. In one or more embodiments, an aqueous composition consists essentially of the antiarrhythmic pharmaceutical agent, the osmolality adjuster, and water.

Solutions can also comprise a buffer or a pH adjusting agent, typically a salt prepared from an organic acid or base. Representative buffers comprise organic acid salts of citric acid, lactic acid, ascorbic acid, gluconic acid, carbonic acid, tartaric acid, succinic acid, acetic acid, or phthalic acid, Tris, tromethamine hydrochloride, or phosphate buffers. Thus, the buffers include citrates, phosphates, phthalates, and lactates.

Besides the above mentioned pharmaceutically acceptable excipients, it can be desirable to add other pharmaceutically acceptable excipients to the pharmaceutical composition to improve particle rigidity, production yield, emitted dose and deposition, shelf-life, and patient acceptance. Such optional pharmaceutically acceptable excipients include, but are not limited to: coloring agents, taste masking agents, buffers, hygroscopic agents, antioxidants, and chemical stabilizers. Further, various pharmaceutically acceptable excipients can be used to provide structure and form to the particle compositions (e.g., latex particles). In this regard, it will be appreciated that the rigidifying components can be removed using a post-production technique such as selective solvent extraction.

The pharmaceutical compositions of one or more embodiments of the present invention can lack taste. In this regard, although taste masking agents are optionally included within the composition, the compositions often do not include a taste masking agent and lack taste even without a taste masking agent.

The pharmaceutical compositions can also include mixtures of pharmaceutically acceptable excipients. For instance, mixtures of carbohydrates and amino acids are within the scope of the present invention.

The compositions of one or more embodiments of the present invention can take various forms, such as solutions, dry powders, reconstituted powders, suspensions, or dispersions comprising a non-aqueous phase, such as propellants (e.g., chlorofluorocarbon, hydrofluoroalkane).

The solutions of the present invention are typically clear. In this regard, many of the antiarrhythmic pharmaceutical agents of the present invention are water soluble.

In some embodiments, the isotonicity of the solution ranges from isotonic to physiologic isotonicity. Physiologic isotonicity is the isotonicity of physiological fluids.

The compositions can have a pH ranging from 3.5 to 8.0, such as from 4.0 to 7.5, or 4.5 to 7.0, or 5.0 to 6.5.

For dry powders, the moisture content can be less than about 15 wt %, such as less than about 10 wt %, less than about 5 wt %, less than about 2 wt %, less than about 1 wt %, or less than about 0.5 wt %. Such powders are described in WO 95/24183, WO 96/32149, WO 99/16419, WO 99/16420, and WO 99/16422, which are incorporated herein by reference in their entireties.

In one version, the pharmaceutical composition is in the form of an inhalable dry powder. Such dry powders can be manufactured by, for instance, solution enhanced dispersion by supercritical fluids (SEDS), which is described in U.S. Pat. Nos. 5,851,453, 6,440,337, 6,576,262, 7,150,766, and 10,798,955, and U.S. Patent Publication Nos. US20060073087A1 and US20020073511A1, each of which is incorporated herein by reference in its entirety.

In another version, the pharmaceutical composition is in the form of an inhalable dry powder formed by technologies described in U.S. Patent Publication No. US20180221849A1, as well as U.S. Pat. Nos. 6,620,351, 7,744,923, and 9,233,348, each of which is incorporated herein by reference in its entirety.

In another version, the pharmaceutical composition is in the form of an inhalable dry powder formed by imprint lithography, which is described in U.S. Pat. Nos. 10,842,748, 9,214,590, 7,855,046, 8,128,393, and 9,545,737, each of which is incorporated herein by reference in its entirety.

In one version, the pharmaceutical composition comprises antiarrhythmic pharmaceutical agent incorporated into a phospholipid matrix. The pharmaceutical composition can comprise phospholipid matrices that incorporate the active agent and that are in the form of particles that are hollow and/or porous microstructures, as described in the aforementioned WO 99/16419, WO 99/16420, WO 99/16422, WO 01/85136, and WO 01/85137, which are incorporated herein by reference in their entireties. The hollow and/or porous microstructures are useful in delivering the antiarrhythmic pharmaceutical agent to the lungs because the density, size, and aerodynamic qualities of the hollow and/or porous microstructures facilitate transport into the deep lungs during a user's inhalation. In addition, the phospholipid-based hollow and/or porous microstructures reduce the attraction forces between particles, making the pharmaceutical composition easier to deagglomerate during aerosolization and improving the flow properties of the pharmaceutical composition making it easier to process.

In one version, the pharmaceutical composition is composed of hollow and/or porous microstructures having a bulk density less than about 1.0 g/$cm^3$, less than about 0.5 g/$cm^3$, less than about 0.3 g/$cm^3$, less than about 0.2 g/$cm^3$, or less than about 0.1 g/$cm^3$. By providing low bulk density particles or particles, the minimum powder mass that can be filled into a unit dose container is reduced, which eliminates the need for carrier particles. That is, the relatively low density of the powders of one or more embodiments of the present invention provides for the reproducible administration of relatively low dose pharmaceutical compounds. Moreover, the elimination of carrier particles will potentially reduce throat deposition and any "gag" effect or coughing, since large carrier particles, e.g., lactose particles, will impact the throat and upper airways due to their size.

In some aspects, the present invention involves high rugosity particles. For instance, the particles can have a rugosity of greater than 2, such as greater than 3, or greater than 4, and the rugosity can range from 2 to 15, such as 3 to 10.

In one version, the pharmaceutical composition is in dry powder form and is contained within a unit dose receptacle which can be inserted into or near the aerosolization apparatus to aerosolize the unit dose of the pharmaceutical composition. This version is useful in that the dry powder form can be stably stored in its unit dose receptacle for a long period of time. In some examples, pharmaceutical compositions of one or more embodiments of the present invention can be stable for at least 2 years. In some versions, no refrigeration is required to obtain stability. In other versions, reduced temperatures, e.g., at 2-8° C., can be used to prolong stable storage. In many versions, the storage stability allows aerosolization with an external power source.

It will be appreciated that the pharmaceutical compositions disclosed herein can comprise a structural matrix that exhibits, defines or comprises voids, pores, defects, hollows, spaces, interstitial spaces, apertures, perforations or holes. The absolute shape (as opposed to the morphology) of the perforated microstructure is generally not critical and any overall configuration that provides the desired characteristics is contemplated as being within the scope of the invention. Accordingly, some embodiments comprise approximately spherical shapes. However, collapsed, deformed or fractured particles are also compatible.

In one version, the antiarrhythmic pharmaceutical agent is incorporated in a matrix that forms a discrete particle, and the pharmaceutical composition comprises a plurality of the discrete particles. The discrete particles can be sized so that they are effectively administered and/or so that they are available where needed. For example, for an aerosolizable pharmaceutical composition, the particles are of a size that allows the particles to be aerosolized and delivered to a user's respiratory tract during the user's inhalation.

The matrix material can comprise a hydrophobic or a partially hydrophobic material. For example, the matrix material can comprise a lipid, such as a phospholipid, and/or a hydrophobic amino acid, such as leucine or tri-leucine. Examples of phospholipid matrices are described in WO 99/16419, WO 99/16420, WO 99/16422, WO 01/85136, and WO 01/85137 and in U.S. Pat. Nos. 5,874,064; 5,855,913; 5,985,309; 6,503,480; and 7,473,433, and in U.S. Published App. No. 20040156792, all of which are incorporated herein by reference in their entireties. Examples of hydrophobic amino acid matrices are described in U.S. Pat. Nos. 6,372,258; 6,358,530; and 7,473,433, which are incorporated herein by reference in their entireties.

When phospholipids are utilized as the matrix material, the pharmaceutical composition can also comprise a polyvalent cation, as disclosed in WO 01/85136 and WO 01/85137, which are incorporated herein by reference in their entireties.

According to another embodiment, release kinetics of the composition containing antiarrhythmic pharmaceutical agent(s) is controlled. According to one or more embodiments, the compositions of the present invention provide immediate release of the antiarrhythmic pharmaceutical agent(s). Alternatively, the compositions of other embodiments of the present invention can be provided as non-homogeneous mixtures of active agent incorporated into a matrix material and unincorporated active agent in order to provide desirable release rates of antiarrhythmic pharmaceutical agent According to this embodiment, antiarrhythmic pharmaceutical agents formulated using the emulsion-based manufacturing process of one or more embodiments of the present invention have utility in immediate release applications when administered to the respiratory tract. Rapid release is facilitated by: (a) the high specific surface area of the low density porous powders; (b) the small size of the drug crystals that are incorporated therein, and; (c) the low surface energy of the particles.

Alternatively, it can be desirable to engineer the particle matrix so that extended release of the active agent(s) is effected. This can be particularly desirable when the active agent(s) is rapidly cleared from the lungs or when sustained release is desired. For example, the nature of the phase behavior of phospholipid molecules is influenced by the nature of their chemical structure and/or preparation methods in spray-drying feedstock and drying conditions and other composition components utilized. In the case of spray-drying of active agent(s) solubilized within a small unilamellar vesicle (SUV) or multilamellar vesicle (MLV), the active agent(s) are encapsulated within multiple bilayers and are released over an extended time.

In contrast, spray-drying of a feedstock comprised of emulsion droplets and dispersed or dissolved active agent(s) in accordance with the teachings herein leads to a phospholipid matrix with less long-range order, thereby facilitating rapid release. While not being bound to any particular theory, it is believed that this is due in part to the fact that the active agent(s) are never formally encapsulated in the phospholipid, and the fact that the phospholipid is initially present on the surface of the emulsion droplets as a monolayer (not a bilayer as in the case of liposomes). The spray-dried particles prepared by the emulsion-based manufacturing process of one or more embodiments of the present invention often have a high degree of disorder. Also, the spray-dried particles typically have low surface energies, where values as low as 20 mN/m have been observed for spray-dried DSPC particles (determined by inverse gas chromatography). Small angle X-ray scattering (SAXS) studies conducted with spray-dried phospholipid particles have also shown a high degree of disorder for the lipid, with scattering peaks smeared out, and length scales extending in some instances only beyond a few nearest neighbors.

It should be noted that a matrix having a high gel to liquid crystal phase transition temperature is not sufficient in itself to achieve sustained release of the active agent(s). Having sufficient order for the bilayer structures is also important for achieving sustained release. To facilitate rapid release, an emulsion-system of high porosity (high surface area), and minimal interaction between the drug substance and phospholipid can be used. The pharmaceutical composition formation process can also include the additions of other composition components (e.g., small polymers such as Pluronic F-68; carbohydrates, salts, hydrotropes) to break the bilayer structure are also contemplated.

To achieve a sustained release, incorporation of the phospholipid in bilayer form can be used, especially if the active agent is encapsulated therein. In this case increasing the $T_m$ of the phospholipid can provide benefit via incorporation of divalent counterions or cholesterol. As well, increasing the interaction between the phospholipid and drug substance via the formation of ion-pairs (negatively charged active+steaylamine, positively charged active+phosphatidylglycerol) would tend to decrease the dissolution rate. If the active is amphiphilic, surfactant/surfactant interactions can also slow active dissolution.

The addition of divalent counterions (e.g., calcium or magnesium ions) to long-chain saturated phosphatidylcholines results in an interaction between the negatively charged phosphate portion of the zwitterionic headgroup and the positively charged metal ion. This results in a displacement of water of hydration and a condensation of the packing of the phospholipid lipid headgroup and acyl chains. Further, this results in an increase in the Tm of the phospholipid. The decrease in headgroup hydration can have profound effects on the spreading properties of spray-dried phospholipid particles on contact with water. A fully hydrated phosphatidylcholine molecule will diffuse very slowly to a dispersed crystal via molecular diffusion through the water phase. The process is exceedingly slow because the solubility of the phospholipid in water is very low (about $10^{-10}$ mol/L for DPPC). Prior art attempts to overcome this phenomenon include homogenizing the crystals in the presence of the phospholipid. In this case, the high degree of shear and radius of curvature of the homogenized crystals facilitates coating of the phospholipid on the crystals. In contrast, "dry" phospholipid powders according to one or more embodiments of this invention can spread rapidly when contacted with an aqueous phase, thereby coating dispersed crystals without the need to apply high energies.

For example, upon reconstitution, the surface tension of spray-dried DSPC/Ca mixtures at the air/water interface decreases to equilibrium values (about 20 mN/m) as fast as a measurement can be taken. In contrast, liposomes of DSPC decrease the surface tension (about 50 mN/m) very little over a period of hours, and it is likely that this reduction is due to the presence of hydrolysis degradation products such as free fatty acids in the phospholipid. Single-tailed fatty acids can diffuse much more rapidly to the air/water interface than can the hydrophobic parent compound. Hence, the addition of calcium ions to phosphatidylcholines can facilitate the rapid encapsulation of crystalline drugs more rapidly and with lower applied energy.

In another version, the pharmaceutical composition comprises low density particles achieved by co-spray-drying nanocrystals with a perfluorocarbon-in-water emulsion. The nanocrystals can be formed by precipitation and can, e.g., range in size from about 45 μm to about 80 μm. Examples of perfluorocarbons include, but are not limited to, perfluorohexane, perfluorooctyl bromide, perfluorooctyl ethane, perfluorodecalin, perfluorobutyl ethane.

In accordance with the teachings herein the particles can be provided in a "dry" state. That is, in one or more embodiments, the particles will possess a moisture content that allows the powder to remain chemically and physically stable during storage at ambient or reduced temperature and remain dispersible. In this regard, there is little or no change in primary particle size, content, purity, and aerodynamic particle size distribution.

As such, the moisture content of the particles is typically less than about 10 wt %, such as less than about 6 wt %, less than about 3 wt %, or less than about 1 wt %. The moisture content is, at least in part, dictated by the composition and is controlled by the process conditions employed, e.g., inlet temperature, feed concentration, pump rate, and blowing agent type, concentration and post drying. Reduction in bound water leads to significant improvements in the dispersibility and flowability of phospholipid based powders, leading to the potential for highly efficient delivery of powdered lung surfactants or particle composition comprising active agent dispersed in the phospholipid. The improved dispersibility allows simple passive DPI devices to be used to effectively deliver these powders.

Yet another version of the pharmaceutical composition includes particle compositions that can comprise, or can be partially or completely coated with, charged species that prolong residence time at the point of contact or enhance penetration through mucosae. For example, anionic charges are known to favor mucoadhesion while cationic charges can be used to associate the formed particle with negatively charged bioactive agents such as genetic material. The charges can be imparted through the association or incorporation of polyanionic or polycationic materials such as polyacrylic acids, polylysine, polylactic acid, and chitosan.

In some versions, the pharmaceutical composition comprises particles having a mass median diameter less than about 20 μm, such as less than about 10 μm, less than about 7 μm, or less than about 5 μm. The particles can have a mass median aerodynamic diameter ranging from about 1 μm to about 6 μm, such as about 1.5 μm to about 5 μm, or about 2 μm to about 4 μm. If the particles are too large, a larger percentage of the particles cannot reach the lungs. If the particles are too small, a larger percentage of the particles can be exhaled.

Unit doses of the pharmaceutical compositions can be placed in a container. Examples of containers include, but are not limited to, syringes, capsules, blow fill seal, blisters, vials, ampoules, or container closure systems made of metal, polymer (e.g., plastic, elastomer), glass, or the like. For instance, the vial can be a colorless Type I borosilicate glass ISO 6R 10 mL vial with a chlorobutyl rubber siliconized stopper, and rip-off type aluminum cap with colored plastic cover.

The container can be inserted into an aerosolization device. The container can be of a suitable shape, size, and material to contain the pharmaceutical composition and to provide the pharmaceutical composition in a usable condition. For example, the capsule or blister can comprise a wall which comprises a material that does not adversely react with the pharmaceutical composition. In addition, the wall can comprise a material that allows the capsule to be opened to allow the pharmaceutical composition to be aerosolized. In one version, the wall comprises one or more of gelatin, hydroxypropyl methylcellulose (HPMC), polyethyleneglycol-compounded HPMC, hydroxyproplycellulose, agar, aluminum foil, or the like. In one version, the capsule can comprise telescopically adjoining sections, as described for example in U.S. Pat. No. 4,247,066 which is incorporated herein by reference in its entirety. The size of the capsule can be selected to adequately contain the dose of the pharmaceutical composition. The sizes generally range from size 5 to size 000 with the outer diameters ranging from about 4.91 mm to 9.97 mm, the heights ranging from about 11.10 mm to about 26.14 mm, and the volumes ranging from about 0.13 mL to about 1.37 mL, respectively. Suitable capsules are available commercially from, for example, Shionogi Qualicaps Co. in Nara, Japan and Capsugel in Greenwood, S.C. After filling, a top portion can be placed over the bottom portion to form a capsule shape and to contain the powder within the capsule, as described in U.S. Pat. Nos. 4,846,876 and 6,357,490, and in WO 00/07572, which are incorporated herein by reference in their entireties. After the top portion is placed over the bottom portion, the capsule can optionally be banded.

For solutions, the amount of the composition in the unit dose typically ranges from about 0.5 ml to about 15 ml, such as about 2 ml to about 15 ml, from about 3 ml to about 10 ml, about 4 ml to about 8 ml, or about 5 ml to about 6 ml.

The compositions of the present invention can be made by any of the various methods and techniques known and available to those skilled in the art.

For instance, a solution of antiarrhythmic pharmaceutical agent can be made using the following procedure. Typically, manufacturing equipment is sterilized before use. A portion of the final volume, e.g., 70%, of solvent, e.g., water for injection, can be added into a suitable container. Antiarrhythmic pharmaceutical agent can then be added. The antiarrhythmic pharmaceutical agent can be mixed until dissolved. Additional solvent can be added to make up the final batch volume. The batch can be filtered, e.g., through a 0.2 μm filter into a sterilized receiving vessel. Filling components can be sterilized before use in filling the batch into vials, e.g., 10 ml vials.

As an example, the above-noted sterilizing can include the following. A 5 liter type 1 glass bottle and lid can be placed in an autoclave bag and sterilized at elevated temperature, e.g., 121° C. for 15 minutes, using an autoclave. Similarly, vials can be placed into suitable racks, inserted into an autoclave bag, and sterilized at elevated temperature, e.g., 121° C. for 15 minutes, using an autoclave. Also similarly, stoppers can be placed in an autoclave bag and sterilized at elevated temperature, e.g., 121° C. for 15 minutes, using an autoclave. Before sterilization, sterilizing filters can be attached to tubing, e.g., a 2 mm length of 7 mm×13 mm silicone tubing. A filling line can be prepared by placed in an autoclave bag and sterilized at elevated temperature, e.g., 121° C. for 15 minutes, using an autoclave.

The above-noted filtration can involve filtration into a laminar flow work area. The receiving bottle and filters can be set up in the laminar flow work area.

The above-noted filling can also be conducted under laminar flow protection. The filling line can be unwrapped and placed into the receiving bottle. The sterilized vials and stoppers can be unwrapped under laminar flow protection. Each vial can be filled, e.g., to a target fill of 5 g, and stoppered. A flip off collar can be applied to each vial. The sealed vials can be inspected for vial leakage, correct overseals, and cracks.

For dry powders, the composition may be formed by spray drying, lyophilization, milling (e.g., wet milling, dry milling), and the like.

As an example, an antiarrhythmic can be prepared by lyophilizing the antiarrhythmic to form a powder for storage. The powder is then reconstituted prior to use. This technique can be used when the antiarrhythmic is unstable in solution.

In some embodiments, the lyophilized powder can be reconstituted in a suitable solvent such that the antiarrhythmic pharmaceutical agent is present at a concentration from about 1 mg/mL to about 150 mg/mL, such as 1 mg/mL to 5 mg/mL, 1 mg/ml to 10 mg/mL, 1 mg/ml to 15 mg/mL, 1 mg/mL to 20 mg/mL, 1 mg/mL to 25 mg/mL, 1 mg/mL to 30 mg/mL, 1 mg/mL to 35 mg/mL, 1 mg/mL to 40 mg/mL, 1 mg/mL to 45 mg/mL, 1 mg/mL to 50 mg/mL, 1 mg/mL to 55 mg/mL, 5 mg/ml to 10 mg/mL, 5 mg/ml to 15 mg/mL, 5 mg/mL to 20 mg/mL, 5 mg/mL to 25 mg/mL, 5 mg/mL to 30 mg/mL, 5 mg/mL to 35 mg/mL, 5 mg/mL to 40 mg/mL, 5 mg/mL to 45 mg/mL, 5 mg/mL to 50 mg/mL, 5 mg/mL to 55 mg/mL, 5 mg/mL to 60 mg/mL; 10 mg/ml to 15 mg/mL, 10 mg/mL to 20 mg/mL, 10 mg/mL to 25 mg/mL, 10 mg/mL to 30 mg/mL, 10 mg/mL to 35 mg/mL, 10 mg/mL to 40 mg/mL, 10 mg/mL to 45 mg/mL, 10 mg/mL to 50 mg/mL, 10 mg/mL to 55 mg/mL, 10 mg/mL to 60 mg/mL, 15 mg/mL to 20 mg/mL, 15 mg/mL to 25 mg/mL, 15 mg/mL to 30 mg/mL, 15 mg/mL to 35 mg/mL, 15 mg/mL to 40 mg/mL, 15 mg/mL to 45 mg/mL, 15 mg/mL to 50 mg/mL, 15 mg/mL to 55 mg/mL, 15 mg/mL to 60 mg/mL, 20 mg/mL to 25 mg/mL, 20 mg/mL to 30 mg/mL, 20 mg/mL to 35 mg/mL, 20 mg/mL to 40 mg/mL, 20 mg/mL to 45 mg/mL, 20 mg/mL to 50 mg/mL, 20 mg/mL to 55 mg/mL, 20 mg/mL to 60 mg/mL, 25 mg/mL to 30 mg/mL, 25 mg/mL to 35 mg/mL, 25 mg/mL to 40 mg/mL, 25 mg/mL to 45 mg/mL, 25 mg/mL to 50 mg/mL, 25 mg/mL to 55 mg/mL, 25 mg/mL to 60 mg/mL, 30 mg/mL to 35 mg/mL, 30 mg/mL to 40 mg/mL, 30 mg/mL to 45 mg/mL, 30 mg/mL to 50 mg/mL, 30 mg/mL to 55 mg/mL, 30 mg/mL to 60 mg/mL, 30 mg/mL to 150 mg/mL, 35 mg/mL to 40 mg/mL, 35 mg/mL to 45 mg/mL, 35 mg/mL to 50 mg/mL, 35 mg/mL to 55 mg/mL, 35 mg/mL to 60 mg/mL, 40 mg/mL to 45 mg/mL, 40 mg/mL to 50 mg/mL, 40 mg/mL to 55 mg/mL, 40 mg/mL to 60 mg/mL, 45 mg/mL to 50 mg/mL, 45 mg/mL to 55 mg/mL, 45 mg/mL to 60 mg/mL, 50 mg/mL to 55 mg/mL, 50 mg/mL to 60 mg/mL, 55 mg/mL to 60 mg/mL, 55 mg/mL to 65 mg/mL, 55 mg/mL to 70 mg/mL, 55 mg/mL to 75 mg/mL, 60 mg/mL to 65 mg/mL, 60 mg/mL to 70 mg/mL, 60 mg/mL to 75 mg/mL, 60 mg/mL to 80 mg/mL, 70 mg/mL to 75 mg/mL, 70 mg/mL to 80 mg/mL, 75 mg/mL to 80 mg/mL, 75 mg/mL to 85 mg/mL, 75 mg/mL to 90 mg/mL, 80 mg/mL to 85 mg/mL, 80 mg/mL to 90 mg/mL, 85 mg/mL to 90 mg/mL, 90 mg/mL to 100 mg/mL, 90 mg/mL to 110 mg/mL, 100 mg/mL to 110 mg/mL, 100 mg/mL to 120 mg/mL, 110 mg/mL to 120 mg/mL, 120 mg/mL to 130 mg/mL, 120 mg/mL to 140 mg/mL, 130 mg/mL to 140 mg/mL, 130 mg/mL to 150 mg/mL, 140 mg/mL to 150 mg/mL, or 145 mg/mL to 150 mg/mL.

The solvent for the solution to be lyophilized can comprise water. The solution can be excipient-free. For instance, the solution can be cryoprotectant-free.

In one or more embodiments, a suitable amount (e.g., 120 g per liter of final solution) of drug substance can be dissolved, e.g., in about the 75% of the theoretical total amount of water for injection under nitrogen bubbling. The dissolution time can be recorded and appearance can be evaluated.

Then, the dilution to the final volume with WFI can be carried out. Final volume can be checked. Density, pH, endotoxin, bioburden, and content by UV can be measured both before and after sterile filtration. The water content of the lyophilized powder is typically less than about 7 wt %, such as less than about 5 wt %, less than about 4 wt %, less than about 3 wt %, less than about 2 wt %, or less than about 1 wt %.

The powder is capable of being reconstituted with water at 25° C. and 1.0 atmosphere and with manual agitation, in less than about 60 seconds, such as less than about 30 seconds, less than about 15 seconds, or less than about 10 seconds. The powder typically has a large specific surface area that facilitates reconstitution. The specific surface area typically ranges from about 5 $m^2/g$ to about 20 $m^2/g$, such as about 8 $m^2/g$ to 15 $m^2/g$, or about 10 $m^2/g$ to 12 $m^2/g$. Upon reconstitution with water, the antiarrhythmic pharmaceutical agent solution typically has a pH that ranges from about 2.5 to about 7, such as about 3 to about 6.

In spray drying, the preparation to be spray dried or feedstock can be any solution, coarse suspension, slurry, colloidal dispersion, or paste that may be atomized using the selected spray drying apparatus. In the case of insoluble agents, the feedstock may comprise a suspension as described above. Alternatively, a dilute solution and/or one or more solvents may be utilized in the feedstock. In one or more embodiments, the feed stock will comprise a colloidal system such as an emulsion, reverse emulsion microemulsion, multiple emulsion, particle dispersion, or slurry.

Pharmaceutical compositions useful in one or more embodiments of the present invention may alternatively be formed by lyophilization. Lyophilization is a freeze-drying process in which water is sublimed from the composition after it is frozen. The lyophilization process is often used because biologics and pharmaceuticals that are relatively unstable in an aqueous solution may be dried without exposure to elevated temperatures, and then stored in a dry state where there are fewer stability problems. With respect to one or more embodiments of the instant invention, such techniques are particularly compatible with the incorporation of peptides, proteins, genetic material and other natural and synthetic macromolecules in pharmaceutical compositions without compromising physiological activity. Lyophilized cake containing a fine foam-like structure can be micronized using techniques known in the art to provide particles of the desired size.

In some embodiments, the potassium channel blocker and sodium channel blocker can be administered via parenteral injection as a single liquid solution, which can include other chemical components, such as carriers, stabilizers, diluents, dispersing agents, suspending agents, thickening agents, preservatives, or excipients. Parenteral injections can be formulated for bolus injection or continuous infusion. The pharmaceutical compositions can be in a form suitable for parenteral injection as a sterile suspension, solution or emulsion in oily or aqueous vehicles, and can contain formulatory agents such as suspending, stabilizing or dispersing agents. Pharmaceutical formulations for parenteral administration include aqueous solutions of the active compounds in water soluble form. For example, compositions described herein can be provided in liquid form, and formulated in saline based aqueous solution of varying pH (5-8), with or without detergents such polysorbate-80 at 0.01-1%, or carbohydrate additives, such mannitol, sorbitol, or trehalose. Commonly used preservatives include chlorobutanol, m-cresol, benzyl alcohol, phenylethyl alcohol, phenol, methylparaben, or propylparaben. Commonly used buffers include histidine, acetate, phosphate, borate, or citrate. Commonly used tonicity adjustors include sodium chloride, mannitol and glycerin. The infusion solution may include 0 to 10% dextrose. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility of the compounds to allow for the preparation of highly concentrated solutions, for example, a cyclodextrin or organic solvent. Organic solvents can include alcohols, for example, $C_1$-$C_4$ linear alkyl, $C_3$-$C_4$ branched alkyl, ethanol, ethylene glycol, glycerin, 2-hydroxypropanol, propylene glycol, maltitol, sorbitol, xylitol; substituted or unsubstituted aryl, and benzyl alcohol. Alternatively, the active ingredient can be in powder form for constitution with a suitable vehicle, e.g., sterile pyrogen-free water, before use.

Non-limiting examples of pharmaceutically-acceptable excipients can be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), each of which is incorporated by reference in its entirety.

The pharmaceutical composition according to one or more embodiments of the invention may, if desired, contain a combination of antiarrhythmic pharmaceutical agent and one or more additional active agents. Examples of additional active agents include, but are not limited to, agents that may be delivered through the lungs.

Additional active agents may comprise, for example, hypnotics and sedatives, psychic energizers, tranquilizers, respiratory drugs, anticonvulsants, muscle relaxants, antiparkinson agents (dopamine antagnonists), analgesics, antiinflammatories, antianxiety drugs (anxiolytics), appetite suppressants, antimigraine agents, muscle contractants, additional anti-infectives (antivirals, antifungals, vaccines) antiarthritics, antimalarials, antiemetics, anepileptics, cytokines, growth factors, anti-cancer agents, antithrombotic agents, antihypertensives, cardiovascular drugs, antiarrhythmics, antioxidants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The additional active agent, when administered by inhalation, may act locally or systemically.

The additional active agent may fall into one of a number of structural classes, including but not limited to small molecules, peptides, polypeptides, proteins, polysaccharides, steroids, proteins capable of eliciting physiological effects, nucleotides, oligonucleotides, polynucleotides, fats, electrolytes, and the like.

Examples of additional active agents suitable for use in this invention include but are not limited to one or more of calcitonin, amphotericin B, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX, insulin, pro-insulin, insulin analogues (e.g., mono-acylated insulin as described in U.S. Pat. No. 5,922,675, which is incorporated herein by reference in its entirety), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIa inhibitor, alpha-1 antitrypsin, phosphodiesterase (PDE) compounds, VLA-4 inhibitors, bisphosponates, respiratory syncytial virus antibody, cystic fibrosis transmembrane regulator (CFFR) gene, deoxyribonuclease (DNase), bactericidal/permeability increasing protein (BPI), anti-CMV antibody, 13-cis retinoic acid, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin, teicoplanin, rampolanin, mideplanin, colistin, daptomycin, gramicidin, colistimethate, polymixins such as polymixin B, capreomycin, bacitracin, penems; penicillins including penicllinase-sensitive agents like penicillin G, penicillin V, penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefinetazole, ceftazidime, loracarbef, and moxalactam, monobactams like aztreonam; and carbapenems such as imipenem, meropenem, pentamidine isethiouate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments, derivatives, and analogs thereof.

Additional active agents for use in the invention can further include nucleic acids, as bare nucleic acid molecules, vectors, associated viral particles, plasmid DNA or RNA or other nucleic acid constructions of a type suitable for transfection or transformation of cells, e.g., suitable for gene therapy including antisense. Further, an active agent may comprise live attenuated or killed viruses suitable for use as vaccines. Other useful drugs include those listed within the Physician's Desk Reference (most recent edition), which is incorporated herein by reference in its entirety.

When a combination of active agents is used, the agents may be provided in combination in a single species of pharmaceutical composition or individually in separate species of pharmaceutical compositions.

EXAMPLES

The following examples are provided to further illustrate some embodiments of the present invention, but are not intended to limit the scope of the invention; it will be understood by their exemplary nature that other procedures, methodologies, or techniques known to those skilled in the art may alternatively be used.

Example 1: Intravenous Administration of Ibutilide in Porcine Model of Paroxysmal Atrial Fibrillation Anesthetization and Monitoring.

Normal Yorkshire pigs are preanesthetized with telazol (4.7 mg/kg, intramuscular) and subsequently further anesthetized using alpha-chloralose (80-mg/kg IV bolus followed by 24-mg/kg/h continuous IV infusion). The pigs are intubated and ventilated at a constant rate of 12 breaths/min and tidal volume of 400 ml per stroke. Blood samples for measurements of plasma levels of ibutilide and flecainide are drawn at the same timepoints that pharmacodynamic measurements are made. Systolic, diastololic and mean arterial pressure (MAP), pulmonary arterial pressure (PAP), LV pressure, and ECG (e.g. heart rate) are continuously monitored. At specific time points (0, 2, 5, 10, 15, 30, 60 min), measurements for pulmonary edge pressure (PWP), LV contractility (LV dp/dt), ECG intervals (e.g. QRS, PR, QT) and atrial depolarization duration (Pa) using an atrial electrocardiogram are made.

Conversion of Atrial Fibrillation to Normal Sinus Rhythm and Pharmacokinetic Analysis.

Intracardiac catheters are positioned under fluoroscopic control. Electrograms are recorded from a decapolar electrode catheter positioned in the LV. Mean arterial pressure (MAP) is continuously recorded from a femoral arterial sheath. LV blood pressure is continuously monitored from a pigtail catheter. A catheter is introduced into the pericardial space via the right atrial appendage for delivery of intrapericardial acetylcholine. Atrial pacing at 160 beats/min is accomplished by delivering electrical stimuli to the right atrial catheter electrodes. Electrograms are monitored from atrial and ventricular sites.

AF is induced with 1 mL of a 102.5 mM solution of acetylcholine bolus delivered through the pericardial catheter, followed by saline flush (2 mL). Burst pacing at a cycle length of 178 ms is performed at 1 minute after intrapericardial administration of ACh. After AF initiation, lavage is carried out with 20 ml of saline. AF duration is compared starting at 2 min after AF was induced, when the IV dose of ibutilide fumarate is administered. Ibutilide fumarate is administered intravenously at 0.1 mg/kg, 1.0 mg/kg, or 5.0 mg/kg of bodyweight in the right jugular vein. Blood samples are collected from the jugular vein catheter into partially evacuated tubes. Blood samples are collected before and at 0, 2, 5, 10, 15, and 30 minutes after ibutilide fumarate administration. A washout period of 120 min was allowed between inductions of each occurrence of AF. Plasma concentration of ibutilide in all blood samples is evaluated using HPLC/MS-MS, and pharmacokinetic and pharmacodynamic parameters are determined.

The average ventricular rate for each AF is obtained by the mean of six measurements of ventricular rate performed each 30 seconds between the IV delivery (sterile water or ibutilide fumarate solution) and the AF conversion to normal sinus rhythm. Contractility (LV dP/dt) and MAP are recorded during atrial pacing at 160 beats/min before AF is induced and after AF termination.

Example 2: Fixed Dose Combination Matrix Study of IV Ibutilide and IV Flecainide in Porcine Model of Paroxysmal Atrial Fibrillation Normal pigs are anesthetized, hemodynamic and ECG parameters are monitored, and AF is induced as in EXAMPLE 1. The effect of several intravenously administered fixed-dose combinations of flecainide acetate and ibutilide fumarate described in TABLE 1 are administered and evaluated for the termination of induced AF per the procedure outlined in EXAMPLE 1.

TABLE 1

Dose combinations for IV FDC matrix study.

| | | Dose ibutilide fumarate (mg/kg) | | |
|---|---|---|---|---|
| | | 0.1 | 1.0 | 5 |
| Dose flecainide acetate (mg/kg) | 0.1 | FDC A1 | FDC B1 | FDC C1 |
| | 0.5 | FDC A2 | FDC B2 | FDC C2 |
| | 2 | FDC A3 | FDC B3 | FDC C3 |

Example 3: Fixed Dose Combination Matrix Study of IV Ibutilide and IV Flecainide in Porcine Model of Persistent Atrial Fibrillation A single-chamber atrial pacemaker is implanted in normal Yorkshire pigs. Burst atrial pacing at 42 Hz with a sinus rhythm detection rate of 180/min is conducted for 10 days, whereupon development of persistent AF is confirmed by ECG measurement. The pigs are anesthetized, and hemodynamic and ECG parameters are monitored as in EXAMPLE 1. The FDCs of TABLE 1 are intravenously administered in the right jugular vein. Blood samples are collected from the jugular vein catheter into partially evacuated tubes. Blood samples are collected before and at 0, 2, 5, 10, 15, and 30 minutes after ibutilide fumarate administration. A washout period of 120 min was allowed between each dose administration. Plasma concentration of ibutilide in all blood samples is evaluated using HPLC/MS-MS, and pharmacokinetic and pharmacodynamic parameters are determined as in EXAMPLE 1.

Example 4: Oral Administration of Dofetilide in Porcine Model of Paroxysmal Atrial Fibrillation Anesthetization and Monitoring.

Normal Yorkshire pigs are preanesthetized with telazol and are subsequently further anesthetized using alpha-chloralose. The pigs are intubated and ventilated at a constant rate of 12 breaths/min and tidal volume of 400 ml per stroke. Blood samples for measurements of plasma levels of dofetilide and flecainide are drawn at the same timepoints that pharmacodynamic measurements are made. Systolic, diastololic and mean arterial pressure (MAP), pulmonary arterial pressure (PAP), LV pressure, and ECG (e.g. heart rate) are continuously monitored. At specific time points (0, 2, 5, 10, 15, 30, 60 min), measurements for pulmonary edge pressure (PWP), LV contractility (LV dp/dt), ECG intervals (e.g. QRS, PR, QT) and atrial depolarization duration (Pa) using an atrial electrocardiogram are made.

Conversion of Atrial Fibrillation to Normal Sinus Rhythm and Pharmacokinetic Analysis.

Conversion of atrial fibrillation to normal sinus rhythm and pharmacokinetic analysis is conducted similarly as described in EXAMPLE 1.

Example 5: Fixed Dose Combination Matrix Study of Oral Tablets in the Treatment of Paroxysmal Atrial Fibrillation in a Porcine Model In this study, the treatment of paroxysmal atrial fibrillation in a porcine model is assessed through the oral administration of tablets containing a potassium channel blocker and a sodium channel blocker. The treatments groups are separated to ascertain the effects of the combination drug tablets: 1) control treatment; 2) dofetilide; 3) sotalol; 4) flecainide; 5) dofetilide+flecainide; 6) sotalol+flecainide; 7) ibutilide; and 8) ibutilide+flecainide.

Normal pigs are anesthetized, hemodynamic and ECG parameters are monitored, and AF is induced similarly as described in EXAMPLE 1. The effect of orally administered tablets composed dofetilide or sotalol in combination with flecainide acetate are administered and evaluated for the termination of induced AF per the procedure outlined in EXAMPLE 1.

Example 6: Fixed Dose Combination Matrix Study of Oral Tablets in the Treatment of Persistent Atrial Fibrillation in a Porcine Model A single-chamber atrial pacemaker is implanted in normal Yorkshire pigs. Burst atrial pacing at 42 Hz with a sinus rhythm detection rate of 180/min is conducted for 10 days, whereupon development of persistent AF is confirmed by ECG measurement. The pigs are anesthetized, and hemodynamic and ECG parameters are monitored as in EXAMPLE 1.

In this study, the treatment of paroxysmal atrial fibrillation in a porcine model is assessed through the oral administration of tablets containing a potassium channel blocker and a sodium channel blocker. The treatments groups are separated to ascertain the effects of the combination drug tablets: 1) control treatment; 2) dofetilide; 3) sotalol; 4) flecainide; 5) dofetilide+flecainide; and 6) sotalol+flecainide.

Normal pigs are anesthetized, hemodynamic and ECG parameters are monitored, and AF is induced similarly as described in EXAMPLE 1. The effect of orally administered tablets composed ibutilide, dofetilide or sotalol in combination with flecainide acetate are administered and evaluated for the termination of induced AF per the procedure outlined in EXAMPLE 1.

Blood samples are collected from the jugular vein catheter into partially evacuated tubes. Blood samples are collected before and at 0, 2, 5, 10, 15, and 30 minutes after dofetilide administration. A washout period was allowed between each dose administration. Plasma concentration of dofetilide in all blood samples is evaluated using HPLC/MS-MS, and pharmacokinetic and pharmacodynamic parameters are determined as in EXAMPLE 1.

Example 7: The Effects of Flecainide and Ibutilide in Prevention of ACh-Mediated AF in a Canine Isolated Coronary-Perfused Model A study was conducted to investigate the effects of flecainide and ibutilide, alone and in combination, on atrial and ventricular electrophysiogical parameters and their effects to prevent the induction of ACh-mediated AF and to terminate AF once induced in a canine isolated coronary-perfused model of AF.

Methods.

Experiments were performed using isolated arterially-perfused canine preparations consisting of right atrium with a rim of right ventricle. The hearts were from Beagles approximately 1 year of age and were stored in ice cold cardioplegic solution for approximately 40 minutes before experimentation.

Electrophysiological Recordings.

During experiments, transmembrane action potential (AP) recordings (sampling rate 41 kHz) were obtained from the atrium and ventricle using floating glass microelectrodes (10-25 MΩ DC resistance). A pseudo-electrocardiogram (ECG) was recorded using two electrodes consisting of Ag/AgCl half cells placed in the Tyrode's solution, bathing the preparation, 1.0 to 1.2 cm from opposite ends of the atrial coronary-perfused preparations (FIG. 1). Effective refractory period (ERP) was measured by delivering premature stimuli after every 10th basic beat at a pacing cycle length (CL) of 500 ms. The diastolic threshold of excitation (DTE) was determined by increasing stimulus intensity in 0.01 mA steps starting from 0.1 mA, until a steady 1:1 activation was achieved. Post-repolarization refractoriness (PRR) was recognized when ERP exceeded APD90 in the ventricle and APD70 in atria. Ventricular ERP coincides with APD90, whereas atrial ERP generally coincides with APD70. The anti-atrial fibrillation (AF) potential of flecainide with and without ibutilide was be tested in an acetylcholine (ACh, 0.5 μM)-mediated AF model. AF was induced by a single premature stimulation and/or by burst of rapid pacing (CL=50 ¬100 ms for 3-10 seconds).

In another experimental series (Series II), the effects of flecainide and ibutilide alone and in combination were examined for their effects in the termination of AF upon induction with burst pacing. Ventricular electrical activity was monitored for the development of early afterdepolarizations (EADs) and torsade de pointes (TdP).

Solutions.

Stock solutions were made by dissolving test article dry powder in distilled water vehicle. Solutions were stored in a refrigerator and used on the day of experimentation. Dilutions of the stock solution were made immediately before experiments. Tyrode's solution composition (in mM): NaCl 129, KCl 4, $NaH_2PO_4$ 0.9, $NaHCO_3$ 20, $CaCl_2$ 1.8, $MgSO_4$ 0.5, glucose 5.5, insulin 1 unit/liter, buffered with 95% $O_2$ and 5% $CO_2$, pH=7.4.

Experimental Series I.

Electrophysiological measurements were performed on isolated arterially-perfused canine right atriums with rims of right ventricles following at least 20 min of perfusion with each concentration of drug as specified in TABLE 2. The electrophysiological measurements were measured at CL of 500 ms.

TABLE 2

| Cohort | Step 1 | Step 2 | Step 3 | Step 4 | Step 5 | Step 6 | N |
|---|---|---|---|---|---|---|---|
| A | Control | Flecainide 1.5 μM | +ACh (0.5 μM) (AF induction) | Washout ACh and Flecainide (AF self-terminate) | Ibutilide (20 nM) | +ACh (0.5 μM) (AF induction) | 2 |
| B | Control | Flecainide (1.5 μM) + Ibutilide (20 nM) | +ACh (0.5 μM) (AF induction) | — | — | — | 2 |

Figure 3:
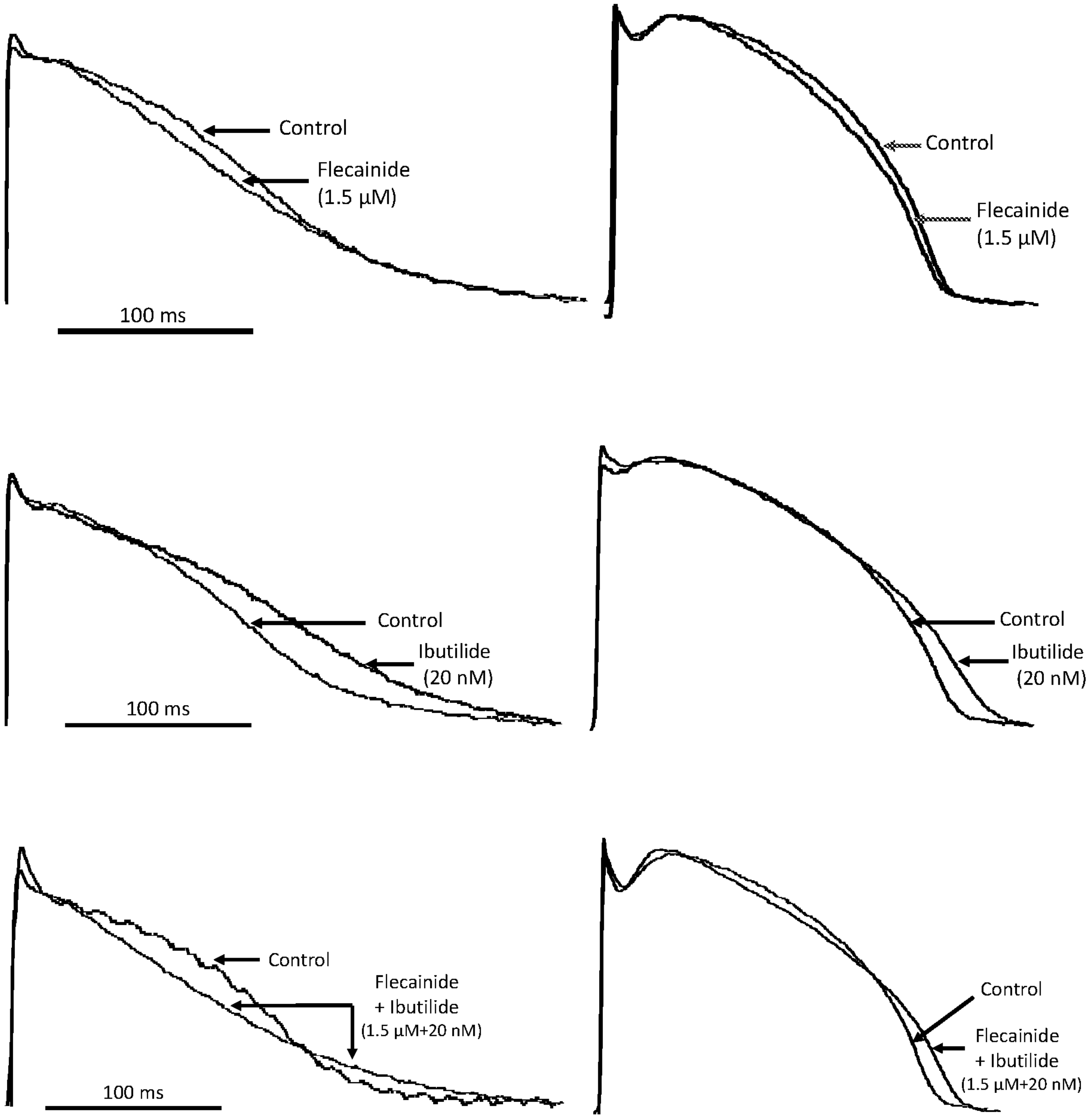
FIG. 3 depicts representative traces showing the effect of flecainide and ibutilide alone and in combination on atrial (left column) and ventricular (right column) action potentials in canine right atrial preparations.

FIG. 3 depicts representative traces showing the effect of flecainide (TABLE 2, A, step 2), ibutilide (A, step 5), and a combination of flecainide and ibutilide on atrial (FIG. 3, left column) and ventricular (FIG. 3, right column) action potentials (B, Step 2) (CL=500 ms).

Figure 4:
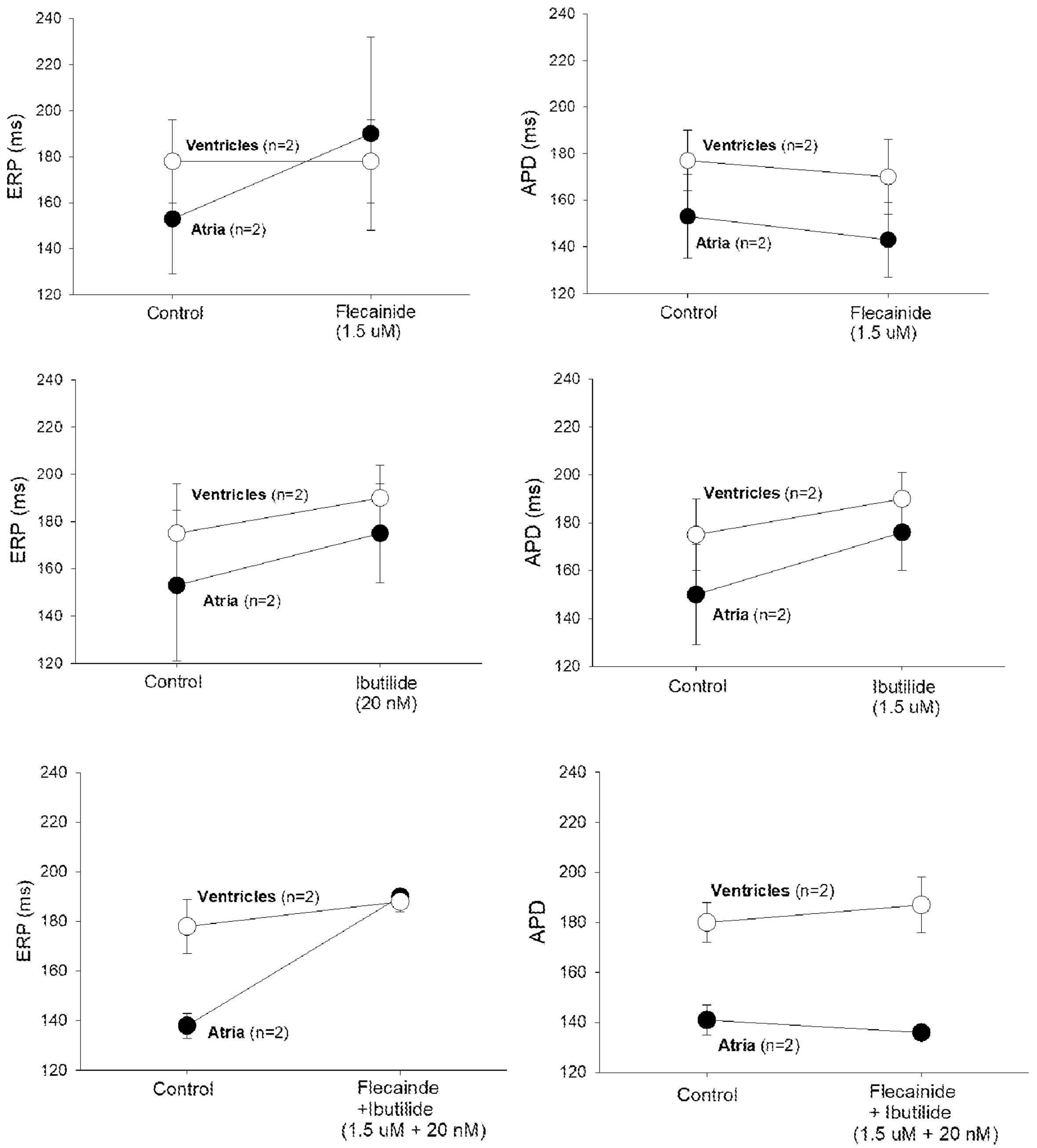
FIG. 4 are charts that show the effect of flecainide, ibutilide, and their combination on atrial and ventricular effective refractory period (ERP) and action potential duration (APD) in canine right atrial preparations.

FIG. 4 provides charts that show the effect of flecainide, ibutilide, and their combination on atrial and ventricular effective refractory period (ERP) and action potential duration (APD). APD70 is provided for atria and APD90 is provided for ventricles (ERPs generally correspond to these levels of APD). Pacing CL=500 ms.

Figure 5:
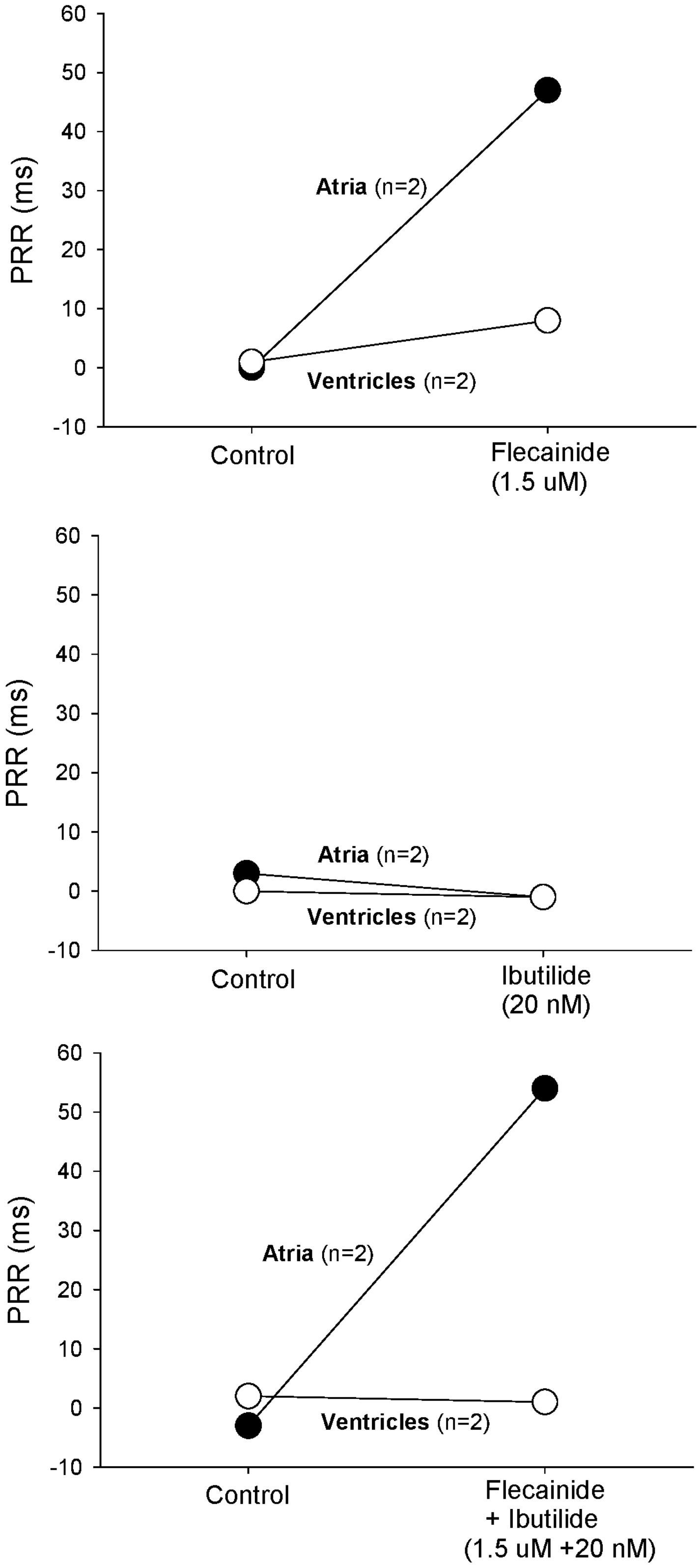
FIG. 5 provides charts that show the effect of flecainide, ibutilide, and their combination on atrial and ventricular post-repolarization refractoriness (PRR) in canine right atrial preparations.

FIG. 5 provides charts that show the effect of flecainide (TABLE 2, A, step 2), ibutilide (A, step 5), and a combination of flecainide and ibutilide on atrial and ventricular post-repolarization refractoriness (PRR). In atria, PRR=ERP minus APD70. In ventricles, PRR=ERP minus APD90. CL=500 ms.

Figure 6:
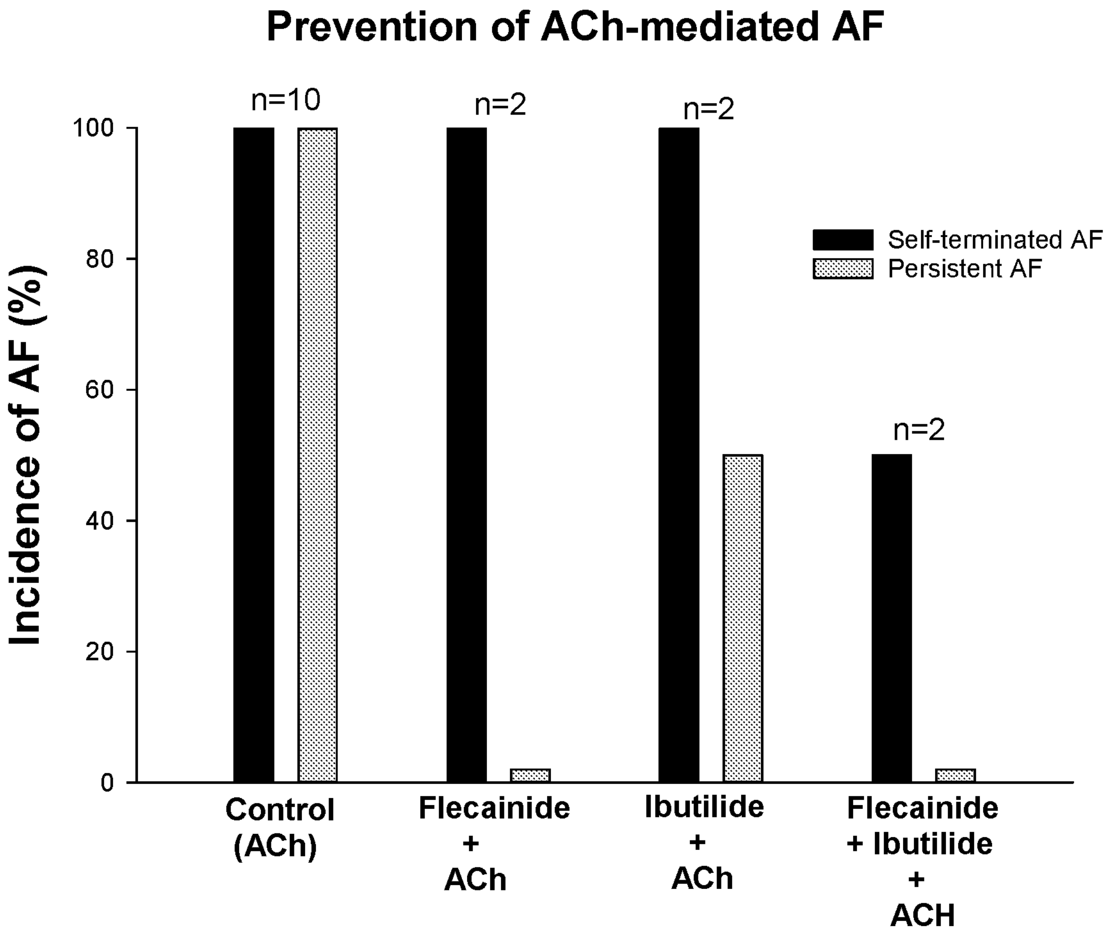
FIG. 6 is a chart that depicts the percent incidence of atrial fibrillation (AF) in canine right atrial preparations treated with flecainide and ibutilide alone and in combination.

FIG. 6 is a chart that depicts the percent incidence of ACh-mediated AF in canine right atrial preparations treated with ibutilide (TABLE 2, A, step 6) flecainide (A, step 3), and a combination of ibutilide and flecainide (B, step 3). ACh (0.5 μM) was added to the coronary perfusate in the presence of flecainide (1.5 μM), ibutilide (20 nM), or a combination of these agents. AF induction was first tested with a single premature beat and, if persistent AF was not induced, rapid pacing was applied.

Figure 7:
FIG. 7 is an example ECG trace depicting repeatedly-induced self-terminating episodes of AF, followed by induction of persistent AF (lasting >1 hour).

In each preparation, before AF became persistent, there were several episodes of self-terminating AF. Self-terminated AF was defined as AF that terminated within 20 sec (in most cases of self-terminating AF, terminated within 1-2 sec). FIG. 7 provides an example ECG trace depicting repeatedly-induced self-terminating episodes of AF, followed by induction of persistent AF (lasting >1 hour).

Experimental Series H.

The effects of flecainide and ibutilide alone and in combination on termination of persistent AF were examined in canine right atriums in experimental groups as specified in TABLE 3. Persistent AF was induced in the presence of ACh (0.5 μM) and the tested drugs were added to the coronary perfusate containing ACh (0.5 μM) on the 5-8th minute of AF.

TABLE 3

| Cohort | Step 1 | Step 2 | Step 3 | N |
|---|---|---|---|---|
| A | ACh 0.5 μM | Persistent AF 5 min | Flecainide | 2 |
| B | ACh 0.5 μM | Persistent AF 5 min | Ibutilide | 3 |
| C | ACh 0.5 μM | Persistent AF 5 min | Flecainide + Ibutilide | 2 |

Figure 8:
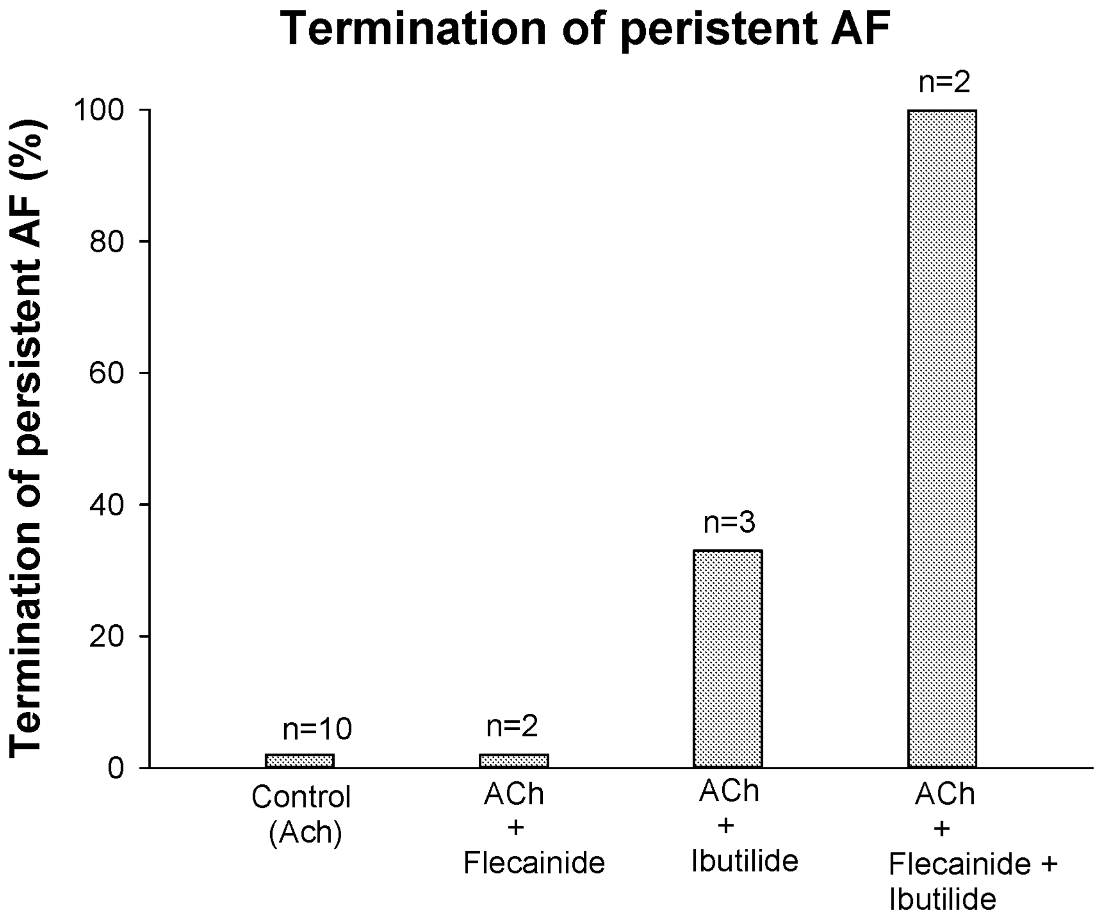
FIG. 8 is a chart depicting the percent of experiments where ACh-induced AF in canine right atrial preparations was terminated upon administration of flecainide and ibutilide alone and in combination.
Figure 9:
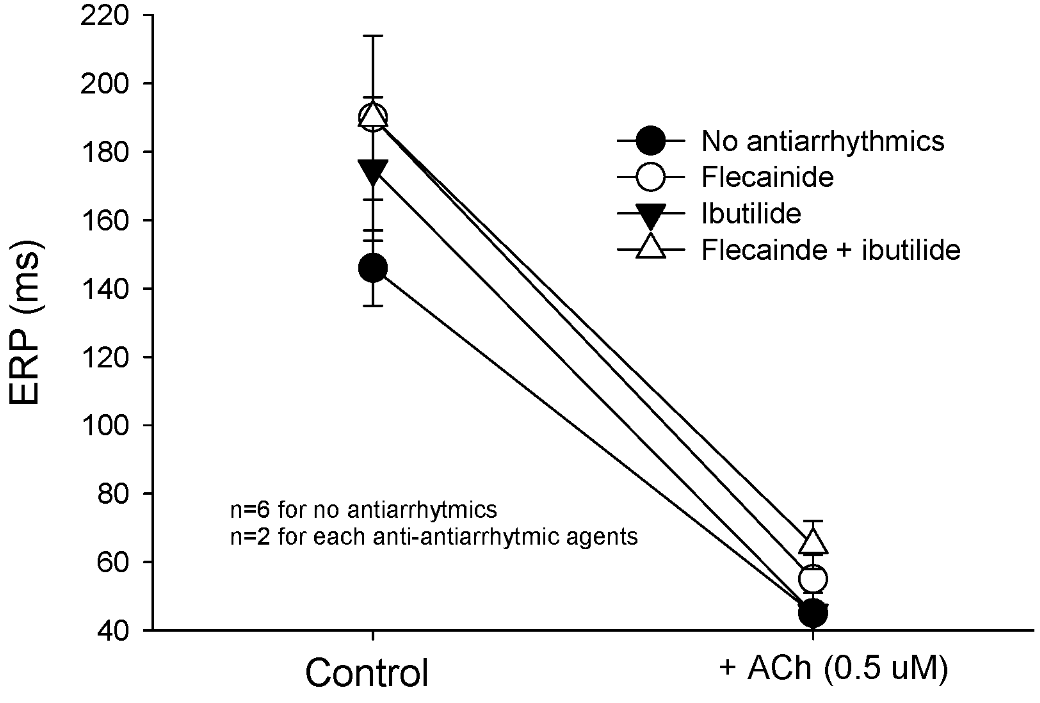
FIG. 9 is a chart that depicts the effect of flecainide (1.5 μM), ibutilide (20 nM), and a combination of flecainide and ibutilide in blunting the effect of ACh-mediated ERP abbreviation in canine right atrial preparations.

FIG. 8 is a chart that shows the percent of preparations where ACh-induced persistent AF in was terminated upon administration of flecainide (TABLE 3, A, Step 3), ibutilide (B, Step 3), or a combination of flecainide and ibutilide (C, Step 3). The combination of flecainide (1.5 μM) and ibutilide (20 nM) terminated persistent AF in all cases after 9 to 17 minutes after exposure to the drug combination (2 out of 2). Flecainide alone was ineffective (0 out of 2) and ibutilide terminated persistent AF in 1 out of 3 test samples. FIG. 9 is a chart that depicts the effect of flecainide (1.5 μM), ibutilide (20 nM), and a combination of flecainide and ibutilide in blunting the effect of ACh-mediated ERP abbreviation (C, Step 3).

Experimental Series III.

An experimental series was performed using canine left ventricular wedge preparations bathed in 3 mM KCl Tyrode's solution and paced at a CL of 2500 msec in order to sensitize the preparation to development of EADs. Drugs were administered in the order and concentrations specified in TABLE 4.

TABLE 4

| Step 1 | Step 2 | N |
|---|---|---|
| Ibutilide 1.5 μM | Flecainide (1.5 μM) + Ibutilide (50 nM) | 5 |
| 3 mM Ko | 3 mM Ko | |
| CL = 2500 msec | CL = 2500 msec | |

Canine left ventricular (LV) wedge preparations were excised from the same hearts used to obtain the right atrial preparations. In cases where ibutilide failed to induce EADs and/or TdP under these conditions preparations were further sensitized by exposure to ATX-II (10-20 nM) to increase late sodium channel current, thus mimicking conditions encountered in the setting of heart failure.

Figure 10:
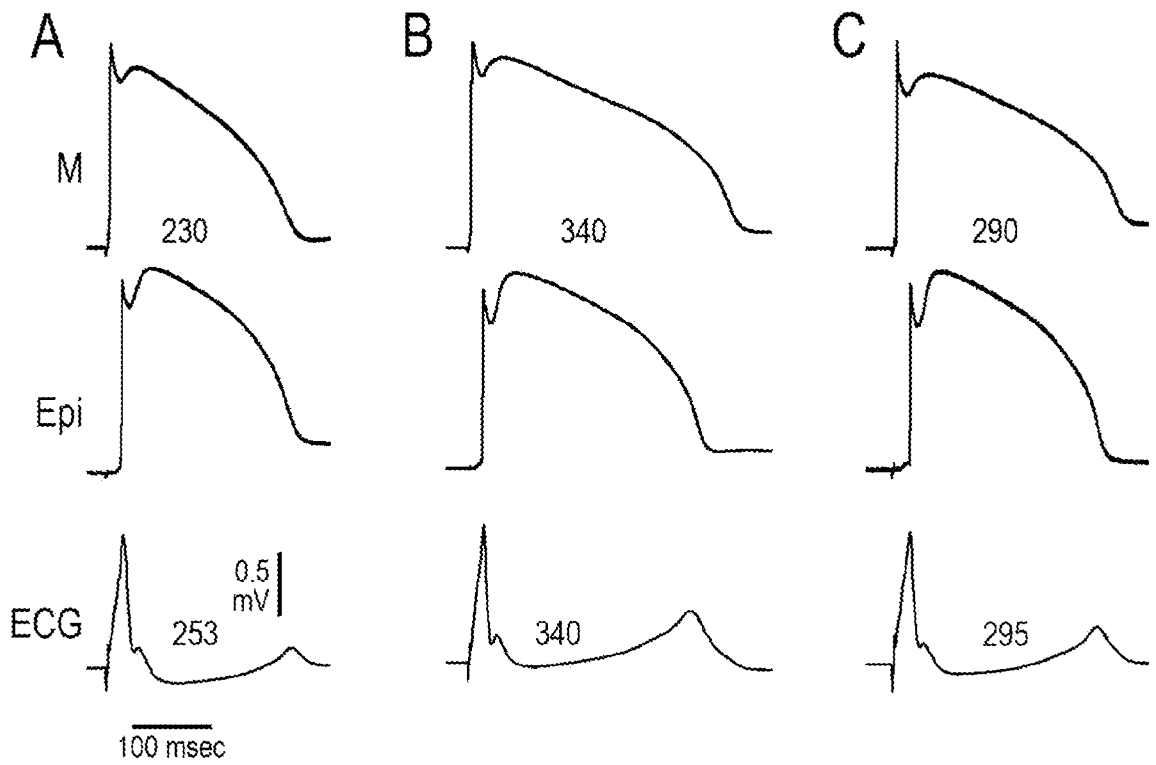
FIG. 10 depicts traces that show the effect of ibutilide (B, 50 nM) and flecainide (C, 1.5 μM) and control (A) in a canine LV wedge preparations.

Resulting traces are depicted in FIG. 10, where, from top bottom, each panel shows M (mid-myocardial) and Epi (epicardial) action potential (AP) recordings and the corresponding ECG (BCL=2000 msec). Panel A: Control. Panel B: Recordings obtained after 40 min of perfusion with ibutilide (50 nM). Panel C: Recordings obtained after the addition of flecainide (1.5 μM; 30 min) to the perfusate. The numbers appearing under M APs indicate APD90 values, and those on the ECG recordings indicate QT interval values. Ibutilide significantly prolonged repolarization (QT interval and Tpeak-Tend were dramatically prolonged). Addition of flecainide partially reversed the effect of ibutilide.

Example 8: Single Dose Pharmacokinetic and Pharmacodynamic Study in Swine

A study was conducted to determine a comparative pharmacokinetic/pharmacodynamic (PK/PD) response of a test article (flecainide or ibutilide) when administered via intravenous injection to study subjects (Sinclair pigs) individually or as a flecainide-ibutilide combination.

Flecainide acetate was provided as a 90 nM acetate buffered solution (pH 5.2) for intravenous injection. Ibutilide hemifumarate was provided as a 90 nM acetate buffered solution (pH 5.2) for intravenous injection.

The study used 9 male Sinclair swine, aged 3-5 months with body weights at study start between 13.5-16 kg.

After the animals were transferred to study, all animals were randomly assigned to treatment groups per the study design described below. This study was designed as a cross-over design with a minimum of 1-week washout between Treatment "A" and Treatment "B". The test articles (flecainide and ibutilide-antiarrhythmic agents) were administered as individual or combined doses via intravenous (IV) infusion at a low dose regimen ("A") and then at a higher dose regimen ("B"). Electrocardiograms (EKGs) were performed prior to infusion and within 30 minutes of dose completion for both "A" and "B" treatments. Infusions were performed under sedation and anesthesia was maintained post-infusion for the duration of the blood collections. Blood was collected following TABLE 5 below: prior to infusion, halfway through infusion, and at 0, 2, 4, 6, 8, 10, 15, 30, 45, 60, and 120 minutes post-infusion completion for both treatment "A" and "B".

TABLE 5

| Group | Target Dose$^{A}$ (mg/kg) | Target Dose$^{B}$ (mg/kg) | Regimen | Blood Collection Timepoints |
|---|---|---|---|---|
| 1 | 1 | 2 | Flecainide | Blood was collected prior to infusion, halfway through infusion, and 0, 2, 4, 6, 8, 10, 15, 30, 45, 60 and 120 minutes post-infusion completion |
| 2 | 0.007 | 0.014 | Ibutilide | |
| 3 | 1 + 0.007 | 2 + 0.014 | Flecainide + Ibutilide | |

$^{A, B}$Treatment "A" precedes treatment "B" by a 1-week washout. Dose was administered at a flow rate of 1 mL/min Test Article and Vehicle Formulation.

The formulations used in the study are specified in TABLE 6.

TABLE 6

| Formulation | Target | Actual |
|---|---|---|
| Formulation 1° | 2 mg/mL flecainide acetate, pH 5.20 | 2.0 mg/mL flecainide acetate, pH 5.20 |
| Formulation 1b | 1 mg/mL flecainide acetate, target pH 5.20 | 1.0 mg/mL flecainide acetate, pH 5.22 |
| Formulation 2° | 0.014 mg/mL ibutilide hemifumarate, target pH 5.20 | 0.0144 mg/mL ibutilide hemifumarate, pH 5.18 |
| Formulation 2b | 0.007 mg/mL ibutilide hemifumarate, target pH 5.20 | 0.0075 mg/mL ibutilide hemifumarate, pH 5.19 |
| Formulation 3° | 2 mg/mL flecainide acetate, 0.014 mg/mL ibutilide fumarate, target pH 5.20 | 2.0 mg/mL flecainide acetate, 0.0151 mg/mL ibutilide hemifumarate, pH 5.21 |
| Formulation 3b | 1 mg/mL flecainide acetate, 0.007 mg/mL ibutilide fumarate, target pH 5.20 | 1.0 mg/mL flecainide acetate, 0.0076 mg/mL ibutilide hemifumarate, pH 5.20 |

Test Article and Vehicle Administration: Intravenous Infusion.

All animals underwent anesthesia for intravenous (IV) infusion (approximately 10 mL/kg over a 10-minute period) of test articles and blood collections per ACL-2010, *Procedures for Injections, Blood Withdrawal, and Dermal Dosing in Swine*. Swine were sedated with target doses of 0.5 mg/kg of midazolam and 25 mg/kg of ketamine (actual doses ranging from 0.5215-0.519 mg/kg and 24.83-25.33 mg/kg, respectively), with the exception of one animal which received half the target doses per veterinary instruction (0.26 mg/kg midazolam and 12.67 mg/kg ketamine). Animals were anesthetized with isoflurane (5% for induction, ~0.5-3% for maintenance) via face mask inhalation for the duration of the infusion and blood collections. All anesthesia and monitoring of vital parameters were performed in accordance with ACL-2011. Animal weights and administered formulation volumes are summarized in TABLE 7.

TABLE 7

| Animal ID | Treatment A Body Weight (kg) | Treatment A Volume (mL) | Treatment B Body Weight (kg) | Treatment B Volume (mL) |
|---|---|---|---|---|
| 1001 | 14.5 | 14.5 | 14.5 | 14.5 |
| 1002 | 13.5 | 13.5 | 15.0 | 15.0 |
| 1003 | 16.0 | 16.0 | 15.0 | 15.0 |
| 2001 | 14.0 | 14.0 | 15.0 | 15.0 |
| 2002 | 14.0 | 14.0 | 15.0 | 15.0 |
| 2003 | 15.0 | 15.0 | 14.5 | 14.5 |
| 3001 | 16.5 | 16.5 | 16.5 | 16.5 |
| 3002 | 14.0 | 14.0 | 13.5 | 13.5 |
| 3003 | 14.5 | 14.5 | 14.0 | 14.0 |

Clinical Observations and Survival.

All animals survived to study completion. Animals underwent clinical observations continuously while the animals are under anesthesia during, pre- and post-dosing through to final blood collection per TXP-1532, Pharmacologic and Toxicological Observations of Experimental Animals, and twice daily per ACL-1974 Receipt, Quarantine and Husbandry of Swine. Abnormal clinical observations included two animals from the ibutilide treatment group who stopped breathing under anesthesia. One of the animals in question was during the high-dose treatment ("B") and was intubated and provided oxygen under the direction of veterinary staff. The other animal was during the low-dose treatment ("A") and returned to breathing normally without need of additional support. Both of these abnormal events were deemed due to anesthesia.

Bodyweights.

Average group body weights are shown in TABLE 8.

TABLE 8

| Group | Randomization Weight Ave (kg) | Randomization Weight SD | Dosing Weight Treatment A Ave (kg) | Dosing Weight Treatment A SD | Dosing Weight Treatment B Ave (kg) | Dosing Weight Treatment B SD |
|---|---|---|---|---|---|---|
| Flecainide | 14.5 | 0.5 | 13.8 | 1.0 | 14.8 | 1.0 |
| Ibutilide | 14.7 | 1.3 | 14.3 | 0.6 | 15.0 | 1.3 |
| Combined | 14.8 | 0.3 | 14.8 | 0.3 | 14.7 | 1.6 |

Electrocardiograms (EKG).

All animals underwent an electrocardiogram (EKG) using the EMKA system. EKGs were collected prior to dosing (any time prior to each dose administration) and within 30 minutes completion of each infusion per TLE-2125, *Physiological Data Collection for Large Animals Using the emkaPACK4g Acquisition System*. ECG waveforms were quantitatively evaluated for heart rate (HR) and PR, QRS, and QT/QTc intervals using a validated ecgAUTO system (v3.5.5, emka TECHNOLOGIES, Paris, France).

QTcB (Bazett's)=QT/$RR_{(1/2)}$

QTcF (Fridericia)=QT/$RR_{(1/3)}$

QTcV (Van de Water)=QT−0.087 (RR−1000)

Where RR=time between successive beats, measured in milliseconds.

In this study, HR was variable at baseline (consistent mean values in the flecainide Group 1 treatments A/B; variable in the ibutilide Group 2, treatment B; and strong reductions in the combined Group 3, treatment B). Post-infusion, all groups with either treatment A or B experienced HR reductions. PR interval prolongations were noted in all groups/treatments post-infusion, driven directly by pharmacological action and indirectly by decreases in HR. QT/QTc was increased in ibutilide for treatments A/B. The QT/QTcV increase was smaller in combined groups, which was deemed due to a counter effect of flecainide.

Baseline-normalized post-infusion physiological parameters are presented in TABLE 9 and TABLE 10 for Treatment A and Treatment B, respectively.

TABLE 9

| Animal ID | | Avg HR % | Avg PR % | Avg QRS % | Avg QT % | Avg QTcB % | Avg QTcF % | Avg ATcV % |
|---|---|---|---|---|---|---|---|---|
| 1001 | | −7.2 | 22.3 | 0.1 | −3.5 | −7.1 | −5.9 | −4.4 |
| 1002 | | −26.5 | 17.5 | −1.3 | −1.6 | −15.7 | −11.2 | −6.0 |
| 1003 | | −9.6 | 8.6 | 3.5 | −1.4 | −6.3 | −4.7 | −2.6 |
| Group 1 | Mean | −14.5 | 16.1 | 0.7 | −2.2 | −9.7 | −7.3 | −4.3 |
| | SD | 10.5 | 7.0 | 2.5 | 1.2 | 5.2 | 3.5 | 1.7 |
| 2001 | | −19.5 | 4.8 | 8.2 | 19.9 | 7.5 | 11.5 | 14.4 |
| 2002 | | −54.7 | 40.7 | 7.3 | 28.1 | −13.4 | −1.4 | 10.5 |
| 2003 | | −28.7 | 7.1 | 4.9 | 11.7 | −5.8 | −0.3 | 5.0 |
| Group 2 | Mean | −34.3 | 17.5 | 6.8 | 19.9 | −3.9 | 3.3 | 10.0 |
| | SD | 18.2 | 20.1 | 1.7 | 8.2 | 10.6 | 7.1 | 4.7 |
| 3001 | | −7.7 | −0.2 | 25.5 | 16.3 | 11.8 | 13.3 | 13.4 |
| 3002 | | −21.0 | 20.4 | 11.1 | 17.0 | 3.9 | 8.1 | 11.4 |
| 3003 | | −21.8 | 25.3 | −3.2 | 6.3 | −6.1 | −2.1 | 1.9 |
| Group 3 | Mean | −16.8 | 15.1 | 11.2 | 13.2 | 3.2 | 6.4 | 8.9 |
| | SD | 8.0 | 13.5 | 14.4 | 6.0 | 9.0 | 7.8 | 6.1 |

TABLE 10

| Animal ID | | Avg HR % | Avg PR % | Avg QRS % | Avg QT % | Avg QTcB % | Avg QTcF % | Avg ATcV % |
|---|---|---|---|---|---|---|---|---|
| 1001 | | 0.4 | 13.3 | 4.4 | 12.6 | 12.8 | 12.7 | 11.4 |
| 1002 | | −18.8 | 9.7 | 3.3 | 2.1 | −8.0 | −4.7 | −2.3 |
| 1003 | | −13.6 | 24.6 | 18.2 | 0.1 | −6.9 | −4.6 | −1.9 |
| Group 1 | Mean | −10.7 | 15.8 | 8.7 | 4.9 | −0.7 | 1.1 | 2.4 |
| | SD | 9.9 | 7.8 | 8.3 | 6.7 | 11.7 | 10.0 | 7.8 |
| 2001 | | −38.3 | 28.2 | 7.7 | 26.6 | −0.6 | 7.8 | 16.1 |
| 2002 | | −12.7 | 2.9 | 16.8 | 16.3 | 8.5 | 11.0 | 13.1 |
| 2003 | | −15.4 | 14.7 | 6.5 | 18.3 | 8.9 | 11.9 | 13.6 |
| Group 2 | Mean | −22.1 | 15.3 | 10.3 | 20.4 | 5.6 | 10.3 | 14.3 |
| | SD | 14.1 | 12.7 | 5.6 | 5.5 | 5.3 | 2.2 | 1.6 |
| 3001 | | −8.7 | 16.7 | 7.3 | 11.6 | 6.6 | 8.3 | 9.2 |
| 3002 | | −3.7 | 16.4 | 17.5 | 10.8 | 8.8 | 9.4 | 9.3 |
| 3003 | | −6.8 | 13.9 | 2.0 | 9.8 | 6.0 | 7.2 | 7.9 |
| Group 3 | Mean | −6.4 | 15.7 | 8.9 | 10.7 | 7.1 | 8.3 | 8.8 |
| | SD | 2.5 | 1.6 | 7.9 | 0.9 | 1.5 | 1.1 | 0.8 |

Bioanalytical.

Blood samples were collected and placed into $K_3$EDTA blood collection tubes at timepoints described above. Tubes were centrifuged, plasma separated, and aliquoted into appropriately labeled vials. Samples were stored at −70 to −90° C. until they were transferred to the for analysis. The $C_{max}$ of test articles was observed either at or near the end of infusion. Additionally, test articles maintained a dose-response between low and high doses (treatments A and B). Test article plasma concentrations were above the lower limit of quantitation at the 120-minute collection timepoint.

Figure 11:
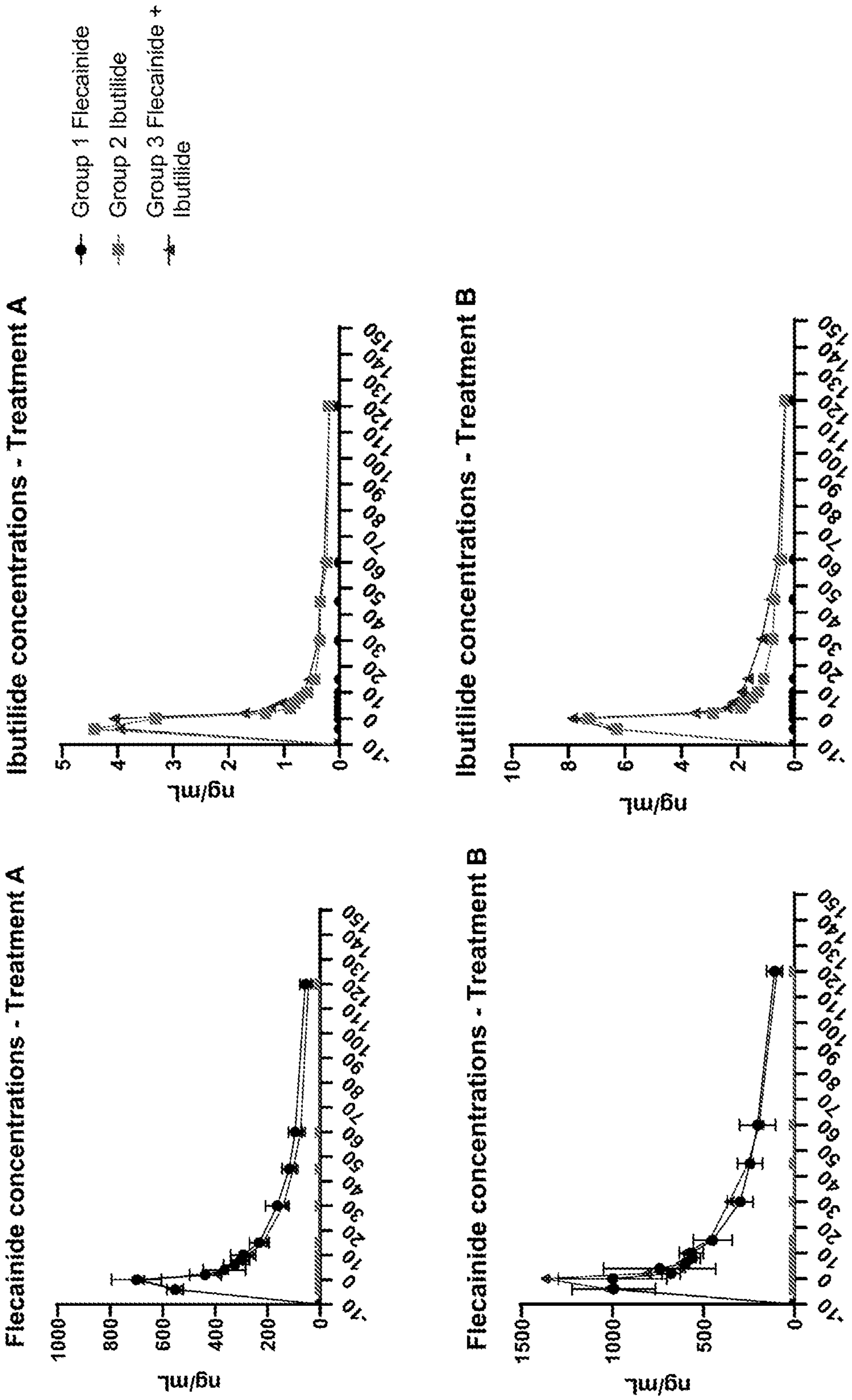
FIG. 11 provides charts summarizing the pharmacokinetic profile of flecainide and ibutilide in animals administered 1 mg/kg flecainide acetate (Treatment A, group 1), 0.007 mg/lg ibutilide hemifumarate (Treatment A, group 2), 1 mg/kg flecainide acetate+0.007 mg/lg ibutilide hemifumarate (Treatment A, group 3), 2 mg/kg flecainide acetate (Treatment B, group 1), 0.014 mg/lg ibutilide hemifumarate (Treatment B, group 2), and 2 mg/kg flecainide acetate+0.014 mg/lg ibutilide hemifumarate (Treatment B, group 3).

FIG. 11 provides charts summarizing the pharmacokinetic profile of flecainide and ibutilide in animals administered 1 mg/kg flecainide acetate (Treatment A, group 1), 0.007 mg/lg ibutilide hemifumarate (Treatment A, group 2), 1 mg/kg flecainide acetate+0.007 mg/lg ibutilide hemifumarate (Treatment A, group 3), 2 mg/kg flecainide acetate (Treatment B, group 1), 0.014 mg/lg ibutilide hemifumarate (Treatment B, group 2), and 2 mg/kg flecainide acetate+0.014 mg/lg ibutilide hemifumarate (Treatment B, group 3).

Quantitative values of flecainide and ibutilide in individual animal plasma are provided in TABLE 11 and TABLE 12, respectively. The following samples were re-extracted and reanalyzed:

Treatment A: Sample ID 2003, 3001, 3002—all timepoints (39 samples)

Treatment B: Sample ID 1002, 1003—0 min and 50% dose (4 samples)

The repeat analysis was performed in duplicate and used a second sample aliquot that was not originally analyzed. The reanalysis is reported based on criteria as follows: If the result of the initial and the mean of the reanalyzed sample is within 20% agreement, the original value is kept. If the result of the initial and the mean of the reanalyzed samples is outside 20% agreement, the mean of the reanalyzed sample is reported.

TABLE 11

| | Time Point (ng/mL) | | | | | | | | | | | | |
|---|---|---|---|---|---|---|---|---|---|---|---|---|---|
| Sample ID | Pre-dose | 0 min | 50% Dose | 2 min | 4 min | 6 min | 8 min | 10 min | 15 min | 30 min | 45 min | 60 min | 120 min |
| | Treatment A | | | | | | | | | | | | |
| 1001 | BQL | 591 | 533 | 386 | 273 | 283 | 271 | 241 | 214 | 154 | 105 | 81.3 | 45.3 |
| 1002 | BQL | 765 | 536 | 502 | 396 | 368 | 341 | 337 | 276 | 213 | 150 | 126 | 80.9 |
| 1003 | BQL | 746 | 589 | 425 | 426 | 328 | 299 | 303 | 209 | 125 | 102 | 79.9 | 44.7 |
| 2001 | BQL | BQL | BQL | BQL | BQL | BQL | BQL | BQL | BQL | BQL | BQL | BQL | BQL |
| 2002 | BQL | BQL | BQL | BQL | BQL | BQL | BQL | BQL | BQL | BQL | BQL | BQL | BQL |
| 2003 | BQL* | BQL* | BQL* | BQL* | BQL* | BQL* | BQL* | BQL* | BQL* | BQL* | BQL* | BQL* | BQL* |
| 3001 | BQL* | 899* | 649* | 587* | 463* | 402* | 339* | 315* | 257* | 160* | 102* | 86.1* | 44.8* |
| 3002 | BQL* | 733* | 590* | 390* | 361* | 315* | 271* | 237* | 186* | 112* | 91.8* | 66.7* | 35.1* |
| 3003 | BQL | 431 | 390 | 201 | 284 | 286 | 271 | 259 | 212 | 148 | 115 | 69.7 | 54.9 |
| | Treatment B | | | | | | | | | | | | |
| 1001 | BQL | 1220 | 928 | 739 | 626 | 596 | 565 | 582 | 438 | 269 | 207 | 171 | 82.5 |
| 1002 | BQL | 661* | 806* | 644 | 509 | 624 | 609 | 627 | 563 | 380 | 325 | 315 | 161 |
| 1003 | BQL | 1120* | 1250* | 656 | 1090 | 574 | 517 | 496 | 352 | 248 | 203 | 127 | 88.7 |
| 2001 | BQL | BQL | BQL | BQL | BQL | BQL | BQL | BQL | BQL | BQL | BQL | BQL | BQL |
| 2002 | BQL | BQL | BQL | BQL | BQL | BQL | BQL | BQL | BQL | BQL | BQL | BQL | BQL |
| 2003 | BQL | BQL | BQL | BQL | BQL | BQL | BQL | BQL | BQL | BQL | BQL | BQL | BQL |
| 3001 | BQL | 1340 | 1140 | 871 | 777 | 785 | 650 | 735 | 558 | 472 | 301 | 242 | 121 |
| 3002 | BQL | 1720 | 1140 | 945 | 631 | 587 | 572 | 589 | 434 | 266 | 202 | 146 | 81.9 |
| 3003 | BQL | 1060 | 815 | 623 | 477 | 512 | 484 | 494 | 414 | 342 | 262 | 198 | 88.9 |

BQL (Below lower quantification limit) < 5.00 ng/mL

*Repeat sample; original value reported. See discussion in paragraphs [0325]-[0326].

TABLE 12

| | Time Point (ng/mL) | | | | | | | | | | | | |
|---|---|---|---|---|---|---|---|---|---|---|---|---|---|
| Sample ID | Pre-dose | 0 min | 50% Dose | 2 min | 4 min | 6 min | 8 min | 10 min | 15 min | 30 min | 45 min | 60 min | 120 min |
| Treatment A | | | | | | | | | | | | | |
| 1001 | BQL | BQL | BQL | BQL | BQL | BQL | BQL | BQL | BQL | BQL | BQL | BQL | BQL |
| 1002 | BQL | BQL | BQL | BQL | BQL | BQL | BQL | BQL | BQL | BQL | BQL | BQL | BQL |
| 1003 | BQL | BQL | BQL | BQL | BQL | BQL | BQL | BQL | BQL | BQL | BQL | BQL | BQL |
| 2001 | BQL | 4.71 | 4.71 | 1.47 | 0.980 | 0.656 | 0.714 | 0.498 | 0.496 | 0.385 | 0.407 | 0.288 | 0.202 |
| 2002 | BQL | 2.59 | 4.88 | 1.67 | 1.09 | 1.31 | 0.914 | 0.753 | 0.532 | 0.387 | 0.360 | 0.235 | 0.265 |
| 2003 | BQL* | 2.64** | 3.67** | 0.862** | 0.607** | 0.466** | 0.544** | 0.498** | 0.327** | 0.284** | 0.293** | 0.160** | 0.123** |
| 3001 | BQL* | 3.76** | 3.52** | 1.91** | 1.36** | 1.16** | 0.750** | 0.753** | 0.655** | 0.417** | 0.303** | 0.319** | 0.206** |
| 3002 | BQL* | 3.69** | 3.31** | 1.55** | 1.23** | 1.26** | 0.954** | 0.684** | 0.494** | 0.322** | 0.280** | 0.267** | 0.148** |
| 3003 | BQL | 4.74 | 5.06 | 1.71 | 1.17 | 0.731 | 0.637 | 0.532 | 0.536 | 0.399 | 0.483 | 0.255 | 0.193 |
| Treatment B | | | | | | | | | | | | | |
| 1001 | BQL | BQL | BQL | BQL | BQL | BQL | BQL | BQL | BQL | BQL | BQL | BQL | BQL |
| 1002 | BQL | BQL* | BQL* | BQL | BQL | BQL | BQL | BQL | BQL | BQL | BQL | BQL | BQL |
| 1003 | BQL | BQL* | BQL* | BQL | BQL | BQL | BQL | BQL | BQL | BQL | BQL | BQL | BQL |
| 2001 | BQL | 9.03 | 6.92 | 3.06 | 2.15 | 1.86 | 1.74 | 1.47 | 1.07 | 0.767 | 0.553 | 0.469 | 0.322 |
| 2002 | BQL | 7.13 | 6.39 | 3.09 | 1.97 | 1.91 | 1.48 | 1.40 | 1.08 | 0.807 | 0.807 | 0.582 | 0.372 |
| 2003 | BQL | 5.69 | 5.56 | 2.49 | 1.52 | 1.54 | 1.21 | 0.984 | 1.10 | 0.736 | 0.742 | 0.378 | 0.265 |
| 3001 | BQL | 6.71 | 6.40 | 3.32 | 2.82 | 2.62 | 2.13 | 2.43 | 1.92 | 1.42 | 1.01 | 0.747 | 0.401 |
| 3002 | BQL | 9.46 | 6.57 | 4.24 | 2.38 | 1.72 | 1.60 | 1.70 | 1.49 | 0.832 | 0.872 | 0.422 | 0.315 |
| 3003 | BQL | 7.44 | 6.31 | 3.04 | 2.00 | 2.21 | 1.62 | 1.53 | 1.55 | 1.27 | 0.736 | 0.604 | 0.293 |

BQL < 0.100 ng/mL

*Reanalyzed sample; original value reported. See discussion in paragraphs [0325]-[0326].

**Reanalyzed sample; mean of duplicate, reanalyzed samples reported. See discussion in paragraphs [0325]-[0326].

SUMMARY

Intravenous administration of the test articles (flecainide and ibutilide-antiarrhythmic agents) were evaluated at a low dose (1 mg/kg, 0.007 mg/kg, or both, respectively) and a high dose (2 mg/kg, 0.014 mg/kg, or both, respectively) regimens to evaluate the short-term pharmacological response by correlating electrocardiograms with circulating blood volumes. Electrocardiograms were performed prior to infusion and within 30 minutes of dose completion for both treatments. Blood was collected prior to infusion, halfway through infusion, and at 0, 2, 4, 6, 8, 10, 15, 30, 45, 60, and 120 minutes post-infusion completion for both treatment groups for bioanalysis.

All animals survived to study completion with no definitive test article clinical observations. The $C_{max}$ of test articles was observed either at or near the end of infusion. Additionally, test articles maintained a dose-response between low and high doses (treatments A and B). Test article plasma concentrations were above the lower limit of quantitation at the 120-minute collection timepoint.

Example 9: In Silico Modeling of Chemical Atrial Defibrillation by Flecainide and Ibutilide An in silico study was conducted to determine if a specialized combination of sodium and potassium channel blocking drugs could be utilized to terminate atrial fibrillation. A comprehensive modeling and simulation approach was applied to determine potential efficacy of flecainide and ibutilide used in combination for chemical defibrillation. An analysis of the potential safety pharmacology impact of this drug combination was also conducted through simulated safety testing on ventricular electrophysiology.

Part 1— Effect of Flecainide and Ibutilide on Atrial Electrophysiology.

Figure 12:
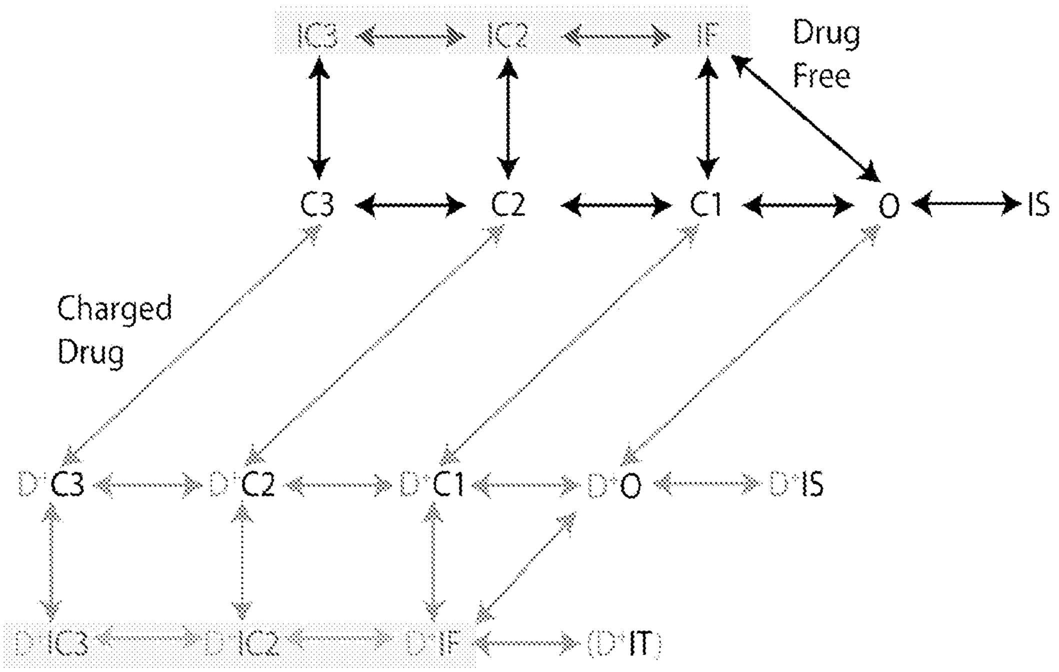
FIG. 12 is a schematic that depicts a Markov model of Na channel-drug interaction used in in silico modeling of chemical atrial defibrillation by flecainide and ibutilide.

A computational framework was formulated via numerical optimization from experimentally derived rate constants to account for the interactions between the Na channel (FIG. 12) and flecainide. FIG. 12 depicts the Markov model of Na channel-drug interaction. Drug free comprises 8 states (top rows in black). Grey lines indicate entry or egress from drug bound states denoted by a D+. Some arrows are omitted for clarity.

Figure 13:
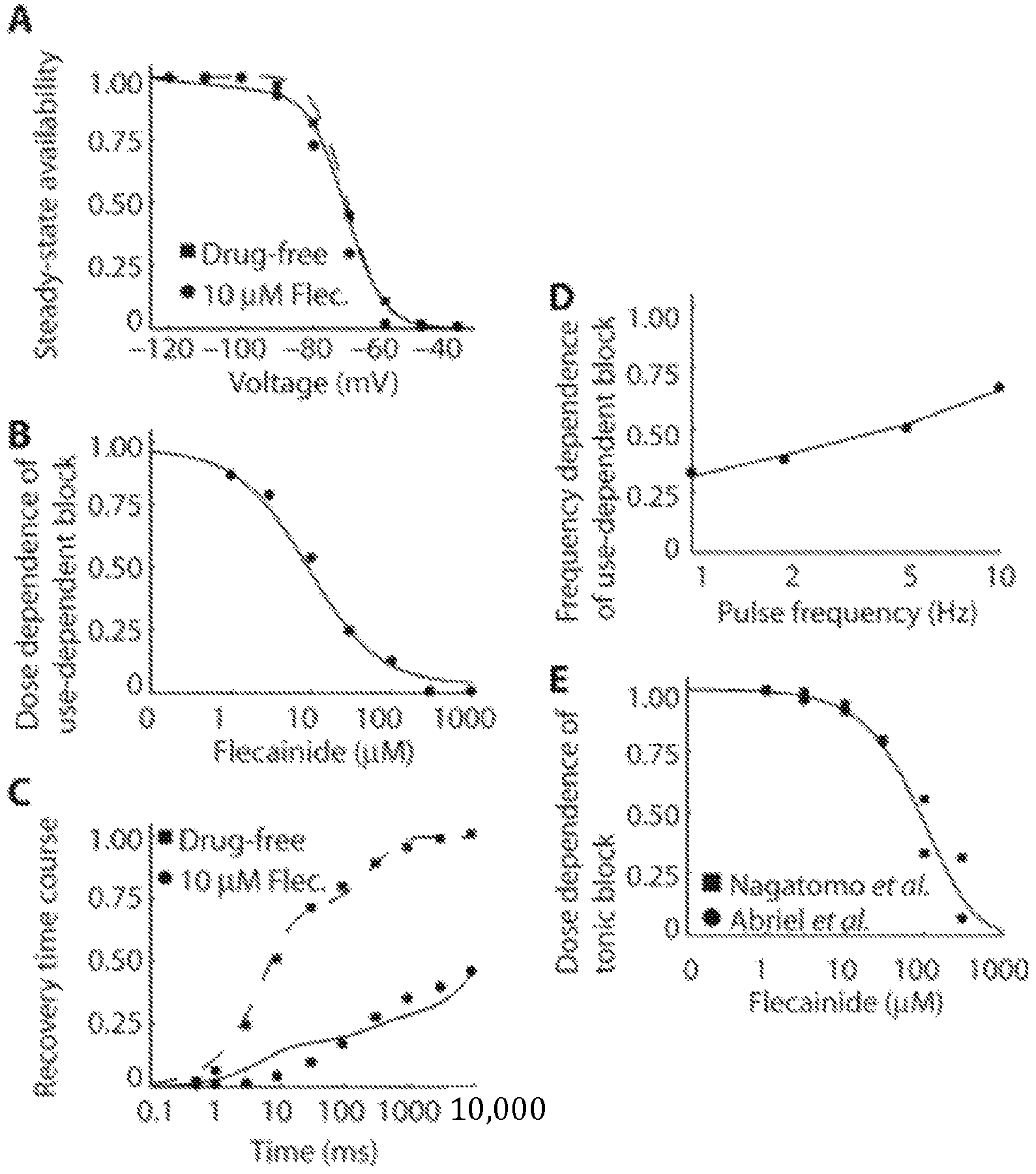
FIG. 13 provides charts that depict simulated (lines) and experimental (symbols) flecainide—Na channel interactions.

The model simulated features including frequency- and use-dependent block, tonic block and time- and voltage-dependent recovery (FIG. 13). FIG. 13 depicts simulated (lines) and experimental (symbols) flecainide—Na channel interactions. Panel A depicts steady-state channel availability, where currents were measured at −10 mV with 10 μM flecainide. Panel B depicts dose-dependence of use-dependent block (UDB) from 300 pulses to −10 mV for 25 ms from −100 mV at 5 Hz with indicated drug dose. Block is peak current for last pulse normalized to first. Panel C depicts recovery from UDB after pulses (to −10 mV for 25 ms at 25 Hz) from −100 mV with 10 μM flecainide. Panel D depicts frequency dependence of UDB, where the protocol is the same as in Panel B with 10 μM flecainide. Panel E depicts a dose dependence of tonic block (TB). One depolarizing pulse from −100 mV to −10 mV was elicited. Block is peak current fraction normalized to drug free conditions.

Figure 14:
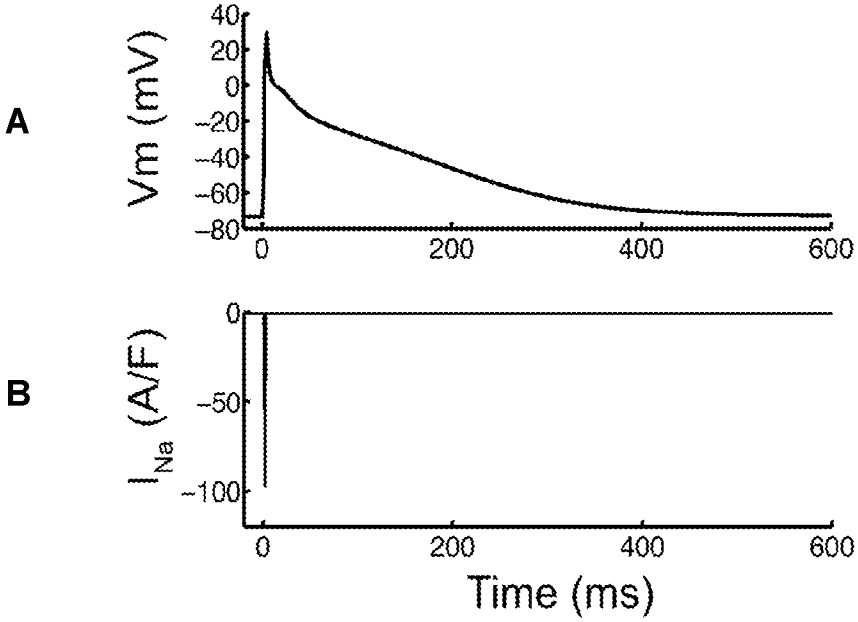
FIG. 14, Panel A provides a simulated atrial cell action potential and atrial Na current generated by a Grandi-Bers human atrial cell model described in EXAMPLE 8, and Panel B shows simulated Na current during the atrial action potential.

A similar approach was used to model the $I_{Kr}$ blocker ibutilide. Peak conductance of $I_{Kr}$ channels in a concentration dependent fashion using a concentration response relationship. The wild-type drug-free $Na^+$ and flecainide model were used as previously described in Moreno, J. D., et al., Sci Transl Med, 2011. 3(98): p. 98ra83. Models of the Na channel and drug interactions as well as the model of hERG (Yang, P. C., et al., Circ Res, 2020. 126(8): p. 947-964) and drug interactions into the Grandi-Bers atrial human cell model were incorporated. An example is provided in FIG. 14, where Panel A provides a simulated atrial cell action potential and atrial Na current generated by the Grandi-Bers human atrial cell model, and Panel B shows simulated Na current during the atrial AP.

Prediction of the Effects of Flecainide and Ibutilide in Simulated Atrial Myocytes ($APD_{90}$).

Figure 15:
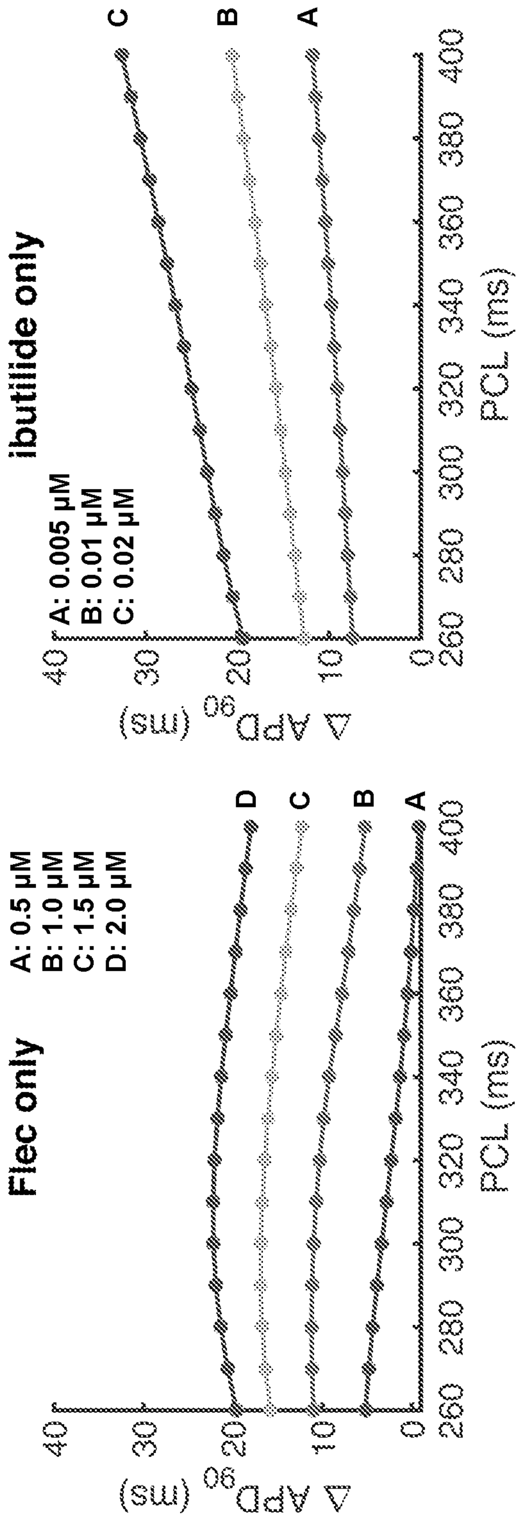
FIG. 15 depicts simulated action potential adaptation curves that show prolonged refractory period indicated as $APD_{90}$ at various pacing frequencies with flecainide alone or ibutilide alone.

When modeled in atrial myocytes, simulations predicted that flecainide alone exhibits rate-dependence reduction in excitability on atrial action potentials, while ibutilide alone exhibits reverse use-dependent prolongation of the action potential duration (FIG. 15). FIG. 15 depicts simulated action potential adaptation curves that show prolonged refractory period indicated as $APD_{90}$ at various pacing frequencies with flecainide alone or ibutilide alone. Cells were paced for 1000 beats at each cycle length, and the last $APD_{90}$ was recorded.

Figure 16:
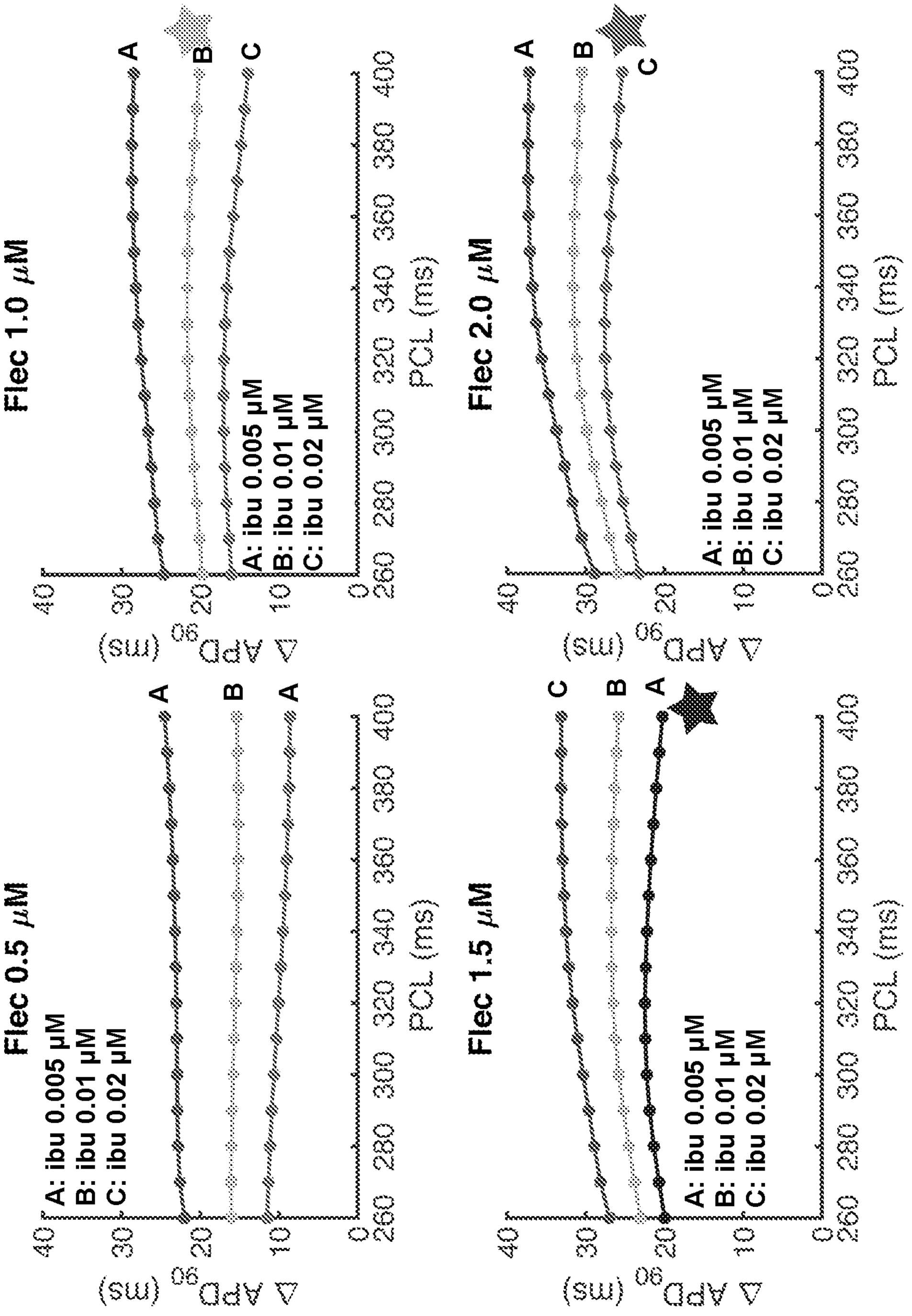
FIG. 16 depicts simulated action potential adaptation curves at various pacing frequencies with combinations of flecainide and ibutilide at various concentrations.

When flecainide and ibutilide were modeled together in atrial myocytes, the combined effects were non-additive and resulted in changes both in the effect on effective refractory period as indicated by $APD_{90}$, but also in the morphology of the action potential as indicated by the change in the slopes of the APD adaptations curves shown in FIG. 16.

Simulations predicted that flecainide reduces the reverse use-dependent prolongation of the action potential duration induced by ibutilide. Moreover, the simulations suggested three possible ideal drug combinations with low concentration of ibutilide (important for ventricular safety) for prolongation of refractory period >20 ms and flattening of the reverse use-dependence curve. These combinations are indicated by stars in the FIG. 16. Flecainide and ibutilide combined effectively prolonged action potential duration while reducing reverse use dependence. Practically, this result indicated that during atrial fibrillation when rate is fast, the drugs are suited to increase refractory period and terminate the arrhythmia. The resulting predicted preferred drug concentrations included 1.0 μM flec+0.01 μM ibu; 1.5 μM flec+0.005 μM ibu; and 2.0 μM flec+0.005 μM ibu.

Prediction of the Effects of Flecainide and Ibutilide in Simulated Atrial Tissue.

Figure 17:
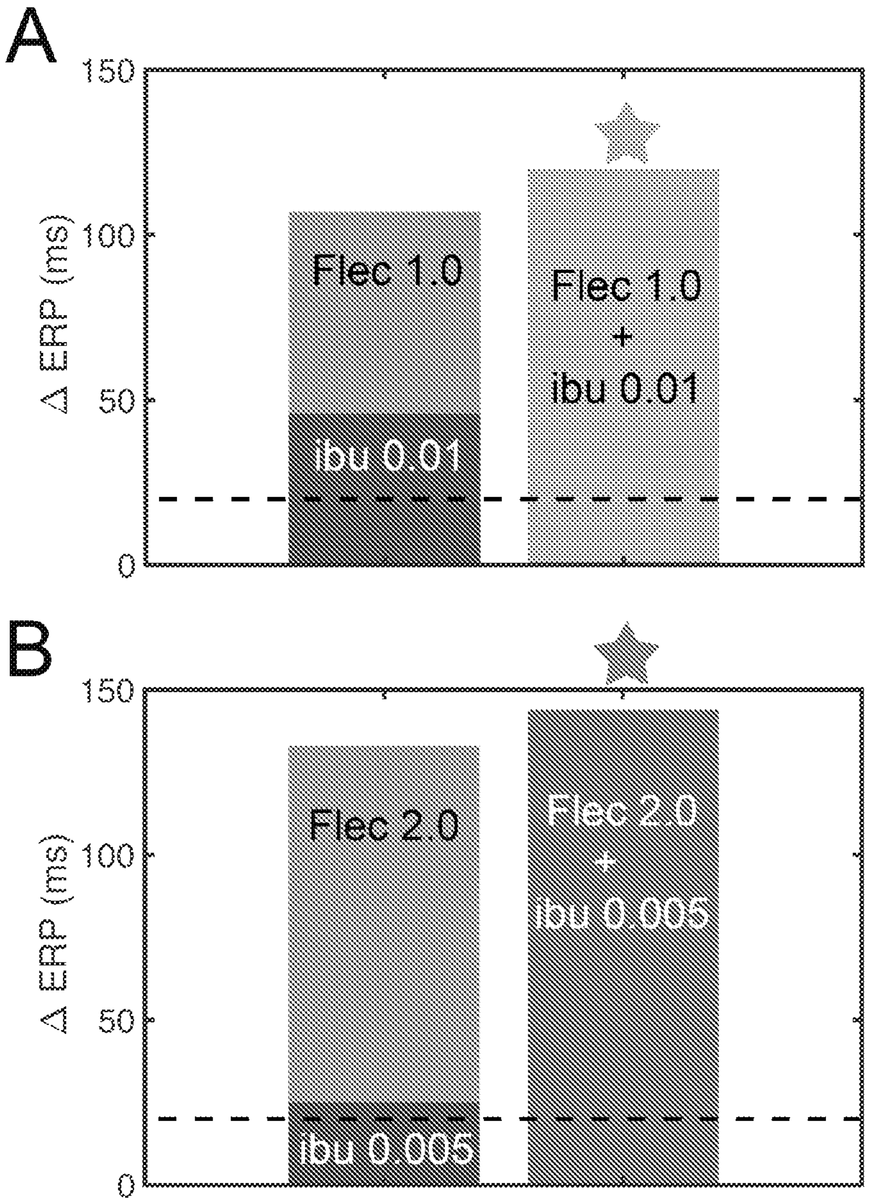
FIG. 17 depicts ΔERP in the presence of flecainide, ibutilide, combinations of flecainide and ibutilide observed in a simulated fiber composed of 165 cells connected by resistances to simulate gap junctions.

The potential for flecainide and ibutilide together to exert synergistic effects on effective refractory period in coupled tissue was explored, which indicated synergistic effects derived from the drug combination. FIG. 17 depicts ΔERP observed in a simulated fiber composed of 165 cells connected by resistances to simulate gap junctions. Refractory periods were recorded in 1D fibers with drug applications alone (left side bars) or combinations (right side bars).

Figure 18:
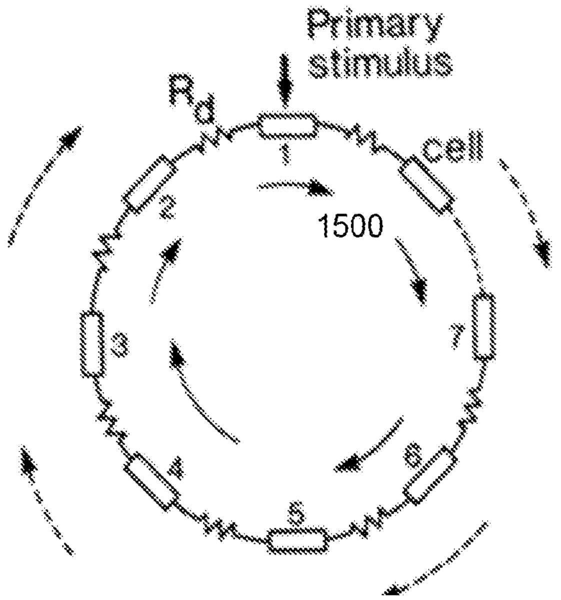
FIG. 18 depicts a simulated self-sustaining model of atrial reentry using a one-dimensional model of Grandi-Bers 1500 simulated cells connected by resistances to simulate gap junctions.

A simulated self-sustaining model of atrial reentry was also developed by constructing a representation of atrial reentry using a one-dimensional model of Grandi-Bers 1500 simulated cells connected by resistances to simulate gap junctions. A stimulus was applied on the first cell to induce propagation along the fiber. The ends of the one-dimensional tissue model were then connected when the voltage in the middle of cell was >−40 to allow continuous propagation around the ring to induced unidirectional reentry. A schematic of the model used to simulate reentrant atrial arrhythmia is depicted in FIG. 18. Wavelength (CV=56 cm/s× CL=400 ms) was set to 22.5 cm. The 1500 Grandi-Bers cells simulated were connected in a ring shape to allow self-sustaining reentrant activity.

Figure 19:
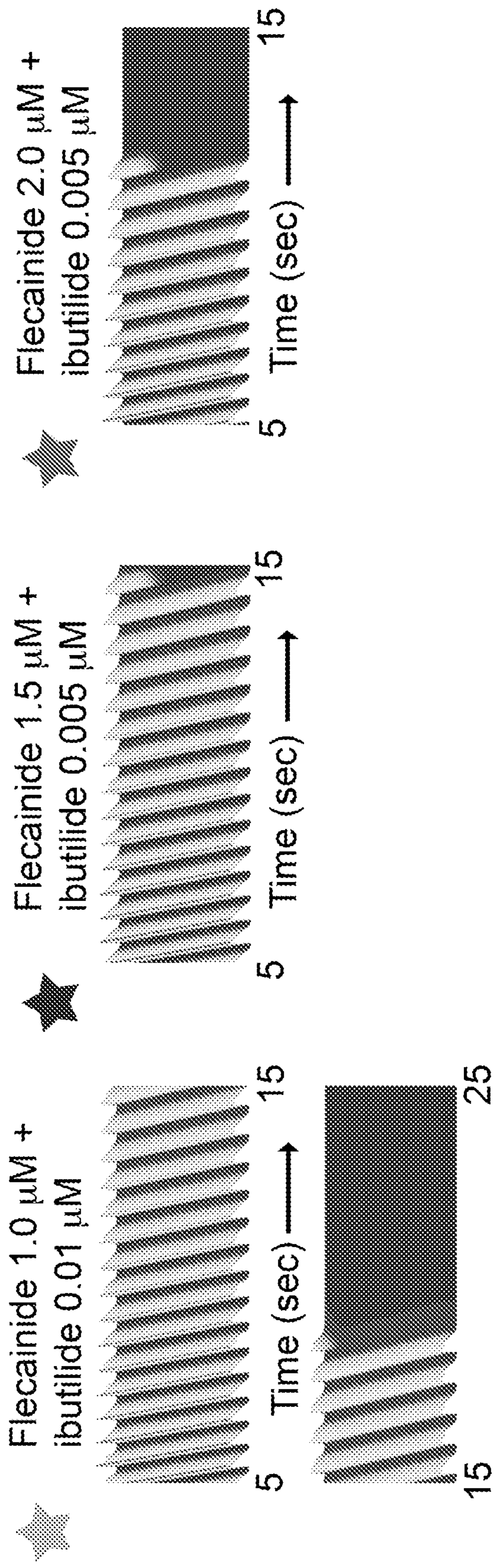
FIG. 19 depicts simulated action potentials over time for each cell in the ring model depicted in FIG. 17 when exposed to various combinations of flecainide and ibutilide, where greyscale darkness represents potential (peaks/troughs=darker) and individual cells are represented by a vertically stacked series of horizontal lines plotted over time, and where the vertical axis position of each line denotes cell position within the ring.

FIG. 19 depicts simulated action potentials in the ring model when exposed to drug combinations of flecainide and ibutilide, where greyscale darkness represents potential (peaks/troughs=darker) and individual cells are represented by a vertically stacked series of horizontal lines plotted over time, and where the vertical axis position of each line denotes cell position within the ring. The examined drug combinations of flecainide and ibutilide terminated sinus rate reentry within 20 seconds. Higher doses of flecainide combined with low dose ibutilide quickly terminated the reentry.

Figure 20:
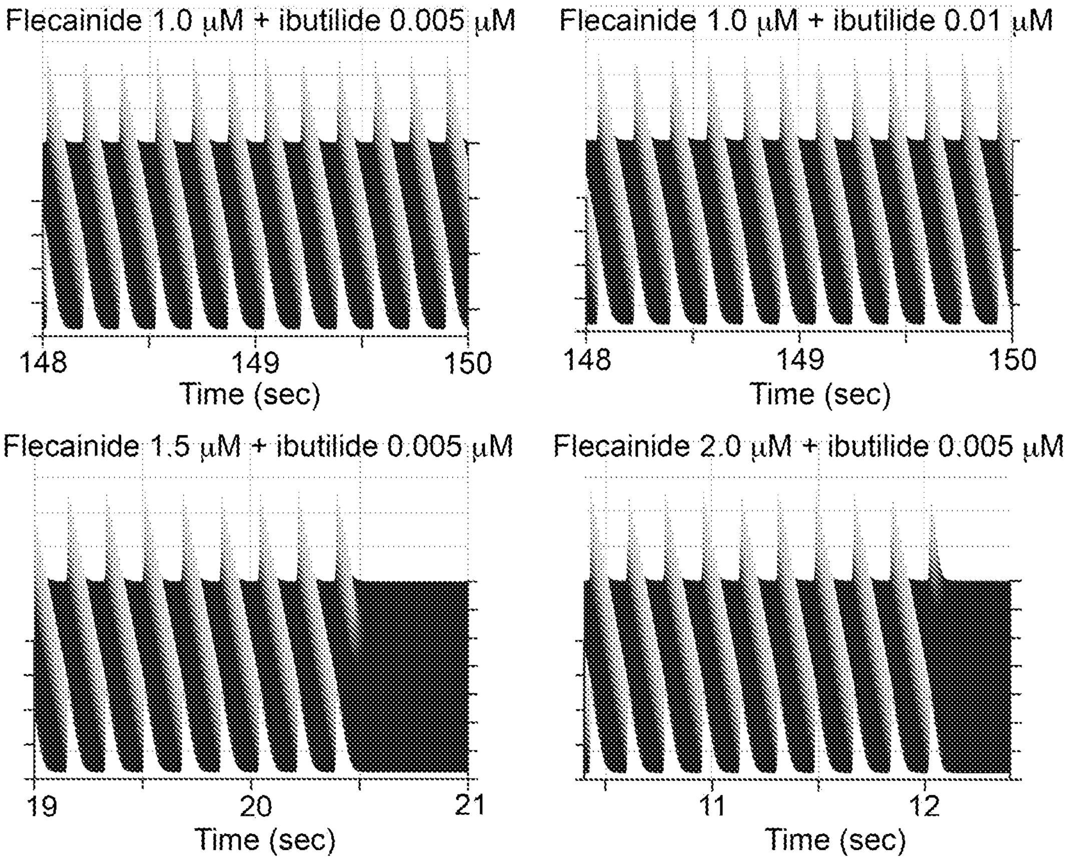
FIG. 20 depicts simulated action potentials in a one-dimensional model of Grandi-Bers 340 simulated cells in the presence of Ach (0.015 μM) when exposed to various combinations of flecainide and ibutilide, where greyscale darkness represents potential (peaks/troughs=darker) and individual cells are represented by a vertically stacked series of horizontal lines plotted over time, and where the vertical axis position of each line denotes cell position within the ring.

Atrial reentry was also simulated using a one-dimensional model of Grandi-Bers 340 simulated cells in the presence of Ach (0.015 μM) to allow self-sustaining reentrant rhythm at a rapid rate (>150 BPM). Wavelength was set to 5 cm in these cases because CL is reduced to 166 ms. As shown in the resulting action potentials depicted in FIG. 20, the lowest doses of flecainide and ibutilide did not terminate the reentry before 150 seconds, but the higher doses of flecainide combined with low dose ibutilide quickly suppressed the reentry.

Part 2: Prediction of the Effects of Flecainide and Ibutilide on Simulated Ventricular Electrophysiology (Safety Pharmacology).

Safety pharmacology computational screening was conducted in O'Hara-Rudy human computational ventricular myocytes for the effect of flecainide and ibutilide alone or in combination to promote proarrhythmia by tracking key parameters. We tracked each parameter in the absence of drug and in the presence of flecainide and ibutilide alone or in combination. The wild-type drug-free Na+ and flecainide and ibutilide models were incorporated as previously described in Moreno, J. D., et al., Sci Transl Med, 2011. 3(98): p. 98ra83, and incorporated into O'Hara-Rudy human ventricular cell model with modification.

Modified ORd Model.

The baseline O'Hara-Rudy model was modified as in Krogh-Madsen, T., et al., Front. Physiol., 2017. 8: p. 1059. The optimized O'Hara-Rudy model with clinical long QT data and with physiological bounds on intracellular calcium and sodium concentrations provides improved predictive power for Torsades de Pointes risk. The optimized model was tested against known arrhythmogenic and non-arrhythmogenic ion channel blockers and was shown to provide an improved risk assessment and reduction of false-positive outcomes generated by the original O'Hara-Rudy model (shown in Appendix below). TABLE 13 provides the modified ionic current conductance in the optimized O'Hara-Rudy model.

TABLE 13

| Currents | Scaling factor |
|---|---|
| $I_{Ks}$ | 8.09 |
| $I_{Kr}$ | 2.2 |
| $I_{CaL}$ | 2.57 |
| $I_{NCX}$ | 3.05 |
| $I_{NaK}$ | 1.91 |
| $I_{NaL}$ | Increased to 0.2% |

TABLE 14 provides ranges of $IC_{50}$ values of drugs for current inhibition tested in the optimized O'Hara-Rudy model. Flecainide $I_{Kr}$ was also assigned an $EC_{50}$ of 0.4 μM.

TABLE 14

| Currents | $IC_{50}$ (μM) |
|---|---|
| $I_{RyR}$ | 20 |
| $I_{Kr}$ | 1.5-3.9 |
| $I_{to}$ | 15.2 |
| $I_{CaL}$ | 27.1 |
| $I_{NaL}$ | 3.4-44.0 |

Figure 21:
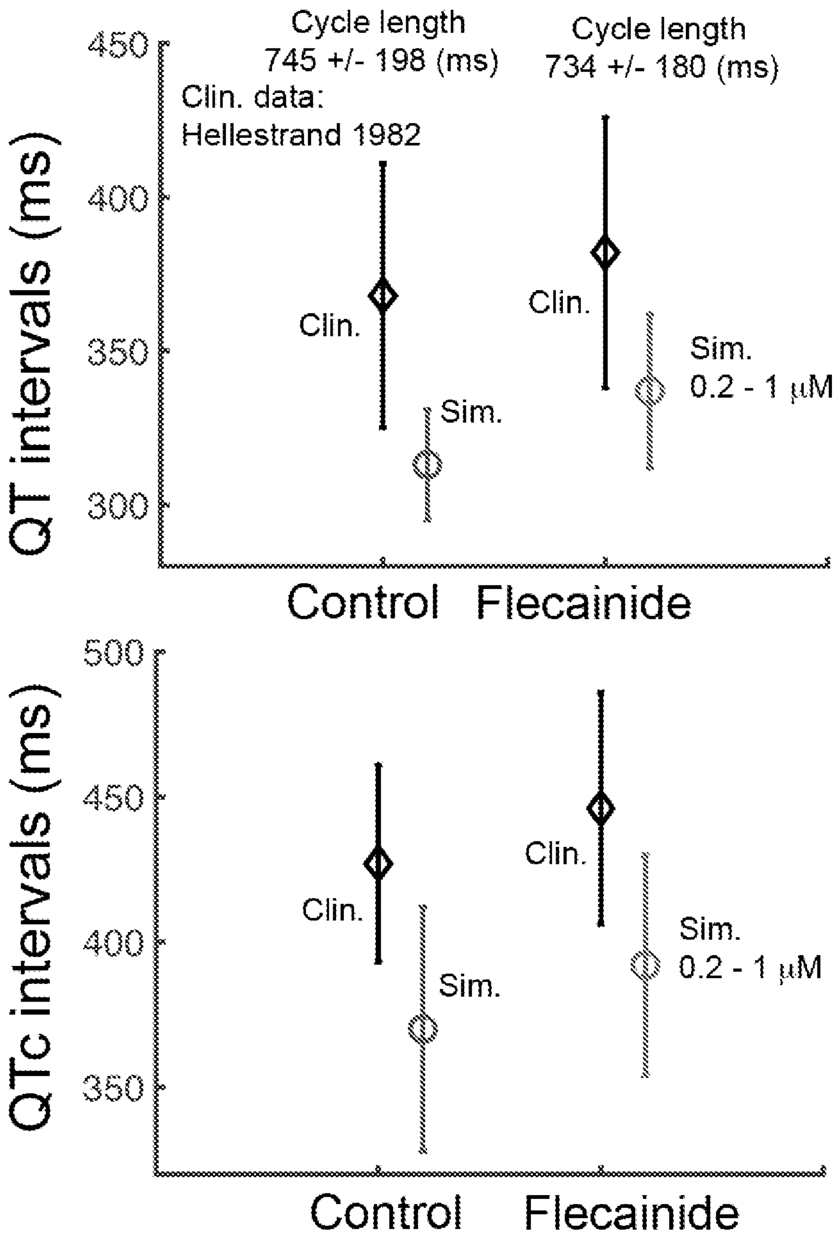
FIG. 21 shows modified O'Hara-Rudy model simulated QT/QTc intervals compared to clinical data.

The optimized O'Hara-Rudy model accurately reproduces the clinically reported effect of flecainide on the rate corrected QT interval in a 4 cm simulation to approximate the size of the human heart. FIG. 21 shows modified ORd simulated QT/QTc intervals compared to clinical data (Hellestrand, K., et al. (1982), Pacing and Clinical Electrophysiology, 5: 180-184.). Cable length was set to 4 cm in the simulations. The cable was paced for 50 beats with varying cycle length.

Figure 22:
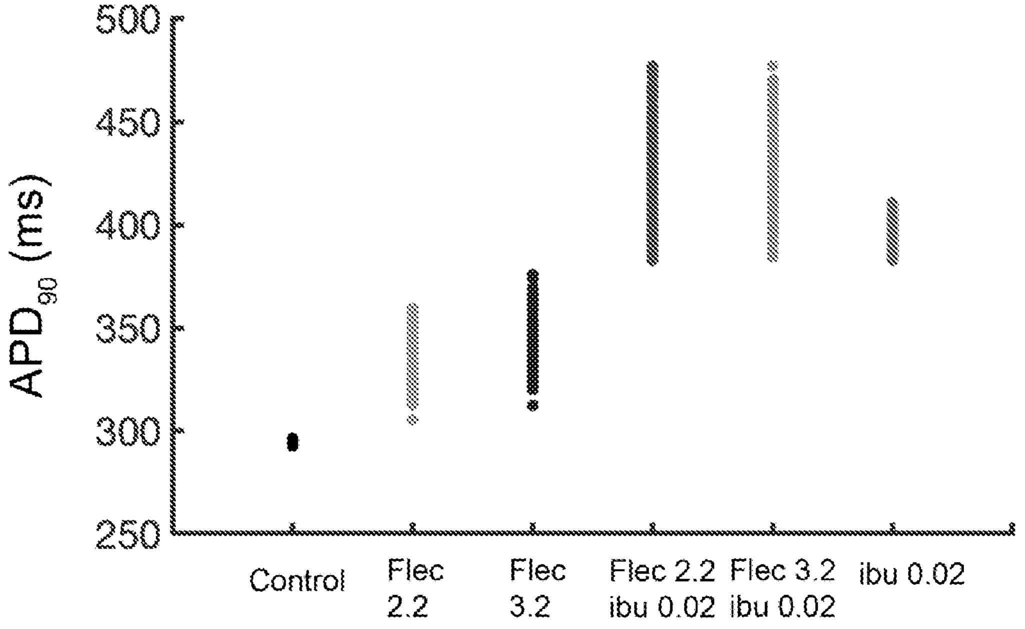
FIG. 22 shows the range of $APD_{90}$ in a population of simulated tissues resulting from application of flecainide and ibutilide alone or in combination.

FIG. 22 shows the range of $APD_{90}$ in a population of simulated tissues resulting from application of flecainide and ibutilide alone or in combination with drug affinities varying randomly within the experimentally reported ranges (combination doses predicted as ideal for eliminating atrial fibrillation in Part 1). 300 dells were generated by randomly varying $IC_{50}$ of flecainide on $I_{Kr}$ between 1.5 and 3.9 μM, $I_{NaL}$ between 3.4 and 44 μM, as well as late $I_{Na}$ current range within 0.1% to 0.2% of peak $I_{Na}$ for each case. Cells were paced at 1 Hz for 500 beats. The last beat was recorded for $APD_{90}$. On average, flecainide was predicted to cause APD prolongation. A low dose of ibutilide on average showed more APD prolongation, while the combination of drugs in doses predicted in experimental settings showed a range of outputs.

Figure 23:
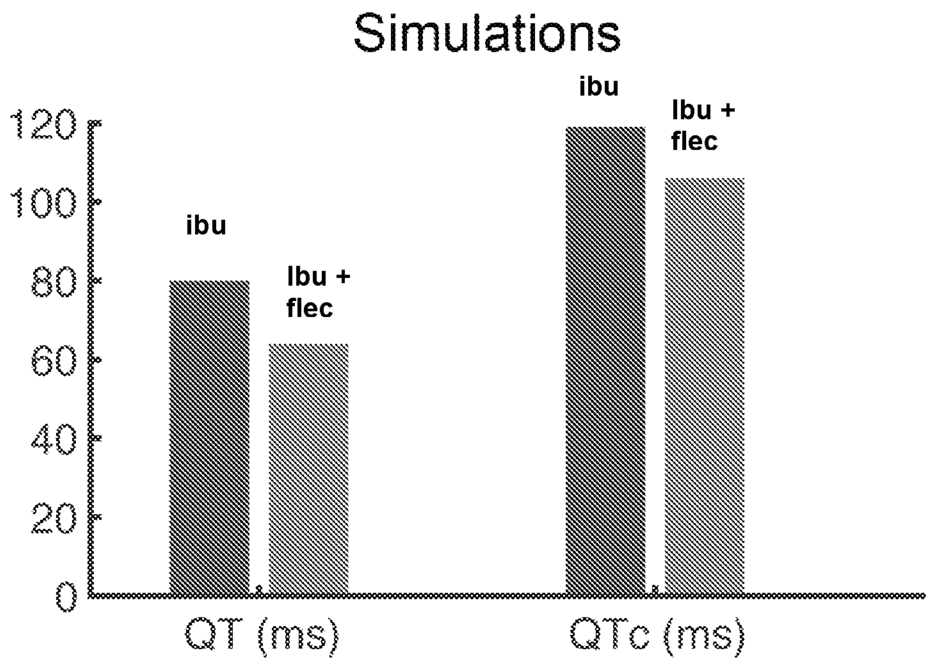
FIG. 23 shows modified O'Hara-Rudy model simulated QT/QTc with ibutilide alone (0.02 μM) or combination (ibutilide 0.02 μM+flecainide 2.2 μM).

The optimized ORd model with $IC_{50}$=3.9 μM for $I_{Kr}$ and $IC_{50}$=3.4 μM for $I_{NaL}$ was then used to simulate the effects of the drug combination on QT intervals. FIG. 23 shows the modified ORd model simulated QT/QTc with ibutilide alone (0.02 μM) or combination (ibutilide 0.02 μM+flecainide 2.2 μM).

Figure 24:
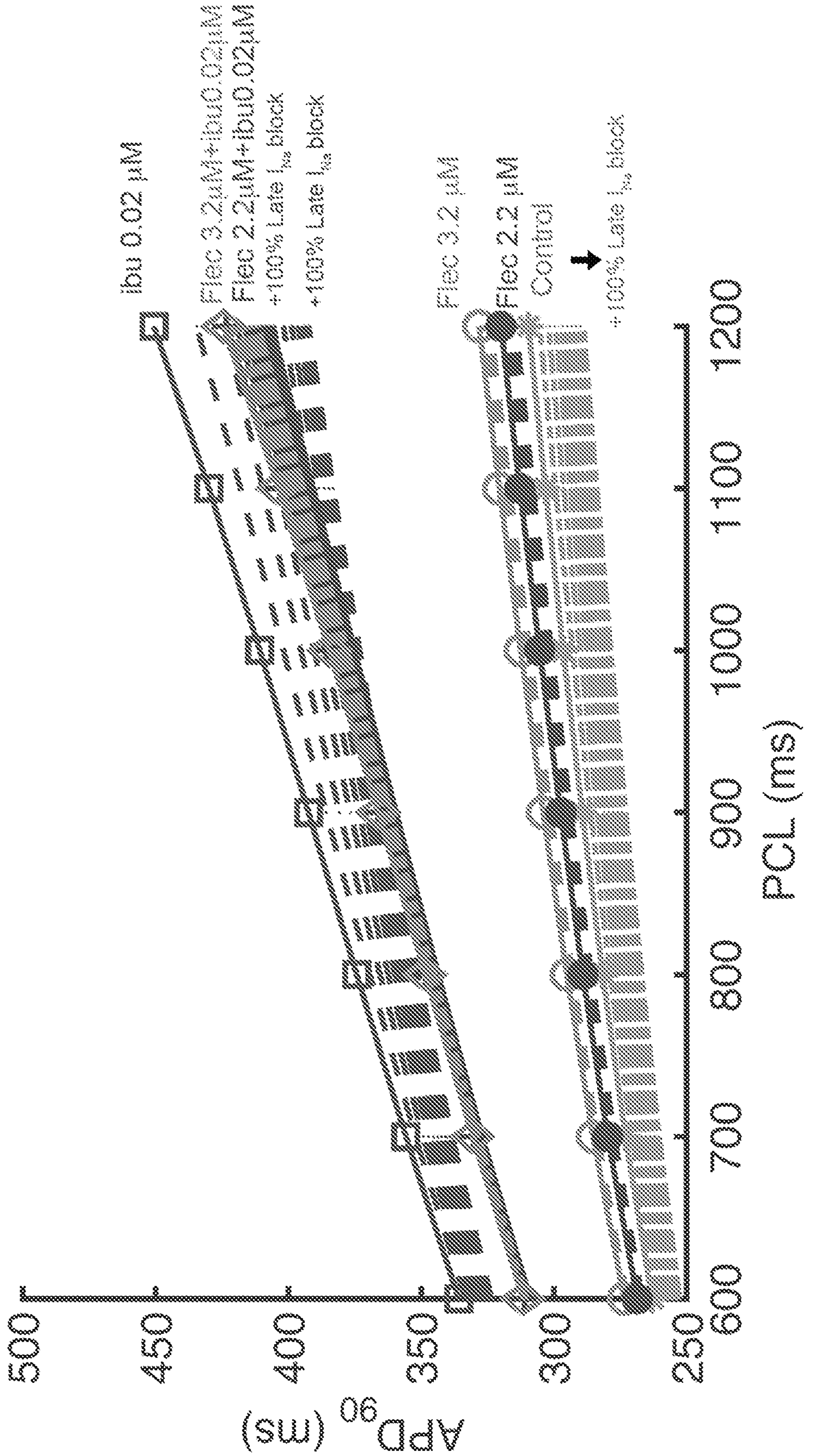
FIG. 24 shows APD adaptation curves (solid lines) from a modified O'Hara-Rudy model with or without drug applications (control cases) constructed from measurement of rate dependence curves measured as $APD_{90}$ at steady state for each pacing cycle length (from 600 ms to 1200 ms).

The effect of adding late Na block to the APD adaptation curves in the modified Ord model was predicted to determine the potential to eliminate reverse use dependence resulting from hERG block. The model predictions show that addition of a late Na current blocker can be considered as an additional adjunctive therapy during chemical atrial defibrillation to improve safety. FIG. 24 shows APD adaptation curves (solid lines) with or without drug applications (control cases) constructed from measurement of rate dependence curves measured as $APD_{90}$ at steady state for each pacing cycle length (from 600 ms to 1200 ms). Curves with additional late $Na^+$ block from 10% to 100% block with 10% increments are shown in dashed lines.

APPENDIX

Figure 25:
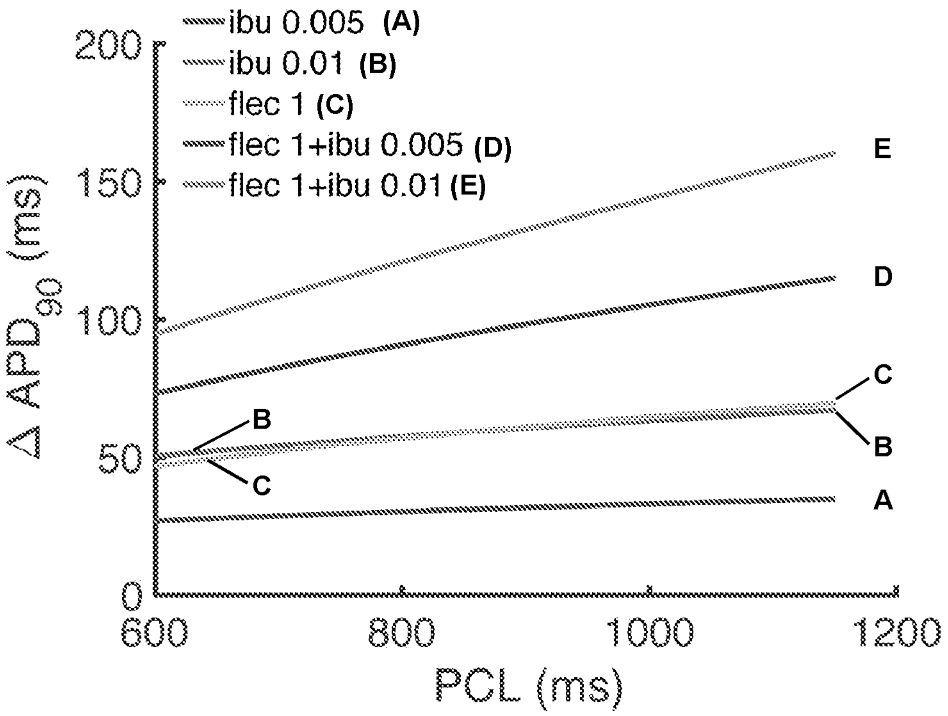
FIG. 25 shows prolonged APD adaptation curves that were constructed from measurement of reverse-use-dependence measured as $APD_{90}$ at steady state for each pacing cycle length (from 600 ms to 1200 ms) for individual drugs and combinations, using the original O'Hara-Rudy ventricular human model.

FIG. 25 shows prolonged APD adaptation curves that were constructed from measurement of reverse-use-dependence measured as $APD_{90}$ using the original O'Hara-Rudy ventricular human model at steady state for each pacing cycle length (from 600 ms to 1200 ms) for individual drugs and combinations.

Figure 26:
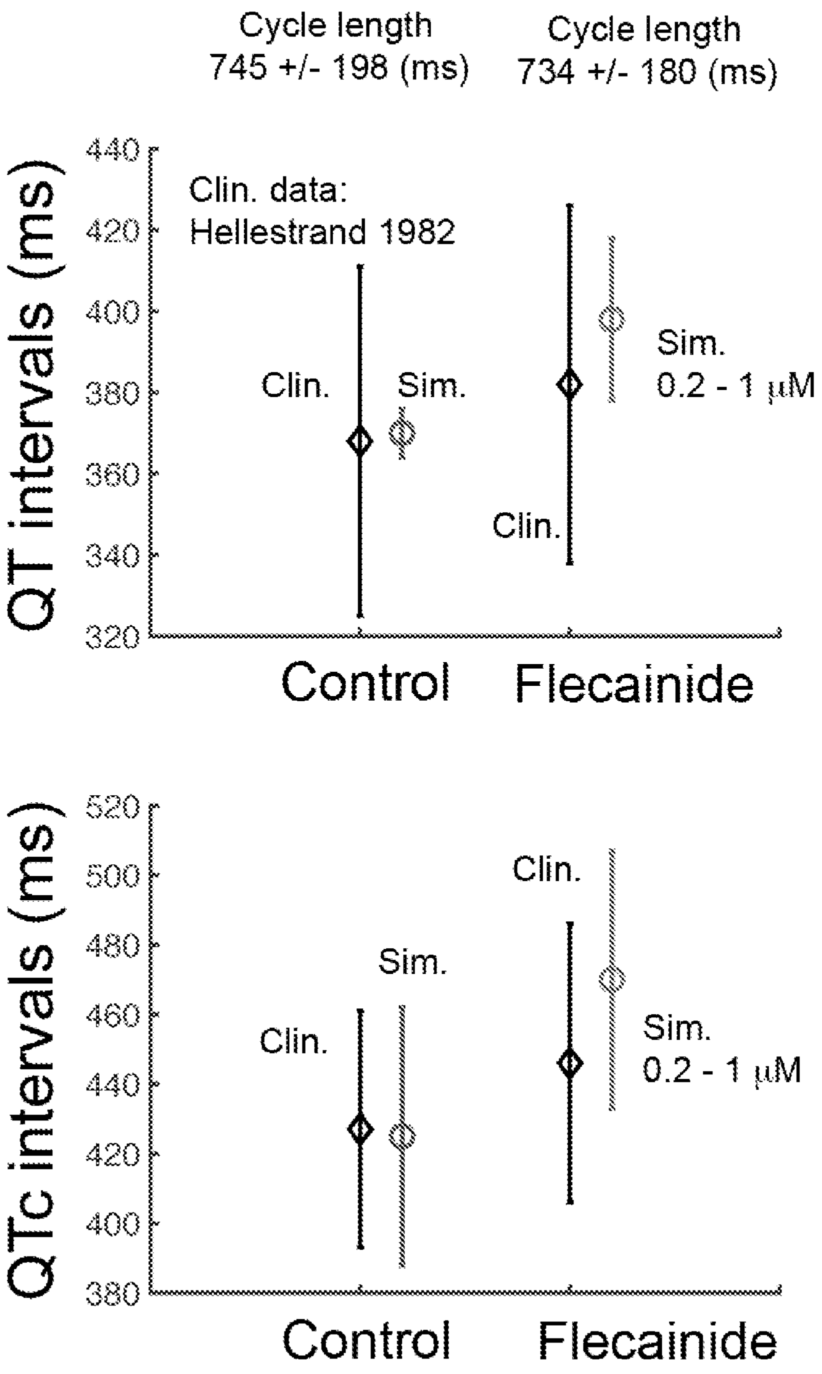
FIG. 26 shows QT/QTc intervals simulated using the original O'Hara-Rudy ventricular human model compared to clinical data.

FIG. 26 shows QT/QTc intervals simulated using the original O'Hara-Rudy ventricular human model compared to clinical data (Hellestrand 1982). Cable length was set to 4 cm in the simulations. The cable was paced for 50 beats with varying cycle length.

Methods.

Figure 27:
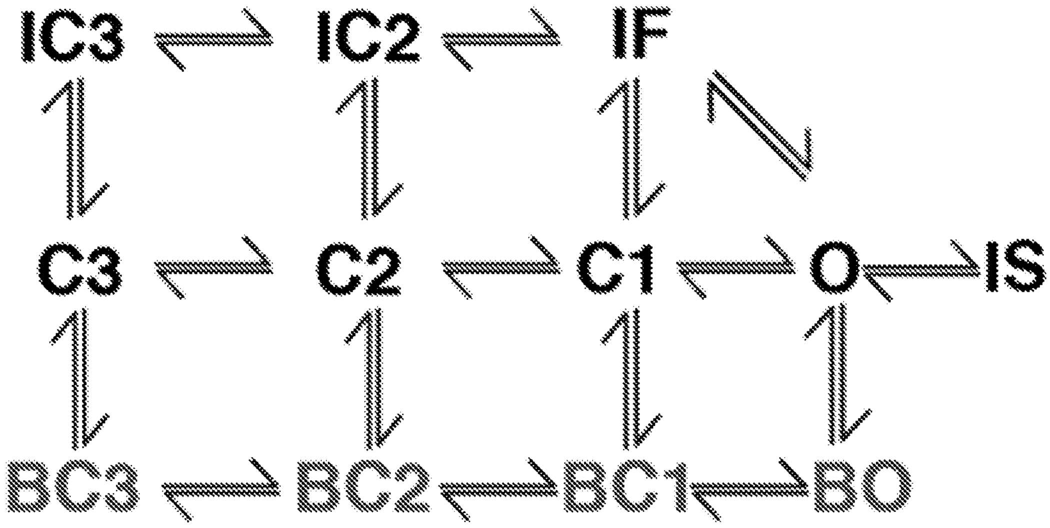
FIG. 27 depicts a drug-bound bursting regime used in a model of flecainide Na channel interactions employed in Part 1 of EXAMPLE 9, where the drug binds to states in grey.

The flecainide model was used as previously described in Moreno, J. D., et al. Sci Transl Med, 2011. 3(98): p. 98ra83., and Yang, P. C., et al., J Physiol, 2016. 594(3): p. 567-93, and included a drug-bound bursting regime (drug binding to grey states as indicated in FIG. 27). Rate constants in the upper (normal mode) states are from Moreno, J. D., et al. Bursting state affinity for the charged form of flecainide was initially set at the value found by assuming the affinity of tonic block of late $I_{Na}$ was equal to Kd at −100 mV. The value for $Kd_0$ was then calculated and used as an initial value in the optimization. For example, the affinity of TB $I_{Na,L}$ for WT is ~3.4 μM. The optimized $Kd_0$, bursting was 0.92 μM. Transition rates are provided in TABLE 15.

TABLE 15

| Transition rates<br>Drug free WT Na+ channel (ms−1) | |
|---|---|
| IC3 → IC2, C3 → C2 | α11 = 8.5539/(7.4392e−2 * exp(−V/17.0) + 2.0373e−1 * exp(−V/150)) |
| IC2 → IF, C2 → C1 | α12 = 8.5539/(7.4392e−2 * exp(−V/15.0) + 2.0373e−1 * exp(−V/150)) |
| C1 → O | α13 = 8.5539/(7.4392e−2 * exp(−V/12.0) + 2.0373e−1 * exp(−V/150)) |
| IC2 → IC3, C2 → C3 | β11 = 7.5215e−2 * exp(−V/20.3) |
| IF → IC2, C1 → C2 | β12 = 2.7574 * exp(−(V−5)/20.3) |
| O → C1 | β13 = 4.7755e−1 * exp(−(V−10)/20.3) |
| IC3 → C3, IC2 → C2, IF → C1 | α3 = 5.1458e−6 * exp(−V/8.2471) |
| C3 → IC3, C2 → IC2, C1 → IF | β3 = 6.1205 * exp(V/12.542) |
| O → IF | α2 = 13.370 * exp(V/43.749) |
| IF → O | β2 = (α13 * α2 * α3)/(β13 * β3) |
| O → IS | αx = 3.4229e−2 * α2 |
| IS → O | βx = 1.7898e−2 * α3 |
| C3, C2, C1, O → BC3, BC2, BC1, BO | μ1 = 2.0462e−7 (WT) |
| BC3, BC2, BC1, BO → C3, C2, C1, O | μ2 = 8.9731e−4 (WT) |
| **Flecainide<br>Transition rates ($ms^{-1}$)** | |
| $k_{on} = k_{closed, on}$ | [D+] * Diffusion |
| $k_{off} = k_{closed, off}$ | $k_{d, open}$ * Diffusion; ($kd_{open}$ = 11.2e−6 * exp(−0.7 * V * F/R * T)) |
| $k_{bursting, on} = k_{closed\ bursting, on}$ | [D+] * Diffusion |
| $k_{bursting, off} = k_{closed\ bursting, off}$ | $kd_{Bursting, Open}$ * Diffusion; ($kd_{Bursting, Open}$ = 95.2165e−6 * exp(−0.7 * V * F/R * T)) |
| $k_{neutral, on}$ | [D] * Diffusion |
| $k_{neutral, off}$ | 400e−6 * Diffusion |
| $k_{neutral, inactivated, on}$ | $k_{neutral, on}/2$ |
| $k_{neutral, inactivated, off}$ | 5.4e−6 * Diffusion |
| $k_{neutral, closed, on}$ | $k_{neutral, on}/2$ |
| $k_{neutral, closed, off}$ | 800e−6 * Diffusion |
| $D^+IC3 → D^+IC2$, $D^+C3 → D^+C2$, DIC3 → DIC2, DC3 → DC2 | α11 |

TABLE 15-continued

| | |
|---|---|
| $D^+IC2 \rightarrow D^+IF$, $D^+C2 \rightarrow D^+C1$, DIC2 → DIF, DC2 → DC1 | α12 |
| $D^+IC2 \rightarrow D^+IC3$, $D^+C2 \rightarrow D^+C3$, DIC2 → DIC3, DC2 → DC3 | β11 |
| $D^+IF \rightarrow D^+IC2$, $D^+C1 \rightarrow D^+C2$, DIF → DIC2, DC1 → DC2 | β12 |
| $D^+O \rightarrow D^+IS$ | αx1 = 5.7839e−05 * αx |
| $D^+IS \rightarrow D^+O$ | βx1 = 1.6689e−08 * βx |
| DO → DIS | αx2 = 2.6126e−01 * αx |
| $D^+C1 \rightarrow D^+O$ | α13c = 3.6324e−03 * a13 |
| DC1 → DO | α13n = 2.6452e+00 * α13 |
| $D^+O \rightarrow D^+C1$ | b13c = (β13 * kcon * koff * α13c)/(kon * kcoff * α13) |
| DO → DC1 | b13n = (β13 * kc_on * α13n * k_off)/(kc_off * α13 * k_on) |
| DIS → DO | βx2 = (βx * k_on * αx2 * ki_off)/(αx * ki_on * k_off) |
| $D^+O \rightarrow D^+IF$ | α22 = 1.4847e+03 * α2 |
| DO → DIF | α_22 = 4.2385e+01 * α2 |
| $D^+IF \rightarrow D^+O$ | β22 = (α13c * α22 * α33)/(β13c * β33) |
| DIF → DO | β_22 = (α_33 * α13n * α_22)/(β_33 * β13n) |
| $D^+C3 \rightarrow D^+IC3$, $D^+C2 \rightarrow D^+IC2$, $D^+C1 \rightarrow D^+IF$ | β33 = 1.7352e−06 * β3 |
| DC3 → DIC3, DC2 → DIC2, DC1 → DIF | β_33 = 2.1181e+00 * β3 |
| $D^+IC3 \rightarrow D^+C3$, $D^+IC2 \rightarrow D^+C2$, $D^+IF \rightarrow D^+C1$ | α33 = 6.7505e−05 * α3 |
| DIC3 → DC3, DIC2 → DC2, DIF → DC1 | α_33 = (ki_off * α3 * kc_on * β_33)/(ki_on * kc_off * β3) |
| Diffusion | 5500 $M^{-1}ms^{-1}$ |

Simulation of $I_{Kr}$, $I_{to}$, or $I_{CaL}$ Blockade.

To simulate the inhibitory effects of flecainide on $I_{Kr}$ $I_{to}$, or $I_{CaL}$ currents, the peak conductance, $G_X$, of each independent channel was decreased in a concentration dependent fashion using a concentration response relationship with a Hill coefficient of 1 (n=1) as follows:

$$G_X = G_{X,max} * \left( \frac{1}{1 + (\text{Drug}/IC_{50})^n} \right)$$

where $G_{X,max}$ is the nominal conductance value obtained from each ventricular myocyte model, and the $IC_{50}$ is the concentration of drug that produces a 50% inhibition of the targeted transmembrane current or intracellular organelle. TABLE 16 provides $IC_{50}$ values of drug for current inhibition.

TABLE 16

| Currents | $IC_{50}$ |
|---|---|
| $I_{RyR}$ | 20 μM |
| $I_{Kr}$ | 3.9 μM |
| $I_{to}$ | 15.2 μM |
| $I_{CaL}$ | 27.1 μM |

Flecainide Increases $I_{K1}$.

$G_{k1}$ was calculated as follows:

$$G_{K1} = G_{K1,max} * \left( 1 + \frac{0.539}{1 + (EC_{50}/\text{Drug})^{2.2}} \right)$$

where flecainide $I_{k1}$ $EC_{50}$=0.4 μM.

Ibutilide $G_{Kr}$.

$G_{Kr}$ was calculated as follows:

$$G_{Kr} = G_{Kr,max} * \left( \frac{1}{1 + (\text{Drug}/IC_{50})^n} \right)$$

where ibutilide $IC_{50}$=0.018 μM.

RyR2—Flecainide Drug-Channel Interaction.

Figure 28:
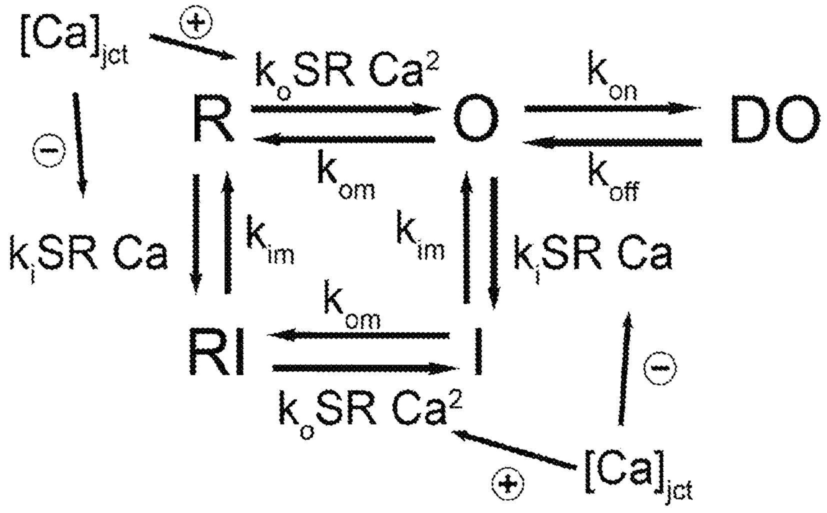
FIG. 28 is a diagram depicting a modified Shannon-Bers Markov model formulation of RyR2 Flecainide drug-channel interactions.

The Shannon-Bers Markov model formulation of the RyR2 (Shannon, T. R., et al., Biophys J, 2004. 87(5): p. 3351-71) was modified to include a drug bound state DO with transitions $k_{on}$=D*[Drug] and $k_{off}$=D*$IC_{50,Drug}$ to and from the open state O, which represent the drug diffusing to the receptor and binding or dissociating from the channel, respectively. FIG. 28 is a diagram depicting this Markov model. The diffusion rate of flecainide was estimated at 5500 $M^{-1}$ $ms^{-1}$.

EMBODIMENTS

Embodiment 1. A pharmaceutical composition comprising a sodium channel blocker, a potassium channel blocker, and one or more pharmaceutically acceptable excipients, diluents, or carriers.

Embodiment 2. The pharmaceutical composition of embodiment 1, wherein said potassium channel blocker is ibutilide, dofetilide, sotalol, methanandamide, anandamide, ambasilide, arachidonamide, A293 (2-(butylsulfonylamino)-N-[(1R)-1-(6-methoxy-3-pyridyl)propyl]-benzamide), bupivacaine, etidocaine, genistein, mepivacaine, phenytoin, quinidine, R-ropivacaine, sematilide, S-ropivacaine, tetracaine, amiodarone, dronedarone, E-4031, vemakalant, or a pharmaceutically acceptable salt thereof.

Embodiment 3. The pharmaceutical composition of embodiment 1, wherein said potassium channel blocker is a class IIIa antiarrhythmic agent.

Embodiment 4. The pharmaceutical composition of embodiment 3, wherein said class IIIa antiarrhythmic agent is ambasilide, amiodarone, dronedarone, dofetilide, ibutilide, sotalol, or vernakalant, or a pharmaceutically acceptable salt thereof.

Embodiment 5. The pharmaceutical composition of embodiment 1, wherein said potassium channel blocker is sotalol or a pharmaceutically acceptable salt thereof.

Embodiment 6. The pharmaceutical composition of embodiment 1, wherein said potassium channel blocker is sotalol hydrochloride.

Embodiment 7. The pharmaceutical composition of embodiment 1, wherein said potassium channel blocker is dofetilide or a pharmaceutically acceptable salt thereof.

Embodiment 8. The pharmaceutical composition of embodiment 1, wherein said potassium channel blocker is ibutilide or a pharmaceutically acceptable salt thereof.

Embodiment 9. The pharmaceutical composition of embodiment 1, wherein said potassium channel blocker is ibutilide hemifumarate.

Embodiment 10. The pharmaceutical composition of any one of embodiments 1-9, wherein said sodium channel blocker is a class Ia antiarrhythmic agent.

Embodiment 11. The pharmaceutical composition of embodiment 10, wherein said class Ia antiarrhythmic agent is quinidine, procainamide, or disopyramide, or a pharmaceutically acceptable salt thereof.

Embodiment 12. The pharmaceutical composition of any one of embodiments 1-9, wherein said sodium channel blocker is a class Ib antiarrhythmic agent.

Embodiment 13. The pharmaceutical composition of embodiment 12, wherein said class Ib antiarrhythmic agent is lidocaine, tocainide, phenytoin, moricizine, or mexiletine, or a pharmaceutically acceptable salt thereof.

Embodiment 14. The pharmaceutical composition of any one of embodiments 1-9, wherein said sodium channel blocker is lidocaine, or a pharmaceutically acceptable salt thereof.

Embodiment 15. The pharmaceutical composition of any one of embodiments 1-9, wherein said sodium channel blocker is lidocaine hydrochloride.

Embodiment 16. The pharmaceutical composition of any one of embodiments 1-9, wherein said sodium channel blocker is mexiletine, or a pharmaceutically acceptable salt thereof.

Embodiment 17. The pharmaceutical composition of any one of embodiments 1-9, wherein said sodium channel blocker is mexiletine hydrochloride.

Embodiment 18. The pharmaceutical composition of any one of embodiments 1-9, wherein said sodium channel blocker is a class Ic antiarrhythmic agent.

Embodiment 19. The pharmaceutical composition of embodiment 18, wherein said class Ic antiarrhythmic agent is flecainide or propafenone, or a pharmaceutically acceptable salt thereof.

Embodiment 20. The pharmaceutical composition of any one of embodiments 1-9, wherein said sodium channel blocker is flecainide or a pharmaceutically acceptable salt thereof.

Embodiment 21. The pharmaceutical composition of any one of embodiments 1-9, wherein said sodium channel blocker is flecainide acetate.

Embodiment 22. The pharmaceutical composition of any one of embodiments 1-9, wherein said sodium channel blocker is propafenone or a pharmaceutically acceptable salt thereof.

Embodiment 23. The pharmaceutical composition of any one of embodiments 1-9, wherein said sodium channel blocker is propafenone hydrochloride.

Embodiment 24. The pharmaceutical composition of embodiment 1, further comprising a $Mg^{2+}$ source.

Embodiment 25. The pharmaceutical composition of embodiment 24, wherein said $Mg^{2+}$ source comprises magnesium citrate, magnesium fumarate, magnesium acetate, magnesium aspartate, magnesium threonate, magnesium glycinate, magnesium chloride, magnesium sulfate, magnesium oxide, or magnesium malate, or a hydrate thereof.

Embodiment 26. The pharmaceutical composition of embodiment 24, wherein said $Mg^{2+}$ source comprises magnesium sulfate, or a hydrate thereof.

Embodiment 27. The pharmaceutical composition of embodiment 24, wherein said $Mg^{2+}$ source comprises magnesium sulfate heptahydrate.

Embodiment 28. The pharmaceutical composition of embodiment 24, wherein said pharmaceutical composition is in a form of a liquid solution.

Embodiment 29. The pharmaceutical composition of any one of embodiments 1, wherein said pharmaceutical composition is in a form of an inhalable dry powder.

Embodiment 30. The pharmaceutical composition of embodiment 29, wherein said dry powder is a spray dried powder.

Embodiment 31. The pharmaceutical composition of embodiment 29, wherein said dry powder is formed by supercritical enhanced dispersion by supercritical fluids (SEDS).

Embodiment 32. The pharmaceutical composition of embodiment 29, wherein said dry powder is formed by supercritical precipitation.

Embodiment 33. The pharmaceutical composition of embodiment 29, wherein said dry powder is formed by imprint lithography.

Embodiment 34. The pharmaceutical composition of embodiment 29, wherein said dry powder is formed by lyophilization.

Embodiment 35. The pharmaceutical composition of embodiment 1, wherein said pharmaceutical composition is in a form of a liquid solution.

Embodiment 36. The pharmaceutical composition of any one of embodiments 1, 29, or 35, wherein said sodium channel blocker is flecainide or a pharmaceutically acceptable salt thereof, and said potassium channel blocker is ibutilide or a pharmaceutically acceptable salt thereof.

Embodiment 37. The pharmaceutical composition of embodiment 36, wherein a mass/mass ratio of said flecainide or pharmaceutically acceptable salt thereof to said ibutilide or pharmaceutically acceptable salt thereof in said pharmaceutical composition is from 60:1 to 240:1.

Embodiment 38. The pharmaceutical composition of embodiment 36, wherein a mass/mass ratio of said flecainide or pharmaceutically acceptable salt thereof to said ibutilide or pharmaceutically acceptable salt thereof in said pharmaceutical composition is about 120:1.

Embodiment 39. The pharmaceutical composition of any one of embodiments 35-38, comprising about 1 mg/mL to about 100 mg/mL flecainide or a pharmaceutically acceptable salt thereof.

Embodiment 40. The pharmaceutical composition of any one of embodiments 35-38, comprising about 50 mg/mL to about 100 mg/mL flecainide or a pharmaceutically acceptable salt thereof.

Embodiment 41. The pharmaceutical composition of any one of embodiments 35-38, comprising about 1 mg/mL to about 30 mg/mL flecainide or a pharmaceutically acceptable salt thereof.

Embodiment 42. The pharmaceutical composition of any one of embodiments 35-38, comprising about 1 mg/mL to about 2 mg/mL flecainide or a pharmaceutically acceptable salt thereof.

Embodiment 43. The pharmaceutical composition of any one of embodiments 35-38, comprising about 75 mg/mL flecainide or a pharmaceutically acceptable salt thereof.

Embodiment 44. The pharmaceutical composition of any one of embodiments 35-38, comprising about 2 mg/mL flecainide or a pharmaceutically acceptable salt thereof.

Embodiment 45. The pharmaceutical composition of any one of embodiments 35-38, comprising about 1 mg/mL flecainide or a pharmaceutically acceptable salt thereof.

Embodiment 46. The pharmaceutical composition of embodiment 35, comprising about 1 mg/mL to about 100 mg/mL flecainide or a pharmaceutically acceptable salt thereof, and about 0.0005 mg/mL to about 5 mg/mL ibutilide or a pharmaceutically acceptable salt thereof.

Embodiment 47. The pharmaceutical composition of embodiment 35, comprising about 50 mg/mL to about 100 mg/mL flecainide or a pharmaceutically acceptable salt thereof, and about 0.0005 mg/mL to about 5 mg/mL ibutilide or a pharmaceutically acceptable salt thereof.

Embodiment 48. The pharmaceutical composition of embodiment 35, comprising about 1 mg/mL to about 30 mg/mL flecainide or a pharmaceutically acceptable salt thereof, and about 0.001 mg/mL to about 1 mg/mL ibutilide or a pharmaceutically acceptable salt thereof.

Embodiment 49. The pharmaceutical composition of embodiment 35, comprising about 1 mg/mL to about 2 mg/mL flecainide or a pharmaceutically acceptable salt thereof, and about 0.001 mg/mL to about 1 mg/mL ibutilide or a pharmaceutically acceptable salt thereof.

Embodiment 50. The pharmaceutical composition of embodiment 28, comprising about 1 mg/mL to about 100 mg/mL flecainide or a pharmaceutically acceptable salt thereof, about 0.0005 mg/mL to about 5 mg/mL ibutilide or a pharmaceutically acceptable salt thereof, and about 5 mg/mL to about 700 mg/mL magnesium sulfate or a hydrate thereof.

Embodiment 51. The pharmaceutical composition of embodiment 28, comprising about 1 mg/mL to about 30 mg/mL flecainide or a pharmaceutically acceptable salt thereof, about 0.01 mg/mL to about 1 mg/mL ibutilide or a pharmaceutically acceptable salt thereof, and about 20 mg/mL to about 700 mg/mL magnesium sulfate or a hydrate thereof.

Embodiment 52. The pharmaceutical composition of embodiment 28, comprising about 1 mg/mL to about 2 mg/mL flecainide or a pharmaceutically acceptable salt thereof, about 0.01 mg/mL to about 1 mg/mL ibutilide or a pharmaceutically acceptable salt thereof, and about 20 mg/mL to about 700 mg/mL magnesium sulfate or a hydrate thereof.

Embodiment 53. The pharmaceutical composition of embodiment 28, comprising about 75 mg/mL flecainide or a pharmaceutically acceptable salt thereof, and about 0.6 mg/mL ibutilide or a pharmaceutically acceptable salt thereof.

Embodiment 54. The pharmaceutical composition of embodiment 28, comprising about 2 mg/mL flecainide or a pharmaceutically acceptable salt thereof, and about 0.014 mg/mL ibutilide or a pharmaceutically acceptable salt thereof.

Embodiment 55. The pharmaceutical composition of embodiment 28, comprising about 1 mg/mL flecainide or a pharmaceutically acceptable salt thereof, and about 0.007 mg/mL ibutilide or a pharmaceutically acceptable salt thereof.

Embodiment 56. The pharmaceutical composition of any one of embodiments 36-38 and 46-55, wherein said ibutilide or pharmaceutically acceptable salt thereof is ibutilide hemifumarate.

Embodiment 57. The pharmaceutical composition of any one of embodiments 1, 29, or 35, wherein said sodium channel blocker is flecainide or a pharmaceutically acceptable salt thereof, and said potassium channel blocker is dofetilide or a pharmaceutically acceptable salt thereof.

Embodiment 58. The pharmaceutical composition of embodiment 36, wherein a mass/mass ratio of said flecainide or pharmaceutically acceptable salt thereof to said dofetilide or pharmaceutically acceptable salt thereof in said pharmaceutical composition is from 60:1 to 480:1.

Embodiment 59. The pharmaceutical composition of embodiment 36, wherein a mass/mass ratio of said flecainide or pharmaceutically acceptable salt thereof to said dofetilide or pharmaceutically acceptable salt thereof in said pharmaceutical composition is about 240:1.

Embodiment 60. The pharmaceutical composition of any one of embodiments 57-59, comprising about 1 mg/mL to about 100 mg/mL flecainide or a pharmaceutically acceptable salt thereof.

Embodiment 61. The pharmaceutical composition of any one of embodiments 57-59, comprising about 50 mg/mL to about 100 mg/mL flecainide or a pharmaceutically acceptable salt thereof.

Embodiment 62. The pharmaceutical composition of any one of embodiments 57-59, comprising about 1 mg/mL to about 30 mg/mL flecainide or a pharmaceutically acceptable salt thereof.

Embodiment 63. The pharmaceutical composition of any one of embodiments 57-59, comprising about 1 mg/mL to about 2 mg/mL flecainide or a pharmaceutically acceptable salt thereof.

Embodiment 64. The pharmaceutical composition of any one of embodiments 57-59, comprising about 75 mg/mL flecainide or a pharmaceutically acceptable salt thereof.

Embodiment 65. The pharmaceutical composition of any one of embodiments 57-59, comprising about 2 mg/mL flecainide or a pharmaceutically acceptable salt thereof.

Embodiment 66. The pharmaceutical composition of any one of embodiments 57-59, comprising about 1 mg/mL flecainide or a pharmaceutically acceptable salt thereof.

Embodiment 67. The pharmaceutical composition of embodiment 35, comprising about 1 mg/mL to about 100 mg/mL flecainide or a pharmaceutically acceptable salt thereof, and about 0.0005 mg/mL to about 5 mg/mL dofetilide or a pharmaceutically acceptable salt thereof.

Embodiment 68. The pharmaceutical composition of embodiment 35, comprising about 1 mg/mL to about 30 mg/mL flecainide or a pharmaceutically acceptable salt thereof, and about 0.001 mg/mL to about 1 mg/mL dofetilide or a pharmaceutically acceptable salt thereof.

Embodiment 69. The pharmaceutical composition of embodiment 35, comprising about 1 mg/mL to about 100 mg/mL flecainide or a pharmaceutically acceptable salt thereof, about 0.0005 mg/mL to about 5 mg/mL dofetilide or a pharmaceutically acceptable salt thereof, and about 5 mg/mL to about 700 mg/mL magnesium sulfate or a hydrate thereof.

Embodiment 70. The pharmaceutical composition of embodiment 35, comprising about 1 mg/mL to about 30 mg/mL flecainide or a pharmaceutically acceptable salt thereof, about 0.01 mg/mL to about 1 mg/mL dofetilide or a pharmaceutically acceptable salt thereof, and about 20 mg/mL to about 700 mg/mL magnesium sulfate or a hydrate thereof.

Embodiment 71. The pharmaceutical composition of any one of embodiments 1, 29, or 35, wherein said sodium channel blocker is flecainide or a pharmaceutically acceptable salt thereof, and said potassium channel blocker is sotalol or a pharmaceutically acceptable salt thereof.

Embodiment 72. The pharmaceutical composition of embodiment 36, wherein a mass/mass ratio of said flecainide or pharmaceutically acceptable salt thereof to said sotalol or pharmaceutically acceptable salt thereof in said pharmaceutical composition is from 0.5:1 to 2:1.

Embodiment 73. The pharmaceutical composition of embodiment 36, wherein a mass/mass ratio of said flecainide or pharmaceutically acceptable salt thereof to said sotalol or pharmaceutically acceptable salt thereof in said pharmaceutical composition is about 1:1.

Embodiment 74. The pharmaceutical composition of any one of embodiments 71-73, comprising about 1 mg/mL to about 100 mg/mL flecainide or a pharmaceutically acceptable salt thereof.

Embodiment 75. The pharmaceutical composition of any one of embodiments 71-73, comprising about 50 mg/mL to about 100 mg/mL flecainide or a pharmaceutically acceptable salt thereof.

Embodiment 76. The pharmaceutical composition of any one of embodiments 71-73, comprising about 1 mg/mL to about 30 mg/mL flecainide or a pharmaceutically acceptable salt thereof.

Embodiment 77. The pharmaceutical composition of any one of embodiments 71-73, comprising about 1 mg/mL to about 2 mg/mL flecainide or a pharmaceutically acceptable salt thereof.

Embodiment 78. The pharmaceutical composition of any one of embodiments 71-73, comprising about 75 mg/mL flecainide or a pharmaceutically acceptable salt thereof.

Embodiment 79. The pharmaceutical composition of any one of embodiments 71-73, comprising about 2 mg/mL flecainide or a pharmaceutically acceptable salt thereof.

Embodiment 80. The pharmaceutical composition of any one of embodiments 71-73, comprising about 1 mg/mL flecainide or a pharmaceutically acceptable salt thereof.

Embodiment 81. The pharmaceutical composition of embodiment 35, comprising about 1 mg/mL to about 100 mg/mL flecainide or a pharmaceutically acceptable salt thereof, and about 0.0005 mg/mL to about 5 mg/mL sotalol or a pharmaceutically acceptable salt thereof.

Embodiment 82. The pharmaceutical composition of embodiment 35, comprising about 1 mg/mL to about 30 mg/mL flecainide or a pharmaceutically acceptable salt thereof, and about 0.01 mg/mL to about 1 mg/mL sotalol or a pharmaceutically acceptable salt thereof.

Embodiment 83. The pharmaceutical composition of embodiment 28, comprising about 1 mg/mL to about 100 mg/mL flecainide or a pharmaceutically acceptable salt thereof, about 0.0005 mg/mL to about 5 mg/mL sotalol or a pharmaceutically acceptable salt thereof, and about 5 mg/mL to about 700 mg/mL magnesium sulfate or a hydrate thereof.

Embodiment 84. The pharmaceutical composition of embodiment 28, comprising about 1 mg/mL to about 30 mg/mL flecainide or a pharmaceutically acceptable salt thereof, about 0.01 mg/mL to about 1 mg/mL sotalol or a pharmaceutically acceptable salt thereof, and about 20 mg/mL to about 700 mg/mL magnesium sulfate or a hydrate thereof.

Embodiment 85. The pharmaceutical composition of any one of embodiments 71-84, wherein said sotalol or pharmaceutically acceptable salt thereof is sotalol hydrochloride.

Embodiment 86. The pharmaceutical composition of any one of embodiments 36-84, wherein said flecainide or a pharmaceutically acceptable salt thereof is flecainide acetate.

Embodiment 87. The pharmaceutical composition of any one of embodiments 36-84, wherein said flecainide or a pharmaceutically acceptable salt thereof is flecainide hydrochloride.

Embodiment 88. A method of treating a subject suffering from atrial arrhythmia, comprising administering to said subject a therapeutically effective amount of said pharmaceutical composition of any one of embodiments 1-87.

Embodiment 89. A method of treating a subject suffering from atrial arrhythmia, comprising administering to said subject:

(i) a sodium channel blocker in a first amount; and (ii) a potassium channel blocker in a second amount, wherein said administration results in a $t_{max}$ of said sodium channel blocker in said subject that occurs no more than about 30 minutes apart from a $t_{max}$ of said potassium channel blocker in said subject, thereby inducing cardioversion of said atrial arrhythmia.

Embodiment 90. The method of embodiment 89, wherein incidence of torsades de pointes (TdP) is decreased in a plurality of experimental subjects in a clinical study relative to incidence of TdP in a control cohort of said clinical study, wherein:

(i) each subject in said plurality of experimental subjects is administered both said sodium channel blocker in said first amount and said potassium channel blocker in said second amount; and (ii) each subject in said control cohort is administered said sodium channel blocker in said first amount without said potassium channel blocker in said second amount, or each subject in said control cohort is administered said potassium channel blocker or pharmaceutically acceptable thereof in said second amount without said sodium channel blocker in said first amount.

Embodiment 91. The method of embodiment 90, wherein said incidence of torsades de pointes (TdP) in said plurality of experimental subjects is decreased by at least about 5% relative to said incidence of TdP in said control cohort.

Embodiment 92. The method of embodiment 90, wherein said incidence of torsades de pointes (TdP) in said plurality of experimental subjects is decreased by at least about 20% relative to said incidence of TdP in said control cohort.

Embodiment 93. The method of embodiment 90, wherein said incidence of torsades de pointes (TdP) in said plurality of experimental subjects is decreased by at least about 35% relative to said incidence of TdP in said control cohort.

Embodiment 94. The method of embodiment 90, wherein said incidence of torsades de pointes (TdP) in said plurality of experimental subjects is decreased by at least about 50% relative to said incidence of TdP in said control cohort.

Embodiment 95. The method of any one of embodiments 89-94, wherein incidence of above-nomogram QT interval is decreased in a plurality of experimental subjects in a clinical study relative to incidence above-nomogram QT interval in a control cohort of said clinical study, wherein:

(i) each subject in said plurality of experimental subjects is administered both said sodium channel blocker in said first amount and said potassium channel blocker in said second amount; and (ii) each subject in said control cohort is administered said sodium channel blocker in said first amount without said potassium channel blocker in said second amount, or each subject in said control cohort is administered said potassium channel blocker in said second amount without said sodium channel blocker in said first amount.

Embodiment 96. The method of embodiment 95, wherein said incidence of above-nomogram QT interval in said plurality of experimental subjects is decreased by at least about 5% relative to said incidence of above-nomogram QT interval in said control cohort.

Embodiment 97. The method of embodiment 95, wherein said incidence of above-nomogram QT interval in said plurality of experimental subjects is decreased by at least about 20% relative to said incidence of above-nomogram QT interval in said control cohort.

Embodiment 98. The method of embodiment 95, wherein said incidence of above-nomogram QT interval in said plurality of experimental subjects is decreased by at least about 35% relative to said incidence of above-nomogram QT interval in said control cohort.

Embodiment 99. The method of embodiment 95, wherein said incidence of above-nomogram QT interval in said plurality of experimental subjects is decreased by at least about 50% relative to said incidence of above-nomogram QT interval in said control cohort.

Embodiment 100. The method of any one of embodiments 89-99, wherein incidence of hypotension is decreased in a plurality of experimental subjects in a clinical study relative to incidence of hypotension in a control cohort of said clinical study, wherein:

(i) each subject in said plurality of experimental subjects is administered both said sodium channel blocker in said first amount and said potassium channel blocker in said second amount; and (ii) each subject in said control cohort is administered said sodium channel blocker in said first amount without said potassium channel blocker in said second amount, or each subject in said control cohort is administered said potassium channel blocker in said second amount without said sodium channel blocker in said first amount, wherein said hypotension comprises, after said administering, a mean arterial pressure (MAP) of less than 70 mmHg sustained for at least 5 minutes.

Embodiment 101. The method of embodiment 100, wherein said incidence of hypotension in said plurality of experimental subjects is decreased by at least about 5% relative to said incidence of hypotension in said control cohort of said clinical study.

Embodiment 102. The method of embodiment 100, wherein said incidence of hypotension in said plurality of experimental subjects is decreased by at least about 20% relative to said incidence of hypotension in said control cohort of said clinical study.

Embodiment 103. The method of embodiment 100, wherein said incidence of hypotension in said plurality of experimental subjects is decreased by at least about 35% relative to said incidence of hypotension in said control cohort of said clinical study.

Embodiment 104. The method of embodiment 100, wherein said incidence of hypotension in said plurality of experimental subjects is decreased by at least about 50% relative to said incidence of hypotension in said control cohort of said clinical study.

Embodiment 105. The method of any one of embodiments 89-104, wherein an average magnitude of increase in $QT_c$ in a plurality of experimental subjects suffering from said atrial arrhythmia in a clinical study relative to average $QT_c$ in a control cohort of said clinical study is no more than 5%, wherein:

(i) each subject in said plurality of experimental subjects is administered both said sodium channel blocker in said first amount and said potassium channel blocker in said second amount; and (ii) each subject in said control cohort is administered said sodium channel blocker in said first amount without said potassium channel blocker in said second amount, or each subject in said control cohort is administered said potassium channel blocker in said second amount without said sodium channel blocker in said first amount.

Embodiment 106. The method of any one of embodiments 89-105, wherein an average magnitude of increase in $QT_c$ in a plurality of experimental subjects in a clinical study relative to average $QT_c$ in a control cohort of said clinical study is no more than about 40 ms, wherein:

(i) each subject in said plurality of experimental subjects is administered both said sodium channel blocker in said first amount and said potassium channel blocker in said second amount; and (ii) each subject in said control cohort is administered said sodium channel blocker in said first amount without said potassium channel blocker in said second amount, or each subject in said control cohort is administered said potassium channel blocker in said second amount without said sodium channel blocker in said first amount.

Embodiment 107. The method of embodiment 106, wherein said average magnitude of increase in $QT_c$ in said plurality of experimental subjects is no more than about 20 ms.

Embodiment 108. The method of embodiment 106, wherein said average magnitude of increase in $QT_c$ in said plurality of experimental subjects is no more than about 10 ms.

Embodiment 109. The method of embodiment 106, wherein said average magnitude of increase in $QT_c$ in said plurality of experimental subjects is no more than about 6 ms.

Embodiment 110. The method of any one of embodiments 105-109, wherein said $QT_c$ is calculated according to the formula $QT_c=QT+0.154*(1-RR)$, where RR is an interval between two successive R waves and QT is a time interval between a beginning of a QRS complex to an end of a subsequent T wave as measured by electrocardiogram (ECG).

Embodiment 111. The method of any one of embodiments 90-110, wherein said experimental subjects are healthy subjects.

Embodiment 112. The method of any one of embodiments 90-110, wherein said experimental subjects suffer from atrial arrhythmia during said administering.

Embodiment 113. The method of any one of embodiments 90-112, wherein subjects of said control cohort are healthy subjects.

Embodiment 114. The method of any one of embodiments 90-112, wherein subjects of said control cohort suffer from atrial arrhythmia during said administering.

Embodiment 115. The method of any one of embodiments 90-114, wherein said sodium channel blocker and said potassium channel blocker are simultaneously administered to said plurality of experimental subjects.

Embodiment 116. The method of any one of embodiments 90-115, wherein a $t_{max}$ of said sodium channel blocker in said plurality of experimental subjects occurs no more than about 30 minutes apart from a $t_{max}$ of said potassium channel blocker in said subject.

Embodiment 117. The method of any one of embodiments 90-115, wherein a $t_{max}$ of said sodium channel blocker in said plurality of experimental subjects occurs no more than about 15 minutes apart from a $t_{max}$ of said potassium channel blocker in said subject.

Embodiment 118. The method of any one of embodiments 90-115, wherein a $t_{max}$ of said sodium channel blocker in said plurality of experimental subjects occurs no more than about 5 minutes apart from a $t_{max}$ of said potassium channel blocker in said subject.

Embodiment 119. The method of any one of embodiments 90-115, wherein a $t_{max}$ of said sodium channel blocker in said plurality of experimental subjects occurs no more than about 3 minutes apart from a $t_{max}$ of said potassium channel blocker in said subject.

Embodiment 120. The method of any one of embodiments 89-119, wherein said atrial arrhythmia is selected from the group consisting of: supraventricular tachycardia, paroxysmal supraventricular tachycardia, atrial fibrillation, paroxysmal atrial fibrillation, persistent and permanent atrial fibrillation, atrial flutter, paroxysmal atrial flutter, and lone atrial fibrillation.

Embodiment 121. The method of any one of embodiments 89-119, wherein said atrial arrhythmia comprises paroxysmal atrial fibrillation.

Embodiment 122. The method of any one of embodiments 89-119, wherein said atrial arrhythmia comprises persistent atrial fibrillation.

Embodiment 123. The method of any one of embodiments 90-119, wherein said experimental subjects is are human subjects.

Embodiment 124. The method of any one of embodiments 90-123, wherein said sodium channel blocker and said potassium channel blocker are intravenously administered.

Embodiment 125. The method of any one of embodiments 90-123, wherein said sodium channel blocker and said potassium channel blocker are orally administered.

Embodiment 126. The method of any one of embodiments 90-123, wherein said sodium channel blocker and said potassium channel blocker are administered via oral inhalation.

Embodiment 127. The method of any one of embodiments 89-124, wherein said subject is a human subject.

Embodiment 128. The method of any one of embodiments 89-124, wherein said subject suffers from paroxysmal atrial fibrillation that is nonresponsive to monotherapy with said sodium channel blocker.

Embodiment 129. The method of any one of embodiments 89-128, wherein said $t_{max}$ of said sodium channel blocker in said subject occurs no more than about 15 minutes apart from said $t_{max}$ of said potassium channel blocker in said subject.

Embodiment 130. The method of any one of embodiments 89-128, wherein said $t_{max}$ of said sodium channel blocker in said subject occurs no more than about 5 minutes apart from said $t_{max}$ of said potassium channel blocker in said subject.

Embodiment 131. The method of any one of embodiments 89-128, wherein said $t_{max}$ of said sodium channel blocker in said subject occurs no more than about 3 minutes apart from said $t_{max}$ of said potassium channel blocker in said subject.

Embodiment 132. The method of any one of embodiments 89-128, wherein said sodium channel blocker is administered no more than 15 minutes apart from administration of said potassium channel blocker.

Embodiment 133. The method of any one of embodiments 89-128, wherein said sodium channel blocker is administered no more than 5 minutes apart from administration of said potassium channel blocker.

Embodiment 134. The method of any one of embodiments 89-128, wherein said sodium channel blocker is administered no more than 3 minutes apart from administration of said potassium channel blocker.

Embodiment 135. The method of any one of embodiments 89-134, wherein said sodium channel blocker comprises a class Ic antiarrhythmic agent.

Embodiment 136. The method of any one of embodiments 89-134, wherein said sodium channel blocker comprises flecainide or a pharmaceutically acceptable salt thereof.

Embodiment 137. The method of any one of embodiments 89-134, wherein said sodium channel blocker comprises flecainide acetate.

Embodiment 138. The method of any one of embodiments 89-134, wherein said sodium channel blocker comprises flecainide hydrochloride.

Embodiment 139. The method of any one of embodiments 136-138, wherein said first amount is about 0.1 mg to about 2 mg per kilogram of said subject.

Embodiment 140. The method of any one of embodiments 136-138, wherein said first amount is about 0.1 mg to about 1 mg per kilogram of said subject.

Embodiment 141. The method of any one of embodiments 136-138, wherein said first amount is about 0.5 mg per kilogram of said subject.

Embodiment 142. The method of any one of embodiments 136-138, wherein said first amount is about 5 mg to about 300 mg.

Embodiment 143. The method of any one of embodiments 136-138, wherein said first amount is about 5 mg to about 150 mg.

Embodiment 144. The method of any one of embodiments 89-143, wherein said potassium channel blocker is ibutilide, dofetilide, sotalol, methanandamide, anandamide, ambasilide, arachidonamide, A293 (2-(butylsulfonylamino)-N-[(1R)-1-(6-methoxy-3-pyridyl)propyl]-benzamide), bupivacaine, etidocaine, genistein, mepivacaine, phenytoin, quinidine, R-ropivacaine, sematilide, S-ropivacaine, tetracaine, amiodarone, dronedarone, E-4031, vemakalant, or a pharmaceutically acceptable salt thereof.

Embodiment 145. The method of any one of embodiments 89-143, wherein said potassium channel blocker is ibutilide, or a pharmaceutically acceptable salt thereof.

Embodiment 146. The method of any one of embodiments 89-143, wherein said ibutilide or pharmaceutically acceptable salt thereof is ibutilide hemifumarate.

Embodiment 147. The method of embodiment 145 or embodiment 146, wherein said second amount is about 0.001 mg to about 0.25 mg per kilogram of said subject.

Embodiment 148. The method of embodiment 145 or embodiment 146, wherein said second amount is about 0.005 mg to about 0.02 mg per kilogram of said subject.

Embodiment 149. The method of embodiment 145 or embodiment 146, wherein said second amount is about 0.01 mg to about 15 mg.

Embodiment 150. The method of embodiment 145 or embodiment 146, wherein said second amount is about 0.25 mg to about 1 mg.

Embodiment 151. The method of any one of embodiments 89-143, wherein said potassium channel blocker is dofetilide or a pharmaceutically acceptable salt thereof.

Embodiment 152. The method of any one of embodiments 89-143, wherein said potassium channel blocker is sotalol or a pharmaceutically acceptable salt thereof.

Embodiment 153. The method of any one of embodiments 89-143, wherein said potassium channel blocker is sotaolol hydrochloride.

Embodiment 154. The method of any one of embodiments 89-153, wherein said sodium channel blocker and said potassium blocker are simultaneously administered to said subject.

Embodiment 155. The method of any one of embodiments 89-134, wherein said sodium channel blocker comprises flecainide or a pharmaceutically acceptable salt thereof, and said potassium channel blocker comprises ibutilide or a pharmaceutically acceptable salt thereof.

Embodiment 156. The method of embodiment 155, wherein said sodium channel blocker is coformulated with said potassium channel blocker in a fixed-dose combination.

Embodiment 157. The method of embodiment 156, wherein said fixed-dose combination is a liquid unit dosage form.

Embodiment 158. The method of embodiment 157, wherein a mass/mass ratio of said flecainide or pharmaceutically acceptable salt thereof to said ibutilide or pharmaceutically acceptable salt thereof in said liquid unit dosage form is from 60:1 to 240:1.

Embodiment 159. The method of embodiment 157, wherein a mass/mass ratio of said flecainide or pharmaceutically acceptable salt thereof to said ibutilide or pharmaceutically acceptable salt thereof in said liquid unit dosage form is about 120:1.

Embodiment 160. The method of any one of embodiments 157-159, wherein said liquid unit dosage form comprises from about 1 mg/mL to about 100 mg/mL flecainide or a pharmaceutically acceptable salt thereof.

Embodiment 161. The method of any one of embodiments 157-159, wherein said liquid unit dosage form comprises from about 50 mg/mL to about 100 mg/mL flecainide or a pharmaceutically acceptable salt thereof.

Embodiment 162. The method of any one of embodiments 157-159, wherein said liquid unit dosage form comprises from about 1 mg/mL to about 30 mg/mL flecainide or a pharmaceutically acceptable salt thereof.

Embodiment 163. The method of any one of embodiments 157-159, wherein said liquid unit dosage form comprises from about 1 mg/mL to about 2 mg/mL flecainide or a pharmaceutically acceptable salt thereof.

Embodiment 164. The method of any one of embodiments 157-159, wherein said liquid unit dosage form comprises from about 75 mg/mL flecainide or a pharmaceutically acceptable salt thereof.

Embodiment 165. The method of embodiment 157, wherein said liquid unit dosage form comprises: about 1 mg/mL to about 100 mg/mL flecainide or a pharmaceutically acceptable salt thereof, about 0.0005 mg/mL to about 5 mg/mL ibutilide or a pharmaceutically acceptable salt thereof; and one or more pharmaceutically acceptable excipients, diluents, or carriers.

Embodiment 166. The method of embodiment 157, wherein said liquid unit dosage form comprises: about 50 mg/mL to about 100 mg/mL flecainide or a pharmaceutically acceptable salt thereof, about 0.0005 mg/mL to about 5 mg/mL ibutilide or a pharmaceutically acceptable salt thereof; and one or more pharmaceutically acceptable excipients, diluents, or carriers.

Embodiment 167. The method of embodiment 157, wherein said liquid unit dosage form comprises: about 1 mg/mL to about 30 mg/mL flecainide or a pharmaceutically acceptable salt thereof, about 0.001 mg/mL to about 1 mg/mL ibutilide or a pharmaceutically acceptable salt thereof; and one or more pharmaceutically acceptable excipients, diluents, or carriers.

Embodiment 168. The method of embodiment 157, wherein said liquid unit dosage form comprises: about 1 mg/mL to about 2 mg/mL flecainide or a pharmaceutically acceptable salt thereof, about 0.001 mg/mL to about 1 mg/mL ibutilide or a pharmaceutically acceptable salt thereof; and one or more pharmaceutically acceptable excipients, diluents, or carriers.

Embodiment 169. The method of any one of embodiments 155-168, wherein said flecainide or pharmaceutically acceptable salt thereof is flecainide acetate, and said ibutilide or pharmaceutically acceptable salt thereof is ibutilide hemifumarate.

Embodiment 170. The method of any one of embodiments 89-134, wherein said sodium channel blocker comprises flecainide or a pharmaceutically acceptable salt thereof, and said potassium channel blocker comprises dofetilide or a pharmaceutically acceptable salt thereof.

Embodiment 171. The method of embodiment 170, wherein said sodium channel blocker is coformulated with said potassium channel blocker in a fixed-dose combination.

Embodiment 172. The method of embodiment 171, wherein said fixed-dose combination is a liquid unit dosage form.

Embodiment 173. The method of 172, wherein a mass/mass ratio of said flecainide or pharmaceutically acceptable salt thereof to said dofetilide or pharmaceutically acceptable salt thereof in said liquid unit dosage form is from 60:1 to 480:1.

Embodiment 174. The method of 172, wherein a mass/mass ratio of said flecainide or pharmaceutically acceptable salt thereof to said dofetilide or pharmaceutically acceptable salt thereof in said liquid unit dosage form is about 240:1.

Embodiment 175. The method of any one of embodiments 172-174, wherein said liquid unit dosage form comprises from about 1 mg/mL to about 100 mg/mL flecainide or a pharmaceutically acceptable salt thereof.

Embodiment 176. The method of any one of embodiments 172-174, wherein said liquid unit dosage form comprises from about 50 mg/mL to about 100 mg/mL flecainide or a pharmaceutically acceptable salt thereof.

Embodiment 177. The method of any one of embodiments 172-174, wherein said liquid unit dosage form comprises from about 1 mg/mL to about 30 mg/mL flecainide or a pharmaceutically acceptable salt thereof.

Embodiment 178. The method of any one of embodiments 172-174, wherein said liquid unit dosage form comprises from about 1 mg/mL to about 2 mg/mL flecainide or a pharmaceutically acceptable salt thereof.

Embodiment 179. The method of any one of embodiments 172-174, wherein said liquid unit dosage form comprises from about 75 mg/mL flecainide or a pharmaceutically acceptable salt thereof.

Embodiment 180. The method of any one of embodiments 172-174, wherein said liquid unit dosage form comprises from about 2 mg/mL flecainide or a pharmaceutically acceptable salt thereof.

Embodiment 181. The method of any one of embodiments 172-174, wherein said liquid unit dosage form comprises from about 1 mg/mL flecainide or a pharmaceutically acceptable salt thereof.

Embodiment 182. The method of embodiment 172, wherein said liquid unit dosage form comprises: about 1 mg/mL to about 100 mg/mL flecainide or a pharmaceutically acceptable salt thereof, about 0.0005 mg/mL to about 5 mg/mL dofetilide or a pharmaceutically acceptable salt thereof; and one or more pharmaceutically acceptable excipients, diluents, or carriers.

Embodiment 183. The method of embodiment 172, wherein said liquid unit dosage form comprises: about 50 mg/mL to about 100 mg/mL flecainide or a pharmaceutically acceptable salt thereof, about 0.0005 mg/mL to about 5 mg/mL dofetilide or a pharmaceutically acceptable salt thereof; and one or more pharmaceutically acceptable excipients, diluents, or carriers.

Embodiment 184. The method of embodiment 172, wherein said liquid unit dosage form comprises: about 1 mg/mL to about 30 mg/mL flecainide or a pharmaceutically acceptable salt thereof, about 0.001 mg/mL to about 1 mg/mL dofetilide or a pharmaceutically acceptable salt thereof; and one or more pharmaceutically acceptable excipients, diluents, or carriers.

Embodiment 185. The method of embodiment 172, wherein said liquid unit dosage form comprises: about 1 mg/mL to about 2 mg/mL flecainide or a pharmaceutically acceptable salt thereof, about 0.001 mg/mL to about 1 mg/mL dofetilide or a pharmaceutically acceptable salt thereof; and one or more pharmaceutically acceptable excipients, diluents, or carriers.

Embodiment 186. The method of any one of embodiments 89-134, wherein said sodium channel blocker comprises flecainide or a pharmaceutically acceptable salt thereof, and said potassium channel blocker comprises sotalol or a pharmaceutically acceptable salt thereof.

Embodiment 187. The method of embodiment 186, wherein said sodium channel blocker is coformulated with said potassium channel blocker in a fixed-dose combination.

Embodiment 188. The method of embodiment 187, wherein said fixed-dose combination is a liquid unit dosage form.

Embodiment 189. The method of embodiment 188, wherein a mass/mass ratio of said flecainide or pharmaceutically acceptable salt thereof to said sotalol or pharmaceutically acceptable salt thereof in said liquid unit dosage form is from 0.5:1 to 2:1.

Embodiment 190. The method of embodiment 188, wherein a mass/mass ratio of said flecainide or pharmaceutically acceptable salt thereof to said sotalol or pharmaceutically acceptable salt thereof in said liquid unit dosage form is about 1:1.

Embodiment 191. The method of any one of embodiments 188-190, wherein said liquid unit dosage form comprises from about 1 mg/mL to about 100 mg/mL flecainide or a pharmaceutically acceptable salt thereof.

Embodiment 192. The method of any one of embodiments 188-190, wherein said liquid unit dosage form comprises from about 50 mg/mL to about 100 mg/mL flecainide or a pharmaceutically acceptable salt thereof.

Embodiment 193. The method of any one of embodiments 188-190, wherein said liquid unit dosage form comprises from about 1 mg/mL to about 30 mg/mL flecainide or a pharmaceutically acceptable salt thereof.

Embodiment 194. The method of any one of embodiments 188-190, wherein said liquid unit dosage form comprises from about 1 mg/mL to about 2 mg/mL flecainide or a pharmaceutically acceptable salt thereof.

Embodiment 195. The method of any one of embodiments 188-190, wherein said liquid unit dosage form comprises from about 75 mg/mL flecainide or a pharmaceutically acceptable salt thereof.

Embodiment 196. The method of any one of embodiments 188-190, wherein said liquid unit dosage form comprises from about 2 mg/mL flecainide or a pharmaceutically acceptable salt thereof.

Embodiment 197. The method of any one of embodiments 188-190, wherein said liquid unit dosage form comprises from about 1 mg/mL flecainide or a pharmaceutically acceptable salt thereof.

Embodiment 198. The method of embodiment 188, wherein said liquid unit dosage form comprises: about 1 mg/mL to about 100 mg/mL flecainide or a pharmaceutically acceptable salt thereof, about 0.0005 mg/mL to about 5 mg/mL sotalol or a pharmaceutically acceptable salt thereof; and one or more pharmaceutically acceptable excipients, diluents, or carriers.

Embodiment 199. The method of embodiment 188, wherein said liquid unit dosage form comprises: about 50 mg/mL to about 100 mg/mL flecainide or a pharmaceutically acceptable salt thereof, about 0.0005 mg/mL to about 5 mg/mL sotalol or a pharmaceutically acceptable salt thereof; and one or more pharmaceutically acceptable excipients, diluents, or carriers.

Embodiment 200. The method of embodiment 188, wherein said liquid unit dosage form comprises: about 1 mg/mL to about 30 mg/mL flecainide or a pharmaceutically acceptable salt thereof, about 0.001 mg/mL to about 1 mg/mL sotalol or a pharmaceutically acceptable salt thereof; and one or more pharmaceutically acceptable excipients, diluents, or carriers.

Embodiment 201. The method of embodiment 188, wherein said liquid unit dosage form comprises: about 1 mg/mL to about 2 mg/mL flecainide or a pharmaceutically acceptable salt thereof, about 0.001 mg/mL to about 1 mg/mL sotalol or a pharmaceutically acceptable salt thereof; and one or more pharmaceutically acceptable excipients, diluents, or carriers.

Embodiment 202. The method of any one of embodiments 198-201, wherein said flecainide or pharmaceutically acceptable salt thereof is flecainide acetate, and said sotalol or pharmaceutically acceptable salt thereof is sotalol hydrochloride.

Embodiment 203. The method of any one of embodiments 155-202, wherein said flecainide or pharmaceutically acceptable salt thereof is flecainide acetate.

Embodiment 204. The method of any one of embodiments 89-202, further comprising administering a $Mg^{2+}$ source in a third amount.

Embodiment 205. The method of embodiment 204, wherein said $Mg^{2+}$ source is administered no more than 0.5 hours apart from administration of said sodium channel blocker.

Embodiment 206. The method of embodiment 204, wherein said $Mg^{2+}$ source is administered no more than 0.5 hours apart from administration of said potassium channel blocker.

Embodiment 207. The method of any one of embodiments 204-206, wherein said third amount is an amount sufficient to administer from about 0.2 mg to about 20 mg $Mg^{2+}$ cation per kilogram of said subject.

Embodiment 208. The method of any one of embodiments 204-206, wherein said third amount is an amount sufficient to administer from about 0.2 g to about 1 g $Mg^{2+}$ cation to said subject.

Embodiment 209. The method of any one of embodiments 204-208, wherein said $Mg^{2+}$ source comprises magnesium citrate, magnesium fumarate, magnesium acetate, magnesium aspartate, magnesium threonate, magnesium glycinate, magnesium chloride, magnesium sulfate, magnesium oxide, or magnesium malate, or a hydrate thereof.

Embodiment 210. The method of any one of embodiments 204-208, wherein said $Mg^{2+}$ source comprises magnesium sulfate, or a hydrate thereof.

Embodiment 211. The method of any one of embodiments 204-208, wherein said $Mg^{2+}$ source comprises magnesium sulfate heptahydrate.

Embodiment 212. The method of embodiment 210 or embodiment 211, wherein said third amount is from about 1 mg to about 100 mg per kilogram of said subject.

Embodiment 213. The method of embodiment 210 or embodiment 211, wherein said third amount is from about 1 g to about 10 g.

Embodiment 214. The method of any one of embodiments 89-134, wherein said sodium channel blocker comprises flecainide or a pharmaceutically acceptable salt thereof, and said potassium channel blocker comprises ibutilide or a pharmaceutically acceptable salt thereof.

Embodiment 215. The method of embodiment 214, further comprising administering a $Mg^{2+}$ source in a third amount.

Embodiment 216. The method of embodiment 215, wherein said flecainide or pharmaceutically acceptable salt thereof, said ibutilide or pharmaceutically acceptable salt thereof, and said $Mg^{2+}$ source are co-formulated in a fixed-dose combination.

Embodiment 217. The method of embodiment 216, wherein said fixed-dose combination is a liquid unit dosage form.

Embodiment 218. The method of embodiment 217, wherein said liquid unit dosage form comprises: about 1 mg/mL to about 100 mg/mL flecainide or a pharmaceutically acceptable salt thereof, about 0.0005 mg/mL to about 5 mg/mL ibutilide or a pharmaceutically acceptable salt thereof, about 1 mg/mL to about 140 mg/mL $Mg^{2+}$ cation; and one or more pharmaceutically acceptable excipients, diluents, or carriers.

Embodiment 219. The method of embodiment 217, wherein said $Mg^{2+}$ source comprises magnesium sulfate, or a hydrate thereof.

Embodiment 220. The method of embodiment 219, wherein said liquid unit dosage form comprises: about 1 mg/mL to about 100 mg/mL flecainide or a pharmaceutically acceptable salt thereof, about 0.0005 mg/mL to about 5 mg/mL ibutilide or a pharmaceutically acceptable salt thereof, about 5 mg/mL to about 700 mg/mL magnesium sulfate or a hydrate thereof; and one or more pharmaceutically acceptable excipients, diluents, or carriers.

Embodiment 221. The method of embodiment 219, wherein said liquid unit dosage form comprises: about 1 mg/mL to about 30 mg/mL flecainide or a pharmaceutically acceptable salt thereof, about 0.001 mg/mL to about 1 mg/mL ibutilide or a pharmaceutically acceptable salt thereof, about 20 mg/mL to about 700 mg/mL magnesium sulfate or a hydrate thereof; and one or more pharmaceutically acceptable excipients, diluents, or carriers.

Embodiment 222. The method of embodiment 219, wherein said liquid unit dosage form comprises: about 1 mg/mL to about 100 mg/mL flecainide or a pharmaceutically acceptable salt thereof, about 0.0005 mg/mL to about 5 mg/mL ibutilide or a pharmaceutically acceptable salt thereof, about 5 mg/mL to about 700 mg/mL magnesium sulfate or a hydrate thereof; and one or more pharmaceutically acceptable excipients, diluents, or carriers.

Embodiment 223. The method of embodiment 219, wherein said liquid unit dosage form comprises: about 1 mg/mL to about 30 mg/mL flecainide or a pharmaceutically acceptable salt thereof, about 0.001 mg/mL to about 1 mg/mL ibutilide or a pharmaceutically acceptable salt thereof, about 20 mg/mL to about 700 mg/mL magnesium sulfate or a hydrate thereof; and one or more pharmaceutically acceptable excipients, diluents, or carriers.

Embodiment 224. The method of any one of embodiments 214-223, wherein said flecainide or pharmaceutically acceptable salt thereof is flecainide acetate.

Embodiment 225. The method of any one of embodiments 157-213 or 217-224, wherein said liquid unit dosage form is intravenously administered.

Embodiment 226. The method of any one of embodiments 89-225, wherein at said $t_{max}$ of said potassium channel blocker in said subject, $QT_c$ of said subject is no more than about 490 ms.

Embodiment 227. The method of any one of embodiments 89-225, wherein between about 30 minutes before and about 30 minutes after said $t_{max}$ of said potassium channel blocker in said subject, $QT_c$ of said subject is no more than about 490 ms.

Embodiment 228. A kit comprising:

(i) a first unit dosage form packaged in a first container, wherein said first unit dosage form comprises a sodium channel blocker and one or more pharmaceutically acceptable excipients, diluents, or carriers; and (ii) a second unit dosage form packaged in a second container, wherein said second unit dosage form comprises a potassium channel blocker or a pharmaceutically acceptable salt thereof and one or more pharmaceutically acceptable excipients, diluents, or carriers, wherein said first unit dosage form or said second unit dosage form further comprises a $Mg^{2+}$ source.

Embodiment 229. The kit of embodiment 228, wherein said potassium channel blocker is sotalol or a pharmaceutically acceptable salt thereof.

Embodiment 230. The kit of embodiment 228, wherein said potassium channel blocker is dofetilide or a pharmaceutically acceptable salt thereof.

Embodiment 231. The kit of embodiment 228, wherein said potassium channel blocker is ibutilide or a pharmaceutically acceptable salt thereof.

Embodiment 232. The kit of embodiment 228, wherein said $Mg^{2+}$ source comprises magnesium citrate, magnesium fumarate, magnesium acetate, magnesium aspartate, magnesium threonate, magnesium glycinate, magnesium chloride, magnesium sulfate, magnesium oxide, or magnesium malate, or a hydrate thereof.

Embodiment 233. The kit of embodiment 228, wherein said sodium channel blocker is a class Ic antiarrhythmic agent.

Embodiment 234. The kit of embodiment 228, wherein said sodium channel blocker is flecainide or a pharmaceutically acceptable salt thereof.

Embodiment 235. The kit of any one of embodiments 231-234, wherein said first unit dosage form or said second unit dosage form is a lyophilized powder.

Embodiment 236. The kit of any one of embodiments 231-234, wherein said first unit dosage form or said second unit dosage form is a liquid solution.

Embodiment 237. The kit of embodiment 236, wherein said $Mg^{2+}$ source is magnesium sulfate or a hydrate thereof.

Embodiment 238. The kit of embodiment 237, wherein said first unit dosage form or said second unit dosage form comprises about 1 mg/mL to about 150 mg/mL $Mg^{2+}$ cation.

Embodiment 239. The kit of embodiment 237, wherein said first unit dosage form or said second unit dosage form comprises about 5 mg/mL to about 700 mg/mL magnesium sulfate or a hydrate thereof.

Embodiment 240. The kit of embodiment 237, wherein said first unit dosage form or said second unit dosage form comprises about 20 mg/mL to about 700 mg/mL magnesium sulfate or a hydrate thereof.

Embodiment 241. The kit of any one of embodiments 236-240, wherein said first unit dosage form comprises from about 1 mg/mL to about 100 mg/mL flecainide or a pharmaceutically acceptable salt thereof.

Embodiment 242. The kit of any one of embodiments 236-240, wherein said first unit dosage form comprises from about 1 mg/mL to about 30 mg/mL flecainide or a pharmaceutically acceptable salt thereof.

Embodiment 243. The kit of any one of embodiments 236-242, wherein said second unit dosage form comprises from about 0.0005 mg/mL to about 5 mg/mL ibutilide or a pharmaceutically acceptable salt thereof.

Embodiment 244. The kit of any one of embodiments 236-242, wherein said second unit dosage form comprises from about 0.001 mg/mL to about 1 mg/mL ibutilide or a pharmaceutically acceptable salt thereof.

Embodiment 245. The kit of any one of embodiments 231-244, wherein said first unit dosage form comprises from about 5 mg to about 300 mg flecainide or a pharmaceutically acceptable salt thereof.

Embodiment 246. The kit of any one of embodiments 231-245, wherein said first unit dosage form comprises from about 5 mg to about 150 mg flecainide or a pharmaceutically acceptable salt thereof.

Embodiment 247. The kit of any one of embodiments 231-245, wherein said second unit dosage form comprises from about 0.001 mg to about 0.25 mg ibutilide or a pharmaceutically acceptable salt thereof.

Embodiment 248. The kit of any one of embodiments 231-245, wherein said second unit dosage form comprises from about 0.005 mg to about 0.02 mg ibutilide or a pharmaceutically acceptable salt thereof.

Embodiment 249. The kit of any one of embodiments 231-248, wherein first unit dosage form or said second unit dosage form comprises from about 0.2 g to about 2 g $Mg^{2+}$ cation.

Embodiment 250. The kit of any one of embodiments 231-247 wherein first unit dosage form or said second unit dosage form comprises from about 1 g to about 10 g magnesium sulfate or a hydrate thereof.

Embodiment 251. The kit of any one of embodiments 231-249, wherein said first unit dosage form and said second unit dosage form are each formulated for intravenous administration.

Embodiment 252. The kit of any one of embodiments 231-251, wherein said sodium channel blocker is flecainide acetate.

Embodiment 253. The kit of any one of embodiments 231-251, wherein said sodium channel blocker is flecainide hydrochloride.

Embodiment 254. The kit of any one of embodiments 231-253, wherein said ibutilide is ibutilide fumarate.

Embodiment 255. The kit of any one of embodiments 228-254, wherein said $Mg^{2+}$ source is magnesium sulfate heptahydrate.

Embodiment 256. The kit of any one of embodiments 228-255, wherein said first container and said second container are each independently a polymer bag, a glass vial, or a prefilled syringe.

Embodiment 257. A method for treating a subject in need thereof, comprising administering said first unit dosage form and said second unit dosage form of any one of embodiments 228-256 to said subject.

Embodiment 258. The method of embodiment 257, wherein said administering comprises administering said first unit dosage form to said subject no more than about 0.5 hours apart from administration of said second unit dosage form.

Embodiment 259. The method of embodiment 257, wherein said administering comprises administering said first unit dosage form to said subject no more than about 15 minutes apart from administration of said second unit dosage form.

Embodiment 260. The method of embodiment 257, wherein said administering comprises administering said first unit dosage form to said subject no more than about 5 minutes apart from administration of said second unit dosage form.

Embodiment 261. The method of embodiment 257, wherein said administering comprises simultaneously administering said first unit dosage form and said second unit dosage form to said subject.

Embodiment 262. The method of embodiment 257, wherein said administering comprises combining said first unit dosage form and said second unit dosage form to provide a combined dosage form, and administering said combined dosage form to said subject.

Embodiment 263. The method of embodiment 257, wherein said subject suffers from atrial arrhythmia.

Embodiment 264. The method of embodiment 263, wherein said administering results in cardioversion of said atrial arrhythmia.

Embodiment 265. A pharmaceutical composition comprising a sodium channel blocker and a potassium channel blocker, and one or more pharmaceutically acceptable excipients, diluents, or carriers.

Embodiment 266. The pharmaceutical composition of embodiment 265, wherein said sodium channel blocker is flecainide, or a pharmaceutically acceptable salt thereof.

Embodiment 267. The pharmaceutical composition of embodiment 266, wherein said potassium channel blocker is ibutilide, or a pharmaceutically acceptable salt thereof.

Embodiment 268. The pharmaceutical composition of embodiment 266, wherein a mass/mass ratio of said flecainide or pharmaceutically acceptable salt thereof to said ibutilide or pharmaceutically acceptable salt thereof in said pharmaceutical composition is from about 60:1 to about 240:1.

Embodiment 269. The pharmaceutical composition of embodiment 266, wherein a mass/mass ratio of said flecainide or pharmaceutically acceptable salt thereof to said ibutilide or pharmaceutically acceptable salt thereof in said pharmaceutical composition is about 120:1.

Embodiment 270. The pharmaceutical composition of any one of embodiments 267-269, wherein said ibutilide or pharmaceutically acceptable salt thereof is ibutilide hemifumarate.

Embodiment 271. The pharmaceutical composition of embodiment 266, wherein said potassium channel blocker is sotalol, or a pharmaceutically acceptable salt thereof.

Embodiment 272. The pharmaceutical composition of embodiment 266, wherein a mass/mass ratio of said flecainide or pharmaceutically acceptable salt thereof to said sotalol or pharmaceutically acceptable salt thereof in said pharmaceutical composition is from about 0.5:1 to about 2:1.

Embodiment 273. The pharmaceutical composition of embodiment 266, wherein a mass/mass ratio of said flecainide or pharmaceutically acceptable salt thereof to said sotalol or pharmaceutically acceptable salt thereof in said pharmaceutical composition is about 1:1.

Embodiment 274. The pharmaceutical composition of any one of embodiments 271-273, wherein said sotalol or pharmaceutically acceptable salt thereof is sotalol hydrochloride.

Embodiment 275. The pharmaceutical composition of embodiment 266, wherein said potassium channel blocker is dofetilide, or a pharmaceutically acceptable salt thereof.

Embodiment 276. The pharmaceutical composition of embodiment 266, wherein a mass/mass ratio of said flecainide or pharmaceutically acceptable salt thereof to said dofetilide or pharmaceutically acceptable salt thereof in said pharmaceutical composition is from about 60:1 to about 480:1.

Embodiment 277. The pharmaceutical composition of embodiment 266, wherein a mass/mass ratio of said flecainide or pharmaceutically acceptable salt thereof to said dofetilide or pharmaceutically acceptable salt thereof in said pharmaceutical composition is about 240:1.

Embodiment 278. The pharmaceutical composition of any one of embodiments 268-277, wherein said pharmaceutical composition is in a form of an inhalable dry powder.

Embodiment 279. The pharmaceutical composition of any one of embodiments 268-277, wherein said dry powder is a spray dried powder.

Embodiment 280. The pharmaceutical composition of any one of embodiments 268-277, wherein said dry powder is formed by supercritical enhanced dispersion by supercritical fluids (SEDS).

Embodiment 281. The pharmaceutical composition of any one of embodiments 268-277, wherein said dry powder is formed by supercritical precipitation.

Embodiment 282. The pharmaceutical composition of any one of embodiments 268-277, wherein said dry powder is formed by imprint lithography.

Embodiment 283. The pharmaceutical composition of any one of embodiments 268-277, wherein said dry powder is formed by lyophilization.

Embodiment 284. The pharmaceutical composition of any one of embodiments 268-277, wherein said pharmaceutical composition is in a form of a liquid solution.

Embodiment 285. The pharmaceutical composition of embodiment 284, comprising about 1 mg/mL to about 100 mg/mL flecainide or a pharmaceutically acceptable salt thereof.

Embodiment 286. The pharmaceutical composition of embodiment 284, comprising about 50 mg/mL to about 100 mg/mL flecainide or a pharmaceutically acceptable salt thereof.

Embodiment 287. The pharmaceutical composition of embodiment 284, comprising about 1 mg/mL to about 30 mg/mL flecainide or a pharmaceutically acceptable salt thereof.

Embodiment 288. The pharmaceutical composition of embodiment 284, comprising about 1 mg/mL to about 2 mg/mL flecainide or a pharmaceutically acceptable salt thereof.

Embodiment 289. The pharmaceutical composition of embodiment 284, comprising about 75 mg/mL flecainide or a pharmaceutically acceptable salt thereof.

Embodiment 290. The pharmaceutical composition of embodiment 284, comprising about 2 mg/mL flecainide or a pharmaceutically acceptable salt thereof.

Embodiment 291. The pharmaceutical composition of embodiment 284, comprising about 1 mg/mL flecainide or a pharmaceutically acceptable salt thereof.

Embodiment 292. The pharmaceutical composition of embodiment 265, wherein said sodium channel blocker is propafenone, or a pharmaceutically acceptable salt thereof.

Embodiment 293. The pharmaceutical composition of embodiment 292, wherein said potassium channel blocker is ibutilide, or a pharmaceutically acceptable salt thereof.

Embodiment 294. The pharmaceutical composition of embodiment 293 wherein a mass/mass ratio of said propafenone or pharmaceutically acceptable salt thereof to said ibutilide or pharmaceutically acceptable salt thereof in said pharmaceutical composition is from about 120:1 to about 480:1.

Embodiment 295. The pharmaceutical composition of embodiment 293, wherein a mass/mass ratio of said propafenone or pharmaceutically acceptable salt thereof to said ibutilide or pharmaceutically acceptable salt thereof in said pharmaceutical composition is about 240:1.

Embodiment 296. The pharmaceutical composition of any one of embodiments 293-295, wherein said ibutilide or pharmaceutically acceptable salt thereof is ibutilide hemifumarate.

Embodiment 297. The pharmaceutical composition of embodiment 292, wherein said potassium channel blocker is sotalol, or a pharmaceutically acceptable salt thereof.

Embodiment 298. The pharmaceutical composition of embodiment 297, wherein a mass/mass ratio of said propafenone or pharmaceutically acceptable salt thereof to said sotalol or pharmaceutically acceptable salt thereof in said pharmaceutical composition is from about 1:1 to about 4:1.

Embodiment 299. The pharmaceutical composition of embodiment 297, wherein a mass/mass ratio of said propafenone or pharmaceutically acceptable salt thereof to said sotalol or pharmaceutically acceptable salt thereof in said pharmaceutical composition is about 2:1.

Embodiment 300. The pharmaceutical composition of any one of embodiments 297-299, wherein said sotalol or pharmaceutically acceptable salt thereof is sotalol hydrochloride.

Embodiment 301. The pharmaceutical composition of embodiment 292, wherein said potassium channel blocker is dofetilide, or a pharmaceutically acceptable salt thereof.

Embodiment 302. The pharmaceutical composition of embodiment 301, wherein a mass/mass ratio of said propafenone or pharmaceutically acceptable salt thereof to said dofetilide or pharmaceutically acceptable salt thereof in said pharmaceutical composition is from about 120:1 to about 900:1.

Embodiment 303. The pharmaceutical composition of embodiment 301, wherein a mass/mass ratio of said propafenone or pharmaceutically acceptable salt thereof to said dofetilide or pharmaceutically acceptable salt thereof in said pharmaceutical composition is about 480:1.

Embodiment 304. The pharmaceutical composition of any one of embodiments 292-303, wherein said pharmaceutical composition is in a form of an inhalable dry powder.

Embodiment 305. The pharmaceutical composition of any one of embodiments 292-303, wherein said dry powder is a spray dried powder.

Embodiment 306. The pharmaceutical composition of any one of embodiments 292-303, wherein said dry powder is formed by supercritical enhanced dispersion by supercritical fluids (SEDS).

Embodiment 307. The pharmaceutical composition of any one of embodiments 292-303, wherein said dry powder is formed by supercritical precipitation.

Embodiment 308. The pharmaceutical composition of any one of embodiments 292-303, wherein said dry powder is formed by imprint lithography.

Embodiment 309. The pharmaceutical composition of any one of embodiments 292-303, wherein said dry powder is formed by lyophilization.

Embodiment 310. The pharmaceutical composition of any one of embodiments 292-303, wherein said pharmaceutical composition is in a form of a liquid solution.

Embodiment 311. The pharmaceutical composition of embodiment 310, comprising about 1 mg/mL to about 100 mg/mL propafenone or a pharmaceutically acceptable salt thereof.

Embodiment 312. The pharmaceutical composition of embodiment 310, comprising about 50 mg/mL to about 100 mg/mL propafenone or a pharmaceutically acceptable salt thereof.

Embodiment 313. The pharmaceutical composition of embodiment 310, comprising about 1 mg/mL to about 30 mg/mL propafenone or a pharmaceutically acceptable salt thereof.

Embodiment 314. The pharmaceutical composition of embodiment 310, comprising about 1 mg/mL to about 2 mg/mL propafenone or a pharmaceutically acceptable salt thereof.

Embodiment 315. The pharmaceutical composition of embodiment 310, comprising about 75 mg/mL propafenone or a pharmaceutically acceptable salt thereof.

Embodiment 316. The pharmaceutical composition of embodiment 310, comprising about 2 mg/mL propafenone or a pharmaceutically acceptable salt thereof.

Embodiment 317. The pharmaceutical composition of embodiment 310, comprising about 1 mg/mL propafenone or a pharmaceutically acceptable salt thereof.

Embodiment 318. The pharmaceutical composition of embodiment 265, wherein said sodium channel blocker is mexiletine, or a pharmaceutically acceptable salt thereof.

Embodiment 319. The pharmaceutical composition of embodiment 318, wherein said potassium channel blocker is ibutilide, or a pharmaceutically acceptable salt thereof.

Embodiment 320. The pharmaceutical composition of embodiment 319, wherein a mass/mass ratio of said mexiletine or pharmaceutically acceptable salt thereof to said ibutilide or pharmaceutically acceptable salt thereof in said pharmaceutical composition is from about 120:1 to about 480:1.

Embodiment 321. The pharmaceutical composition of embodiment 319, wherein a mass/mass ratio of said mexiletine or pharmaceutically acceptable salt thereof to said ibutilide or pharmaceutically acceptable salt thereof in said pharmaceutical composition is about 240:1.

Embodiment 322. The pharmaceutical composition of any one of embodiments 319-321, wherein said ibutilide or pharmaceutically acceptable salt thereof is ibutilide hemifumarate.

Embodiment 323. The pharmaceutical composition of embodiment 318, wherein said potassium channel blocker is sotalol, or a pharmaceutically acceptable salt thereof.

Embodiment 324. The pharmaceutical composition of embodiment 323, wherein a mass/mass ratio of said mexiletine or pharmaceutically acceptable salt thereof to said sotalol or pharmaceutically acceptable salt thereof in said pharmaceutical composition is from about 1:1 to about 4:1.

Embodiment 325. The pharmaceutical composition of embodiment 323, wherein a mass/mass ratio of said mexiletine or pharmaceutically acceptable salt thereof to said sotalol or pharmaceutically acceptable salt thereof in said pharmaceutical composition is about 2:1.

Embodiment 326. The pharmaceutical composition of any one of embodiments 323-325, wherein said sotalol or pharmaceutically acceptable salt thereof is sotalol hydrochloride.

Embodiment 327. The pharmaceutical composition of embodiment 318, wherein said potassium channel blocker is dofetilide, or a pharmaceutically acceptable salt thereof.

Embodiment 328. The pharmaceutical composition of embodiment 327, wherein a mass/mass ratio of said mexiletine or pharmaceutically acceptable salt thereof to said dofetilide or pharmaceutically acceptable salt thereof in said pharmaceutical composition is from about 120:1 to about 900:1.

Embodiment 329. The pharmaceutical composition of embodiment 327, wherein a mass/mass ratio of said mexiletine or pharmaceutically acceptable salt thereof to said dofetilide or pharmaceutically acceptable salt thereof in said pharmaceutical composition is about 480:1.

Embodiment 330. The pharmaceutical composition of any one of embodiments 318-329, wherein said pharmaceutical composition is in a form of an inhalable dry powder.

Embodiment 331. The pharmaceutical composition of any one of embodiments 318-329, wherein said dry powder is a spray dried powder.

Embodiment 332. The pharmaceutical composition of any one of embodiments 318-329, wherein said dry powder is formed by supercritical enhanced dispersion by supercritical fluids (SEDS).

Embodiment 333. The pharmaceutical composition of any one of embodiments 318-329, wherein said dry powder is formed by supercritical precipitation.

Embodiment 334. The pharmaceutical composition of any one of embodiments 318-329, wherein said dry powder is formed by imprint lithography.

Embodiment 335. The pharmaceutical composition of any one of embodiments 318-329, wherein said dry powder is formed by lyophilization.

Embodiment 336. The pharmaceutical composition of any one of embodiments 318-329, wherein said pharmaceutical composition is in a form of a liquid solution.

Embodiment 337. The pharmaceutical composition of embodiment 336 comprising about 1 mg/mL to about 100 mg/mL mexiletine or a pharmaceutically acceptable salt thereof.

Embodiment 338. The pharmaceutical composition of embodiment 336, comprising about 50 mg/mL to about 100 mg/mL mexiletine or a pharmaceutically acceptable salt thereof.

Embodiment 339. The pharmaceutical composition of embodiment 336, comprising about 1 mg/mL to about 30 mg/mL mexiletine or a pharmaceutically acceptable salt thereof.

Embodiment 340. The pharmaceutical composition of embodiment 336, comprising about 1 mg/mL to about 2 mg/mL mexiletine or a pharmaceutically acceptable salt thereof.

Embodiment 341. The pharmaceutical composition of embodiment 336, comprising about 75 mg/mL mexiletine or a pharmaceutically acceptable salt thereof.

Embodiment 342. The pharmaceutical composition of embodiment 336, comprising about 2 mg/mL mexiletine or a pharmaceutically acceptable salt thereof.

Embodiment 343. The pharmaceutical composition of embodiment 336, comprising about 1 mg/mL mexiletine or a pharmaceutically acceptable salt thereof.

Embodiment 344. The pharmaceutical composition of any one of embodiments 265-291, wherein said flecainide or pharmaceutically acceptable salt thereof is flecainide acetate.

Embodiment 345. The pharmaceutical composition of any one of embodiments 292-317, wherein said propafenone or pharmaceutically acceptable salt thereof is propafenone hydrochloride.

Embodiment 346. The pharmaceutical composition of any one of embodiments 318-343, wherein said mexiletine or pharmaceutically acceptable salt thereof is mexiletine hydrochloride.

Embodiment 347. A method of treating a subject suffering from atrial arrhythmia, comprising administering to said subject a therapeutically effective amount of said pharmaceutical composition of any one of embodiments 265-346.

What is claimed is:

1. A method of treating a subject suffering from atrial arrhythmia, comprising intravenously administering to said subject a pharmaceutical composition, wherein the pharmaceutical composition comprises a sodium channel blocker that is flecainide or a pharmaceutically acceptable salt thereof; and a potassium channel blocker selected from the group consisting of: ibutilide or a pharmaceutically acceptable salt thereof, and dofetilide or a pharmaceutically acceptable salt thereof.

2. The method of claim 1, wherein said sodium channel blocker is flecainide acetate.

3. The method of claim 1, wherein said sodium channel blocker is flecainide hydrochloride.

4. The method of claim 2, wherein said administering comprises administering flecainide acetate in an amount that is about 0.1 mg to about 2 mg per kilogram of said subject.

5. The method of claim 2, wherein said administering comprises administering flecainide acetate in an amount that is about 1 mg per kilogram of said subject.

6. The method of claim 2, wherein said administering comprises administering flecainide acetate in an amount that is about 5 mg to about 300 mg.

7. The method of claim 1, wherein said potassium channel blocker is ibutilide or a pharmaceutically acceptable salt thereof.

8. The method of claim 1, wherein said potassium channel blocker is ibutilide hemifumarate.

9. The method of claim 8, wherein said administering comprises administering ibutilide hemifumarate in an amount that is about 0.001 mg to about 0.25 mg per kilogram of said subject.

10. The method of claim 8, wherein said administering comprises administering ibutilide hemifumarate in an amount that is about 0.007 mg per kilogram of said subject.

11. The method of claim 8, wherein said administering comprises administering ibutilide hemifumarate in an amount that is about 0.01 mg to about 15 mg.

12. The method of claim 1, wherein said pharmaceutical composition is in liquid unit dosage form.

13. The method of claim 7, wherein a mass/mass ratio of said flecainide or pharmaceutically acceptable salt thereof to said ibutilide or pharmaceutically acceptable salt thereof is from 60:1 to 240:1.

14. The method of claim 7, wherein a mass/mass ratio of said flecainide or pharmaceutically acceptable salt thereof to said ibutilide or pharmaceutically acceptable salt thereof is about 120:1.

15. The method of claim 12, wherein said pharmaceutical composition comprises from about 1 mg/mL to about 10 mg/mL flecainide or pharmaceutically acceptable salt thereof.

16. The method of claim 12, wherein said pharmaceutical composition comprises about 0.001 mg/mL to about 1 mg/mL ibutilide or pharmaceutically acceptable salt thereof.

17. The method of claim 1, wherein said atrial arrhythmia is selected from the group consisting of: supraventricular tachycardia, paroxysmal supraventricular tachycardia, atrial fibrillation, paroxysmal atrial fibrillation, persistent and permanent atrial fibrillation, atrial flutter, paroxysmal atrial flutter, and lone atrial fibrillation.

18. The method of claim 1, wherein said atrial arrhythmia comprises paroxysmal atrial fibrillation.

19. The method of claim 1, wherein said atrial arrhythmia comprises persistent atrial fibrillation.

20. The method of claim 1, wherein said potassium channel blocker is dofetilide or a pharmaceutically acceptable salt thereof.

21. The method of claim 20, wherein said administering comprises administering dofetilide in an amount that is about 1 μg to about 5 μg per kilogram of said subject.

22. The method of claim 20, wherein said administering comprises administering dofetilide in an amount that is about 0.002 mg to about 2 mg.

23. The method of claim 20, wherein a mass/mass ratio of said flecainide or pharmaceutically acceptable salt thereof to said dofetilide or pharmaceutically acceptable salt thereof is from 60:1 to 480:1.

24. The method of claim 20, wherein said pharmaceutical composition comprises about 1 μg/mL to about 40 μg/mL dofetilide or pharmaceutically acceptable salt thereof.

* * * * *